(12) United States Patent
Chobotov

(10) Patent No.: US 8,864,814 B2
(45) Date of Patent: *Oct. 21, 2014

(54) METHOD OF DELIVERING ADVANCED ENDOVASCULAR GRAFT AND SYSTEM

(75) Inventor: Michael V. Chobotov, Santa Rosa, CA (US)

(73) Assignee: Trivascular, Inc., Santa Rosa, CA (US)

(*) Notice: Subject to any disclaimer, the term of this patent is extended or adjusted under 35 U.S.C. 154(b) by 149 days.

This patent is subject to a terminal disclaimer.

(21) Appl. No.: 13/246,651

(22) Filed: Sep. 27, 2011

(65) Prior Publication Data

US 2012/0022636 A1 Jan. 26, 2012

Related U.S. Application Data

(63) Continuation of application No. 12/566,808, filed on Sep. 25, 2009, now abandoned, and a continuation of (Continued)

(51) Int. Cl.
| | | |
|---|---|---|
| *A61F 2/06* | (2013.01) | |
| *A61F 2/962* | (2013.01) | |
| *A61F 2/07* | (2013.01) | |
| *A61F 2/95* | (2013.01) | |
| *A61M 25/01* | (2006.01) | |
| *A61F 2/954* | (2013.01) | |
| *A61F 2/848* | (2013.01) | |
| *A61F 2/89* | (2013.01) | |

(52) U.S. Cl.
CPC . *A61F 2/07* (2013.01); *A61F 2/962* (2013.01); *A61F 2002/9517* (2013.01); *A61F 2002/9505* (2013.01); *A61F 2220/005* (2013.01);

(58) Field of Classification Search
USPC .......... 623/1.11, 1.13–1.16, 1.23, 1.35–1.36; 606/108
See application file for complete search history.

(56) References Cited

U.S. PATENT DOCUMENTS

| 3,657,744 A | 4/1972 | Ersek |
| 4,140,126 A | 2/1979 | Choudhury |

(Continued)

FOREIGN PATENT DOCUMENTS

| EP | 0 646 365 B1 | 4/1995 |
| EP | 0 664 107 B1 | 7/1995 |

(Continued)

OTHER PUBLICATIONS

Japanese Office Action for JP Patent Application No. 2008-303094, mailed May 24, 2011.

(Continued)

*Primary Examiner* — Paul Prebilic
(74) *Attorney, Agent, or Firm* — John S. Sopko; Hoffmann & Baron, LLP

(57) ABSTRACT

A flexible low profile delivery system for delivery of an expandable intracorporeal device, specifically, an endovascular graft, which has at least one belt circumferentially disposed about the device in a constraining configuration. The belt is released by a release member, such as a release wire, by retracting the wire from looped ends of the belt. Multiple belts can be used and can be released sequentially so as to control the order of release and placement of the endovascular graft. An outer protective sheath may be disposed about the endovascular graft while in a constrained state which must first be refracted or otherwise removed prior to release of the graft from a constrained state. The delivery system can be configured for delivery over a guiding device such as a guidewire. The delivery system can also be configured for delivery of bifurcated intracorporeal devices.

30 Claims, 66 Drawing Sheets

Related U.S. Application Data application No. 11/333,595, filed on Jan. 17, 2006, now Pat. No. 7,766,954, which is a continuation of application No. 10/091,641, filed on Mar. 5, 2002, now abandoned, which is a continuation of application No. 10/029,559, filed on Dec. 20, 2001, now Pat. No. 7,147,661.

(52) U.S. Cl.
CPC .. *A61F 2250/0036* (2013.01); *A61F 2002/065* (2013.01); *A61F 2002/9511* (2013.01); *A61M 2025/0177* (2013.01); *A61F 2/954* (2013.01); *A61F 2002/075* (2013.01); *A61F 2250/0003* (2013.01); *A61F 2220/0058* (2013.01); *A61F 2002/8486* (2013.01); *A61F 2/89* (2013.01)
USPC .................. 623/1.14; 623/1.36; 623/1.13

(56) References Cited

U.S. PATENT DOCUMENTS

| | | |
|---|---|---|
| 4,562,596 A | 1/1986 | Kornberg |
| 4,577,631 A | 3/1986 | Kreamer |
| 4,580,568 A | 4/1986 | Gianturco |
| 4,733,665 A * | 3/1988 | Palmaz .................. 606/108 |
| 4,787,899 A | 11/1988 | Lazarus |
| 4,793,348 A * | 12/1988 | Palmaz .................. 606/194 |
| 4,987,775 A | 1/1991 | Chobotov |
| 4,994,071 A | 2/1991 | MacGregor |
| 4,994,077 A | 2/1991 | Dobben |
| 5,035,706 A * | 7/1991 | Giantureo et al. ........... 606/198 |
| 5,052,998 A | 10/1991 | Zimmon |
| 5,104,399 A | 4/1992 | Lazarus |
| 5,151,105 A | 9/1992 | Kwan-Gett |
| 5,156,620 A | 10/1992 | Pigott |
| 5,163,955 A | 11/1992 | Love et al. |
| 5,167,614 A | 12/1992 | Tessmann et al. |
| 5,250,059 A | 10/1993 | Andreas et al. |
| 5,275,622 A | 1/1994 | Lazarus et al. |
| 5,344,426 A * | 9/1994 | Lau et al. ................ 623/1.11 |
| 5,350,398 A | 9/1994 | Pavcnik et al. |
| 5,354,329 A | 10/1994 | Whalen |
| 5,360,443 A | 11/1994 | Barone et al. |
| 5,383,887 A | 1/1995 | Nadal |
| 5,387,235 A | 2/1995 | Chuter |
| 5,391,147 A | 2/1995 | Imran et al. |
| 5,397,344 A | 3/1995 | Garfield et al. |
| 5,397,345 A | 3/1995 | Lazarus |
| 5,397,355 A * | 3/1995 | Marin et al. .................. 623/1.2 |
| 5,405,378 A | 4/1995 | Strecker |
| 5,415,634 A | 5/1995 | Glynn et al. |
| 5,423,885 A * | 6/1995 | Williams .................. 623/1.17 |
| 5,456,694 A | 10/1995 | Marin et al. |
| 5,456,713 A | 10/1995 | Chuter |
| 5,464,449 A | 11/1995 | Ryan et al. |
| 5,478,330 A | 12/1995 | Imran et al. |
| 5,480,423 A | 1/1996 | Ravenscroft et al. |
| 5,489,295 A | 2/1996 | Piplani et al. |
| 5,507,769 A | 4/1996 | Marin et al. |
| 5,522,880 A | 6/1996 | Barone et al. |
| 5,522,883 A | 6/1996 | Slater et al. |
| 5,562,724 A | 10/1996 | Vorwerk et al. |
| 5,562,726 A | 10/1996 | Chuter |
| 5,562,728 A | 10/1996 | Lazarus et al. |
| 5,575,818 A | 11/1996 | Pinchuk |
| 5,578,071 A | 11/1996 | Parodi |
| 5,578,072 A | 11/1996 | Barone et al. |
| 5,591,229 A | 1/1997 | Parodi |
| 5,609,625 A | 3/1997 | Piplani et al. |
| 5,609,627 A | 3/1997 | Goicoechea et al. |
| 5,626,599 A | 5/1997 | Bourne et al. |
| 5,628,783 A | 5/1997 | Quiachon et al. |
| 5,632,772 A | 5/1997 | Alcime et al. |
| 5,639,278 A | 6/1997 | Dereume et al. |
| 5,656,029 A | 8/1997 | Imran et al. |
| 5,662,675 A | 9/1997 | Polanskyj Stockert et al. |
| 5,662,700 A | 9/1997 | Lazarus |
| 5,665,115 A | 9/1997 | Cragg |
| 5,669,936 A | 9/1997 | Lazarus |
| 5,676,671 A | 10/1997 | Inoue |
| 5,676,696 A | 10/1997 | Marcade |
| 5,676,697 A | 10/1997 | McDonald |
| 5,683,449 A | 11/1997 | Marcade |
| 5,683,451 A | 11/1997 | Lenker et al. |
| 5,690,644 A | 11/1997 | Yurek et al. |
| 5,693,083 A | 12/1997 | Baker et al. |
| 5,693,084 A | 12/1997 | Chuter |
| 5,693,087 A | 12/1997 | Parodi |
| 5,693,088 A | 12/1997 | Lazarus |
| 5,709,701 A | 1/1998 | Parodi |
| 5,709,703 A | 1/1998 | Lukie et al. |
| 5,713,917 A | 2/1998 | Leonhardt et al. |
| 5,720,776 A | 2/1998 | Chuter et al. |
| 5,723,004 A | 3/1998 | Dereume et al. |
| 5,733,325 A | 3/1998 | Robinson et al. |
| 5,733,330 A * | 3/1998 | Cox ........................ 623/1.15 |
| 5,749,920 A | 5/1998 | Quiachon et al. |
| 5,749,921 A | 5/1998 | Lenker et al. |
| 5,766,203 A | 6/1998 | Imran et al. |
| 5,769,885 A | 6/1998 | Quiachon et al. |
| 5,769,887 A * | 6/1998 | Brown et al. .............. 623/1.23 |
| 5,776,142 A | 7/1998 | Gunderson |
| 5,782,838 A | 7/1998 | Beyar et al. |
| 5,782,909 A | 7/1998 | Quiachon et al. |
| 5,800,508 A | 9/1998 | Goicoechea et al. |
| 5,800,518 A | 9/1998 | Piplani et al. |
| 5,800,526 A * | 9/1998 | Anderson et al. ............ 623/1.16 |
| 5,817,102 A | 10/1998 | Johnson et al. |
| 5,824,037 A | 10/1998 | Fogarty et al. |
| 5,824,039 A | 10/1998 | Piplani et al. |
| 5,824,041 A | 10/1998 | Lenker et al. |
| 5,824,044 A | 10/1998 | Quiachon et al. |
| 5,824,058 A | 10/1998 | Ravenscroft et al. |
| 5,827,322 A * | 10/1998 | Williams .................... 623/1.18 |
| 5,833,707 A | 11/1998 | McIntyre et al. |
| 5,843,158 A | 12/1998 | Lenker et al. |
| 5,843,162 A | 12/1998 | Inoue |
| 5,843,164 A | 12/1998 | Frantzen et al. |
| 5,843,167 A | 12/1998 | Dwyer et al. |
| 5,855,598 A | 1/1999 | Pinchuk |
| 5,871,536 A | 2/1999 | Lazarus |
| 5,873,906 A | 2/1999 | Lau et al. |
| 5,906,619 A | 5/1999 | Olson et al. |
| 5,911,754 A | 6/1999 | Kanesaka et al. |
| 5,919,204 A | 7/1999 | Lukic et al. |
| 5,944,750 A | 8/1999 | Tanner et al. |
| 5,954,729 A | 9/1999 | Bachmann et al. |
| 5,957,973 A | 9/1999 | Quiachon et al. |
| 5,968,068 A | 10/1999 | Dehdashtian et al. |
| 5,972,023 A | 10/1999 | Tanner et al. |
| 5,976,179 A | 11/1999 | Inoue |
| 5,976,650 A | 11/1999 | Campbell et al. |
| 5,984,964 A | 11/1999 | Roberts et al. |
| 5,993,481 A | 11/1999 | Marcade et al. |
| 6,001,123 A | 12/1999 | Lau |
| 6,004,347 A | 12/1999 | McNamara et al. |
| 6,004,348 A | 12/1999 | Banas et al. |
| 6,015,431 A | 1/2000 | Thornton et al. |
| 6,017,364 A | 1/2000 | Lazarus |
| 6,019,778 A | 2/2000 | Wilson et al. |
| 6,019,779 A | 2/2000 | Thorud et al. |
| 6,024,763 A | 2/2000 | Lenker et al. |
| 6,030,413 A | 2/2000 | Lazarus |
| 6,030,414 A | 2/2000 | Taheri |
| 6,036,413 A | 3/2000 | Chandrasekar |
| 6,036,702 A | 3/2000 | Bachinski et al. |
| 6,036,723 A | 3/2000 | Anidjar et al. |
| 6,036,725 A | 3/2000 | Avellanet |
| 6,039,758 A | 3/2000 | Quiachon et al. |
| 6,042,589 A | 3/2000 | Marianne |
| 6,042,605 A | 3/2000 | Martin et al. |
| 6,045,557 A | 4/2000 | White et al. |
| 6,051,020 A | 4/2000 | Goicoechea et al. |
| 6,059,821 A | 5/2000 | Anidjar et al. |
| 6,070,589 A | 6/2000 | Keith et al. |

(56) References Cited

U.S. PATENT DOCUMENTS

| | | | |
|---|---|---|---|
| 6,077,297 A | 6/2000 | Robinson et al. |
| 6,090,128 A | 7/2000 | Douglas |
| 6,098,630 A | 8/2000 | Papazoglou |
| 6,110,198 A | 8/2000 | Fogarty et al. |
| 6,126,685 A | 10/2000 | Lenker et al. |
| 6,132,457 A | 10/2000 | Chobotov |
| 6,132,459 A | 10/2000 | Piplani et al. |
| 6,139,572 A | 10/2000 | Campbell et al. |
| 6,142,973 A | 11/2000 | Carleton et al. |
| 6,143,014 A | 11/2000 | Dehdashtian et al. |
| 6,143,016 A | 11/2000 | Bleam et al. |
| 6,143,021 A | 11/2000 | Staehle |
| 6,146,389 A | 11/2000 | Geitz |
| 6,152,944 A | 11/2000 | Holman et al. |
| 6,156,063 A | 12/2000 | Douglas |
| 6,159,229 A | 12/2000 | Jendersee et al. |
| 6,165,210 A | 12/2000 | Lau et al. |
| 6,165,213 A | 12/2000 | Goicoechea et al. |
| 6,165,214 A | 12/2000 | Lazarus |
| 6,168,610 B1 | 1/2001 | Marin et al. |
| 6,168,616 B1 | 1/2001 | Brown, III |
| 6,168,617 B1 | 1/2001 | Blaeser et al. |
| 6,168,618 B1 | 1/2001 | Frantzen |
| 6,168,620 B1 | 1/2001 | Kerr |
| 6,183,481 B1 | 2/2001 | Lee et al. |
| 6,183,504 B1 | 2/2001 | Inoue |
| 6,187,036 B1 | 2/2001 | Shaolian et al. |
| 6,193,745 B1 | 2/2001 | Fogarty et al. |
| 6,196,230 B1 | 3/2001 | Hall et al. |
| 6,197,046 B1 | 3/2001 | Piplani et al. |
| 6,197,049 B1 | 3/2001 | Shaolian et al. |
| 6,200,339 B1 | 3/2001 | Leschinsky et al. |
| 6,203,550 B1 | 3/2001 | Olson |
| 6,203,568 B1 | 3/2001 | Lombardi et al. |
| 6,210,422 B1 | 4/2001 | Douglas |
| 6,210,434 B1 | 4/2001 | Quiachon et al. |
| 6,210,435 B1 | 4/2001 | Piplani et al. |
| 6,214,038 B1 | 4/2001 | Piplani et al. |
| 6,224,609 B1 | 5/2001 | Ressemann et al. |
| 6,235,050 B1 | 5/2001 | Quiachon et al. |
| 6,235,051 B1 | 5/2001 | Murphy |
| 6,241,759 B1 | 6/2001 | Piplani et al. |
| 6,245,097 B1 | 6/2001 | Inoue |
| 6,245,101 B1 | 6/2001 | Drasler et al. |
| 6,251,132 B1 | 6/2001 | Ravenscroft et al. |
| 6,254,593 B1 | 7/2001 | Wilson |
| 6,254,632 B1 | 7/2001 | Wu et al. |
| 6,258,073 B1 | 7/2001 | Mauch |
| 6,261,316 B1 | 7/2001 | Shaolian et al. |
| 6,261,317 B1 | 7/2001 | Inoue |
| 6,264,662 B1 | 7/2001 | Lauterjung |
| 6,280,466 B1 | 8/2001 | Kugler et al. |
| 6,283,991 B1 | 9/2001 | Cox et al. |
| 6,287,315 B1 | 9/2001 | Wijeratne et al. |
| 6,287,329 B1 | 9/2001 | Duerig et al. |
| 6,287,330 B1 | 9/2001 | Johansson et al. |
| 6,287,335 B1 | 9/2001 | Drasler et al. |
| 6,290,728 B1 | 9/2001 | Phelps et al. |
| 6,293,969 B1 | 9/2001 | Chuter |
| 6,302,891 B1 | 10/2001 | Nadal |
| 6,302,906 B1 | 10/2001 | Goicoechea et al. |
| 6,302,908 B1 | 10/2001 | Parodi |
| 6,306,145 B1 | 10/2001 | Leschinsky |
| 6,312,462 B1 | 11/2001 | McDermott et al. |
| 6,319,276 B1 | 11/2001 | Holman et al. |
| 6,322,587 B1 | 11/2001 | Quiachon et al. |
| 6,325,819 B1 | 12/2001 | Pavcnik et al. |
| 6,325,825 B1 | 12/2001 | Kula et al. |
| 6,328,749 B1 | 12/2001 | Kalmann et al. |
| 6,331,186 B1 | 12/2001 | Wang et al. |
| 6,331,190 B1 | 12/2001 | Shokoohi et al. |
| 6,331,191 B1 | 12/2001 | Chobotov |
| 6,344,044 B1 | 2/2002 | Fulkerson et al. |
| 6,344,054 B1 | 2/2002 | Parodi |
| 6,352,553 B1 | 3/2002 | van der Burg et al. |
| 6,352,561 B1 | 3/2002 | Leopold et al. |
| 6,355,060 B1 | 3/2002 | Lenker et al. |
| 6,371,979 B1 | 4/2002 | Beyar et al. |
| 6,383,213 B2 | 5/2002 | Wilson et al. |
| 6,387,330 B1 | 5/2002 | Bova et al. |
| 6,391,050 B1 | 5/2002 | Broome |
| 6,395,019 B2 | 5/2002 | Chobotov |
| 6,395,022 B1 | 5/2002 | Piplani et al. |
| 6,413,269 B1 | 7/2002 | Bui et al. |
| 6,416,535 B1 | 7/2002 | Lazarus |
| 6,416,536 B1 | 7/2002 | Yee |
| 6,416,542 B1 | 7/2002 | Marcade et al. |
| 6,425,898 B1 | 7/2002 | Wilson et al. |
| 6,428,566 B1 | 8/2002 | Holt |
| 6,428,567 B2 | 8/2002 | Wilson et al. |
| 6,432,129 B2 | 8/2002 | DiCaprio |
| 6,432,131 B1 | 8/2002 | Ravenscroft |
| 6,436,104 B2 | 8/2002 | Hojeibane |
| 6,443,979 B1 | 9/2002 | Stalker et al. |
| 6,447,501 B1 | 9/2002 | Solar et al. |
| 6,447,522 B2 | 9/2002 | Gambale et al. |
| 6,451,053 B1 | 9/2002 | Dehdashtian et al. |
| 6,464,721 B1 | 10/2002 | Marcade et al. |
| 6,468,301 B1 * | 10/2002 | Amplatz et al. ............. 623/1.13 |
| 6,471,718 B1 | 10/2002 | Staehle et al. |
| 6,471,722 B1 | 10/2002 | Inoue |
| 6,475,166 B1 | 11/2002 | Escano |
| 6,475,208 B2 | 11/2002 | Mauch |
| 6,478,807 B1 | 11/2002 | Foreman et al. |
| 6,478,808 B2 | 11/2002 | Nowakowski |
| 6,485,515 B2 | 11/2002 | Strecker |
| 6,488,694 B1 | 12/2002 | Lau et al. |
| 6,488,700 B2 | 12/2002 | Klumb et al. |
| 6,488,701 B1 | 12/2002 | Nolting et al. |
| 6,494,875 B1 | 12/2002 | Mauch |
| 6,494,904 B1 | 12/2002 | Love |
| 6,494,909 B2 | 12/2002 | Greenhalgh |
| 6,500,202 B1 | 12/2002 | Shaolian et al. |
| 6,500,203 B1 | 12/2002 | Thompson et al. |
| 6,514,281 B1 | 2/2003 | Blaeser et al. |
| 6,517,573 B1 | 2/2003 | Pollock et al. |
| 6,517,574 B1 | 2/2003 | Chuter |
| 6,520,983 B1 | 2/2003 | Colgan et al. |
| 6,520,984 B1 | 2/2003 | Garrison et al. |
| 6,530,947 B1 | 3/2003 | Euteneuer et al. |
| 6,533,806 B1 | 3/2003 | Sullivan et al. |
| 6,533,807 B2 | 3/2003 | Wolinsky et al. |
| 6,533,811 B1 | 3/2003 | Ryan et al. |
| 6,540,778 B1 | 4/2003 | Quiachon et al. |
| 6,554,858 B2 | 4/2003 | Dereume et al. |
| 6,562,063 B1 | 5/2003 | Euteneuer et al. |
| 6,565,597 B1 * | 5/2003 | Fearnot et al. ............. 623/1.14 |
| 6,575,994 B1 | 6/2003 | Marin et al. |
| 6,592,544 B1 | 7/2003 | Mooney et al. |
| 6,602,280 B2 | 8/2003 | Chobotov |
| 6,641,606 B2 | 11/2003 | Ouriel et al. |
| 6,652,580 B1 | 11/2003 | Chuter et al. |
| 6,663,664 B1 * | 12/2003 | Pacetti ............. 623/1.2 |
| 6,695,875 B2 | 2/2004 | Stelter et al. |
| 6,733,521 B2 | 5/2004 | Chobotov et al. |
| 6,736,839 B2 | 5/2004 | Cummings |
| 6,761,733 B2 | 7/2004 | Chobotov et al. |
| 6,773,453 B2 | 8/2004 | Ravenscroft |
| 6,776,604 B1 | 8/2004 | Chobotov et al. |
| 7,014,653 B2 | 3/2006 | Ouriel et al. |
| 7,056,325 B1 | 6/2006 | Makower et al. |
| 7,066,951 B2 | 6/2006 | Chobotov |
| 7,081,129 B2 | 7/2006 | Chobotov |
| 7,081,132 B2 | 7/2006 | Cook et al. |
| 7,090,693 B1 | 8/2006 | Chobotov et al. |
| 7,125,464 B2 | 10/2006 | Chobotov et al. |
| 7,128,754 B2 | 10/2006 | Bolduc |
| 7,147,455 B2 | 12/2006 | Chobotov et al. |
| 7,147,660 B2 | 12/2006 | Chobotov et al. |
| 7,147,661 B2 | 12/2006 | Chobotov et al. |
| 7,150,758 B2 | 12/2006 | Kari et al. |
| 7,166,125 B1 | 1/2007 | Baker et al. |
| 7,232,459 B2 | 6/2007 | Greenberg et al. |
| 7,338,518 B2 | 3/2008 | Chobotov |

(56) References Cited

U.S. PATENT DOCUMENTS

| | | | |
|---|---|---|---|
| 8,177,833 B2* | 5/2012 | Chuter et al. | 623/1.36 |
| 8,668,730 B2* | 3/2014 | McGuckin et al. | 623/1.14 |
| 2001/0003801 A1 | 6/2001 | Strecker | |
| 2001/0004706 A1 | 6/2001 | Hojeibane | |
| 2001/0007954 A1 | 7/2001 | Shaolian et al. | |
| 2001/0007955 A1 | 7/2001 | Drasler et al. | |
| 2001/0012943 A1 | 8/2001 | Shaolian et al. | |
| 2001/0014794 A1 | 8/2001 | Moll et al. | |
| 2001/0014813 A1 | 8/2001 | Saadat et al. | |
| 2001/0014823 A1 | 8/2001 | Ressemann et al. | |
| 2001/0020184 A1 | 9/2001 | Dehdashtian et al. | |
| 2001/0034547 A1 | 10/2001 | Hall et al. | |
| 2001/0037142 A1 | 11/2001 | Stelter et al. | |
| 2001/0039445 A1 | 11/2001 | Hall et al. | |
| 2001/0047150 A1 | 11/2001 | Chobotov | |
| 2001/0047164 A1 | 11/2001 | Teague et al. | |
| 2001/0049534 A1 | 12/2001 | Lachat | |
| 2001/0049551 A1* | 12/2001 | Tseng et al. | 623/1.15 |
| 2002/0002397 A1 | 1/2002 | Martin et al. | |
| 2002/0002400 A1 | 1/2002 | Drasler et al. | |
| 2002/0010508 A1 | 1/2002 | Chobotov | |
| 2002/0019659 A1 | 2/2002 | Goicoechea et al. | |
| 2002/0077692 A1 | 6/2002 | Besselink | |
| 2002/0099405 A1 | 7/2002 | Yurek et al. | |
| 2002/0099431 A1 | 7/2002 | Armstrong et al. | |
| 2002/0099432 A1 | 7/2002 | Yee | |
| 2002/0099433 A1 | 7/2002 | Fischell et al. | |
| 2002/0099435 A1 | 7/2002 | Stinson | |
| 2002/0099437 A1 | 7/2002 | Anson et al. | |
| 2002/0100484 A1 | 8/2002 | Hall et al. | |
| 2002/0103525 A1 | 8/2002 | Cummings | |
| 2002/0111633 A1 | 8/2002 | Stoltze et al. | |
| 2002/0111665 A1 | 8/2002 | Lauterjung | |
| 2002/0111666 A1 | 8/2002 | Hart et al. | |
| 2002/0111675 A1 | 8/2002 | Wilson | |
| 2002/0116046 A1 | 8/2002 | DiCaprio et al. | |
| 2002/0116047 A1 | 8/2002 | Vardi et al. | |
| 2002/0120321 A1 | 8/2002 | Gunderson et al. | |
| 2002/0123032 A1 | 9/2002 | Rothschild et al. | |
| 2002/0123794 A1 | 9/2002 | Ellis et al. | |
| 2002/0138081 A1 | 9/2002 | Blaeser et al. | |
| 2002/0138127 A1 | 9/2002 | Stiger et al. | |
| 2002/0138128 A1 | 9/2002 | Stiger et al. | |
| 2002/0143381 A1 | 10/2002 | Gilligan et al. | |
| 2002/0143383 A1 | 10/2002 | Parodi | |
| 2002/0143387 A1 | 10/2002 | Soetikno et al. | |
| 2002/0151953 A1 | 10/2002 | Chobotov et al. | |
| 2002/0151956 A1 | 10/2002 | Chobotov et al. | |
| 2002/0156489 A1 | 10/2002 | Gellman et al. | |
| 2002/0165602 A1 | 11/2002 | Douglas et al. | |
| 2002/0165603 A1 | 11/2002 | Thornton et al. | |
| 2002/0173837 A1 | 11/2002 | Lauterjung | |
| 2002/0177890 A1 | 11/2002 | Lenker | |
| 2002/0183825 A1 | 12/2002 | Solem | |
| 2002/0183826 A1 | 12/2002 | Dorn et al. | |
| 2002/0183827 A1 | 12/2002 | Derus et al. | |
| 2002/0183832 A1 | 12/2002 | Penn et al. | |
| 2002/0188341 A1 | 12/2002 | Elliott | |
| 2002/0193863 A1 | 12/2002 | Rourke et al. | |
| 2002/0193867 A1 | 12/2002 | Gladdish, Jr. et al. | |
| 2002/0193873 A1 | 12/2002 | Brucker et al. | |
| 2002/0198587 A1 | 12/2002 | Greenberg et al. | |
| 2002/0198588 A1 | 12/2002 | Armstrong et al. | |
| 2003/0004560 A1 | 1/2003 | Chobotov et al. | |
| 2003/0009211 A1 | 1/2003 | DiCarlo | |
| 2003/0009212 A1 | 1/2003 | Kerr | |
| 2003/0014101 A1 | 1/2003 | Harrison | |
| 2003/0040803 A1 | 2/2003 | Rioux et al. | |
| 2003/0050684 A1 | 3/2003 | Abrams et al. | |
| 2003/0050686 A1 | 3/2003 | Raeder-Devens et al. | |
| 2003/0050694 A1* | 3/2003 | Yang et al. | 623/2.11 |
| 2003/0074048 A1 | 4/2003 | Sherry | |
| 2003/0074050 A1 | 4/2003 | Kerr | |
| 2003/0114735 A1 | 6/2003 | Silver et al. | |
| 2003/0120331 A1 | 6/2003 | Chobotov et al. | |
| 2003/0120339 A1 | 6/2003 | Banik et al. | |
| 2003/0125797 A1 | 7/2003 | Chobotov et al. | |
| 2003/0176912 A1 | 9/2003 | Chuter et al. | |
| 2003/0216802 A1 | 11/2003 | Chobotov | |
| 2003/0220681 A1 | 11/2003 | Chobotov | |
| 2003/0220683 A1 | 11/2003 | Minasian et al. | |
| 2003/0234570 A1 | 12/2003 | Fischbacher et al. | |
| 2004/0034407 A1 | 2/2004 | Sherry | |
| 2004/0073287 A1 | 4/2004 | Goicoechea et al. | |
| 2004/0088044 A1 | 5/2004 | Brown et al. | |
| 2004/0093078 A1 | 5/2004 | Moll et al. | |
| 2004/0098079 A1 | 5/2004 | Hartley et al. | |
| 2004/0098115 A1 | 5/2004 | Goicoechea et al. | |
| 2004/0106974 A1 | 6/2004 | Greenberg et al. | |
| 2004/0106977 A1 | 6/2004 | Sullivan et al. | |
| 2004/0106978 A1 | 6/2004 | Greenberg et al. | |
| 2004/0138734 A1 | 7/2004 | Chobotov et al. | |
| 2004/0220664 A1 | 11/2004 | Chobotov | |
| 2005/0027347 A1 | 2/2005 | Chobotov et al. | |
| 2005/0090804 A1 | 4/2005 | Chobotov et al. | |
| 2006/0009833 A1 | 1/2006 | Chobotov et al. | |
| 2006/0020319 A1 | 1/2006 | Kim et al. | |
| 2006/0173533 A1 | 8/2006 | Chobotov | |
| 2006/0178732 A1 | 8/2006 | Chobotov et al. | |
| 2006/0206193 A1 | 9/2006 | Chobotov et al. | |
| 2006/0224227 A1 | 10/2006 | Chobotov | |
| 2006/0224232 A1 | 10/2006 | Chobotov | |
| 2007/0012396 A1 | 1/2007 | Chobotov et al. | |
| 2007/0219627 A1 | 9/2007 | Chu et al. | |
| 2007/0239273 A1 | 10/2007 | Allen | |
| 2008/0058759 A1 | 3/2008 | Makower et al. | |
| 2008/0114441 A1 | 5/2008 | Rust et al. | |
| 2008/0114442 A1 | 5/2008 | Mitchell et al. | |
| 2008/0114443 A1 | 5/2008 | Mitchell et al. | |
| 2008/0228255 A1 | 9/2008 | Rust et al. | |
| 2009/0082844 A1* | 3/2009 | Zacharias et al. | 623/1.13 |

FOREIGN PATENT DOCUMENTS

| | | | |
|---|---|---|---|
| EP | 0 712 614 A1 | 5/1996 | |
| EP | 0 792 627 B1 | 9/1997 | |
| EP | 0 808 140 B1 | 11/1997 | |
| EP | 0 819 411 A2 | 1/1998 | |
| EP | 0 821 979 B1 | 2/1998 | |
| EP | 0 943 302 B1 | 9/1999 | |
| EP | 1 093 772 A2 | 4/2001 | |
| EP | 1 138 280 A2 | 10/2001 | |
| EP | 1 208 817 B1 | 5/2002 | |
| EP | 1 212 987 B1 | 6/2002 | |
| EP | 1 212 988 B1 | 6/2002 | |
| EP | 1 212 989 B1 | 6/2002 | |
| EP | 1 327 422 A1 | 7/2003 | |
| EP | 1 923 020 A2 | 5/2008 | |
| JP | 6-23031 A | 2/1994 | |
| JP | 11-501526 A | 2/1999 | |
| WO | 95/01761 A2 | 1/1995 | |
| WO | 96/14808 A1 | 5/1996 | |
| WO | 96/24308 A1 | 8/1996 | |
| WO | 98/06355 A1 | 2/1998 | |
| WO | 98/07388 A1 | 2/1998 | |
| WO | 98/27894 A1 | 7/1998 | |
| WO | 98/36708 A1 | 8/1998 | |
| WO | 98/41167 A1 | 9/1998 | |
| WO | 98/53761 A1 | 12/1998 | |
| WO | 99/11199 A1 | 3/1999 | |
| WO | 99/39662 A1 | 8/1999 | |
| WO | 99/43378 A1 | 9/1999 | |
| WO | 99/43379 A1 | 9/1999 | |
| WO | 99/65419 A1 | 12/1999 | |
| WO | 00/13613 A1 | 3/2000 | |
| WO | 00/18322 A1 | 4/2000 | |
| WO | 00/33769 A1 | 6/2000 | |
| WO | 00/42947 A2 | 7/2000 | |
| WO | 00/42948 A2 | 7/2000 | |
| WO | 00/53251 A1 | 9/2000 | |
| WO | 00/67675 A1 | 11/2000 | |
| WO | 01/05331 A1 | 1/2001 | |
| WO | 01/08599 A1 | 2/2001 | |
| WO | 01/56500 A2 | 8/2001 | |

(56) References Cited

FOREIGN PATENT DOCUMENTS

| WO | 01/58387 | A1 | 8/2001 |
|---|---|---|---|
| WO | 01/67993 | A2 | 9/2001 |
| WO | 01/74270 | A2 | 10/2001 |
| WO | 01/76509 | A1 | 10/2001 |
| WO | 02/056798 | A2 | 7/2002 |
| WO | 02/060345 | A2 | 8/2002 |
| WO | 02/087651 | A1 | 11/2002 |
| WO | 03/008005 | A2 | 1/2003 |
| WO | 03/022181 | A1 | 3/2003 |
| WO | 03/053288 | A1 | 7/2003 |
| WO | 2004/002371 | A2 | 1/2004 |
| WO | 2004/021932 | A1 | 3/2004 |

OTHER PUBLICATIONS

European Search Report for EP 09009090.3, dated Jul. 26, 2010.
Examination Report dated Oct. 25, 2011 from the Australian Patent Office for a subject-matter-related foreign counter-part application.
European Search Report for Application No. EP 10 00 5904.
Office Action dated Nov. 14, 2011 for U.S. Appl. No. 13/245,661.
Office Action dated Sep. 1, 2011 for U.S. Appl. No. 12/491,336.

* cited by examiner

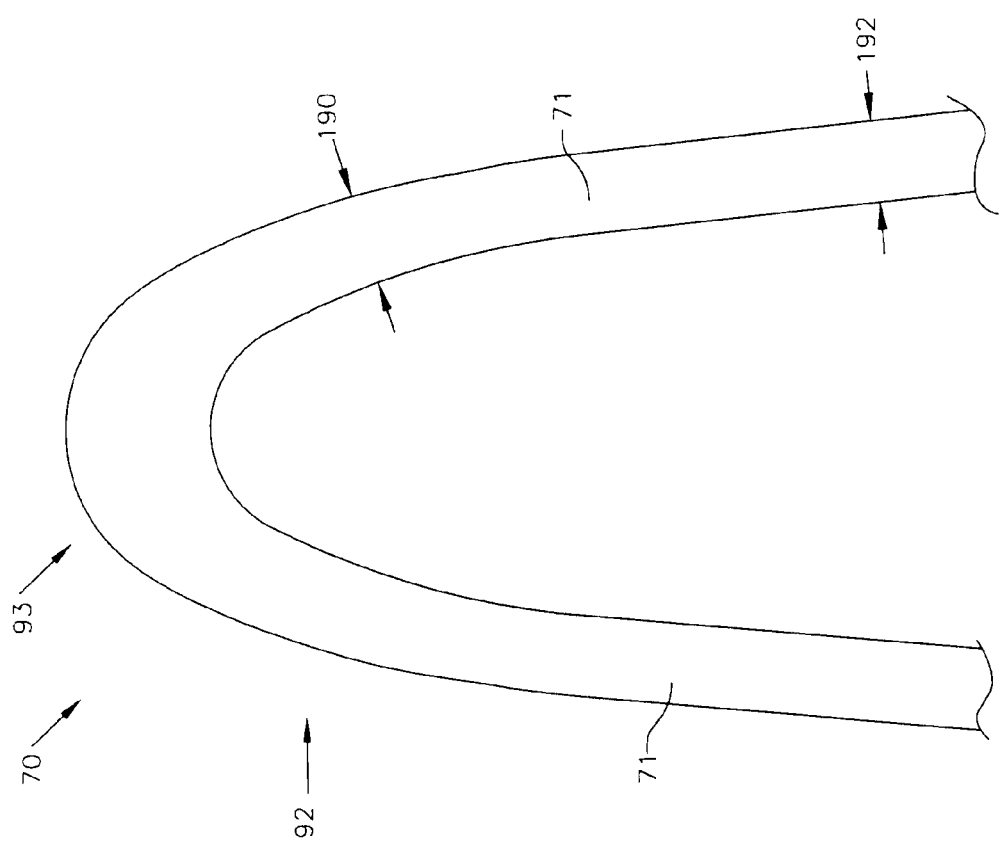

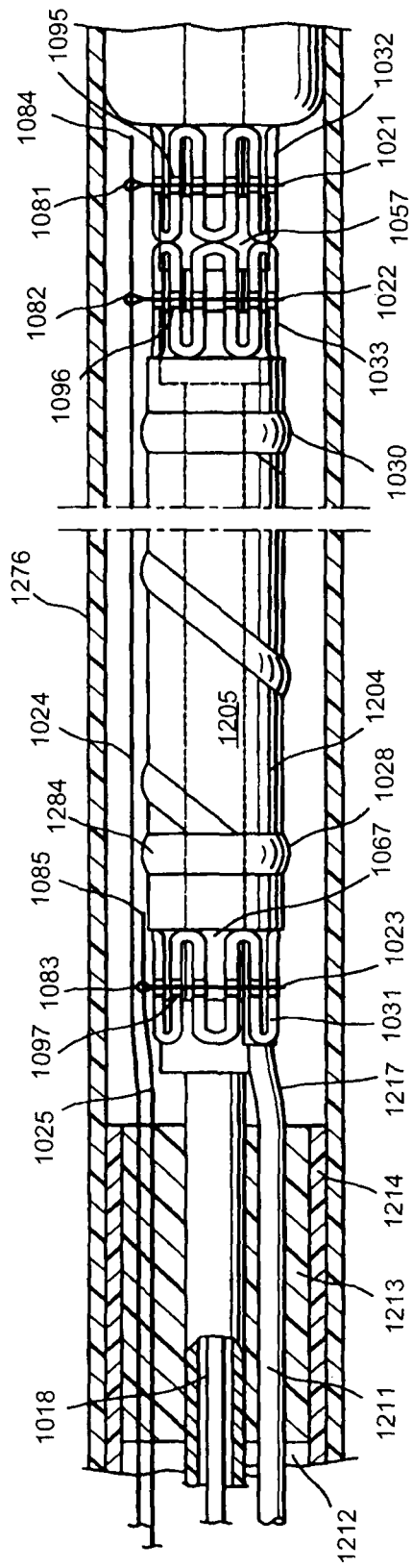
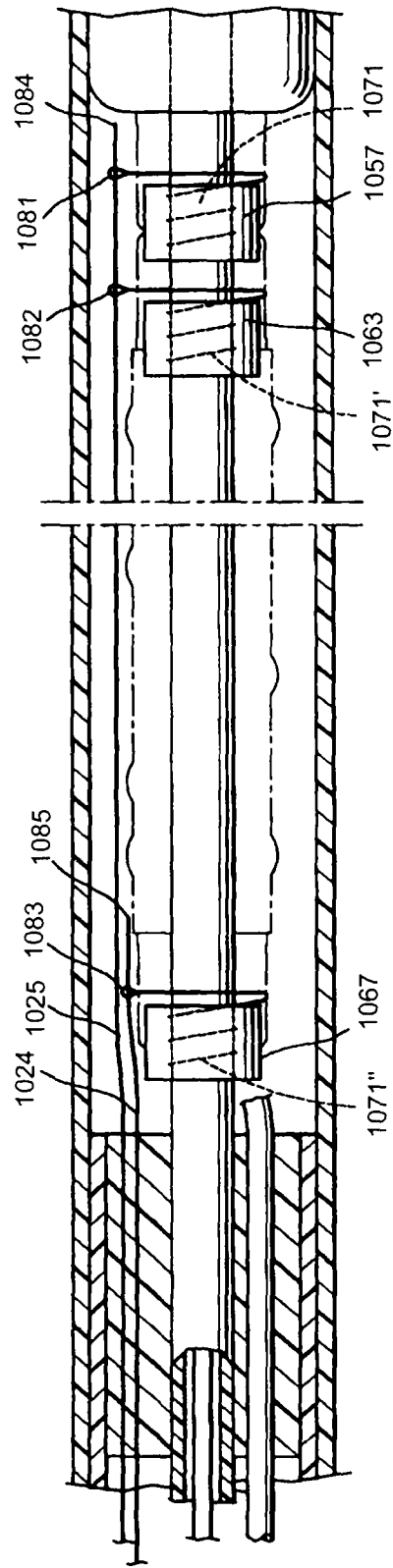
FIG. 19A
FIG. 19B

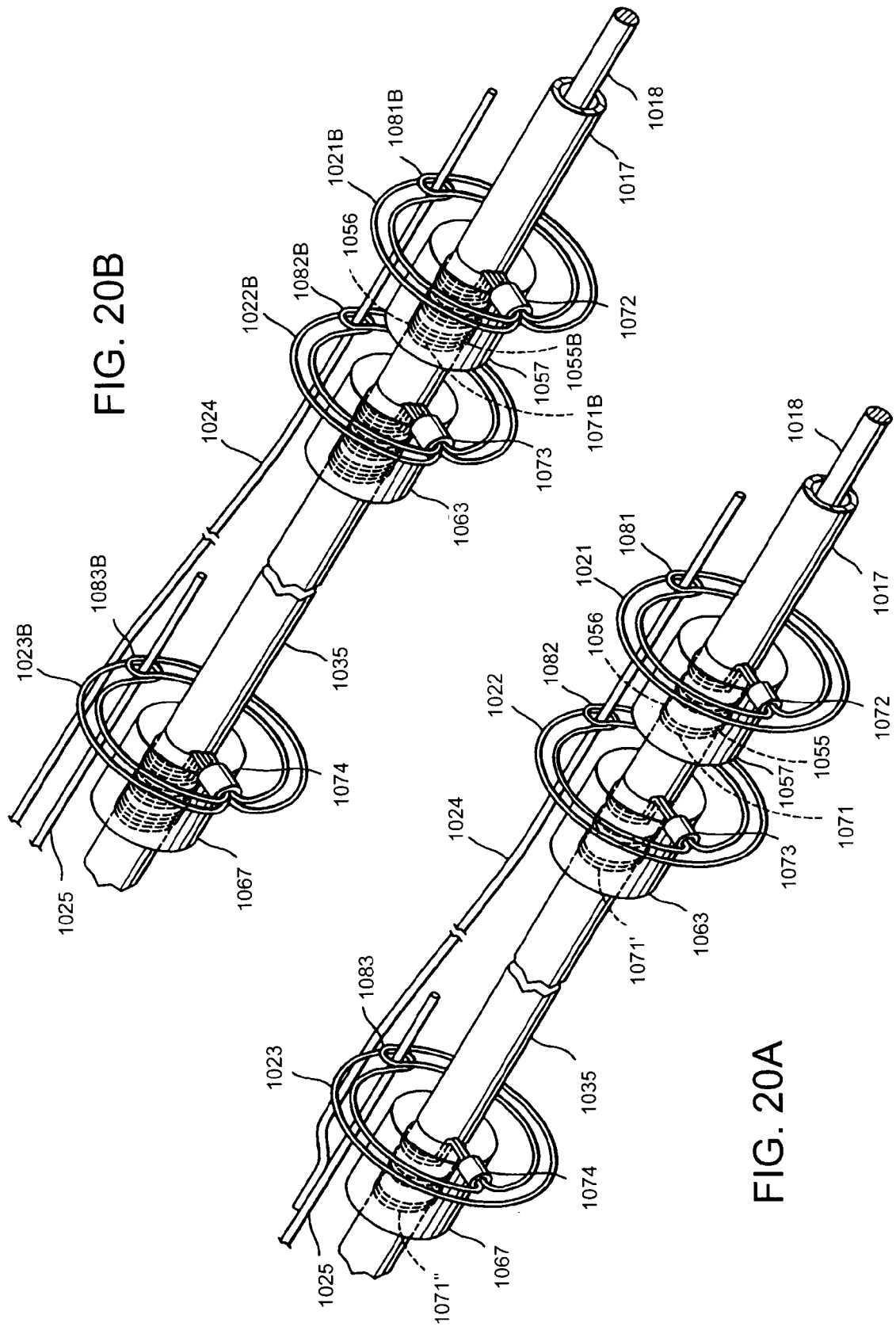

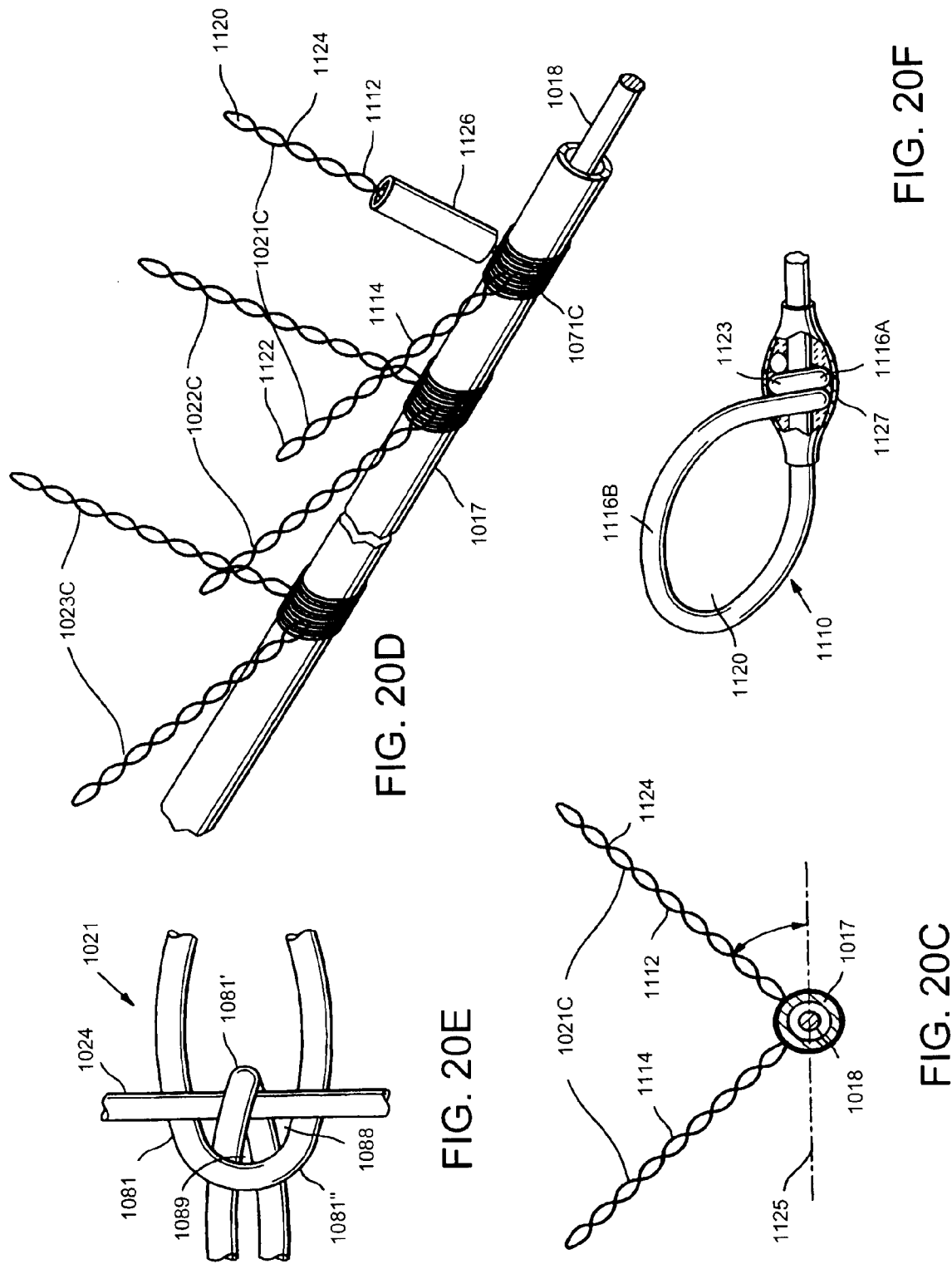

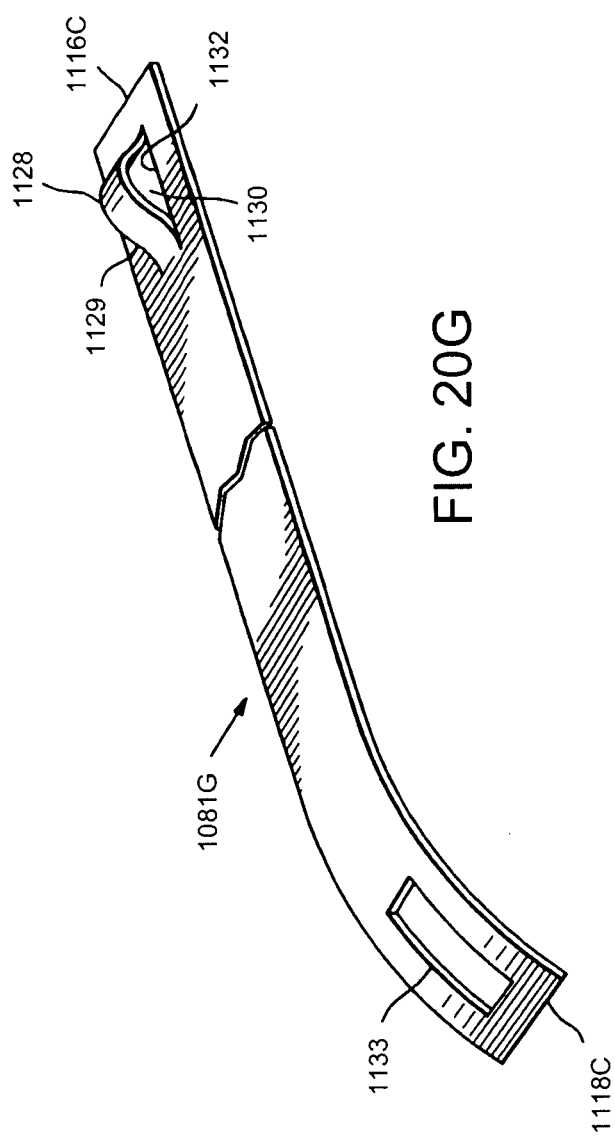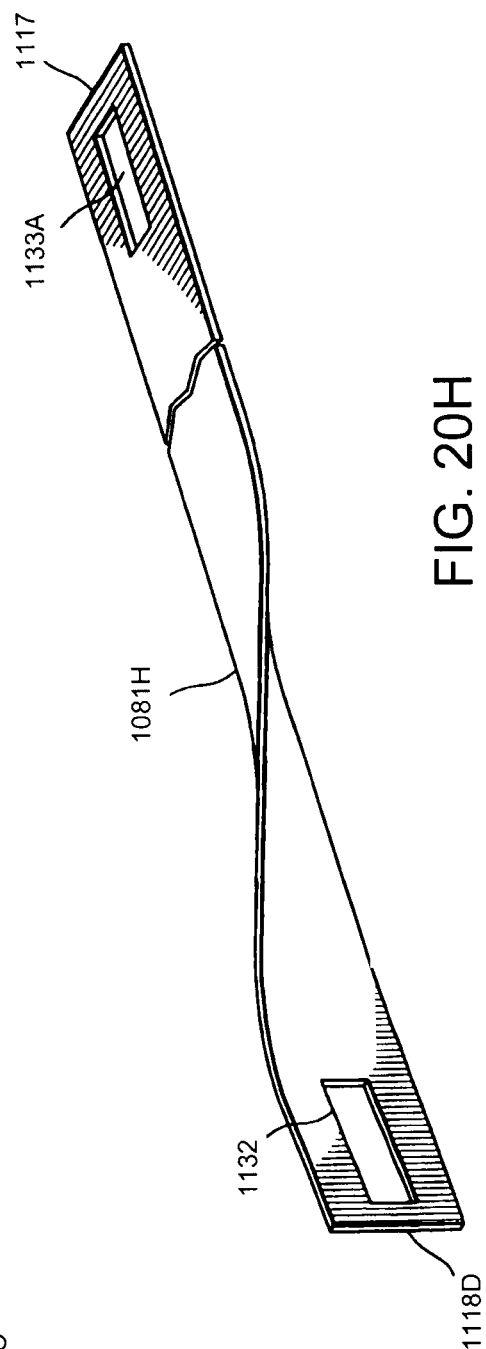

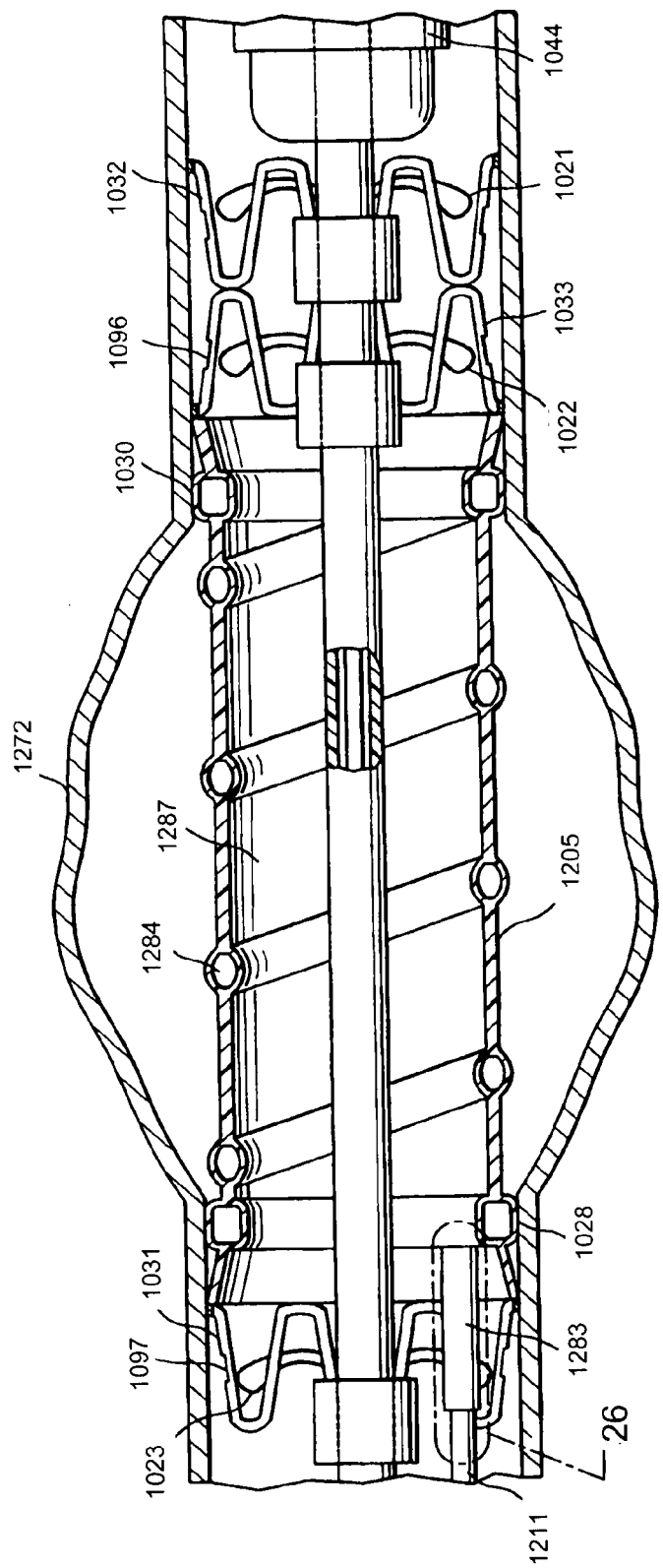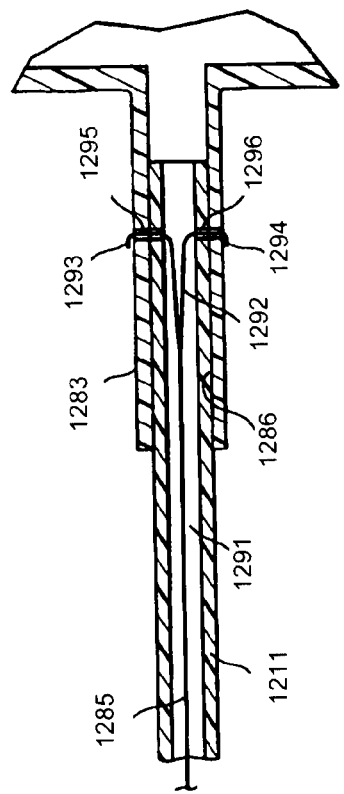
FIG. 25
FIG. 26

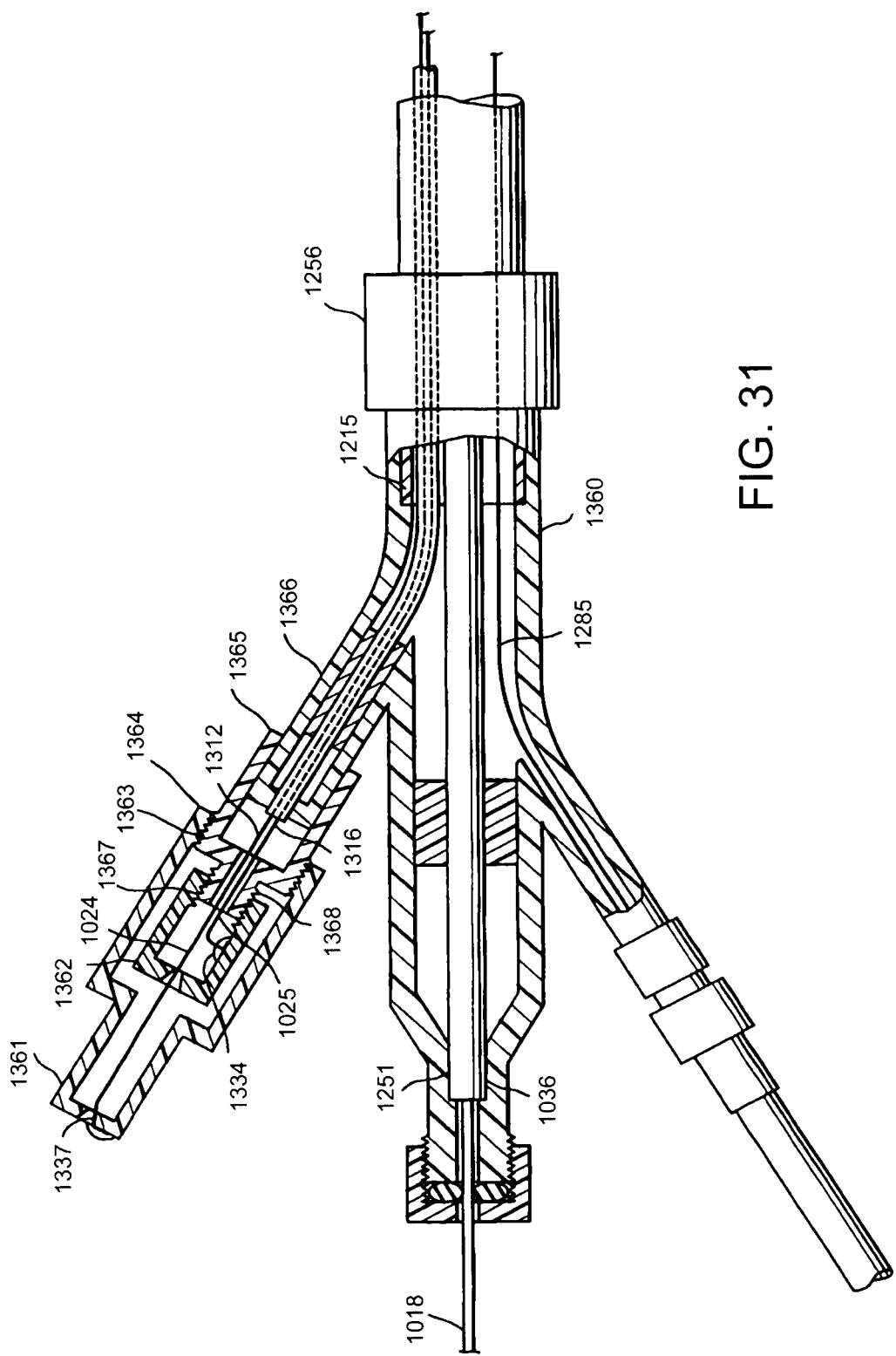

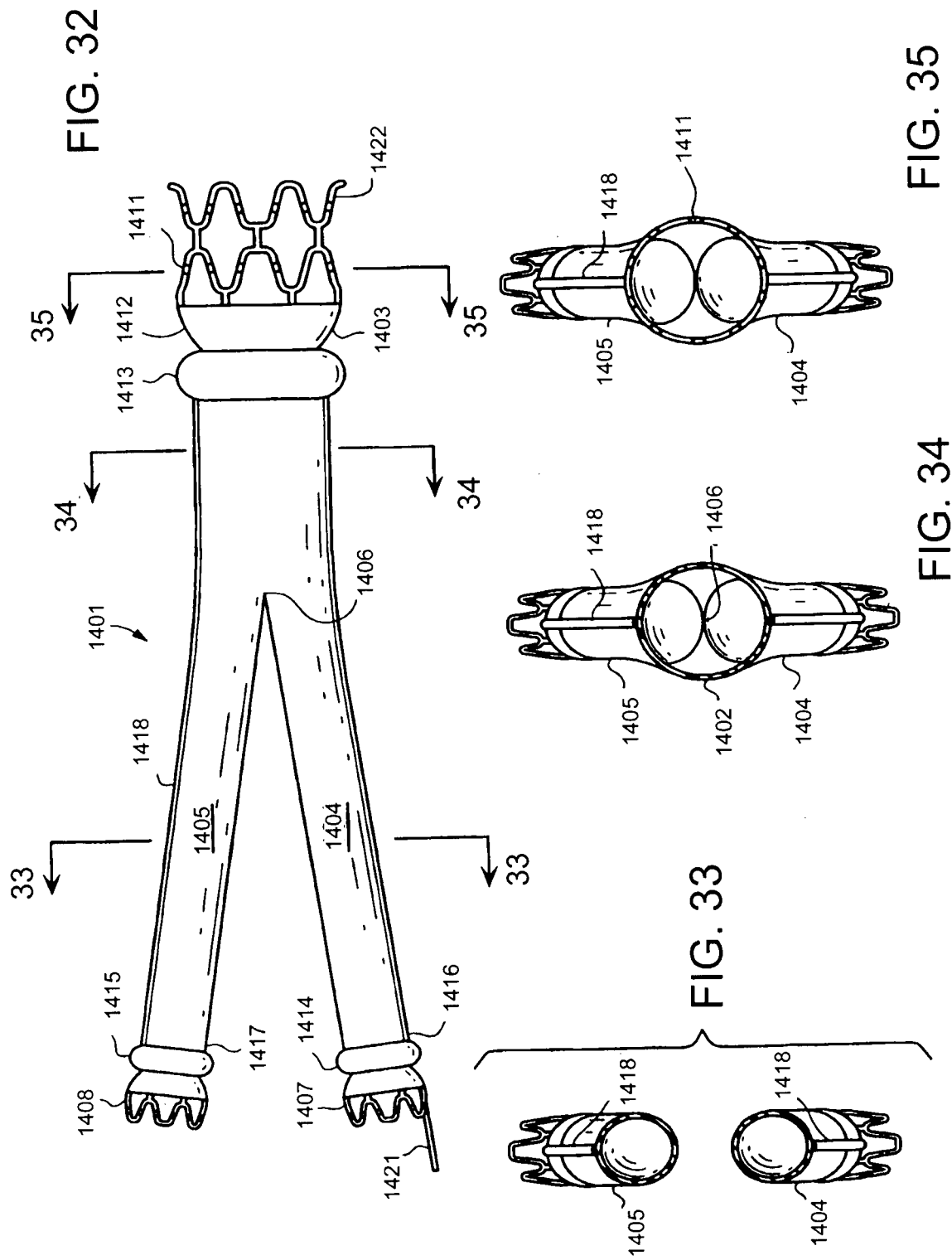

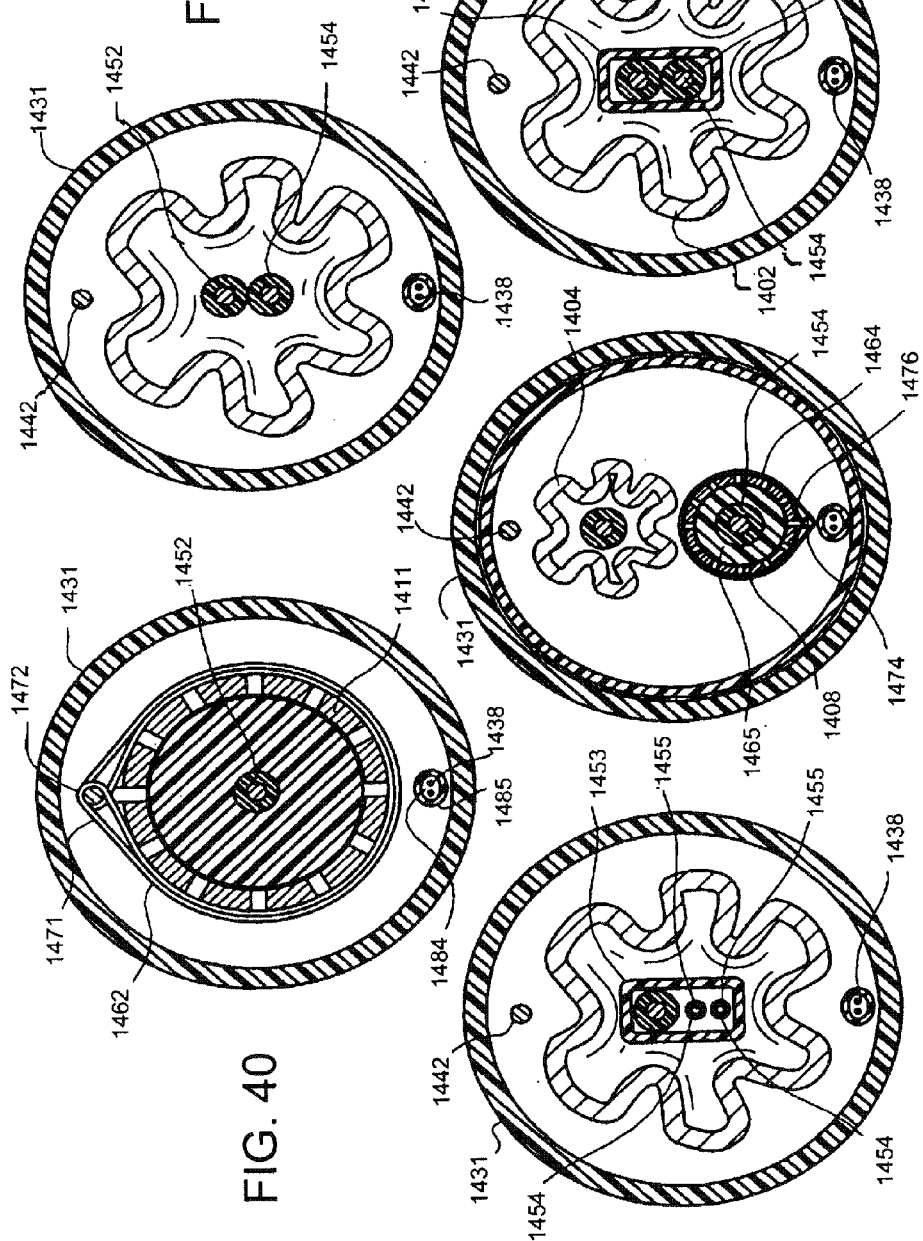

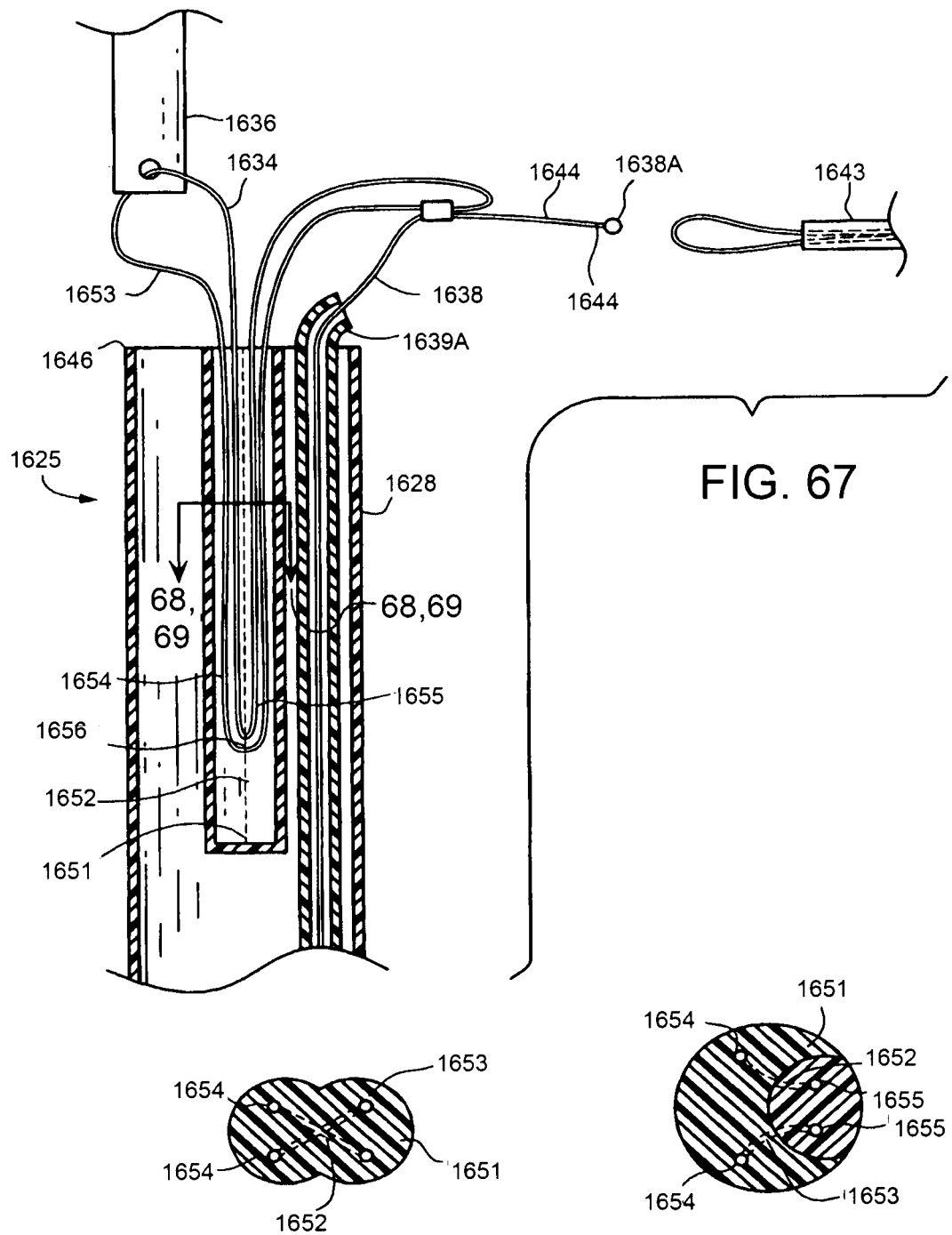

METHOD OF DELIVERING ADVANCED ENDOVASCULAR GRAFT AND SYSTEM

CROSS-REFERENCE TO RELATED APPLICATIONS

This application is a continuation of U.S. patent application Ser. No. 12/566,808, filed Sep. 25, 2009, now abandoned, which is a continuation of U.S. patent application Ser. No. 11/333,595, filed Jan. 17, 2006, now U.S. Pat. No. 7,766,954, which is a continuation of U.S. patent application Ser. No. 10/091,641, filed Mar. 5, 2002, now abandoned, which is a continuation of U.S. patent application Ser. No. 10/029,559, filed Dec. 20, 2001, now U.S. Pat. No. 7,147,661, the contents of which are incorporated by reference herein.

FIELD OF THE INVENTION

The present invention relates to a system for the treatment of disorders of the vasculature. More specifically, the invention relates to a system for the treatment of disease or injury that potentially compromises the integrity of a flow conduit in the body. For example, an embodiment of the invention is useful in treating indications in the digestive and reproductive systems as well as indications in the cardiovascular system, including thoracic and abdominal aortic aneurysms, arterial dissections (such as those caused by traumatic injury), etc. Such cardiovascular indications often require intervention due to the severity of the sequelae, which frequently is death. In addition, this application is related to U.S. patent application Ser. No. 10/029,570 (now U.S. Pat. No. 6,776,604), filed Dec. 20, 2001, entitled "Method and Apparatus for Shape Forming Endovascular Graft Material" by Chobotov et al., U.S. patent application Ser. No. 10/029,584 (now U.S. Pat. No. 7,090,693), filed Dec. 20, 2001, entitled "Endovascular Graft Joint and Method for Manufacture" by Chobotov et al., U.S. patent application Ser. No. 10/029,557 (now U.S. Pat. No. 7,125,464), filed Dec. 20, 2001, entitled "Method and Apparatus for Manufacturing an Endovascular Graft Section", by Chobotov et al. All of the above applications are commonly owned. All of the above applications are hereby incorporated herein by reference, each in its entirety.

BACKGROUND

For indications such as abdominal aortic aneurysms, traditional open surgery is still the conventional and most widely-utilized treatment when the aneurysm's size has grown to the point that the risk of aneurysm rupture outweighs the drawbacks of surgery. Surgical repair involves replacement of the section of the vessel where the aneurysm has formed with a graft. An example of a surgical procedure is described by Cooley in Surgical Treatment of Aortic Aneurysms, 1986 (W.B. Saunders Company).

Despite its advantages, however, open surgery is fraught with high morbidity and mortality rates, primarily because of the invasive and complex nature of the procedure. Complications associated with surgery include, for example, the possibility of aneurysm rupture, loss of function related to extended periods of restricted blood flow to the extremities, blood loss, myocardial infarction, congestive heart failure, arrhythmia, and complications associated with the use of general anesthesia and mechanical ventilation systems. In addition, the typical patient in need of aneurysm repair is older and in poor health, facts that significantly increase the likelihood of complications.

Due to the risks and complexities of surgical intervention, various attempts have been made to develop alternative methods for treating such disorders. One such method that has enjoyed some degree of success is the catheter-based delivery of a bifurcated stent-graft via the femoral arteries to exclude the aneurysm from within the aorta.

Endovascular repair of aortic aneurysms represents a promising and attractive alternative to conventional surgical repair techniques. The risk of medical complications is significantly reduced due to the less-invasive nature of the procedure. Recovery times are significantly reduced as well, which concomitantly diminishes the length and expense of hospital stays. For example, open surgery requires an average six-day hospital stay and one or more days in the intensive care unit. In contrast, endovascular repair typically requires a two-to-three day hospital stay. Once out of the hospital, patients benefiting from endovascular repair may fully recover in two weeks while surgical patients require six to eight weeks.

Despite these and other significant advantages, however, endovascular-based systems have a number of shortcomings. Present bifurcated stent-grafts require relatively large delivery catheters, often up to 24 French and greater in diameter. These catheters also tend to have a high bending stiffness. Such limitations result in the need for a surgical cut-down to deliver the stent-graft and make delivery through the often narrow and irregular arteries of diseased vessels difficult and risky. Because of this, endovascular treatment of aortic aneurysmal disease is not available to many patients who could otherwise benefit from it. For instance, women statistically tend to have smaller vessels and therefore some are excluded from many current endovascular therapies simply due to this reason. There is therefore a need for an endovascular stent-graft capable of being delivered via a smaller and more flexible delivery catheter. Even greater advantages may be realized if such an endovascular stent-graft is capable of being delivered percutaneously.

Further, an endovascular stent-graft must withstand tremendous pulsatile forces over a substantial period of time while remaining both seated and sealed within the vessel. In order to achieve these objectives, the device, which may comprise component parts and/or materials, must remain intact. The device must resist axial migration from the site of deployment while being subjected to significant pulsatile forces, and it should have sufficient radial compliance to conform to the vessel anatomy within which it is deployed so as to prevent blood leakage between the device and the vessel wall at both its proximal, or cephalic, end as well as at its distal, or caudal end or ends (where the net force may be retrograde). Such a device should conform to the morphology of the treated vessel, without kinking or twisting, over the life of the patient.

SUMMARY

The present invention generally is directed to a system for the endovascular treatment of body passageways that includes a medical device implantable within a body lumen such as a blood vessel. Some embodiments of this invention include an endovascular graft for treating vascular disease.

One embodiment includes a graft with a graft body section having a proximal end and a distal end, and, disposed or affixed on at least one end, a connector member having one or more connector member connector elements. The connector member may be embedded within multiple layers of the graft body section. A stent may be coupled or affixed to the one or more connector member connector elements via one or more stent connector elements. The graft may include a proximal stent and connector member only, a distal stent and connector member only, or both proximal and distal stents and their respective connector members.

Both the connector member connector elements and the stent connector elements may have a proximal end and a distal end that comprise opposing shoulder portions. The graft may further have one or more coupling members, such as a wire coil, configured to couple or connect the one or more connector member connector elements to the one or more stent connector elements.

Both the connector members and the stents may be formed of a serpentine ring having one or more apices. One embodiment includes a graft having single stage distal and/or proximal stents in which the associated connector member may have twice as many apices as the stent. In another embodiment, the graft has two-stage distal and/or proximal stents with twice as many apices in a first region as in a second region while the associated connector member has the twice the number of apices as in the first region of the stent. For example, a useful embodiment is one in which a twelve-apex connector member is connected to a first six-apex or six-crown region of a proximal or distal stent and that stent has a second three-apex or three-crown region integral with or joined to the six-crown region.

In alternative embodiments, grafts that include various combinations of single and multiple-stage proximal and distal stents with their associated connector members are possible.

The stents may also include one or more barbs. Typically, the barbs on a proximal stent are oriented distally to engage the stent into the tissue wall in the proximal-to-distal flow field in which the graft is typically disposed. Likewise, in applications in which the graft is deployed to treat an abdominal or thoracic aortic aneurysm, the barbs on one or more distal stents are typically oriented proximally to engage the stent into the tissue wall to oppose the typically retrograde migration forces. The barbs may range in length from about 1 to about 5 mm. They will typically project radially outward from a longitudinal axis of their respective stent and form a barb radial angle from about 10 to about 45 degrees with respect to the graft proximal neck portion inlet axis when the stent is deployed in vivo. The barbs may also be laterally biased in a plane that is orthogonal to a plane in which the barb radial angle is formed to form a barb kick angle.

The stent or stents (proximal and/or distal) comprise struts having one or more optional barb tuck pads integral to the struts such that when the proximal stent is in a reduced profile delivery configuration, each barb is retained by the stent strut. When the endovascular graft is in a deployed configuration, the one or more barbs are released.

The stent or stents may also comprise optional barb tuck slots configured to receive the barbs such that each barb is retained by a slot when the stent is in a delivery configuration. In a deployed configuration, the barbs are released from their corresponding barb tuck slots.

In addition, the stent may comprise grooves. In a typical delivery system, some type of belts or sutures may be used to help retain the endovascular graft in its compressed delivery configuration. The grooves may accommodate these belts or sutures without increasing the small diameter delivery of the device.

The graft body section may also have one or more inflatable cuffs disposed on or near the graft body section proximal end, distal end, or both. The inflatable cuffs provide a sufficiently stiff structure when inflated which help to support the graft body section and provide a conformable surface to seal the graft against the interior surface of the vessel in which it is deployed.

The graft body section may also include one or more inflatable channels. The channel or channels typically may be disposed between and in fluid communication with either or both proximal and distal inflatable cuffs. The channel or channels enhance the graft body section stiffness upon their inflation, help to prevent kinking of the graft body section, and may also facilitate deployment of the graft within a patient's body passageway. The inflatable channel or channels can be in a longitudinal and/or linear configuration with respect to the graft body section, but alternatively may take on a helical or circumferential configuration. Other orientations such as interconnecting grids or rings may also be suitable alone or in combination with any of the other configurations.

During deployment of the graft, the inflatable cuff or cuffs and channel or channels may be inflated or injected with a material that may comprise one or more of a solid, fluid (gas and/or liquid), gel or other medium. According to the invention, a useful inflation medium includes the combination polyethylene glycol diacrylate, pentaerthyritol tetra 3(mercaptopropionate) and a buffer such as glycylglycine or triethanolamine in phosphate-buffered saline. Saline or another inert biocompatible liquid may be added to this three-component inflation medium in amounts up to about sixty percent of the total inflation medium volume. Radiopaque materials such as tantalum, iodinated contrast agents, barium sulfate, etc. may be added to this three-component medium, typically in the buffer, so to render the inflation medium visible under fluoroscopy.

In another embodiment of the invention, the graft may comprise a main body portion and a first bifurcated portion forming a continuous lumen that is configured to confine a flow of fluid therethrough. The graft may also include a second bifurcated portion in fluid communication with the main body portion. At least one inflatable cuff may be disposed at either or both a proximal end of the main body portion and a distal end of the first bifurcated portion. One or more inflatable channels may be disposed between the inflatable cuffs as previously described, and may extend over some or all of the main body portion. The cuffs and channels may be filled with an inflation medium, optionally diluted with an inert biocompatible material such as saline or other liquid, as described above.

In yet another embodiment of the invention, the graft may comprise a main body portion in fluid communication with a first and a second bifurcated portion forming a continuous bifurcated lumen, said lumen configured to confine a flow of fluid therethrough. At least one inflatable cuff may be disposed at or near either or both a proximal end of the main body portion and a distal end of the first and second bifurcated portions. One or more inflatable channels may be disposed between the inflatable cuffs as previously described, and may extend over some or all of the main body portion.

The proximal ends of the graft main body portion may have connector members comprising one or more connector elements, and a proximal stent coupled to the one or more connector elements. One or both of the first and/or second bifurcated portions may likewise have first and/or second distal connector members comprising one or more connector elements disposed on their respective distal ends, and a distal stent coupled to the first and/or second distal connector members.

The present invention is also a system for implanting a tubular medical device within a body lumen having a wall, including a stent for affixing the medical device to the body lumen wall and a connector member for coupling the stent to the medical device, wherein the stent and the connector member are coupled to one another by at least one set of connector elements.

One or more barbs may also be included in this system. In addition, one or more barb tuck pads may be included in which the one or more barbs are configured to be retained by the one or more barb tuck pads when the system is in a delivery configuration and released by the one or more barb tuck pads when the system moves to a deployed configuration. The stent may further include optional slots configured to receive the barbs when the system is in a delivery configuration and wherein the barbs are configured to be released from the slots when the system is in a deployed configuration.

The invention also includes an endovascular graft comprising a graft body section with a proximal end and a distal end and a proximal connector member affixed to the proximal end of the graft body section. The proximal connector member may have one or more connector elements.

The graft may also have a proximal stent comprising one or more distally oriented barbs and one or more proximal stent connector elements coupled to the one or more proximal connector member connector elements and a distal connector member affixed to the distal end of the graft body section. The distal connector member may include one or more connector elements.

The graft of this embodiment further includes a distal stent comprising one or more proximally oriented barbs and comprising one or more distal stent connector elements coupled to the one or more distal connector member connector elements, one or more inflatable cuffs disposed at or near each of the proximal and distal ends of the graft body section, and wherein the graft body section comprises an inflatable channel in fluid communication with the proximal and distal cuffs.

In addition, the proximal and distal connector member connector elements may each have opposing shoulder portions on their proximal and distal ends, as may the proximal and distal stent connector elements. One or more coupling members may couple the proximal connector member connector elements to the proximal stent connector elements and likewise couple the one or more distal connector member connector elements to the one or more distal stent connector elements.

At least one of the inflatable channel, the distal inflatable cuff, and the proximal inflatable cuff may contain an inflation medium comprising the combination polyethylene glycol diacrylate, pentaerthyritol tetra 3(mercaptopropionate), and a buffer.

The proximal stent barbs or distal stent barbs of this embodiment may have a length from about 1 to about 5 mm, and the graft body section may comprise ePTFE.

In yet still a further bifurcated embodiment of the present invention, the device includes a main body portion with a distal end and a proximal end with a connector member disposed on the proximal end. The connector member may include one or more connector elements.

The proximal stent of this embodiment may comprise one or more distally oriented barbs and one or more proximal stent connector elements that are coupled to the connector member connector elements.

This embodiment further includes a first bifurcated portion and a second bifurcated portion forming a continuous lumen with the main body portion. This lumen is configured to confine a flow of fluid therethrough.

A distal connector member may be disposed on distal ends of each of the first and second bifurcated portions. Each of these distal connector members includes one or more connector elements. In addition, this embodiment has one or more distal stents with at least one proximally oriented barb and comprising one or more distal stent connector elements. The distal stent connector elements are coupled to the distal connector member connector elements on one or both of the first and second bifurcated portions.

This embodiment also includes at least one inflatable channel extending from one or both of the first and second bifurcated portions to the main body portion, at least one inflatable cuff disposed at or near a proximal end of the main body portion in fluid communication with the at least one channel, and an inflatable cuff disposed at or near a distal end of each of the first and second bifurcated portions.

The proximal and distal connector member connector elements may each have opposing shoulder portions on their proximal and distal ends, as may the proximal and distal stent connector elements. One or more coupling members may couple the proximal connector member connector elements to the proximal stent connector elements and likewise couple the one or more distal connector member connector elements to the one or more distal stent connector elements.

At least one of the inflatable channel, the first bifurcated portion distal inflatable cuff, the second bifurcated portion distal inflatable cuff, and the proximal inflatable cuff may contain an inflation medium comprising the combination polyethylene glycol diacrylate, pentaerthyritol tetra 3(mercaptopropionate), and a buffer.

The proximal and/or distal stent barbs may have a length from about 1 to about 5 mm. The graft main body portion as well as the first and second bifurcated portions may comprise ePTFE.

The invention is also directed generally to a delivery system for delivery of an expandable intracorporeal device, specifically, an endovascular graft. Embodiments of the invention are directed to percutaneous non-invasive delivery of endovascular grafts which eliminate the need for a surgical cut-down in order to access the afflicted artery or other intracorporeal conduit of the patient being treated. Such a noninvasive delivery system and method result in shorter procedure duration, expedited recovery times and lower risk of complication. The flexible low profile properties of some embodiments of the invention also make percutaneous non-invasive procedures for delivery of endovascular grafts available to patient populations that may not otherwise have such treatment available. For example, patients with small anatomies or particularly tortuous vasculature may be contraindicated for procedures that involve the use of delivery systems that do not have the flexible or low profile characteristics of embodiments of the present invention.

In one embodiment, the delivery system has an elongate shaft with a proximal section and a distal section. The distal section of the elongate shaft includes a portion having an expandable intracorporeal device. An elongate belt support member is disposed adjacent a portion of the expandable intracorporeal device and a belt is secured to the belt support member and circumferentially disposed about the expandable intracorporeal device. The belt member constrains at least a portion of the expandable intracorporeal device. A release member releasably secures the belt in the constraining configuration.

Another embodiment of the invention is directed to a delivery system that has an elongate shaft with a proximal section and a distal section. The distal section of the elongate shaft has an elongate belt support member disposed adjacent a portion of the expandable intracorporeal device. A belt is secured to the belt support member and is circumferentially disposed about the expandable intracorporeal device. The belt has a configuration which constrains the expandable intracorporeal device and a release member releasably secures the belt in the constraining configuration. The belt may constrain any portion of the expandable intracorporeal device, such as a self-expanding portion of the expandable intracorporeal device. A self-expanding portion of the device may include a self-expanding member such as a tubular stent.

In a particular embodiment of the invention, a plurality of belts are secured to various axial positions on the belt support member, are circumferentially disposed about the expandable intracorporeal device and have a configuration which constrains the expandable intracorporeal device. At least one release member releasably secures the belts in the constraining configuration. Each belt can be released by a single separate release member which engages each belt separately, or multiple belts can be released by a single release member. The order in which the belts are released can be determined by the axial position of the belts and the direction of movement of the release member.

Another embodiment of the invention is directed to a delivery system for delivery of a self-expanding endovascular graft with a flexible tubular body portion and at least one self-expanding member secured to an end of the endovascular graft. The delivery system has an elongate shaft having a proximal section and a distal section. The distal section of the elongate shaft has an elongate belt support member disposed within the self-expanding member of the endovascular graft and a belt which is secured to the belt support member adjacent the self-expanding member. The belt is also circumferentially disposed about the self-expanding member and has a configuration which constrains the self-expanding member. A release wire releasably secures ends of the belt in the constraining configuration.

A further embodiment of the invention includes a delivery system for delivery of an endovascular graft with a flexible tubular body portion and a plurality of self-expanding members secured to ends of the endovascular graft. The delivery system has an elongate shaft with a proximal section and a distal section. The distal section of the elongate shaft has an elongate guidewire tube disposed within the endovascular graft in a constrained state. A plurality of shape memory thin wire belts are secured to the guidewire tube respectively adjacent the self-expanding members. The belts are circumferentially disposed about the respective self-expanding members and have a configuration which constrains the respective self-expanding members. A first release wire releasably secures ends of the belts disposed about the self-expanding members at the proximal end of the endovascular graft in a constraining configuration. A second release wire releasably secures ends of the belts disposed about the self-expanding members at a distal end of the endovascular graft in the constraining configuration.

The invention also is directed to a method for deploying an expandable intracorporeal device within a patient's body. The method includes providing a delivery system for delivery of an expandable intracorporeal device including an elongate shaft having a proximal section and a distal section. The distal section of the elongate shaft has an elongate belt support member disposed adjacent a portion of the expandable intracorporeal device and a belt which is secured to the belt support member. The belt is circumferentially disposed about the expandable intracorporeal device and has a configuration which constrains the expandable intracorporeal device. A release member releasably secures the belt in the constraining configuration.

Next, the distal end of the delivery system is introduced into the patient's body and advanced to a desired site within the patient's body. The release member is then activated, releasing the belt from the constraining configuration. Optionally, the delivery system may also have an outer protective sheath disposed about the endovascular graft in a constrained state, the belt in its constraining configuration and at least a portion of the release wire disposed at the belt. In such an embodiment, the method of deployment of an expandable intracorporeal device also includes retraction of the outer protective sheath from the endovascular graft prior to activation of the release member.

In an embodiment of the invention directed to delivery of bifurcated intracorporeal device, an elongate shaft has a proximal section and a distal section. The distal section of the shaft has an elongate primary belt support member and at least one primary belt disposed on the primary belt support member. The primary belt support member is configured to be circumferentially disposed about a bifurcated intracorporeal device and at least partially constrain the device. A primary release member is configured to engage and releasably secure the primary belt in a constraining configuration. At least one elongate secondary belt support member is disposed adjacent the elongate primary belt support member. At least one secondary belt is disposed on the secondary belt support member. This at least one secondary belt is configured to be circumferentially disposed about a bifurcated intracorporeal device and at least partially constrain the device. A secondary release member is configured to engage and releasably secure the secondary belt in a constraining configuration.

In a method for deploying a bifurcated intracorporeal device within a patient's body, a delivery system for delivery and deployment of a bifurcated intracorporeal device is provided. The delivery system includes an elongate shaft having a proximal section and a distal section. The bifurcated intracorporeal device is disposed on the distal section of the elongate shaft. The distal section of the elongate shaft also includes an elongate primary belt support member and at least one primary belt secured to the primary belt support member. The primary belt is configured to be circumferentially disposed about a bifurcated intracorporeal device and at least partially constrain the device. A primary release member engages and releasably secures the primary belt in the constraining configuration. The distal section of the elongate shaft also includes at least one elongate secondary belt support member disposed adjacent the elongate primary belt support member. At least one secondary belt is secured to the secondary belt support member and is configured to be circumferentially disposed about a bifurcated intracorporeal device to at least partially constrain the device. A secondary release member engages and releasably secures the secondary belt in a constraining configuration.

The distal end of the delivery system is introduced into the patient's body and advanced to a desired site within the patient's body. The release members are then activated to release the belts from the constraining configuration and the device is deployed. Thereafter, the delivery system can be removed from the patient's body. In some embodiments of the invention, the secondary belt support member is detached and removed from the delivery system prior to withdrawal of the delivery system from the patient. In another embodiment, the secondary belt support member is displaced laterally towards the primary belt support member so as to be substantially parallel to the primary belt support member and enable withdrawal of the delivery system through an ipsilateral side of the bifurcated intracorporeal device.

These and other advantages of the invention will become more apparent from the following detailed description of the invention when taken in conjunction with the accompanying exemplary drawings.

BRIEF DESCRIPTION OF THE DRAWINGS

FIG. 5A is an enlarged side view of FIG. 5 at Detail A.

FIG. 12 shows detail of a stent section comprising a tapered strut section.

FIG. 19A is an enlarged elevational view in partial section of the delivery system in FIG. 14.

FIG. 19B is an enlarged elevational view in partial section of the delivery system of FIG. 14 with portions of the graft and self-expanding members cut away for clarity of view of the belt bushings.

FIG. 20A is a perspective view showing release belt configurations having features of the invention.

FIG. 20B is a perspective view showing an alternative embodiment of release belts.

FIG. 20C is an end view showing an alternative embodiment of release belts.

FIG. 20D is a perspective view of the embodiment of FIG. 20C.

FIG. 20E is an enlarged view of a particular coupling configuration between end loops of release belts.

FIG. 20F is a perspective view, partially cut away, of a particular embodiment of an end loop of a release belt.

FIG. 20G is a perspective view of an alternative embodiment of a release belt.

FIG. 20H is a perspective view of an alternative embodiment of a release belt.

FIG. 25 is an enlarged diagrammatic view of a delivery system having features of the invention disposed within an artery of a patient with an expandable intracorporeal device being deployed within the artery.

FIG. 26 is an elevational view in partial section of a connection between an inflation tube and an inflation port of an endovascular graft.

FIG. 31 is an elevational view in partial section of an alternative embodiment of the proximal adapter of the delivery system shown in FIG. 27 with a nested handle configuration.

FIG. 32 is an elevational view of a bifurcated stent graft suitable for delivery and deployment by embodiments of the invention.

FIG. 33 is a transverse cross sectional view of the stent graft of FIG. 32 taken along lines 33-33 in FIG. 32.

FIG. 34 is a transverse cross sectional view of the stent graft of FIG. 32 taken along lines 34-34 of FIG. 32.

FIG. 35 is a transverse cross sectional view of the stent graft of FIG. 32 taken along lines 35-35 of FIG. 32.

FIG. 40 is a transverse cross sectional view of the delivery system of FIG. 39 taken along lines 40-40 of FIG. 39.

FIG. 41 is a transverse cross sectional view of the delivery system of FIG. 39 taken along lines 41-41 of FIG. 39.

FIG. 41A is a transverse cross sectional view of an alternative embodiment of a secondary belt support member of a delivery system similar in function to that shown in FIG. 41.

FIG. 42 is a transverse cross sectional view of the delivery system of FIG. 39 taken along lines 42-42 of FIG. 39.

FIG. 43 is a transverse cross sectional view of the delivery system of FIG. 39 taken along lines 43-43 in FIG. 39.

FIGS. 66-70 illustrate a number of alternative catheter distal shaft arrangements in which a well is provided to facilitate the orderly and tangle-free withdrawal of the release strand from the delivery catheter.

DETAILED DESCRIPTION

Figure 1:
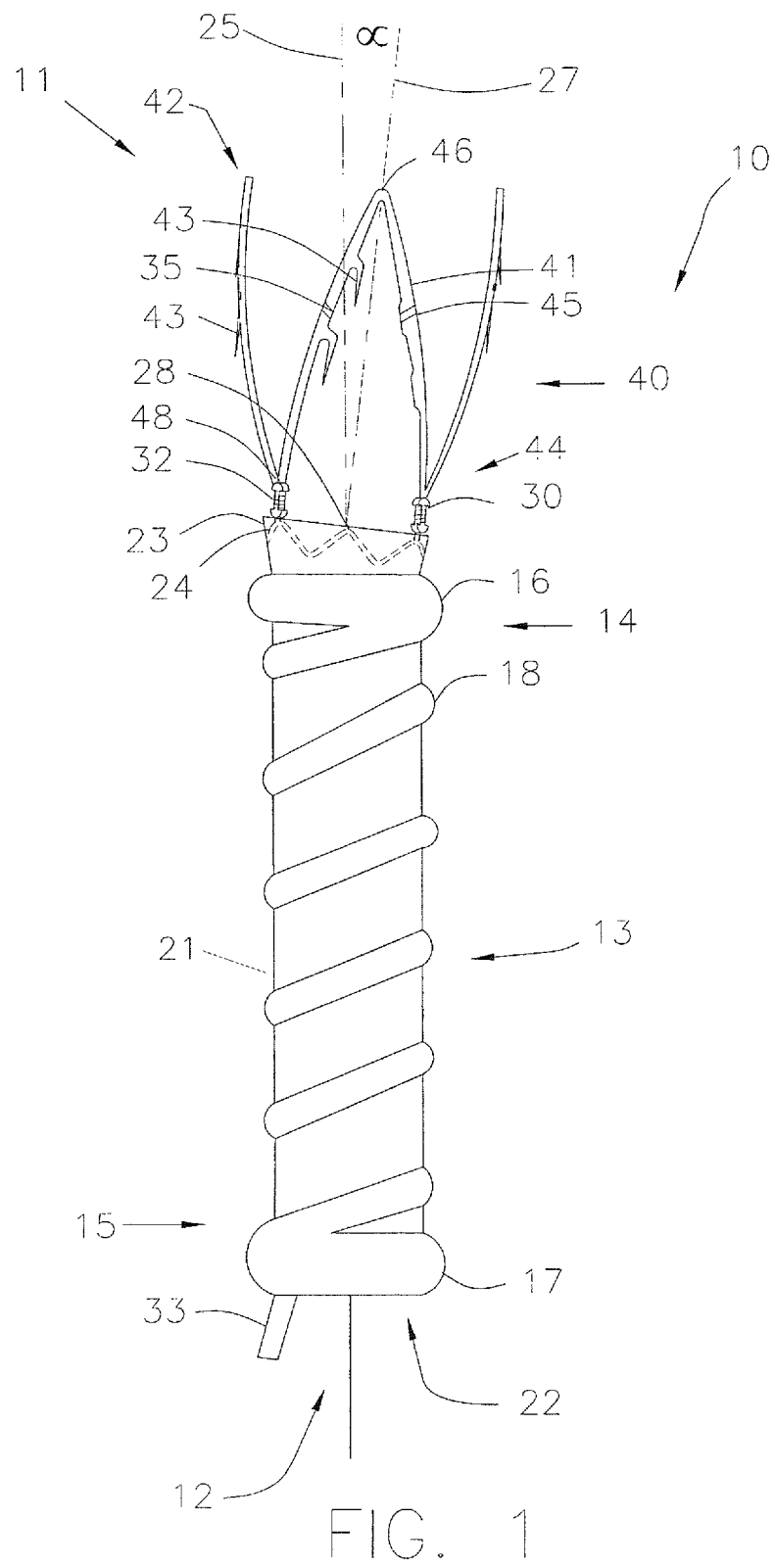
FIG. 1 shows an endovascular graft according to an embodiment of the present invention.

FIG. 1 shows an endovascular graft 10 in its deployed configuration. Unless otherwise stated, the term "graft" or "endovascular graft" is used herein to refer to a prosthesis capable of repairing and/or replacing diseased vessels or portions thereof, including generally tubular and bifurcated devices and any components attached or integral thereto. For purposes of illustration, the graft embodiments described below are assumed to be most useful in the endovascular treatment of abdominal aortic aneurysms (AAA). For the purposes of this application, with reference to endovascular graft devices, the term "proximal" describes the end of the graft that will be oriented towards the oncoming flow of bodily fluid, typically shows a flat pattern blood, when the device is deployed within a body passageway. The term "distal" therefore describes the graft end opposite the proximal end. Finally, while the drawings in the various figures are accurate representations of the various embodiments of the present invention, the proportions of the various components thereof are not necessarily shown to exact scale within and among or between any given figure(s).

Graft 10 has a proximal end 11 and a distal end 12 and includes a generally tubular structure or graft body section 13 comprised of one or more layers of fusible material, such as expanded polytetrafluoroethylene (ePTFE). A proximal inflatable cuff 16 is disposed at or near a proximal end 14 of graft body section 13 and an optional distal inflatable cuff 17 is disposed at or near a graft body section distal end 15. Graft body section 13 forms a longitudinal lumen 22 configured to confine a flow of fluid therethrough and may range in length from about 5 to about 30 cm; specifically from about 10 to about 20 cm.

As will be described in greater detail below, inflation of cuffs 16 and 17 will cause them to assume a generally annular shape (especially when graft body section 13 is in an unconstrained state). Inflatable cuffs 16 and 17 will generally, however, conform to the shape of the vessel within which it is deployed. When fully inflated, cuffs 16 and 17 may have an outside diameter ranging from about 10 to about 45 mm; specifically from about 16 to about 32 mm.

At least one inflatable channel 18 may be disposed between and in fluid communication with proximal inflatable cuff 16 and distal inflatable cuff 17. Inflatable channel 18 provides structural support to graft body section 13 when inflated to contain an inflation medium. Inflatable channel 18 further prevents kinking and twisting of the tubular structure or graft body section when it is deployed within angled or tortuous anatomies as well as during remodeling of body passageways (such as the aorta and iliac arteries) within which graft 10 is deployed. Together with proximal and distal cuffs 16 and 17, inflatable channel 18 forms a network of inflatable cuffs and channels in fluid communication with one other.

We have found the helical configuration of channel 18 in the FIG. 1 embodiment to be particularly effective in providing the needed kink resistance for effectively treating diseased body passageways such as AAAs, in which highly angled and tortuous anatomies are frequently found. In alternative embodiments, however, other cuff and channel configurations are possible. Inflatable channel 18 may be disposed helically as shown in FIG. 1, it may take on a more circumferential or annular rib and spine configuration as shown in the FIG. 2 embodiment, or otherwise. Similarly, the longitudinal and radial dimensions of inflatable channel 18 may vary as necessary both between different graft body sections and even within a single graft body section, depending on the indication for which graft 10 is intended to treat. Further, inflatable channel 18 may be oriented at various angles with respect to the longitudinal axis 25 of graft body section 13, and the pitch (the distance between helical or parallel windings of channel 18) may vary as necessary.

In the embodiment of FIG. 1, the channel pitch, or distance between each helical inflatable channel 18 winding, may range from about 2 to about 20 mm, depending on the overall size of graft body section 13 and the desired degree of kink resistance. We have found that a pitch of between about 4 and about 10 mm is effective for tubular embodiments of the present invention and a pitch of between about 3 and about 10 mm to be useful in bifurcated graft embodiments. The helix angle of each channel winding (measured with respect to a plane perpendicular to the graft body section longitudinal axis 25) may range from about 10 to about 45 degrees; more specifically, from about 20 to about 35 degrees in tubular and bifurcated graft embodiments. Finally, the width of inflatable channel 18 typically ranges from about 1 to about 8 mm; more specifically, from about 2 to about 4 mm.

Graft body section or tubular structure 13 and its associated components may be made from a variety of suitable materials, including ultra high molecular weight polyethylene, polyesters, and the like. As previously discussed, we have found constructing graft body section 13 primarily from one or more layers of ePTFE to be particularly useful. Details of how graft 10 may be fabricated (as well as all of the other grafts discussed herein) are more fully described in parent U.S. patent application Ser. No. 10/029,559 (now U.S. Pat. No. 7,147,661) and in U.S. patent application Ser. No. 10/029,570 (now U.S. Pat. No. 6,776,604), Ser. No. 10/029,584 (now U.S. Pat. No. 7,090,584), and Ser. No. 10/029,557 (now U.S. Pat. No. 7,125,464), each to Chobotov et al. and, in addition, U.S. patent application Ser. No. 09/133,978 to Chobotov, filed Feb. 9, 1998 and entitled "Endovascular Graft", now U.S. Pat. No. 6,395,019 and U.S. patent application Ser. No. 09/917,371 to Chobotov et al., filed Jul. 27, 2001 and entitled "Bifurcated Stent-Graft Delivery System and Method", now U.S. Pat. No. 6,761,733, the entirety of each of which is hereby incorporated herein by reference, teach a useful endovascular stent-graft and delivery system, respectively.

A proximal neck portion 23 is disposed in the vicinity of graft body section proximal end 14 and serves as an additional means to help seal the deployed graft against the inside of a body passageway. Proximal neck portion 23 has an inlet axis 27 that forms an inlet axis angle α in relation to graft body section longitudinal axis 25. This angled inlet axis 27 allows the graft to better conform to the morphology of a patient's vasculature in patients who have an angled vessel morphology, such as is often the case in the neck region of abdominal aortic aneurysms. The inlet axis angle α may range in any direction with respect to longitudinal axis 25 from about zero to about 90 degrees, preferably from about 20 to about 30 degrees. Proximal neck portion 23 may be tapered or flared to a larger diameter in the proximal direction to facilitate this sealing function. Proximal neck portion 23 also serves as a means of providing a smooth fluid flow transition into graft lumen 22.

The network of inflatable cuffs 16, 17 and channel 18 may be inflated, most usefully in vivo, by introduction or injection of a material or medium through an injection port 33 that is in fluid communication with cuff 17 and the associated cuff/channel network. The material may comprise one or more of a solid, fluid (gas and/or liquid), gel or other medium. The material may contain a contrast medium that facilitates imaging the device while it is being deployed within a patient's body. For example, radiopaque materials containing elements such as bismuth, barium, gold, iodine, platinum, tantalum or the like may be used in particulate, liquid, powder or other suitable form as part of the inflation medium. Liquid iodinated contrast agents are a particularly suitable material to facilitate such imaging. Radiopaque markers may also be disposed on or integrally formed into or on any portion of graft 10 for the same purpose, and may be made from any combination of biocompatible radiopaque materials.

A connector member 24 is affixed to or integrally formed in graft body section 13, or as shown in FIG. 1, at or near graft body section proximal end 14 and proximal neck portion 23. Connector member 24 is a serpentine ring structure comprising apices 28. Connector member 24 may be made from any suitable material that permits expansion from a constrained state, most usefully a shape memory alloy having superelastic properties such as nickel titanium (NiTi). Other suitable connector member 24 materials include stainless steel, nickel-cobalt alloys such as MP35N, tantalum and its alloys, polymeric materials, composites, and the like. Connector member 24 (as well as all stents and connector members described herein) may be configured to self-expand from a radially constrained state or be configured to expand as a result of an applied force (such as from an inflated balloon), or, in the case of some shape memory materials, a temperature change.

The configuration of connector member 24 shown in FIG. 1 comprises eight apices 28 (put more precisely, the FIG. 1 connector member 24 comprises eight proximal apices and eight distal apices; however, unless otherwise mentioned, the term "apices" refers in this context to either the proximal or distal set of apices in a single connector member, stent, or stent portion). Another particularly useful configuration is one shown in FIGS. 2-7 in which the connector member comprises twelve apices. Any number of apices up to twenty-four or more may be used in connector member 24. In general terms, as the number of apices 28 on connector member 24 increase, connector member 24 will exhibit a greater conformability to the vessel wall when it is expanded from a radially constrained state.

No matter the number of apices present, one function of connector member 24 is to work in conjunction with proximal neck 23 in which it is typically embedded to help seal the deployed graft against the inside of a body passageway as previously described. It can also play a role in helping to keep graft 10 in place within the vessel wall and may also facilitate the opening of graft body section proximal end 14 during deployment.

Some apices 28 may also comprise a connector member connector element 30, described more fully below with respect to the embodiment of FIG. 2. In the FIG. 1 embodiment, in which connector member 24 comprises eight (proximal) apices 28, a connector element 30 is distributed on every other apex 28. We have found this configuration to be suitable for meeting the various performance requirements of the present invention. Other configurations are possible, including the twelve-apex connector member 24 shown in FIGS. 2-7 comprising six connector elements 30 distributed on every other apex 28. Other configurations in which, for example, connector elements are distributed on every apex, every third or fourth apex, or any other pattern are within the scope of the present invention.

Graft 10 further comprises a proximal stent 40 having a proximal end 42 and a distal end 44. Although other configurations are possible, proximal stent 40 in the FIG. 1 embodiment comprises a serpentine ring having four apices 46, or half the number of apices 28 of connector member 24. Note that proximal stent 40 in FIG. 1 takes on an optional tulip-shaped tapered profile in which the stent's diameter varies along its length. Such a profile serves to present sufficient radial force upon radial expansion of stent 40 to reliably anchor graft 10 to the vessel or lumen wall within which it is deployed while, at its tapered distal end near graft body section 13, refraining from interfering with the sealing function performed by proximal cuff 16, proximal neck portion 23, and connector member 24. This profile also accommodates any taper that may be present in the host vessel or lumen.

As shown in FIG. 1, proximal stent 40 is disposed generally proximal to graft body section 13 and connector member 24. Proximal stent is typically, though not necessarily, made a part of graft 10 by being affixed or connected to connector member 24 via connector elements as described in detail below. Proximal stent 40 may also be affixed or embedded directly to or in proximal neck portion 23 and/or other portions of graft body section 13. In addition, the present invention includes embodiments wherein the connector member and proximal stent are not mechanically or otherwise fastened to one another but rather unified, formed of a monolithic piece of material such as NiTi.

This configuration of proximal stent 40, connector member 24, proximal neck portion 23, and proximal cuff 16 helps to separate the sealing function of proximal cuff 16, which requires conformation and apposition to the vessel wall within which graft 10 is deployed without excessive radial force, from the anchoring function of proximal stent 40 (connector member 24 and proximal neck portion 23 play intermediate roles). This allows the sealing and anchoring functions each to be optimized without compromising the other. In addition, in part because proximal stent 40, connector member 24, and inflatable cuff 16 are longitudinally distributed along the graft body section longitudinal axis 25, a smaller, more flexible delivery profile ranging from about 10 to about 16 French is possible; preferably below 12 French.

Proximal stent 40 may be manufactured from any of the materials suitable for connector member 24. When manufactured from a shape memory alloy having superelastic properties such as NiTi, proximal stent 40 may be configured to self-expand upon release from a constrained state.

Proximal stent 40 further comprises proximal stent connector elements 48 that are affixed to connector member connector elements 30 via coupling members as described more fully below in relation to FIGS. 2-6. Note that in the FIG. 1 embodiment, there is one proximal stent connector element 48 for every connector member connector element 30.

Proximal stent 40 also comprises struts 41 and may also comprise one or more barbs 43. A barb can be any outwardly directed protuberance, typically terminating in a sharp point that is capable of at least partially penetrating a body passageway in which graft 10 is deployed (typically the intimal and medial layers of a blood vessel such as the abdominal aorta).

When proximal stent 40 is deployed in the abdominal aorta, for example, typically in a location proximal to the aneurysm and any diseased tissue, barbs 43 are designed to work in conjunction with the distally-oriented blood flow field in this location to penetrate tissue and prevent axial migration of graft 10. This is why barbs 43 in the FIG. 1 embodiment are oriented distally with respect to graft body section 13.

In alternative embodiments, depending upon the material used in the manufacture of proximal stent 40, the clinical demands and other factors, the degree to which barbs 43 help maintain the position of graft 10 within the vessel may vary. Consequently, the number, dimensions, configuration and orientation of barbs 43 may vary significantly, yet be within the scope of the present invention.

The length of barbs 43 in any of the embodiments of the present invention may range from about 1 to about 5 mm; more particularly, from about 2 to about 4 mm.

Figure 1A:
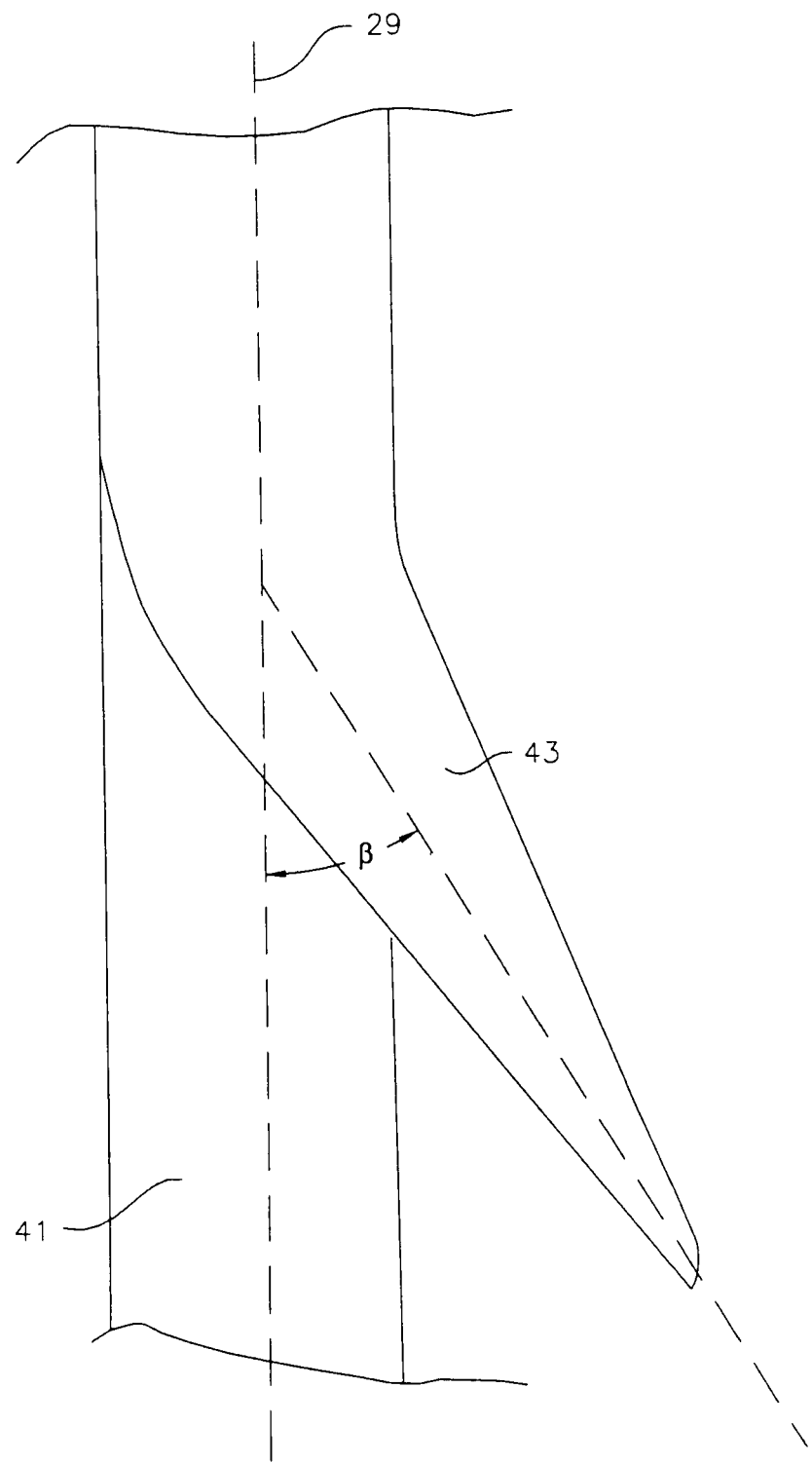
FIGS. 1A-1B detail two angles at which a stent barb may be oriented on the graft of an embodiment of the present invention.

As shown in their free expanded configuration in FIG. 1 and as shown in greater detail in FIG. 1A, barbs 43 may be oriented in a distal direction and form an elevation angle $\beta$ ranging from about 10 to about 45 degrees or higher with respect to a longitudinal axis 29 of strut 41, projecting generally radially outward from graft lumen 22 away from proximal neck inlet axis 27. Disposing barbs at angle $\beta$ provides the necessary embedding force to anchor graft 10 into the vessel or lumen in which it is deployed. Although not shown in the figures, the barb elevation may also be described when the graft 10 is deployed in vivo in a body lumen or vessel by a second angle $\beta'$ measured relative to proximal neck inlet axis 27. This second barb elevation angle $\beta'$ will typically range from about 5 to about 45 degrees. For both barb elevation angles $\beta$ and $\beta'$, similar orientations may be found with barbs in other embodiments of the present invention.

Figure 1B:
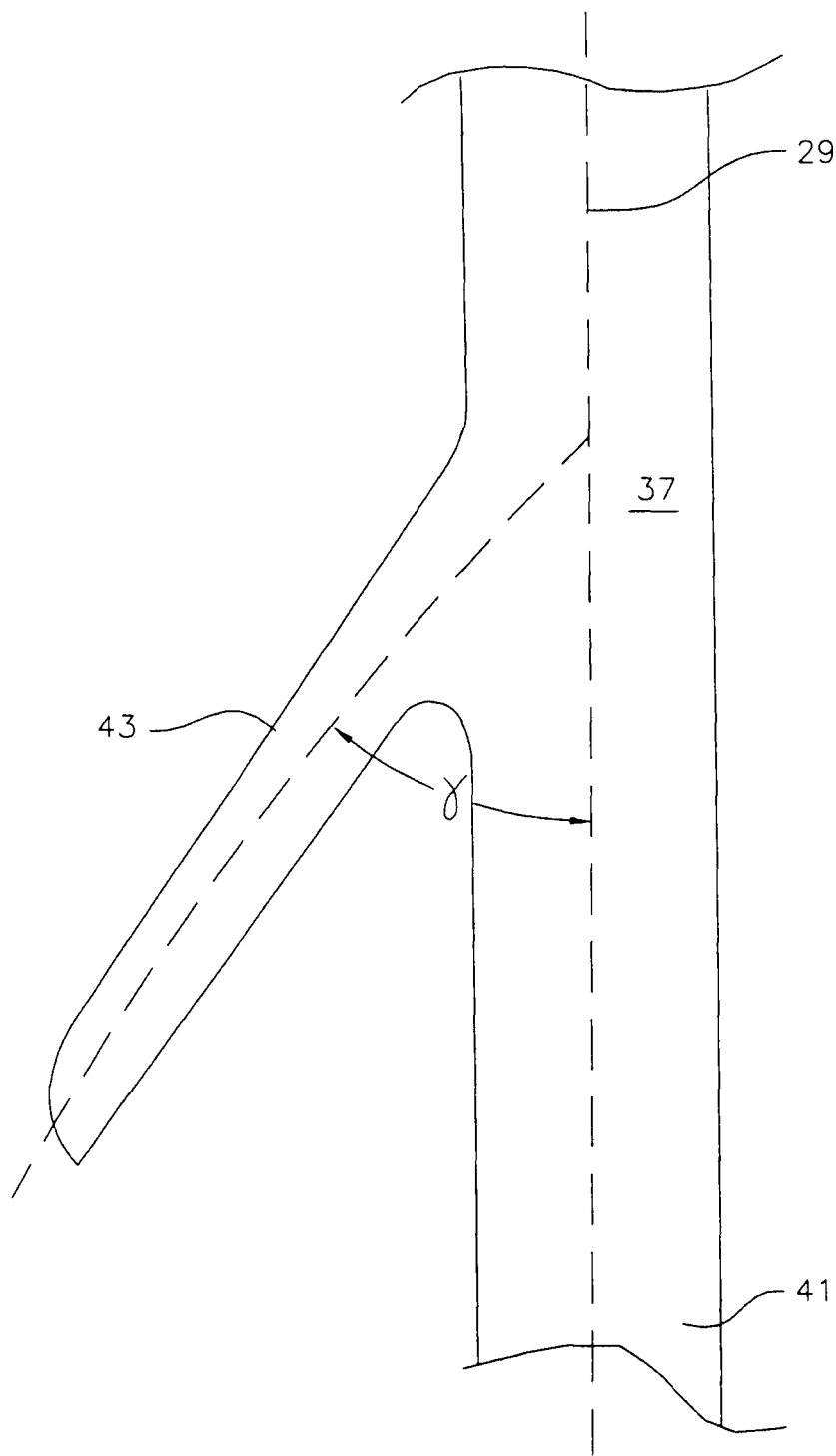

It is generally desirable that barbs 43 be oriented in a position generally parallel to the axis of the lumen in which they are deployed so that they are in a position to best resist the drag loads imposed by the flow field in vivo in certain applications. To this end, we have found it useful for one or more of barbs 43 to form an optional second barb azimuth or "kick" angle $\gamma$ with respect to strut longitudinal axis 29 as shown in FIG. 1B. In this view, barb 43 is laterally biased in a plane that is tangent to an outside surface 37 of strut 41 and generally orthogonal to a plane in which angle $\gamma$ is formed. The term "strut outside surface 37" generally refers to that portion of the surface of strut 41 located opposite the proximal neck inlet axis 27, or that portion of strut 41 that when deployed will be in direct contact with the vessel or lumen wall. We have also found that providing lateral kick angle $\gamma$ to barbs 43 contributes to greater barb stability when the barb is tucked behind an adjacent strut or tuck pad in a reduced diameter delivery configuration. In proximal stent 40, $\gamma$ may range from between about 5 and about 70 degrees relative to strut axis 41. Similar orientations may be found with barbs in other embodiments of the present invention.

The number of barbs, the length of each barb, each of the barb angles described above, and the barb orientation may vary from barb to barb within a single stent or between multiple stents within a single graft.

Note that although the various barbs (and tuck pads 45 discussed below) discussed herein may be attached to or fixed on the stent struts 41, we have found it useful that, as shown in the various figures, they be integrally formed as part of the stent struts. In other words, they can be mere extensions of the struts in which no joint or other connection exists. Because there is no joint, we have found the strength of the barb/strut interface to be very high, as is the fatigue resistance of the barbs. With no mechanical connection to join the barbs to the struts, reliability of the barb/strut interface is higher. In addition, the lack of a heat-affected zone in which the mechanical properties of a welded or brazed joint may be deleteriously affected is another significant advantage to having the barbs and tuck pads be integral to the stent.

Struts 41 may also comprise optional integral tuck pads 45 disposed opposite each barb 43. As is the case with the barbs, the number, dimensions, configuration and orientation of barb tuck pads 45 may vary significantly.

During preparation of graft 10 (and therefore proximal stent 40) into its reduced diameter delivery configuration, each barb 43 is placed behind a corresponding strut 41 (and optional tuck pad 45, if present) so to thereby prevent that barb from contacting the inside of a delivery sheath or catheter during delivery of the device and from undesired contact with the inside of a vessel wall. As described in copending U.S. patent application Ser. No. 09/917,371 to Chobotov et al., now U.S. Pat. No. 6,761,733, a release belt disposed in one or more grooves 35 disposed on struts 41 retain proximal stent 40 in this delivery configuration.

Upon deployment of graft 10, and more particularly, proximal stent 40, (typically accomplished in part by release of this and other belts), the radial expansion of stent 40 results in a displacement of struts 41 so that the distance between them increases. Eventually this displacement becomes large enough so to free the barbs from behind the adjacent strut (and optional tuck pad 45, if present) and engage the wall of the lumen being treated. During experiments in which stents of the present invention having barbs described herein are released from a constrained delivery configuration to assume an expanded or deployed configuration, high speed video confirms that the barbs tend to release with a time constant that is generally an order of magnitude lower than the time constant associated with the radial expansion of the stent. In other words, during the stent deployment process, their barbs complete their deployment before the stent is fully expanded, so that the barbs may engage the vessel or lumen wall with maximum effectiveness.

Alternatively, and especially in the case when a different material such as stainless steel is used for proximal stent 40, an optional balloon may be used to expand stent 40 to free barbs 43 from their tuck pads 45 and to cause barbs 43 to engage tissue as desired. Even if a superelastic self-expanding proximal stent 40 is used in graft 10, such a balloon may be used to help further implant barbs 43 into their desired position to ensure proper placement of graft 10.

Figure 2:
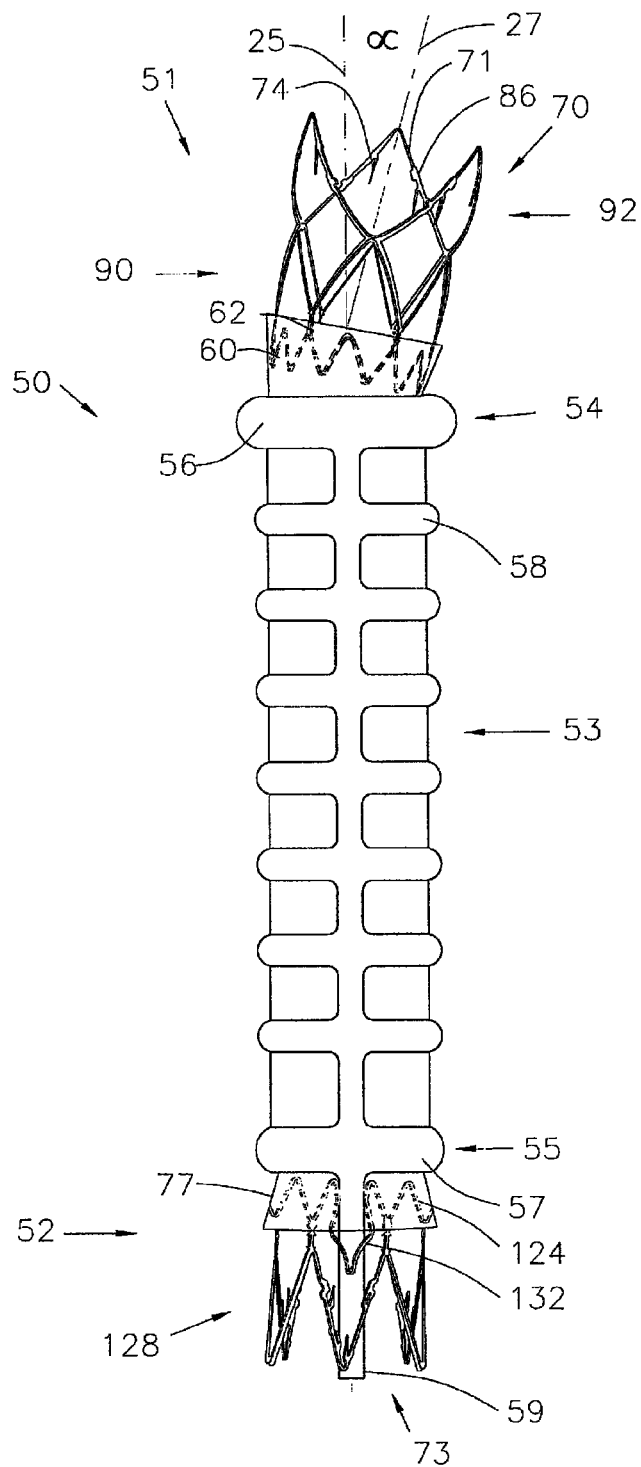
FIG. 2 shows a second endovascular graft according to an embodiment of the present invention.

Turning now to FIG. 2, another endovascular graft having features of the present invention is illustrated. Graft 50 has a proximal end 51 and a distal end 52 and comprises a tubular structure or graft body section 53 with a proximal end 54 and distal end 55. As with the FIG. 1 embodiment, graft body section 53 forms a longitudinal lumen 73 configured to confine a flow of fluid therethrough and may range in length from about 5 to about 30 cm; specifically from about 10 to about 20 cm. Proximal inflatable cuff 56 and optional distal inflatable cuff 57 form a seal when inflated to help prevent transmission of pressure (hemodynamic pressure when the fluid is blood) to the lumen or vessel walls in the region between the proximal and distal cuffs. In addition, the cuffs help to prevent flow of fluid such as blood around the outer surface of graft body section 53.

Inflatable channel 58 comprises an inflatable longitudinal channel or spine in fluid communication with a series of approximately parallel inflatable circumferential channels or ribs. We have found this configuration to be particularly useful in providing effective kink resistance while allowing for rapid and relatively easy inflation of the cuffs and channels when using more viscous inflation materials. Channel 58 is in fluid communication with proximal and distal cuffs 56 and 57, forming a network of inflatable cuffs and channels in fluid communication with each other. Fill port 59 is in fluid communication with distal cuff 57, inflatable channel 58, and proximal cuff 56, adding to this network for the introduction of an inflation medium into graft body section 53. Features of the FIG. 1 embodiment not discussed herein may be present in the FIG. 2 device.

Graft 50 of FIG. 2 also comprises a twelve-crown or twelve-apex proximal connector member 60, a two-stage six- and three-crown proximal stent 70, distal neck portion 77, distal connector member 124, and distal stent 128. Distal connector member 124 and distal stent 128 are analogous to connector member 60 and proximal stent 70 except that the distal stent in the FIG. 2 embodiment is single-stage and its optional barbs face in the opposite, or proximal direction relative to the barbs 74 of proximal stent 70. Distal connector member 124 is affixed or attached to distal stent 128, both of which are more fully described in relation to a bifurcated version of the present invention shown in FIGS. 8 and 9, respectively. Distal connector member 124 and distal stent 128 may be manufactured from materials and according to methods that are suitable for connector member 60 and proximal stent 70. Further, distal connector member 124 may be attached to, affixed to, formed integrally with tubular structure or graft body section 53, or more typically, distal neck portion 77. Distal connector member 124 further comprises fill port bridge 132.

Figure 3:
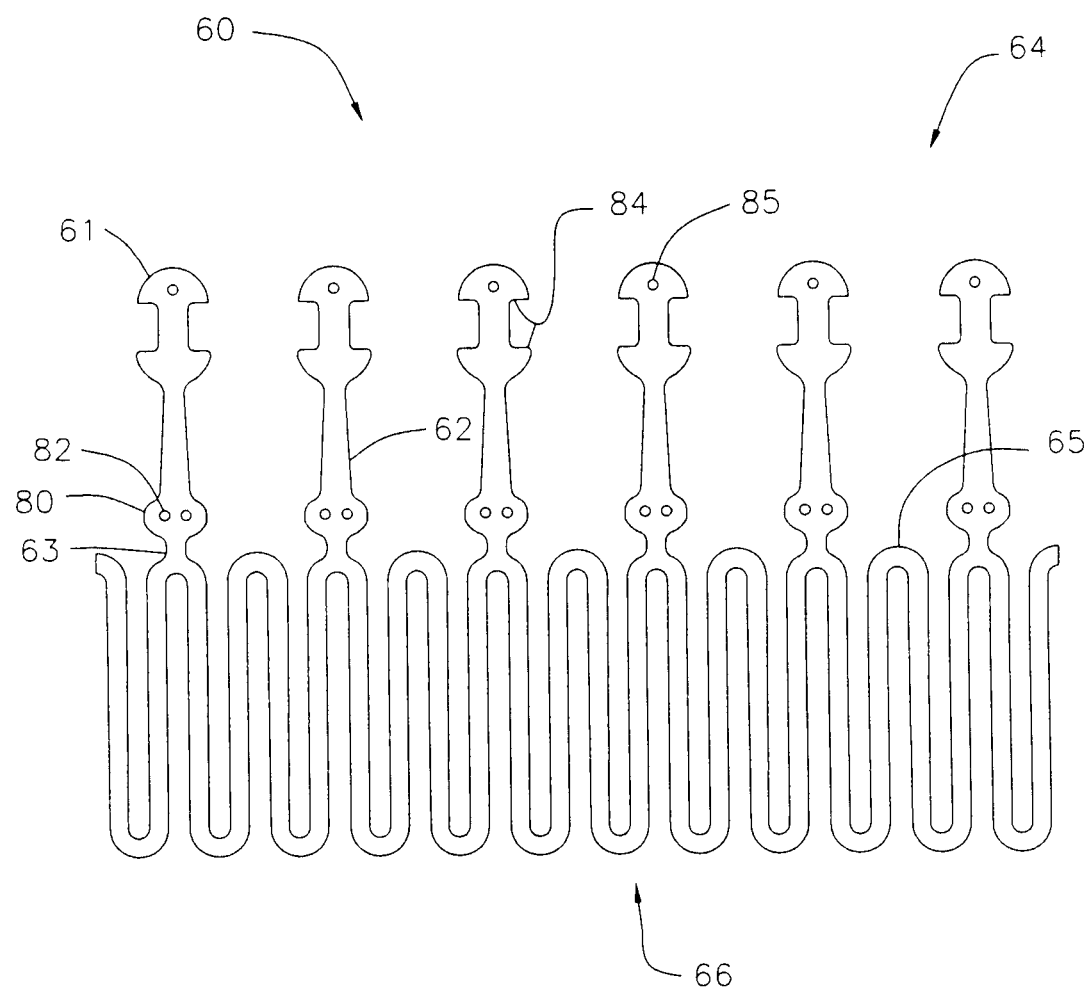
FIG. 3 shows a flat pattern of a component of the endovascular graft of FIG. 2.
Figure 4:
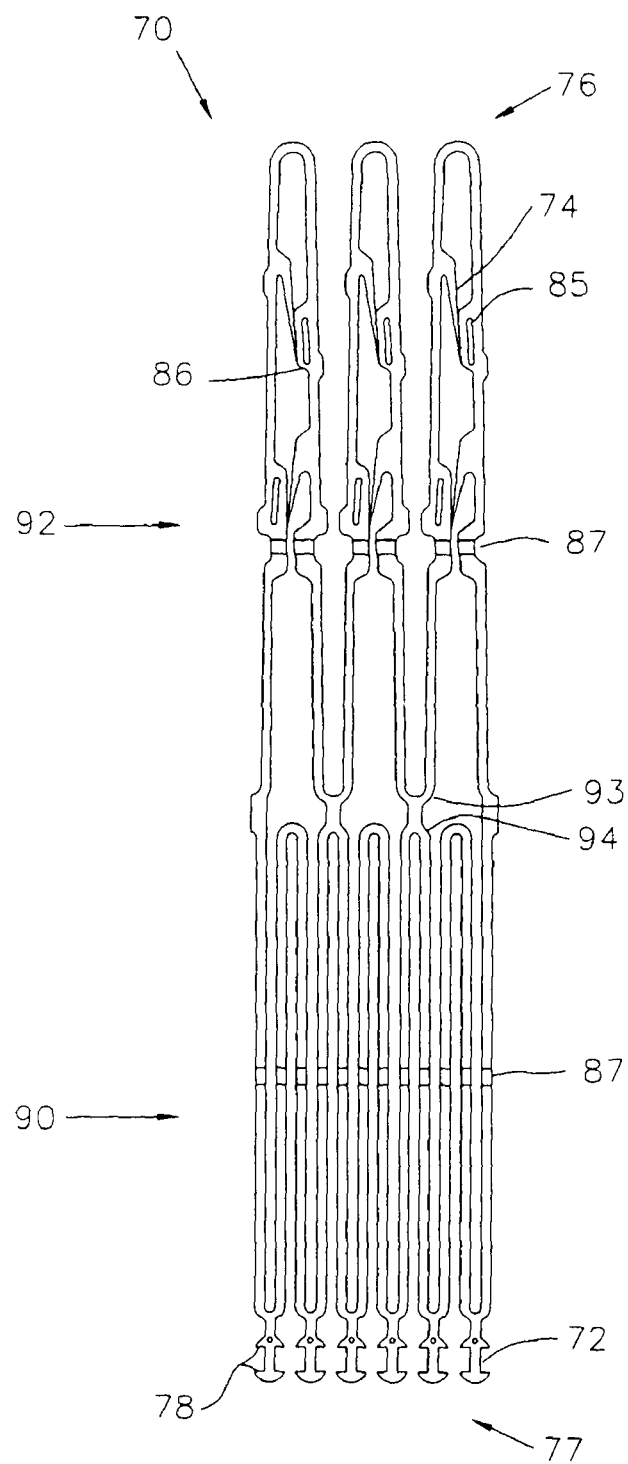
FIG. 4 shows a flat pattern of another component of the endovascular graft of FIG. 2.

FIG. 3 shows a detailed flat pattern view of the proximal connector member 60 shown in FIG. 2. Proximal connector member 60 comprises a distal end 66 and a proximal end 64 having twelve crowns or apices 65. Alternate proximal apices 65 comprise proximal connector member connector elements 62. These connector elements 62 each in turn comprises a proximal end 61, a distal end 63, and optional ears 80 disposed near distal end 63. Ears 80 provide for increased surface area on connector elements 62 to aid in maximizing the strength of the bond between connector element and graft proximal neck portion and further comprises one or more optional apertures 82 to further enhance such a bond as previously discussed. Opposing shoulder portions 84 may have rounded corners so to minimize their potential to snag, tear, or otherwise interfere with other components of the graft or the lumen in which it is deployed. Shoulder portions 84 also have one or more optional shoulder holes 85. These shoulder holes 85 are useful in helping to stabilize the proximal stent 70 and proximal connector member 60 device as they are coupled during assembly as discussed below in conjunction with FIG. 5A.

As illustrated in FIGS. 4-5 and 6-7, two-stage proximal stent 70 has a proximal end 76 and a distal end 77 with proximal stent connector elements 72. Proximal stent connector elements 72 have opposing shoulder portions 78 that may mirror opposing shoulder portions 84 of distal stent connector elements 62.

Figure 6:
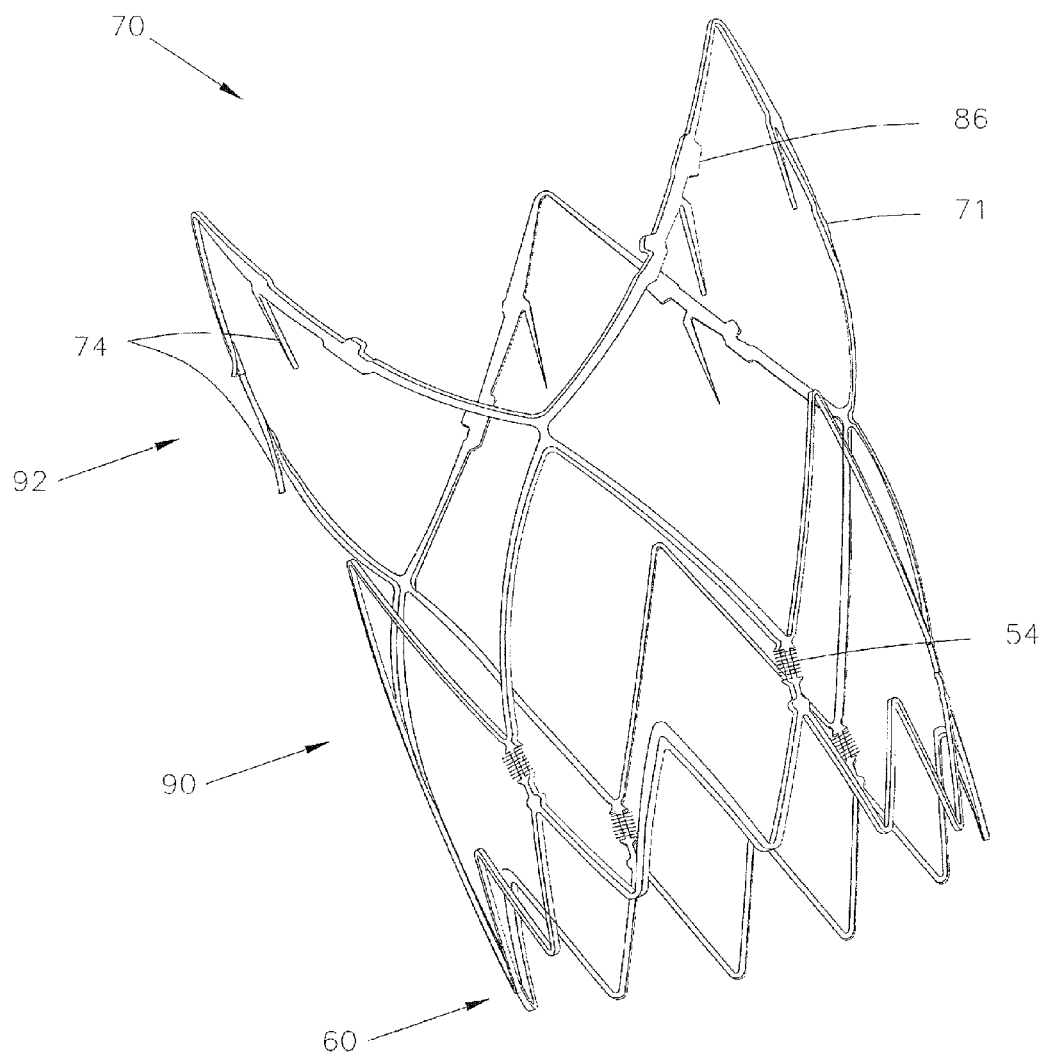
FIG. 6 is an enlarged view of a portion of an endovascular graft having features of an embodiment of the present invention.

Proximal stent 70 comprises struts 71, any one of which may further comprise one or more barbs 74. Optional barb tuck pads 86 near each barb serve to shield barbs 74 when graft 50 is in its reduced diameter delivery configuration. Struts 71 or tuck pads 86 may also contain an optional barb tuck slot 85 to help retain barbs 74 while graft 50 (and consequently proximal stent 70) is in its delivery configuration. Upon deployment of graft 50 as previously described with respect to the FIG. 1 embodiment, barbs 74 are released from barb tuck slots 85 and are placed in their operational, or deployed configuration, as shown in FIGS. 2 and 6. When so deployed in a patient vessel, proximal stent 70 is expanded, forcing barbs 74 at least partially into the vessel wall to emplace graft 50 therein and to resist fluid flow forces that might otherwise dislodge graft 50.

Proximal stent 70 also may comprise one or more sets of optional grooves 87 for housing device release bands as previously discussed.

Unlike proximal stent 40 of FIG. 1, however, proximal stent 70 is a two-stage component having a first, or six-crown region 90 and a second, or three-crown region 92. The first, or six-crown region 90 comprises a serpentine ring having six apices 94 (i.e., six distal and six proximal apices). Likewise, the second, or three-crown region 92 comprises a serpentine ring having three apices 93, the distal apices of which connect to every other proximal apex 94 of six-crown region 90. Note that proximal stent 70 is typically made from a single piece of material such that there are no joints or connections between each stage (such as a mechanical connection or a weld, etc.). However, other configurations in which two or more stages may be so joined or connected from separate parts or stents to form a single stent are possible; likewise, single-piece stents having more than two stages are also possible.

Proximal stent 70 may exhibit a greater outward radial force at three-crown region 92 than in six-crown region 90. Such a design is particularly useful in a clinical setting in which it is desired that such outward radial force be applied within a healthier section of vessel, more remote from the site of disease. Proximal stent 70 may accordingly perform the anchoring function within a portion of vessel that can accommodate such radial force.

Figure 5:
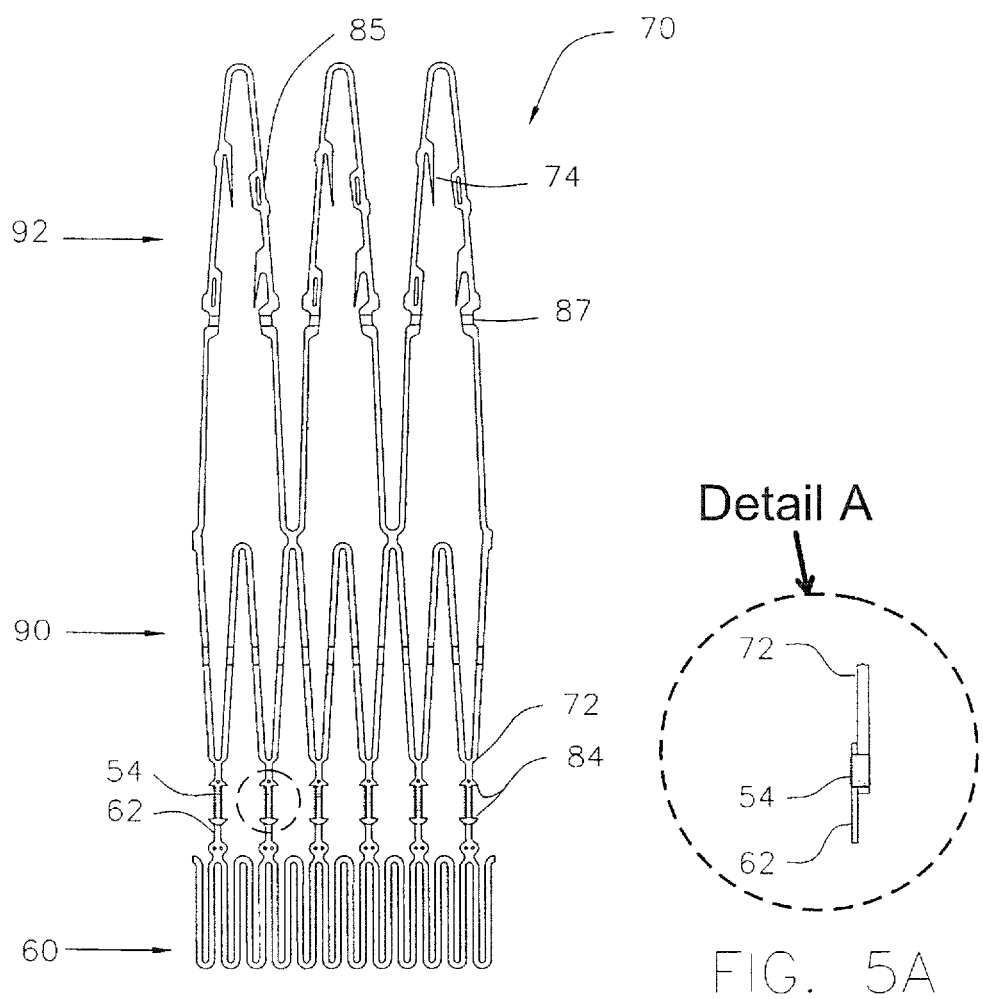
FIG. 5 shows a flat pattern of a portion of the endovascular graft of FIG. 2.

FIG. 5 is a flat pattern view of connector member 60 joined to proximal stent 70. For this embodiment, there is a relationship among the various apices 65, 93 and 94 of the connector member 60 and the two stages of proximal stent 70, respectively, in which there are twelve connector member apices 65, six apices 94 in the proximal stent first or six-crown region 90 and three apices 93 in the proximal stent second or three-crown region 92.

While the actual number of apices may vary as previously discussed, this more generally illustrates a useful convention for the present invention in which the relationship among the various apices may be described: for instance, if the number of connector member 60 apices 65 is denoted "n", "n/2" then denotes the number of proximal stent 70 first or six-crown region 90 apices 94 and "n/4" as the number of proximal stent 70 second or three-crown region 92 apices 93. Other useful embodiments include those in which there are "n" connector member apices, "n" proximal stent first region apices, and "n/2" proximal stent second region apices. These ratios may vary as appropriate; these particular sets of ratios are merely illustrative.

Note also in FIG. 5 that connector member connector elements 62 are coupled to proximal stent connector elements 72 via coupling members 54.

FIG. 5A is a side view of proximal stent connector element 72, connector member connector element 62, and coupling member 54. Coupling member 54 is a wire or similar element wrapped to form a coil around the overlapping connector member connector element 62 and proximal stent connector element 72 to mechanically join connector member 60 to proximal stent 70. Alternatively, any other suitable joining technique, such as welding, brazing, soldering, mechanical means, adhesive, etc. may be used to join these components of the graft 50. We have found, however, that mechanical means such as coupling member 54 is most useful in that it avoids problems presented by techniques such as welding, etc., where possible heat-affected zones some distance from the joint may deleteriously affect the microstructure of the stent/connector element material, especially when that material is nickel titanium, thus having a negative impact on the joint strength, fatigue life, and ultimately the integrity of graft 50.

Any suitable member may be used for coupling member 54 although we have found a wire or wire-like member having a circular cross-sectional shape to be useful (although any shape may be used). Optimally, the wire coupling member 54 may be formed of a suitable metal such as nickel, stainless steel, nickel-titanium, etc. The wire may have a diameter ranging from about 0.002 to about 0.006 inch; more specifically from about 0.003 to about 0.005 inch.

To secure the connector elements 62 and 72 to one another, coupling member 54 may be wound around the matched connector elements one or more times. We have found that providing enough windings to present a single layer of wire in which the windings are immediately adjacent one another from shoulder 78, 84 to shoulder 78, 84 provides sufficient strength and stiffness to the joint thus created without detracting from the low delivery profile afforded by the novel design of graft 50. Thus the number of optimal windings from graft to graft will vary but typically ranges from about 6 to about 18 windings in most applications. With coupling members 54 in place, connector member connector elements 62 and proximal stent connector elements 72 are securely coupled to one another. The features and advantages of coupling member 54 discussed herein may be utilized by any of the embodiments of the present invention herein discussed.

FIG. 6 is a perspective view of connector member 60 joined to proximal stent 70 in this way in their expanded, or deployed configuration. Graft body section 53 and other graft components are removed for clarity of illustration. Barbs 74 are shown in their deployed state, released from optional barb tuck pads 86.

Figure 7:
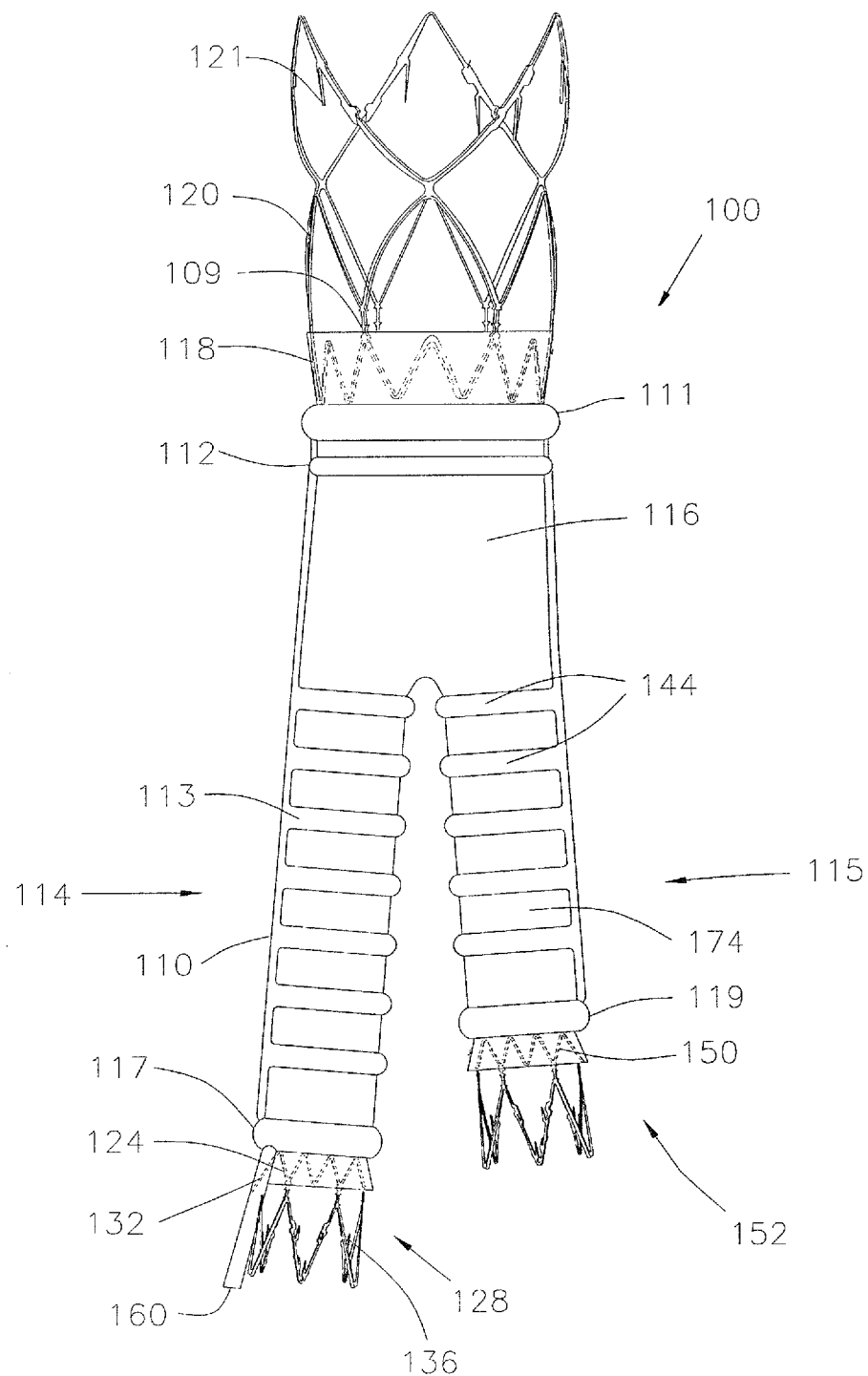
FIG. 7 shows a bifurcated endovascular graft according to embodiments of the present invention.

FIG. 7 illustrates another embodiment of the invention in the form of a bifurcated endovascular graft 100. A bifurcated device such as endovascular graft 100 may be utilized to repair a diseased lumen at or near a bifurcation within the vessel, such as, for example, in the case of an abdominal aortic aneurysm in which the aneurysm to be treated may extend into the anatomical bifurcation or even into one or both of the iliac arteries distal to the bifurcation. In the following discussion, the various features of the graft embodiments previously discussed may be used as necessary in the bifurcated graft 100 embodiment unless specifically mentioned otherwise.

Graft 100 comprises a first bifurcated portion 114, a second bifurcated portion 115 and main body portion 116. The size and angular orientation of the bifurcated portions 114 and 115, respectively, may vary—even between portion 114 and 115—to accommodate graft delivery system requirements and various clinical demands. For instance, each bifurcated portion or leg is shown in FIG. 7 to have a different length, but this is not necessary. First and second bifurcated portions 114 and 115 are generally configured to have an outer inflated diameter that is compatible with the inner diameter of a patient's iliac arteries. First and second bifurcated portions 114 and 115 may also be formed in a curved shape to better accommodate curved and even tortuous anatomies in some applications.

Together, main body portion 116 and first and second bifurcated portions 114, 115 form a continuous bifurcated lumen, similar to lumens 22 and 73, which is configured to confine a flow of fluid therethrough. And although not shown in FIG. 7, graft 100 does not have to have a second bifurcated portion 115, in which case the bifurcated lumen is formed between main body portion 116 and first bifurcated portion 114.

First and second bifurcated portions 114 and 115 each comprises a network of inflatable cuffs and channels as discussed with respect to the FIG. 2 embodiment, including inflatable channel 113. Channel 113 comprises one or more optional inflatable longitudinal channels 110 in fluid communication with one or more approximately parallel inflatable circumferential channels 144, all of which are in fluid communication with optional distal inflatable cuffs 117 and 119.

As with the embodiments previously discussed, the number of inflatable circumferential channels 144 may vary with the specific configuration of the graft as adapted to a given indication. Generally, however, the number of inflatable circumferential channels 144 per bifurcated portion may range from 1 to about 30, preferably about 10 to about 20. Similarly, the dimensions, spacing, angular orientation, etc. of circumferential inflatable channels 144 may vary as well.

For instance, the distance between and width of each circumferential inflatable channel 144 may vary along the length of the graft or may be constant. The pitch or inter-ring distance may range from about 2 to about 20 mm; specifically, it may range from about 3 to about 10 mm. Circumferential inflatable channels 144 are each typically between about 2 and about 4 mm wide, but may be from about 1 to about 8 mm wide. Each longitudinal channel 110 is typically from about 2 to about 4 mm wide, but may vary, together or independently, to be from about 1 to about 8 mm wide.

In the embodiment of FIG. 7, channel 113 forms a continuous cuff and channel network extending from first bifurcated portion 114 to main body portion 116 to second bifurcated portion 115. Accordingly, inflatable channel 113 fluidly connects into a network with proximal inflatable cuff 111, secondary proximal cuff 112, circumferential inflatable channels 144, optional distal inflatable cuff 117 and optional distal inflatable cuff 119. Note that longitudinal channels 110 extend proximally along main body portion 116 to be in fluid communication with cuffs 111 and 112.

In alternative embodiments of the graft of FIG. 7 as well as that of FIGS. 1 and 2, numerous other inflatable channel and cuff configurations are possible. The inflatable channel for instance may be disposed longitudinally, horizontally, in a helical fashion, or otherwise. One or more additional cuffs may be disposed on either or both bifurcated portions 114 and 115 as well as main body portion 116. In other embodiments, graft 100 may have compartmentalized channels and cuffs requiring multiple sites from which they are inflated and may use multiple inflation materials to optimize properties in each region.

Second bifurcated portion 115 may be of a similar construction to first bifurcated portion 114. In the FIG. 7 embodiment of graft 100, second bifurcated portion 115 is of a unitary, continuous construction with first bifurcated portion 114 and main body portion 116. Alternatively, first and second bifurcated portion 114 and 115 respectively may be singly or jointly formed separately from a main body portion and may be joined to the main body portion before deployment in the body passageway or in vivo after such deployment.

First and second bifurcated portions 114 and 115 may be generally cylindrical in shape when deployed, and will generally conform to the shape of a vessel interior within which they are deployed. Their length as measured from main body portion 116 may range from about 1 to about 10 cm or more. The nominal inflated outside diameter of the distal ends of the first and second bifurcated portions 114 and 115 at cuffs 117 and 119 may range from about 2 to about 30 mm, preferably from about 5 to about 20 mm.

Main body portion 116 comprises a proximal inflatable cuff 111 and an optional secondary proximal inflatable cuff 112 in fluid communication with one or more inflatable longitudinal channels 110. As with other embodiments, proximal cuff 111 serves primarily to seal graft 100 firmly against a lumen wall. Secondary proximal inflatable cuff 112 has been found to confer additional kink resistance on graft 100, particularly in those clinical applications in which the vessel in which the graft is deployed is highly angled or tortuous. The nominal inflated outside diameter of secondary proximal inflatable cuff 112 may range from about 10 to about 45 mm, preferably from about 15 to about 30 mm, while the nominal inflated outside diameter of proximal cuff 111 may range from about 10 to about 45 mm, preferably from about 16 to about 32 mm. Main body portion 116 may range in length from about 2 to about 10 cm; preferably from about 4 to about 8 cm.

Endovascular graft 100 further comprises a proximal connector member 118, proximal stent 120, and proximal neck portion 146 all of which may be similar to those components discussed above in reference to FIGS. 2-6. Coupling members (not shown) may join proximal stent 120 and proximal connector member 118 as discussed with respect to the embodiments of FIGS. 1-6. Proximal connector members and proximal stents as discussed in conjunction with the FIG. 1 embodiment are also possible for use in bifurcated graft 100.

In bifurcated embodiments of grafts having features of the invention which also have a biased proximal end that forms an inlet axis angle, the direction of the bias or angulation can be important with regard to achieving a proper fit between the graft and the morphology of the deployment site. Generally, the angular bias of the proximal end of the graft, proximal neck portion or proximal anchor can be in any direction. Preferably, the angular bias is in a direction and of a magnitude consistent with the mean angulation of the type of lesion (e.g. abdominal aortic aneurysm) intended for treatment with the graft.

As with proximal stent 70 of the embodiments shown in FIGS. 2 and 4-6, proximal stent 120 comprises barbs 121 which are oriented in a distal direction for reliable anchoring against the direction of pulsatile forces in vivo when the device is implanted in the abdominal aorta, for instance, to treat an abdominal aortic aneurysm.

One or both bifurcated portions 114 and/or 115 may further comprise a distal connector member 124 and/or 150, a distal stent 128, and a distal neck portion 154. The embodiment of FIG. 7 has distal connector member 124 and distal stent 128 disposed at the distal ends of each of first and second bifurcated portions 114 and 115, respectively. Distal connector member 124 and distal stent 128 are shown in greater detail in FIGS. 8 and 9.

Figure 8:
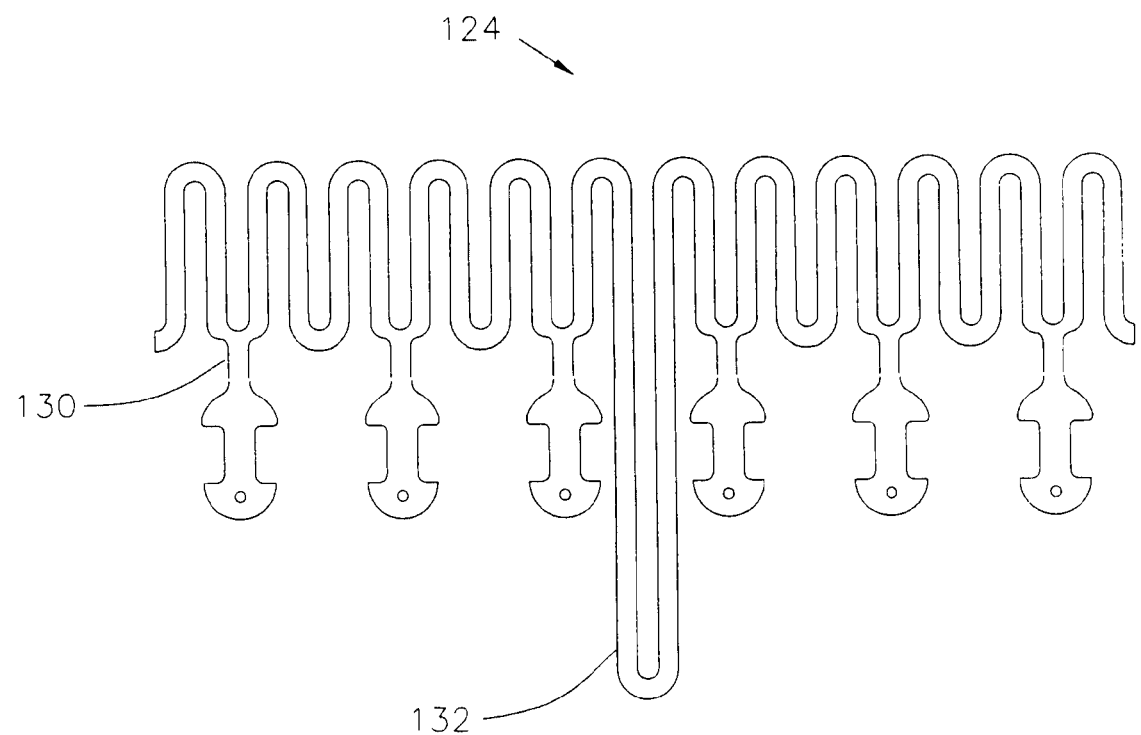
FIG. 8 shows a flat pattern of yet another component of the endovascular graft of FIG. 2.

As discussed with respect to the FIG. 2 embodiment and as shown more clearly in FIG. 8, distal connector member 124 disposed at or near first bifurcated portion 114 comprises distal connector member connector elements 130 and an optional fill-port bridge 132. Fill-port bridge 132 serves to prevent interference by distal connector member 124 with the manufacture of graft 100 and with the injection of an inflation medium, while preserving the continuous ring structure of distal connector member 124.

Inflatable channels 113 (and other inflatable members of the invention) are in communication with a fill port 160 through distal inflatable cuff 117. Fill port 160 may be disposed alternatively on second bifurcated portion 115 or graft main body portion 116, and more than one fill port may be used. Fill port 160 is configured to accept a pressurized source of fluid (gas and/or liquid), particles, gel or combination thereof as previously discussed.

Figure 9:
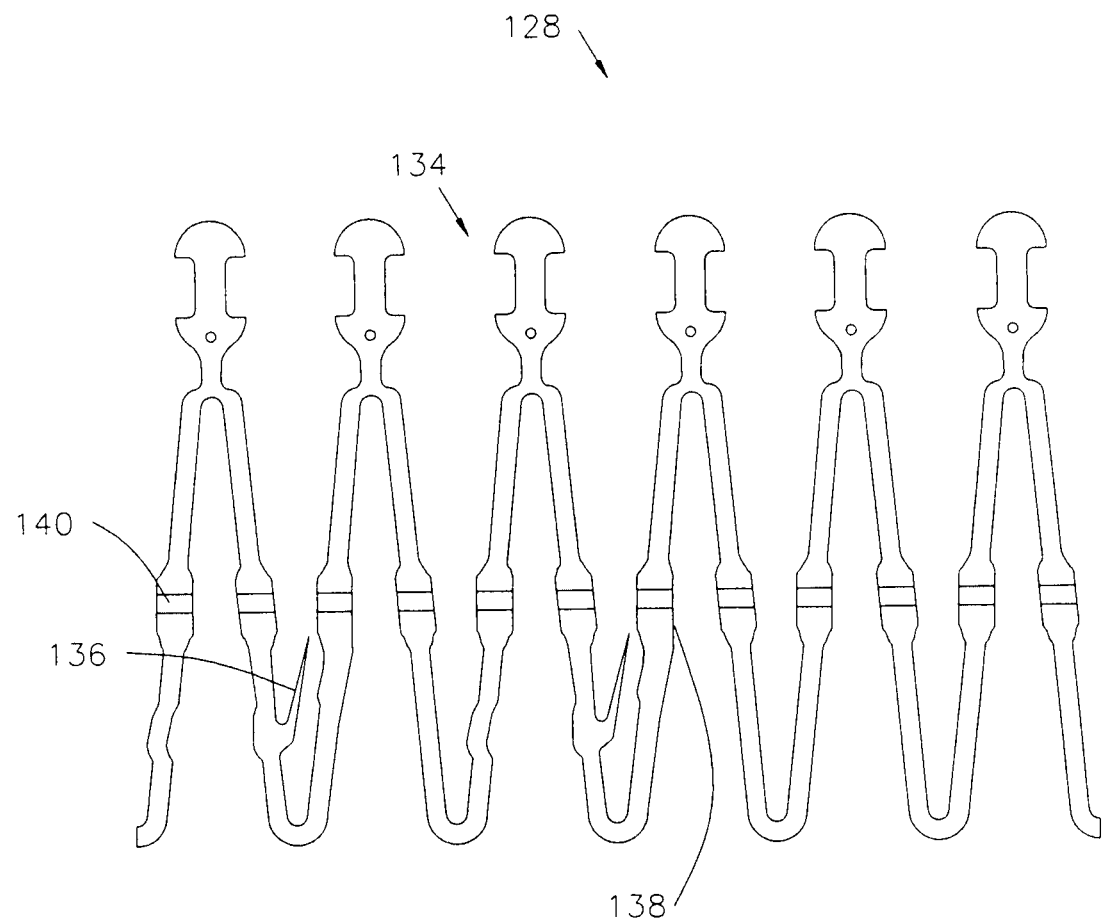
FIG. 9 shows a flat pattern of another component of the endovascular graft of FIG. 2.

As discussed with respect to the FIG. 2 embodiment, FIG. 9 details a flat pattern of distal stent 128, which includes distal stent connector elements 134. Distal connector member connector elements 130 are configured to be coupled with distal stent connector elements 134 via coupling members (not shown) similar to those discussed with respect to the FIGS. 1-6 embodiments. Distal stent 128 comprises one or more optional distal stent barbs 136, one or more optional distal stent barb tuck pads 138 and one or more optional distal stent barb tuck slots 140, each of which functions in a similar fashion to the corresponding features of embodiments discussed above. Distal stent barbs 136 are oriented proximally, opposite the direction of orientation of barbs 121, to accommodate the environment often found in the iliac arteries that can cause the bifurcated portions 114 and 115 to migrate proximally in vivo. Note that only two distal stent barbs 136 are shown in FIG. 9 for the purposes of clarity of illustration despite a larger number being depicted in the FIG. 7 embodiment of the present invention. It is understood that all embodiments of the present invention includes proximal and distal stents each of which may optionally comprise one, two, or any number of barbs.

The optional distal connector member 150, disposed in the FIG. 7 embodiment at or near distal end 152 of second bifurcated portion 115, has a structure similar to that of first bifurcated portion 114, with the exception of the absence of fill-port bridge 132. Other embodiments of the invention include bifurcated grafts in which the distal connector member 150 includes a fill-port bridge.

FIGS. 10-13 illustrate additional features of the present invention that may be used in any of the various stents and connector rings of the present invention, in any combination.

Figure 10:
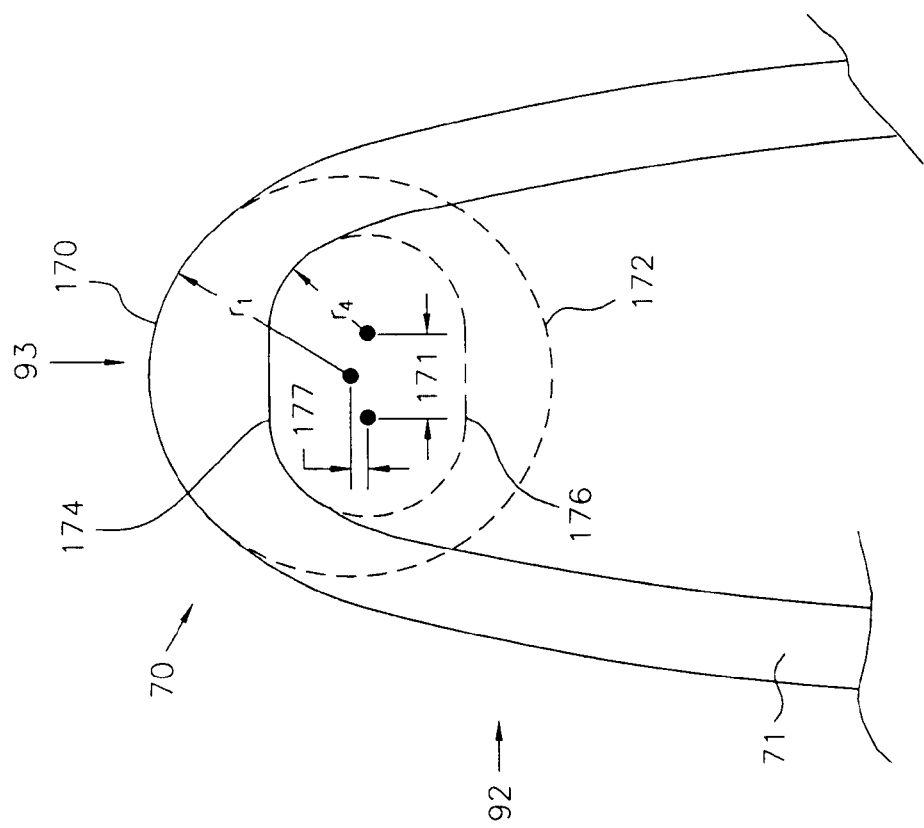
FIG. 10 shows detail of a stent apex detail that comprises offset circular and elliptical radii.

Turning to FIG. 10, a simplified detail of a proximal apex 93 of the second or three-crown region 92 of proximal stent 70 is shown. An outer surface 170 of apex 93 takes on a circular radius of curvature as defined by circle 172 having a radius $r_1$. An inner surface 174 of the stent strut apex 93 takes on an elliptical shape as shown by ellipse 176. In the configuration of FIG. 10, circle 172 and ellipse 176 offset as shown by reference numeral 177; however, they may share a common center. Radius $r_4$ shown at one of the foci of ellipse 176; the foci are shown as separated by a distance 171 in FIG. 10.

We have found that for the NiTi stents used in the present invention, such a configuration provides for a more diffuse strain distribution in the stent and reduces the peak strains experienced during assembly and in vivo, while also allowing for a smaller delivery profile as compared to other configurations, particularly in the proximal apex 93 of the second or three-crown region 92 of proximal stent 70. However, the stent apex configuration of FIG. 10 may be used in any other stent or connector member apex described herein, and may be used for components comprising material other than NiTi.

In the example of FIG. 10 wherein proximal apex 93 of the second or three-crown region 92, we have found that for NiTi components radius $r_1$ of between about 0.030 and about 0.070 inch; specifically about 0.050 inch is useful, while an offset 171 of between about zero and about 0.050 inch; specifically about 0.0025 inch, is effective. A radius $r_4$ of between about 0.010 and about 0.030 inch; specifically about 0.020 inch, is useful as well.

Figure 11:
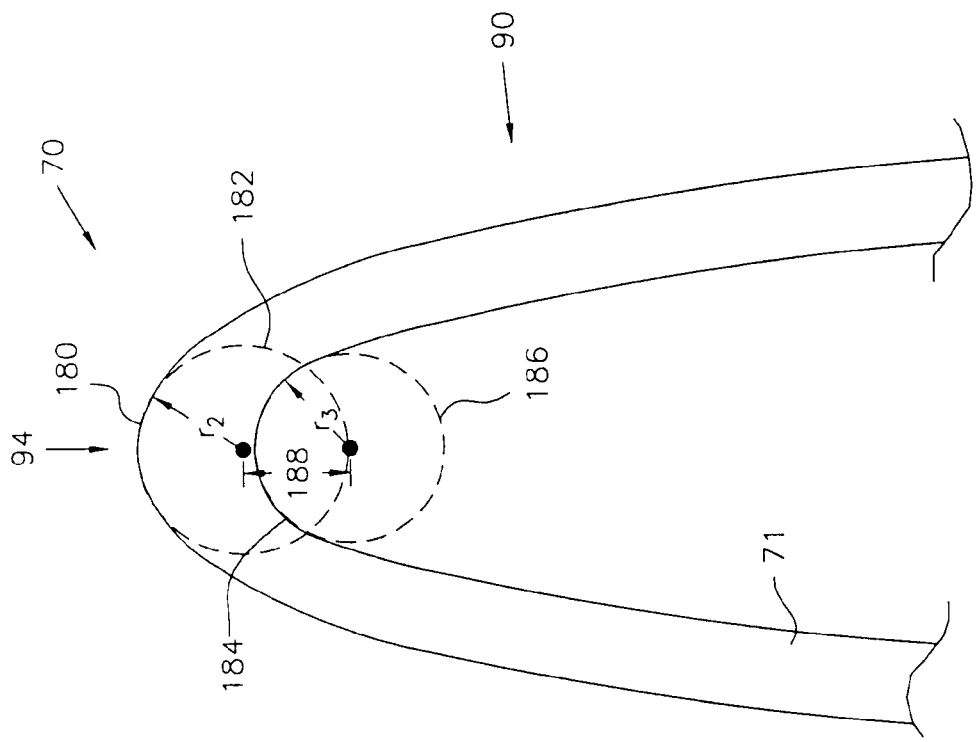
FIG. 11 shows detail of a stent apex detail that comprises offset circular radii.

FIG. 11 details an alternative offset circular apex configuration. Here, a simplified detail of proximal apex 94 in the first or six-crown region 90 of proximal stent 70 is shown (without a transition region to the second or three-crown stent region as seen in, e.g., FIG. 4 for clarity of illustration). An outer surface 180 of apex 94 takes on a circular radius of curvature as defined by circle 182 having a radius $r_2$. An inner surface 184 of apex 94 takes on a circular radius of curvature defined by circle 186 having a radius $r_3$. Radius $r_2$ may be equal to or greater than radius $r_3$ and be within the scope of the present invention. The centers of circles 182 and 186 are offset from each other as indicated by reference numeral 188 in FIG. 11. This offset 188 may be equal to, greater than, or less than the width of the strut 71 in the region of apex 94.

We have found that when NiTi is used for the stents and connector members of the present invention, such a configuration is effective in distributing the peak strains experienced in the stent from the apex 94 to stent strut 71 as compared to other configurations, particularly in the proximal apex 94 of the first or six-crown region 90 of proximal stent 70. However, the offset circular apex configuration of FIG. 11 may be used in any other stent or connector member apex described herein, and may be used for components comprising material other than NiTi.

When used in the proximal apex 94 of the proximal stent first or six-crown region 90, we have found offset values ranging from about zero to about 0.030 inch; particular about 0.020 inch, to be effective in NiTi stents having expanded, or deployed diameters ranging from about 16 to about 26 mm. We have also found effective a configuration in which radius $r_2$ ranges from about 0.020 to about 0.040 inch; more particularly about 0.035 inch, and in which radius $r_3$ ranges from about 0.005 to about 0.020 inch; in particular about 0.010 inch.

Optional taper or tapers may be incorporated into the struts 41 and 71 of the various stent embodiments of the present invention as well as the various proximal and distal connector members. In general, incorporating one or more tapers into the struts on both proximal and distal stents provide greater space in the tapered region to accommodate alternative features such as barbs and tuck pads. It allows for a smaller deployment profile when the component is in a radially collapsed delivery configuration. We have found that when configuring the various stents and connector elements of the present invention into this reduced diameter delivery profile, the stents experience a large degree of bending strain that is often poorly or locally distributed. Tapering certain stent struts in particular locations helps to distribute this strain more evenly throughout the stent or connector member and to manage the peak strains. The examples of FIGS. 12 and 13 are now introduced and discussed below.

In FIG. 12, a simplified section of the second or three-crown region 92 of proximal stent 70 is depicted in which the stent struts 71 taper from a maximum width 190 (which may or may not equal a width of strut 71 in region of apex 93) to a minimum width 192. The optional taper, expressed as the ratio of the maximum width 190 to the minimum width 192, may vary widely depending on the particular region of the stent or connector member, the material used, and other factors. Taper ratios ranging from 1 to about 10 or greater are within the scope of the present invention. It is also within the scope of the present invention for the stent struts 71 to exhibit no taper.

For example, in a proximal stent 70 three-crown region 92 made from NiTi, we have found effective a maximum strut width 190 ranging from about 0.016 to about 0.032 inch; particularly from about 0.022 and about 0.028 inch, and a minimum strut width 192 of between about 0.010 and about 0.026 inch; particularly from about 0.012 and about 0.022 inch. The optional tapered strut feature described herein and shown in FIG. 12 may be used in any other stent or connector member described herein, and may be used for components comprising material other than NiTi.

Figure 13:
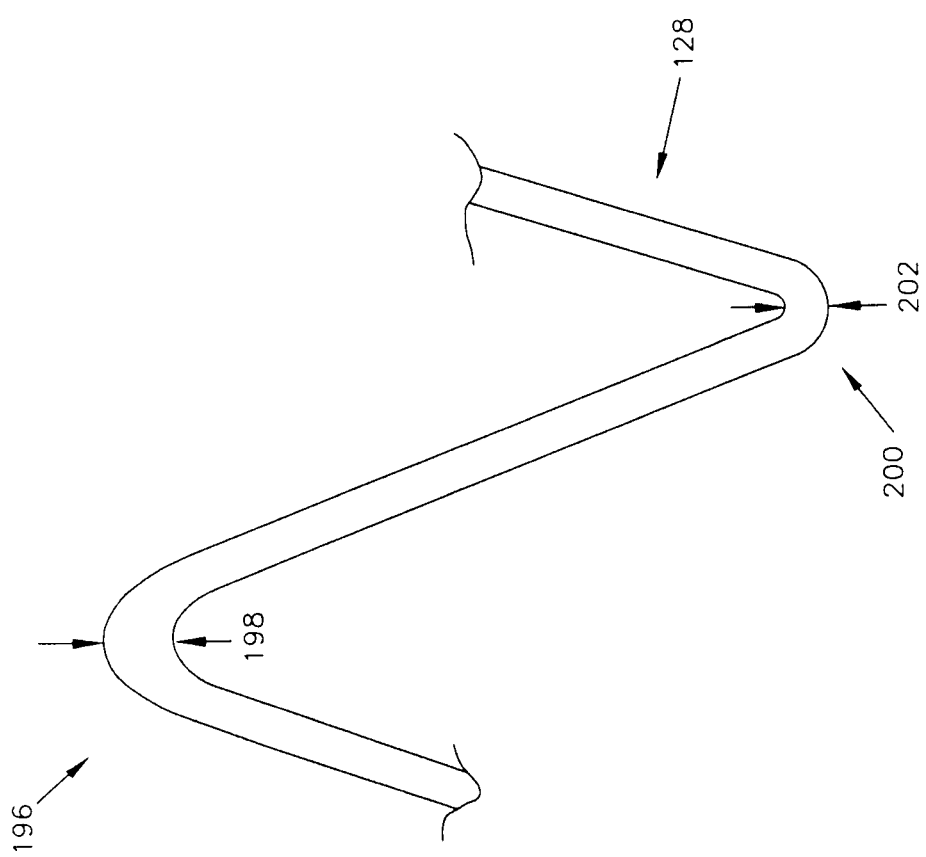
FIG. 13 shows detail of a stent section comprising another configuration for a tapered strut section.

Turning now to FIG. 13, a simplified section of distal stent 128 is shown as an example of optional tapering that results in asymmetric crowns. In this example, distal stent 128 comprises a distal apex or crown 196 exhibiting a width 198 and a proximal apex or crown (with connector element 134 removed for clarity of illustration) 200 exhibiting a smaller width 202. It is within the scope of the present invention for width 198 and width 202 to be equal.

We have found that, especially for the distal stents of the present invention, an asymmetric crown in which the distal apex 200 has a smaller strut width than that of the proximal apex 196 results in a difference in the expansion force exerted between each of the proximal and distal apices. When deployed in a diseased lumen or vessel, the proximal apices of such a stent having this configuration will tend to exert a smaller expansion force near the graft seal zone, reducing the potential for such a stent to cause trauma to tissue in the seal zone near the cuffs (where weaker, more diseased tissue tends to reside). Such a configuration also facilitates a consistent, safe and predictable deployment when the component moves from a reduced diameter delivery profile to an expanded treatment profile. Finally, such a taper reduces the flare exhibited by the distal apex 200; this in turn provides for a smaller distal stent delivery profile when the distal stent is in a reduced-diameter configuration. Taper ratios (defined in the same manner above as the ratio between width 198 and width 202) ranging from 1 to about 10 or higher are within the scope of the present invention.

For distal stent 128 comprising NiTi, we have found that a width 202 ranging from about 0.010 to about 0.026 inch; specifically from about 0.012 and about 0.024 inch to be useful, and we have found a width 198 ranging from about 0.016 to about 0.032 inch; specifically from about 0.017 to about 0.028 inch to be useful.

Of course, the various types of offset radii and combinations of elliptical and circular apex radii may be used to effect these tapers and ratios so to further cause the desired behavior during assembly into a reduced-diameter delivery configuration, effective delivery and performance in vivo.

Useful inflation media generally include those formed by the mixing of multiple components and that have a cure time ranging from a few minutes to tens of minutes, preferably from about three and about twenty minutes. Such a material should be biocompatible, exhibit long-term stability (preferably on the order of at least ten years in vivo), pose as little an embolic risk as possible, and exhibit adequate mechanical properties, both pre- and post-cure, suitable for service in the graft of the present invention in vivo. For instance, such a material should have a relatively low viscosity before solidification or curing to facilitate the graft cuff and channel fill process. A desirable post-cure elastic modulus of such an inflation medium is from about 50 to about 400 psi—balancing the need for the filled graft to form an adequate seal in vivo while maintaining clinically relevant kink resistance of the graft. The inflation media ideally should be radiopaque, both acute and chronic, although this is not absolutely necessary.

Details of compositions suitable for use as an inflation medium in the present invention are described in greater detail in U.S. patent application Ser. No. 09/496,231 to Hubbell et al., filed Feb. 1, 2000 and entitled "Biomaterials Formed by Nucleophilic Addition Reaction to Conjugated Unsaturated Groups", now U.S. Pat. No. 7,744,912, and U.S. patent application Ser. No. 09/586,937 to Hubbell et al., filed Jun. 2, 2000 and entitled "Conjugate Addition Reactions for the Controlled Delivery of Pharmaceutically Active Compounds", now U.S. Pat. No. 6,958,212. The entirety of each of these patent applications is hereby incorporated herein by reference.

We have found one particular three-component medium formed by the Michael addition process to be particularly useful in serving as an inflation medium for the present invention. This medium comprises:

polyethylene glycol diacrylate (PEGDA), present in a proportion ranging from about 50 to about 55 weight percent; specifically in a proportion of about 52 weight percent, pentaerthyritol tetra 3(mercaptopropionate) (QT) present in a proportion ranging from about 22 to about 27 weight percent; specifically in a proportion of about 24 weight percent, and glycylglycine buffer present in a proportion ranging from about 22 to about 27 weight percent; specifically in a proportion of about 24 weight percent.

Variations of these components and other formulations as described in U.S. patent application Ser. No. 09/496,231, now U.S. Pat. No. 7,744,912, and Ser. No. 09/586,937, now U.S. Pat. No. 6,958,212, both to Hubbell et al., may be used as appropriate. In addition, we have found PEGDA having a molecular weight ranging from about 350 to about 850 to be useful; PEGDA having a molecular weight ranging from about 440 to about 560 are particularly useful.

Radiopaque materials as previously discussed may be added to this 3-component system. We have found that adding radiopacifiers such as barium sulfate, tantalum powder, and soluble materials such as iodine compounds to the glycylglycine buffer is useful.

We have found that triethanolamine in phosphate-buffered saline may be used as an alternative to glycylglycine buffer as the third component described above to form an alternative curable gel suitable for use in embodiments of the present invention.

An alternative to these three-component systems is a gel made via polymer precipitation from biocompatible solvents. Examples of such suitable polymers include ethylene vinyl alcohol and cellulose acetate. Examples of such suitable biocompatible solvents include dimethylsulfoxide (DMSO), n-methyl pyrrolidone (NMP) and others. Such polymers and solvents may be used in various combinations as appropriate.

Alternatively, various siloxanes may be used as inflation gels. Examples include hydrophilic siloxanes and polyvinyl siloxanes (such as STAR-VPS from Danville Materials of San Ramon, Calif. and various silicone products such as those manufactured by NuSil, Inc. of Santa Barbara, Calif.).

Other gel systems useful as an inflation medium or material for the present invention include phase change systems that gel upon heating or cooling from their initial liquid or thixotropic state. For example, materials such as n-isopropyl-polyacrylimide (NIPAM), BASF F-127 pluronic polyoxyamer, and polyethylene glycol (PEG) chemistries having molecular weights ranging between about 500 and about 1,200 are suitable.

Effective gels may also comprise thixotropic materials that undergo sufficient shear-thinning so that they may be readily injected through a conduit such as a delivery catheter but yet still are able to become substantially gel-like at zero or low shear rates when present in the various channels and cuffs of the present invention.

In the case of the three-component PEDGA-QT-glycylglycine formulation described above, a careful preparation and delivery protocol should be followed to ensure proper mixing, delivery, and ultimately clinical efficacy. Each of the three components is typically packaged separately in sterile containers such as syringes until the appropriate time for deploying the endovascular graft. The QT and buffer (typically glycylglycine) are first continuously and thoroughly mixed, typically between their respective syringes for approximately two minutes. PEGDA is then mixed thoroughly with the resulting two-component mixture for approximately three minutes. This resulting three-component mixture is then ready for introduction into the graft body section as it will cure into a gel having the desired properties within the next several minutes. Cure times may be tailored by adjusting the formulations, mixing protocol, and other variables according to the requirements of the clinical setting. Details of suitable delivery protocols for these materials are discussed in U.S. patent application Ser. No. 09/917,371 to Chobotov et al., now U.S. Pat. No. 6,761,733.

We have found the post-cure mechanical properties of these gels to be highly tailorable without significant changes to the formulation. For instance, these gels may exhibit moduli of elasticity ranging from tens of psi to several hundred psi; the formulation described above exhibits moduli ranging from about 175 to about 250 psi with an elongation to failure ranging from about 30 to about 50 percent.

Notably, we have found it helpful to add an inert biocompatible material to the inflation material. In particular, we have found that adding a fluid such as saline to the PEGDA-QT-glycylglycine formulation (typically after it has been mixed but before significant curing takes place) lowers the viscosity of the formulation and results in greater ease when injecting the formulation into the graft body section network of inflatable cuffs and channels without sacrificing the desired physical, chemical, and mechanical properties of the formulation or its clinical efficacy. In the appropriate volume percentages, adding materials such as saline may also reduce the potential for the inflation material such as PEGDA-QT-glycylglycine to pose an embolic risk in case of spillage or leakage. Saline concentrations as a volume percentage of the final saline/three-component formulation combination may range from zero to as high as sixty percent or more; particularly suitable are saline concentrations ranging from about twenty to about forty percent. We have found a saline volume concentration of about thirty percent to be most suitable. Alternatives to saline may include biocompatible liquids, including buffers such as glycylglycine.

In more general terms, it is desirable to use an inflation medium in which each of its components is biocompatible and soluble in blood. A biocompatible inflation medium is desirable so to manage any toxicity risk in the case the inflation medium were inadvertently released into the patient's vasculature. A soluble inflation medium is desirable so to manage any embolism risk if released into the vasculature. Such an inflation medium should not disperse nor gel or solidify if spilled into flowing blood before curing. In the event of a spill, the normal blood flow would then rapidly disperse the components and their concentration would fall below the level required for crosslinking and formation of a solid. These components would then be eliminated by the body through standard pathways without posing an embolic risk to the patient. Among the many possibilities of an inflation medium example in which all of the components are soluble in blood is the combination polyethylene glycol diacrylate, a thiolated polyethyleneamine, and a buffer.

As previously discussed, more than one type of inflation medium, or more than one variant of a single type of inflation medium may be used in a single graft to optimize the graft properties in the region in which it is disposed.

For example, in the proximal and distal cuffs of the various embodiments of the present invention, the inflation material serves as a conformable sealing medium to provide a seal against the lumen wall. Desirable mechanical characteristics for the inflation medium in the proximal and distal cuffs would therefore include a low shear strength so to enable the cuff to deform around any luminal irregularities (such as calcified plaque asperities) and to conform to the luminal profile, as well as a high volumetric compressibility to allow the fill material to expand the cuffs as needed to accommodate any late lumen dilatation and maintain a seal.

In the channel or channels, by contrast, the inflation medium serves primarily to provide structural support to the lumen within which the graft is placed and kink resistance to the graft. Desirable mechanical characteristics for the inflation medium in the channel or channels therefore includes a high shear strength, to prevent inelastic deformation of a channel or channel segment due to external compression forces from the vessel or lumen (due, for example, to neointimal hyperproliferation) and low volumetric compressibility to provide stable support for adjacent channels or channel segments that may be in compressive contact with each other, thereby providing kink resistance to the graft.

Given these contrasting requirements, it may be useful to have different inflation materials fill different portions of the graft, such as one inflation medium for the proximal and distal cuffs and a second in the channel or channels.

In the various embodiments of the present invention, it is desirable that the inflation medium be visible through the use of techniques such as fluoroscopy during the time of deployment in which the graft cuffs and channels are being filled with the inflation medium. Such visibility allows the clinician to verify that the cuffs and channels are filling correctly and to adjust the filling procedure if they are not. It also provides an opportunity to detect any leakage or otherwise undesirable flow of inflation material out of the graft so that injection may be stopped, thereby minimizing the amount of leaked inflation material.

After the graft has been deployed into a patient, it is desirable that the graft be visible through the use of follow-up imaging techniques such as computed tomography (CT) and the like. However, the inflation material at this point in time is ideally not so radiopaque that it produces a dense CT image as such an image could potentially mask clinically significant endoleaks that would be visualized by opacifying the blood with a contrast agent.

Balancing these two objectives is difficult, however, since CT techniques are much more sensitive in detecting small amounts of radiopaque matter than are fluoroscopy techniques. One solution is to use an inflation medium that becomes less radiopaque over time, such as for example by using a blend of radiopaque materials in which one or more will diffuse out of the inflation medium over time, thereby reducing the inflation medium's radiopacity. For instance, a blend of a soluble contrast agent such as an iodinated aqueous solution and an insoluble contrast agent such as barium sulfate may serve this purpose. The soluble contrast agent will diffuse through the graft body section pores some time after the graft has been implanted, resulting in a progressive decrease in radiopacity of the inflation material over time. A fill material radiopacifier prepared from a combination of about two percent barium sulfate (by weight) and about 20 percent iodinated contrast solution (by weight) is useful in this capacity.

FIGS. 14-21 and 23 illustrate an embodiment of delivery system 1010 for delivering a variety of expandable intracorporeal devices; specifically, an expandable endovascular graft 1011. One such expandable endovascular graft 1011 useful for delivery and deployment at a desired site within a patient is disclosed in co-pending U.S. patent application Ser. No. 09/133,978 (now U.S. Pat. No. 6,395,019), filed Aug. 27, 1998, by M. Chobotov, which is hereby incorporated by reference in its entirety.

Figure 14:
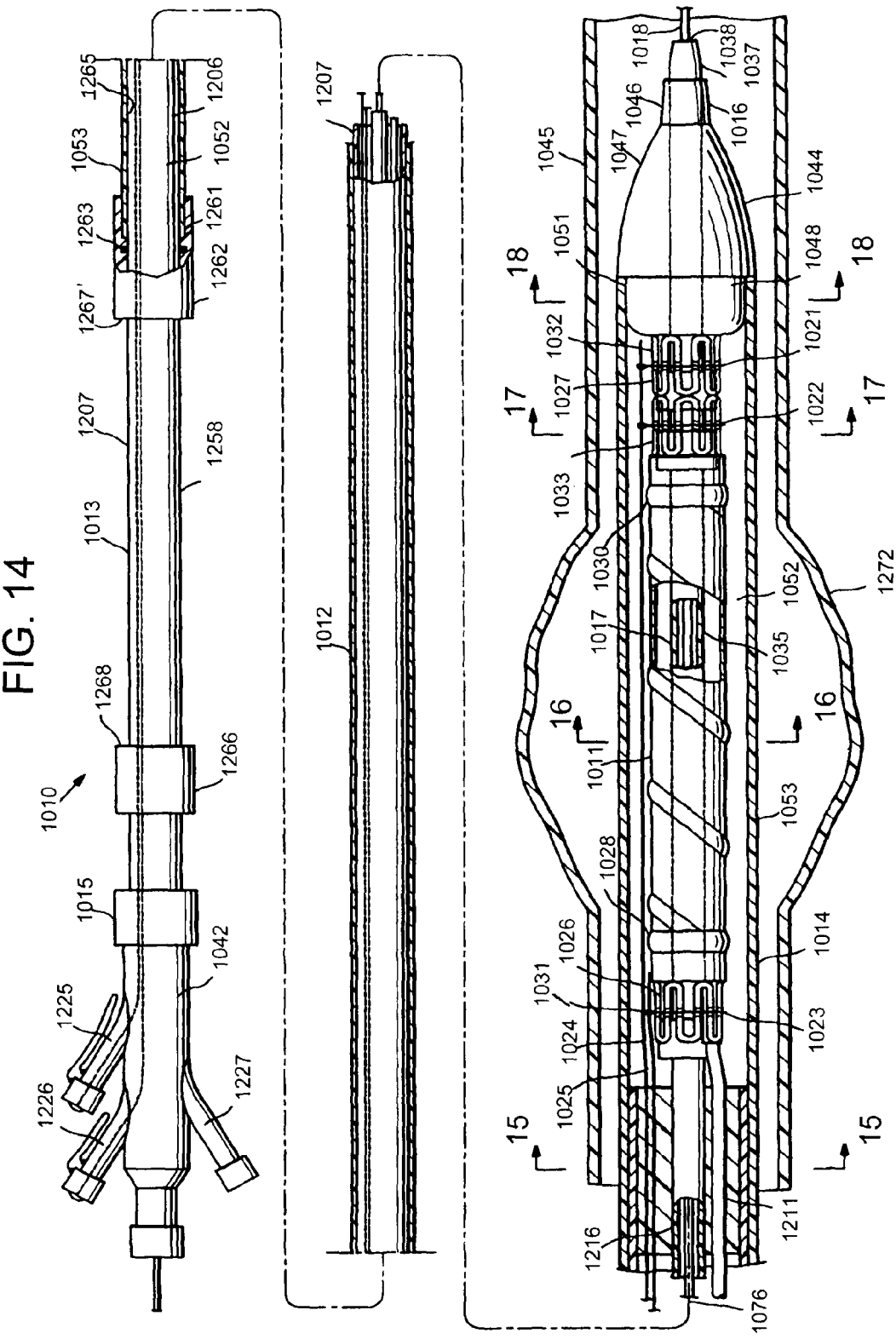
FIG. 14 is an elevational view in partial longitudinal section illustrating an embodiment of a delivery system for an expandable intracorporeal device having features of the invention.

Delivery system 1010 in FIG. 14 has an elongate shaft 1012 with a proximal section 1013, a distal section 1014, a proximal end 1015 and a distal end 1016. The distal section 1014 has an elongate belt support member in the form of a guidewire tube 1017 disposed adjacent a portion of the expandable endovascular graft 1011. A guidewire 1018 is disposed within guidewire tube 1017. A plurality of belts 1021, 1022, and 1023 are secured to the guidewire tube 1017 and are circumferentially disposed about portions of the endovascular graft 1011. FIG. 14 shows the belts in a configuration that constrains the endovascular graft 1011. First and second release members 1024 and 1025 releasably secure belts 1021, 1022, and 1023 in a constraining configuration as shown.

The endovascular graft 1011 has a proximal end 1026, a distal end 1027, a proximal inflatable cuff 1028, a distal inflatable cuff 1030, a proximal self-expanding member 1031, a first distal self-expanding member 1032 and a second distal self-expanding member 1033. As defined herein, the proximal end of the elongate shaft is the end 1015 proximal to an operator of the delivery system during use. The distal end of the elongate shaft is the end 1016 that enters and extends into the patient's body. The proximal and distal directions for the delivery system 1010 and endovascular graft 1011 loaded within the delivery system 1010 as used herein are the same. This convention is used throughout the specification for the purposes of clarity, although other conventions are commonly used. For example, another useful convention defines the proximal end of an endo vascular graft as that end of the graft that is proximal to the source of blood flow going into the graft. Such a convention is used in the previously discussed co-pending patent application Ser. No. 09/133,978 (now U.S. Pat. No. 6,395,019), although that convention is not adopted herein.

Figure 15:
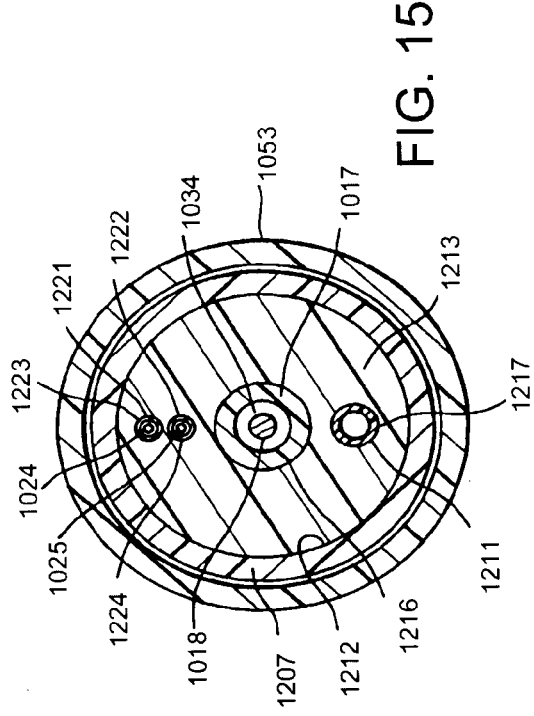
FIG. 15 is a transverse cross sectional view of the delivery system of FIG. 14 taken along lines 15-15 of FIG. 14.
Figure 21:
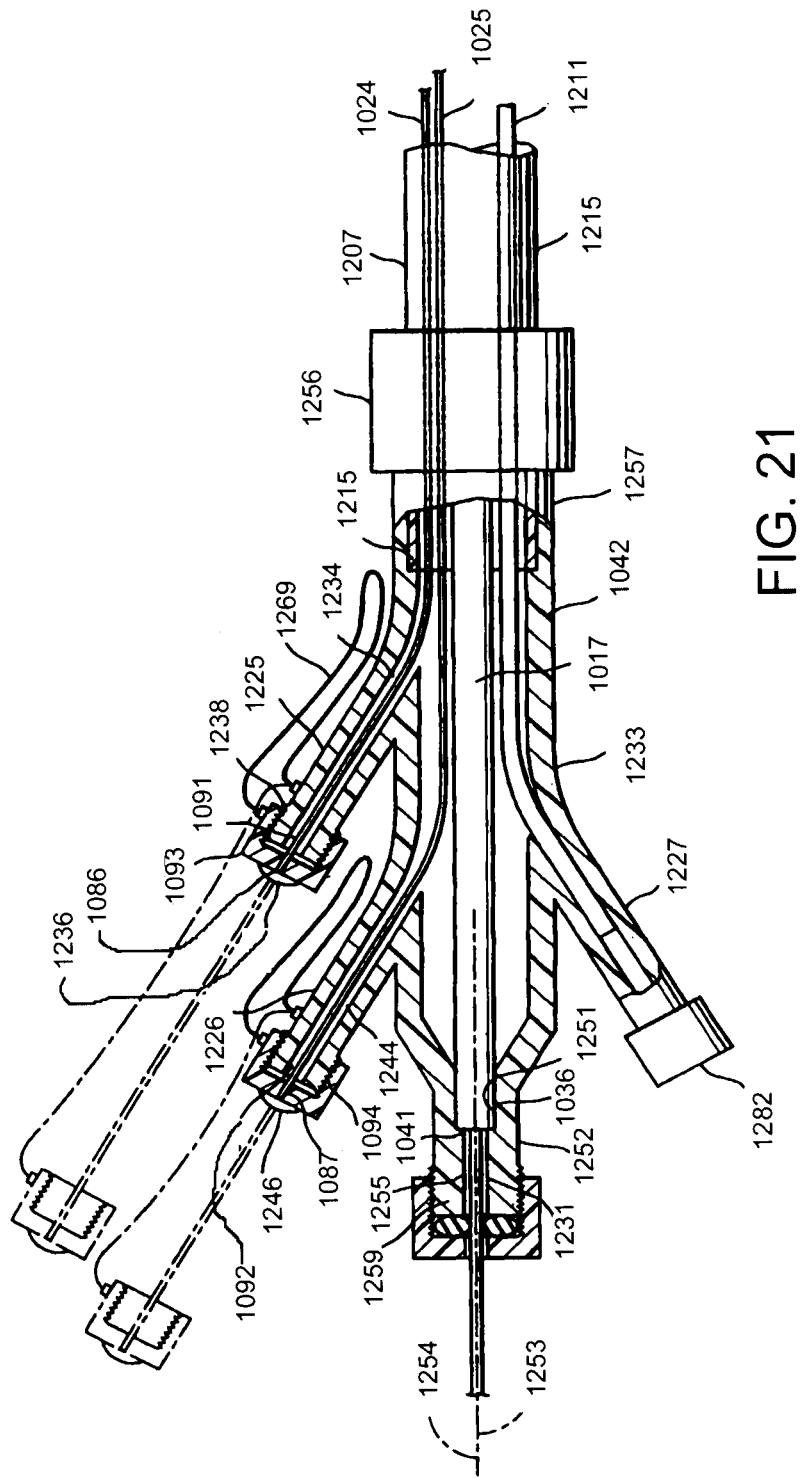
FIG. 21 is an elevational view in partial section of the proximal adapter shown in FIG. 14.
Figure 23:
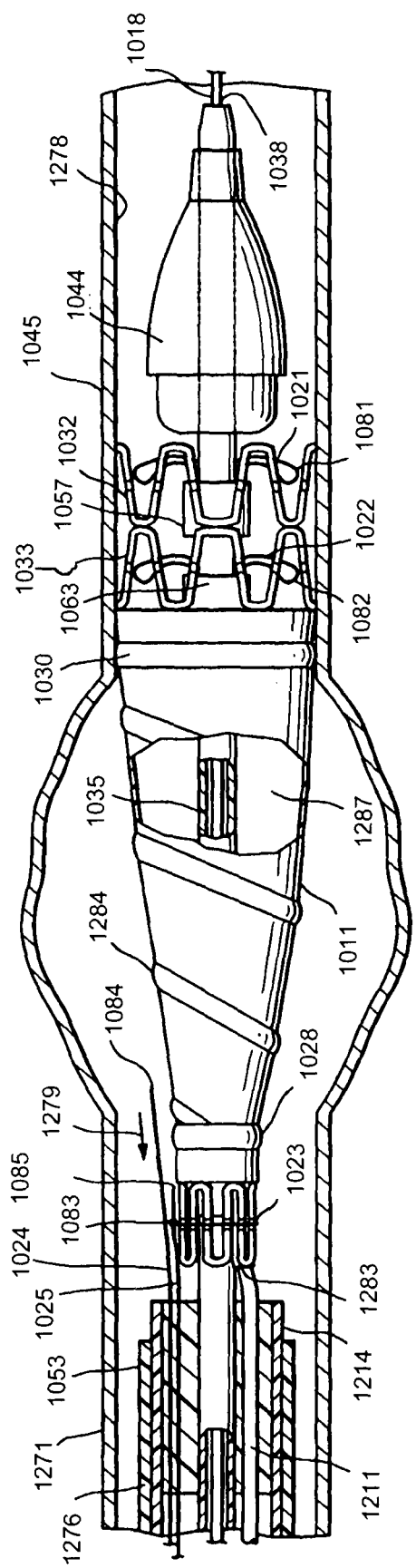
FIG. 23 is a diagrammatic view of a delivery system having features of the invention disposed within an artery of a patient with an expandable intracorporeal device being deployed within the artery.

The guidewire tube 1017 has an inner lumen 1034, as shown in FIG. 15, a distal section 1035, a proximal end 1036, as shown in FIG. 21, and a distal end 1037. The inner lumen 1034 of the guidewire tube 1017 terminates at the distal end 1037 with a distal guidewire tube port 1038, as shown in FIG. 23. As seen in FIG. 21, the proximal end 1036 of guidewire tube 1017 terminates in a port 1041 disposed in the proximal adapter 1042. The port 1041 is typically a tapered fitting such as a Luer lock fitting which facilitates the attachment of a hemostasis valve (not shown). The guidewire tube 1017 is a hollow tubular member that normally has an annular cross section, although oval cross-sectional profiles and others are also suitable.

Figure 18:
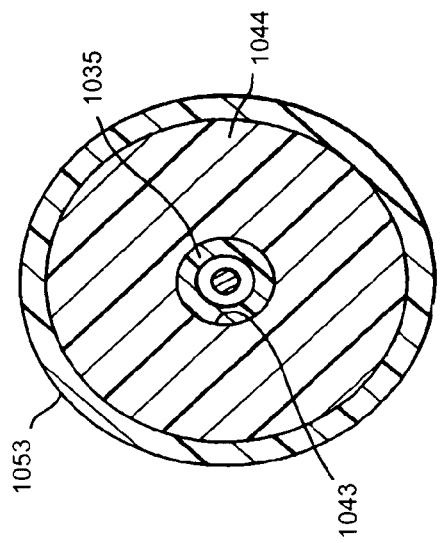
FIG. 18 is a transverse cross sectional view of the delivery system of FIG. 14 taken along lines 18-18 of FIG. 14.

A portion of the distal section 1035 of the guidewire tube 1017, shown in FIG. 14, is disposed within an inner lumen 1043 of a distal nose piece 1044, as shown in FIG. 18. Distal nose piece 1044 is configured in a streamlined bullet shape for easy passage within a patient lumen or vessel such as aorta 1045. Guidewire tube 1017 may be bonded to the inner lumen 1043 of the nose piece 1044, or it may be molded into the nose piece 1044 during manufacture. Referring to FIG. 14, the nose piece 1044 has a distal portion 1046, an intermediate portion 1047 and a proximal shoulder portion 1048 configured to slidingly engage the distal portion 1051 of an inner lumen 1052 of an outer tubular member 1053.

Referring to FIGS. 14, 19A, 19B and 20A, on the distal section 1035 of guidewire tube 1017, proximal to the proximal shoulder portion 1048 of nose piece 1044, a first distal belt 1021 is secured to the guidewire tube 1017. The first distal belt may be secured to the guidewire tube 1017 with any suitable adhesive such as cyanoacrylate, epoxy or the like. Both free ends 1055 and 1056 of the first distal belt 1021 are secured to the guidewire tube 1017. The guidewire tube 1017 may be made from a variety of suitable materials including polyethylene, teflon, polyimide and the like.

Referring to FIGS. 15-18, the inner lumen 1034 of the guidewire tube 1017 has an inside diameter that can accommodate a guidewire suitable for guiding a device such as delivery system 1010. The inner lumen 1034 of the guidewire tube 1017 may have an inside diameter of about 0.015 inch to about 0.045 inch; specifically, about 0.020 inch to about 0.040 inch. The outer diameter of the guidewire tube 1017 may range from about 0.020 inch to about 0.060 inch; specifically, about 0.025 inch to about 0.045 inch.

Referring again to FIGS. 19A, 19B and 20A, an optional first distal belt bushing 1057 is disposed about the guidewire tube 1017 so as to cover the portions of the free ends 1055 and 1056 of the first distal belt 1021 that are secured to the distal section 1035 of the guidewire tube 1017. This bushing 1057 may also serve to control the constrained configuration of the belted self-expanding members, and may include geometric features to engage or support the belted members. A similar configuration is present at a second distal belt 1022 which has free ends secured to the guidewire tube 1017 proximal to the first distal belt 1021. A second distal belt bushing 1063 is disposed about the guidewire tube 1017 so as to cover the portions of the free ends of the second distal belt 1022 that are secured to the guidewire tube 1017. A proximal belt 1023 has free ends secured to the guidewire tube 1017 proximal to the second distal belt 1022 and has an optional proximal belt bushing 1067, as shown in FIG. 19, configured similarly to the first and second distal belt bushings 1057 and 1063.

The belts 1021, 1022 and 1023 can be made from any high strength, resilient material that can accommodate the tensile requirements of the belt members and remain flexible after being set in a constraining configuration. Typically, belts 1021, 1022 and 1023 are made from solid ribbon or wire of a shape memory alloy such as nickel titanium or the like, although other metallic or polymeric materials are possible. Belts 1021, 1022 and 1023 may also be made of braided metal filaments or braided or solid filaments of high strength synthetic fibers such as Dacron®, Spectra or the like. An outside transverse cross section of the belts 1021, 1022 and 1023 may range from about 0.002 to about 0.012 inch, specifically, about 0.004 to about 0.007 inch. The cross sections of belts 1021, 1022 and 1023 may generally take on any shape, including rectangular (in the case of a ribbon), circular, elliptical, square, etc.

In general, we have found that a ratio of a cross sectional area of the belts to a cross sectional area of the release members, 1024 and 1025, of about 1:2 is useful to balance the relative strength and stiffness requirements. Other ratios, however, may also be used depending on the desired performance characteristics.

Figure 17:
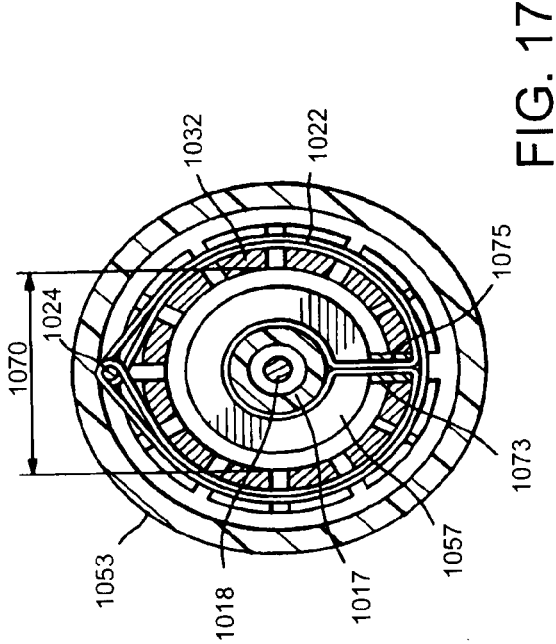
FIG. 17 is a transverse cross sectional view of the delivery system of FIG. 14 taken along lines 17-17 of FIG. 14.

The inner diameters of belt bushings 1057, 1063 and 1067 are sized to have a close fit over the guidewire tube 1017 and secured portion 1071, as shown in FIG. 20A, of the free ends of the belts 1021, 1022 and 1023 that are secured to the guidewire tube 1017. Typically, the inner diameter of the belt bushings 1057, 1063 and 1067 range from about 0.025 inch to about 0.065 inch; specifically, about 0.030 inch to about 0.050 inch. In addition, the outer diameter of belt bushing 1057 may be sized to approximate an inner diameter 1070, as shown in FIG. 17, of the respective first distal self-expanding member 1032 of the endovascular graft 1011 when the member 1032 is in a fully constrained state. The other belt bushings 1063 and 1067 may be similarly configured with respect to the second distal self-expanding member 1033 and the proximal self-expanding member 1031.

Such an arrangement keeps the self-expanding members 1031, 1032 and 1033 properly situated when in a constrained state and prevents the various portions of the self-expanding members 1031, 1032 and 1033 from overlapping or otherwise entangling portions thereof while in a constrained state. The outer diameter of the belt bushings 1057, 1063 and 1067 may range from about 0.040 inch to about 0.200 inch; specifically, about 0.060 inch to about 0.090 inch. The material of the belt bushings 1057, 1063 and 1067 may be any suitable polymer, metal, alloy or the like that is bondable. Generally, the belt bushings 1057, 1063 and 1067 are made from a polymer such as polyurethane, silicone rubber or PVC plastic.

As shown in FIG. 20A, belts 1021, 1022 and 1023 extend radially from the guidewire tube 1017 through optional standoff tubes 1072, 1073 and 1074. Standoff tubes 1072, 1073 and 1074 are disposed about belts 1021-1023 adjacent the guidewire tube 1017 and act to prevent separation of belts 1021-1023 in a circumferential direction as tension is applied to the belts. Standoff tubes 1072-1074 also prevent belts 1021-1023 from applying other undesirable forces on portions of the endovascular graft 1011 that are constrained by the belts. Specifically, the standoff tubes 1072-1074 prevent the belts 1021-1023 from spreading the self-expanding members 1031-1033, or portions thereof, at those locations where the belts 1021-1023 extend radially through the self-expanding members.

The standoff tubes 1072-1074 typically have a length substantially equal to a single wall thickness of the self-expanding members 1031, 1032 and 1033. The length of the standoff tubes 1072-1074 may range from about 0.010 inch to about 0.030 inch. An inner diameter of an inner lumen 1075 of the standoff tubes, as shown in FIG. 17, may range from about 0.004 to about 0.024 inch, with a wall thickness of the standoff tubes being about 0.002 inch to about 0.006 inch. Typically, the standoff tubes 1072-1074 are made from a high strength metal or alloy such as stainless steel, although they may be polymeric as well.

Belts 1021-1023 exit the outer apertures of standoff tubes 1072-1074 and extend circumferentially about the respective portions of the expandable intracorporeal device 1011. The term "circumferential extension" as used with regard to extension of the belts 1021-1023 is meant to encompass any extension of a belt in a circumferential direction. The belts may extend circumferentially a full 360 degrees, or any portion thereof. For example, belts or belt segments may extend partially about an endovascular device, and may be combined with other belts or belt segments that also partially extend circumferentially about an endovascular device. Typically, a plane formed by each of the belts 1021-1023 when in a constraining configuration is generally perpendicular to a longitudinal axis 1076, shown in FIG. 14, of the distal section 1014 of shaft 1012. As shown in FIGS. 19A and 19B, loop ends 1081, 1082 and 1083 of the belts 1021, 1022 and 1023, respectively, are releasably locked together by one or more release members. For example, in the embodiment shown in FIG. 14, a release member in the form of a first release wire 1024 is shown disposed within end loops 1081 of the first distal belt 1021 and end loops 1082 of the second distal belt 1022 so as to secure the first and second distal belts 1021 and 1022 in a constraining configuration about the endovascular graft 1011. Another release member in the form of a second release wire 1025 is shown disposed within end loops 1083 of the proximal belt 1023 so as to secure the proximal belt 1023 in a constraining configuration about the endovascular graft 1011.

A single release wire may also be used to perform the function of each of the first and second release wires, 1024 and 1025, so that first distal belt 1021, second distal belt 1022, and proximal belt 1023 may be releasably secured by a single release wire. A highly controlled, sequential belt deployment scheme may be realized with the use of a single release wire.

Any number of release wires and belts as may be needed to effectively secure and deploy graft 1011, in combination, are within the scope of the present invention.

In some embodiments of the invention, when constrained, the end loops of any single belt touch each other or are spaced closely together such that the belt as a whole forms a substantially circular constraint lying substantially in a plane. Release wire 1024 and 1025 may be made from suitable high strength materials such as a metal or alloy (e.g., stainless steel) which can accommodate the torque force applied to the release wire by the belt end loops 1083 when the belts 1023 are under tension from the outward radial force of the constrained portions of the endovascular graft 1011, i.e., the self-expanding members 1032 and 1033.

The release wires 1024 and 1025 may generally have an outer diameter ranging from about 0.006 to about 0.027 inch. Distal end portions 1084 and 1085 of release wires 1024 and 1025, respectively, may terminate at any appropriate site distal of the end loops 1081-1083 of belts 1021-1023. As shown in FIG. 21, the proximal ends 1086 and 1087 of the release wires 1024 and 1025 extend through the elongate shaft 1012 of the delivery system 1010 through proximal ports 1091 and 1092 on the proximal adapter 1042, respectively, and terminate at respective release wire handles 1093 and 1094 which are releasably secured to the proximal adapter 1042.

FIG. 20B illustrates an alternative embodiment of the belts 1021-1023 of FIG. 20A. In FIG. 20A, belts 1021-1023 are shown as each consisting of a single strand of wire formed into the end loops 1081-1083, respectively, with the end loops in an overlapping configuration. Free ends 1055 and 1056 of belt 1081 are shown secured to the distal section 1035 of the guidewire tube 1017. In contrast, FIG. 20B, wherein like elements with regard to FIG. 20A are shown with like reference numerals, shows belts 1021B, 1022B and 1023B formed of two strands of wire, with each strand formed into a single loop which overlaps a loop of the other strand to form end loops 1081B, 1082B and 1083B. The free ends of the belts 1021B-1023B may be secured in a similar manner to those of free ends 1055 and 1056 of FIG. 20A.

Turning now to FIGS. 20C and 20D, alternative embodiments for portions of the delivery system of the present invention are shown. FIGS. 20C and 20D illustrate alternative belts 1021C, 1022C and 1023C disposed on guidewire tube 1017. Single or multiple belts 1021C-1023C may be deployed at various locations along guidewire tube 1017 as desired. In addition, the members comprising belts 1021C-1023C are shown as a single line. However, belts 1021C-1023C may be of a single- or multiple strand or filament design with various cross-sectional shapes as previously described. A single solid ribbon or wire is particularly useful.

Belts 1021C-1023C shown in FIGS. 20C and 20D are a single strand filament wrapped around guidewire tube 1017 and fixed thereon via any number of suitable techniques, such as gluing with adhesive, mechanical fixation, etc. Especially useful is fixing the belt with an ultraviolet-curable adhesive.

Alternatively, belts 1021C-1023C may comprise two strand filaments each wrapped around guidewire tube 1017 so that, for instance, belt 1021C is a two-filament component.

Belt 1021C includes belt arms 1112 and 1114, each of which, in the embodiments shown, is a loop of filament twisted upon itself to form a helix. Any number of twists may be imparted to arms 1112 and 1114 to provide a relatively loose or relatively tight helix as desired. Typically the number of twists (with a single twist being defined as a single overlap of wire segment) in each belt arm 1112 and 1114 numbers from zero to about 50 or more; specifically, about two to about 10. The choice of material used for belt 1021C is an important factor in determining the optimum number of twists for each belt arm. Belt arms 1112 and 1114 may be formed into other configurations (e.g., braid, double helix, etc.) as well.

Disposed within the end loops of the belt arms 1112 and 1114 are distal apertures or openings 1120, 1122, respectively. During assembly of the delivery system, a release wire (such as wire 1024) is passed through each aperture 1120, 1122 after the belt arms are wrapped around the graft self-expanding member, preferably in a circumferential groove as further described below. The release wire may also be disposed through any aperture created along the length of belt arms 1112, 1114 by each helix twist, although the distal-most apertures 1120, 1122 are preferred.

The wire optionally may be welded, glued, or otherwise fixed to itself at discrete points or along all or any portion of belt arms 1112, 1114, save their corresponding apertures 1120 and 1122. For instance, the belt arm wire may be glued or welded to itself at the overlap or twist points, such as points 1124.

FIG. 20D shows an optional belt arm sleeve 1126 that may be used to enclose a portion of one or both belt arms 1112, 1114, or any of the other belt embodiments contemplated herein. Belt 1112 is shown in FIG. 20D being constrained or covered over a length thereof by a flexible sleeve or coating 1126 (or alternatively, a coil wrapping or by fixing the loop to itself by adhesives, welding, soldering, brazing, etc.). Sleeve or coating 1126 may optionally be shrink-wrapped, crimped, or otherwise configured to constrain or cover belt arm 1112 therein. These fixation and sleeve features help to minimize the potential of belt arm untwisting and tend to close or block some or all of the helix apertures along the length except those through which the release wire are intended to pass. They can also provide greater structural and operational stability to the catheter system as a whole.

Belt arm sleeve 1126 can be configured to have a transverse dimension that is sized to fit a twisted belt arm with fixed nodal points such as the belt arm 1112 shown in FIG. 20D. In order to accommodate such a twisted belt arm 1112, the inner diameter and outer diameter would be large relative to a transverse dimension of the wire material that forms the belt arm 1112. However, the belt arm sleeve 1126 can also be only slightly larger in transverse dimension that the wire that forms the belt arm. For example, embodiments of belt arms that do not have twisted wires may have a sleeve 1126 that fits closely or tightly over two strands of wire forming a belt arm. The sleeve 1126 can cover substantially the entire length of such an untwisted belt arm from at least the guidewire tube to just proximal of the distal loop, such as distal loop 1120. The distal loop should remain exposed for engagement by a release wire. In such an embodiment, the sleeve covered portion of the belt arm may also be wrapped around and secured to the guidewire tube just as the unsleeved belt portion of the belt arm 1112 shown in FIG. 20D is shown at 1071C. This type of low profile belt arm sleeve may also be used to cover twisted belt arm embodiments, although a slightly larger diameter sleeve would be required.

It may be desirable to impart a particular free resting angle to the belt arms 1112, 1114 to improve the reliability of the system and further reduce the possibility of the arms 1112 and 1114 interfering with other components of the prosthesis or delivery system. The FIG. 20C view shows belt arms 1112, 1114 symmetrically disposed at an angle α as measured from a horizontal plane 1125. This angle a may range from zero to 180 degrees. For example, one or both belt arm 1112, 1114 may lie along plane 1125 or they may rest in the configuration shown (α=45 degrees). Any known techniques may be used to impart a desired resting configuration to the system, such as, for example, cold working or shape-setting by way of an athermal phase transformation (in the case of shape memory alloys).

Figure 20I:
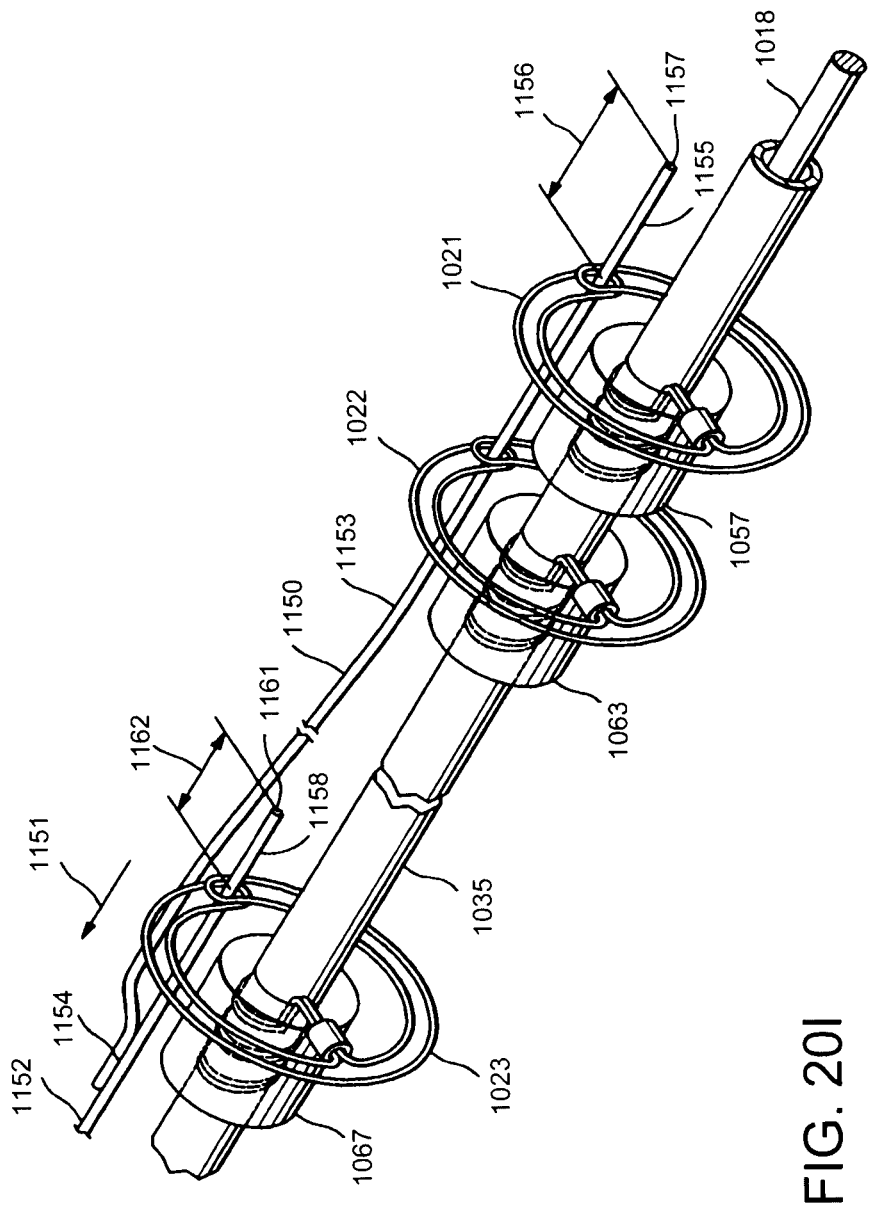
FIG. 20I is a perspective view of an alternative embodiment of a branched release wire.
Figure 20K:
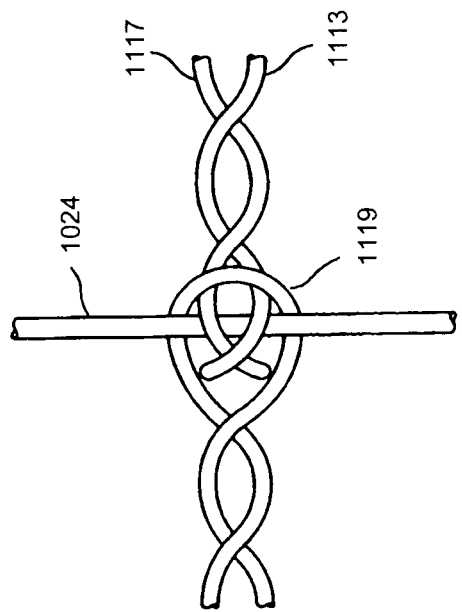
FIG. 20K is a transverse cross sectional view showing the alternative embodiment of the release belt configuration of FIG. 20J constraining a self-expanding member.
Figure 20L:
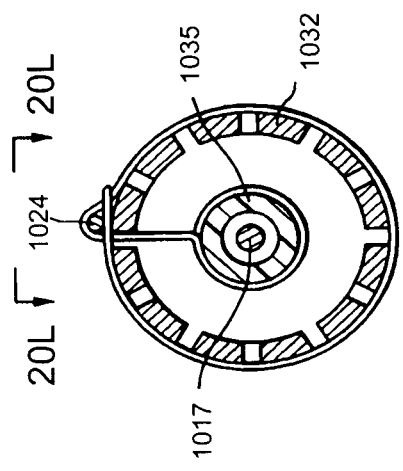
FIG. 20L is a detail of the connection formed where a release wire is used with the alternative release belt embodiment of FIGS. 20J-20K.
Figure 20J:
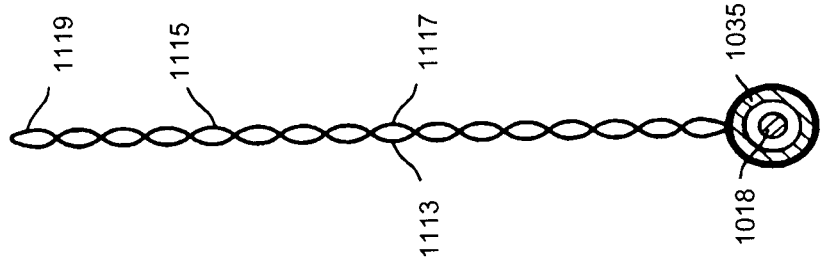
FIG. 20J is an end view showing an alternative embodiment of a release belt.

FIG. 20J shows a single belt example of the version shown in FIGS. 20C and 20D. Here, a single belt arm 1113 is shown disposed about the distal end 1035 of guidewire tube 1017. Belt arm 1113 is significantly longer than either belt arm 1112 or 1114 of the FIGS. 20C-20D embodiment so that it may extend at least around the circumference of any one of self-expanding members 1031, 1032, or 1033. The distal portion 1115 of belt arm 1113 meets a more proximal portion 1117 where one or both strands (when the belt arm 1113 is a twisted variety) extends through an end loop 1119 in the belt arm 1115 distal portion. As discussed with other embodiments, a release member such as release wire 1024 may be inserted through end loop 1119 and the intersecting portion of the belt arm proximal portion 1117 to releasably secure belt arm 1113 in a constraining configuration about the endovascular graft 1011. FIG. 20K depicts a simplified schematic cross-sectional view of belt arm 1113 (shown here untwisted) held in place by a release wire 1024 about an exemplary self-expanding member 1032. FIG. 20L is a detail of the connection formed where release wire 1024 intersects the distal and proximal portions, 1115 and 1117, respectively, of belt arm 1113.

All of the features discussed herein with respect to the, FIGS. 20C-20D embodiment may be employed in the embodiment of FIGS. 20J-20K as well.

This helix configuration shown in the embodiments of FIGS. 20C-20D and 20J-20L is a particularly reliable configuration. It reduces the possibility that a portion of belt 1021C becomes entangled with a self-expanding member (such as members 1031, 1032 and 1033) or otherwise interferes with the safe and effective deployment of the prosthesis.

FIG. 20E depicts a particularly useful arrangement for configuring the belt end loops 1081-1083 with release wires 1024-1025 during assembly of delivery system 1010. In this example, first and second end loops 1081' and 1081" of belt 1021 are shown connected via release wire 1024. To achieve the configuration of FIG. 20E, first end loop 1081' is passed through aperture 1088 disposed in second end loop 1081". A portion of aperture 1089 disposed in first end loop 1081' should extend through the plane created by second end loop 1081" as shown in FIG. 20E.

Next, release wire 1024 is passed through the portion of aperture 1089 that extends beyond this plane so that wire 1024 "locks" the two looped ends 1081' and 1081" together as shown. We have found that this is a stable configuration that lends itself well to a reliable and safe deployment protocol.

Other techniques for assembling wire 1024 and first and second end loops 1081' and 1081" may be used; the method described above is merely exemplary. Wire 1024 may simply pass through loop ends as configured and as shown at reference numerals 1081, 1082 and 1083 in FIG. 20A, and 1081B, 1082B and 1083B of FIG. 20B as well.

In the embodiment of FIG. 20F, belt 1110 is a member in the shape of a wire formed into an end loop 1116B having an aperture 1120 for receiving a release wire. This arrangement may be used on one or both ends of belt 1110 or, alone if belt 1110 is in the form of a single belt arm as discussed above. Connection 1122 is shown in FIG. 20F as a simple wrapping of the distal end 1116A of the wire comprising belt 1110. Connection 1122 need not be limited to such a tapered or cylindrical sleeve or coating, however. Other methods to form end loop 1116B are contemplated, including, for example, the use of adhesives, welding, brazing, soldering, crimping, etc. An optional protective sleeve or coating 1127 (shown in sectional view in FIG. 20F) covers or is part of connection 1122 and serves to protect the patient as well as components of the delivery system and prosthesis from damage.

Turning now to FIGS. 20G and 20H, two alternative embodiments of a ribbon-like belt 1081G and 1081H are shown. In FIG. 20G, a section 1128 of material has been partially displaced from belt 1081G distal end 1116C and worked into a loop-like member 1129 such that two generally orthogonal apertures 1130, 1132 are formed in belt distal end 1116C. A set of hinges or other protective mechanism or material may be used on each end of this member 1128 so that further tearing or peeling of this member may be prevented. Section 1128 may be formed integrally from the belt distal end 1116C as shown in FIG. 20G or may be a separate component that is attached to the belt distal end by any suitable means.

Second belt distal end 1118C in FIG. 20G is shown as having an aperture 1133 disposed therein. In use, a half-twist is imparted to the ribbon-like belt 1081G as the second distal end 1118C is brought through aperture 1130 such that apertures 1132 and 1133 are at least partially aligned. A release wire (such as wire 1024) is then brought through apertures 1132 and 1133 to releasably join ends 1116C and 1118C.

FIG. 20H shows yet another embodiment of a belt 1081H where a simple rectangular aperture 1133A is disposed in the distal end 1117 of belt 1081H through which another belt end and release wire may be disposed as taught herein. As with the embodiment of FIG. 20G, a half-twist is imparted to the belt 1081H in use so that the second distal end 1118D is brought through aperture 1133. A release wire may then be threaded through apertures 1132 and 1133 to releasably join ends 1117 and 1118D. In this embodiment, aperture 1132 should be large enough to accommodate both second distal end 1118D and a release wire.

FIG. 20I shows a perspective view of a belt assembly similar to that shown in FIG. 20A, wherein like elements are shown with like reference numerals. An alternative embodiment of a release wire consisting of a branched release wire 1150 is illustrated in FIG. 20I. The branched release wire 1150 engages belts 1021-1023 and is configured to release belts 1021-1023 at different times with a proximal withdrawal movement of the branched release wire 1150, the direction of which is indicated by arrow 1151. Branched release wire 1150 has a main portion 1152 and a branch portion 1153. Branch portion 1153 is secured to main portion 1152 by a solder joint 1154. The joint 1154 could also be made by any other suitable means, such as welding, bonding with an epoxy, mechanically binding the joint, or the like. The embodiment of the branched release wire shown in FIG. 20L consists of wire which is generally round in cross section. The wire of the branched release wire can have the same or similar material and mechanical properties to the wire of the release wires 1024 and 1025 discussed above. Branch portion 1153 engages first distal belt 1021 and second distal belt 1022. A distal segment 1155 has a length L indicated by arrow 1156 which extends distally from first distal belt 1021 to the distal end 1157 of branch portion 1153.

Main portion 1152 of the branched release wire 1150 engages the proximal belt 1023 and has a distal segment 1158 that extends distally from the proximal belt 1023 to a distal end 1161 of the main portion. The length L' of the distal segment 1158 of the main portion 1152 is indicated by arrow 1162. Length L of distal segment 1155 is greater than length L' of distal segment 1158. In this way, as the branched release wire is withdrawn proximally, proximal belt 1023 is released first, first distal belt 1021 is released second and second distal belt is released last. Such a branched release wire allows a wide variety of belt release timing with a single continuous withdrawal or movement of a proximal end (not shown) of the branched release wire 1150. The proximal end of the branched release wire may be terminated and secured to a release wire handle or the like, as discussed herein with regard to other embodiments of release wires. The ability to deploy multiple release wires in a desired timing sequence with a single branched release wire 1150 gives the designer of the delivery system great flexibility and control over the deployment sequence while making the deployment of the belts simple and reliable for the operator of the delivery system. Although the branched release wire 1150 has been shown with only a single branch, any number of branches or desired configuration could be used to achieve the deployment sequence required for a given embodiment of a delivery system. For example, a separate branch could be used for each belt in a multiple belt system, with varying distal segment length used to control the sequence of deployment. Also, multiple branched release wires, or the like, could be used in a single delivery system to achieve the desired results.

A number of embodiments for the belt and belt arm components of the present invention are described herein. In general, however, we contemplate any belt or belt arm configuration in which the belt may be used to releasably hold or restrain an implant member in conjunction with a release member. The particular embodiments disclosed herein are not meant to be limiting, and other variations not explicitly disclosed herein, such as those in which multiple apertures (which may have varying shapes and sizes) are disposed along the belt length, those in which the belt or belt arm distal ends comprises a separate material or element that is affixed to the belt or belt arm, etc. are within the scope of the invention. Furthermore, various embodiments of the ends of the belts or belt arms taught herein may exist in any combination in a single delivery system.

Turning now to FIG. 19A, belts 1021-1023 lie within circumferential grooves or channels 1095, 1096 and 1097, respectively, formed into the respective self-expanding members 1031, 1032 and 1033. Grooves 1095-1097 prevent axial displacement of the belts 1021-1023 prior to activation or release of the releasable members 1024 and 1025, i.e., proximal retraction of the first and second release wires. Although grooves 1095-1097 are illustrated in the embodiment shown, other alternatives are possible to achieve the same or similar function of the grooves. For example, abutments extending slightly from the self-expanding members 1031-1033 on either side of the belts 1021-1023 in their constraining configuration could prevent axial movement of the belts. A detachable adhesive or the like could also be used.

As shown in FIG. 23, the release of end loops 1081-1083 occurs when the distal end portions 1084 and 1085 of the release wires 1024 and 1025, respectively, pass from within the overlapped end loops 1081-1083. If the end loops 1081-1083 move axially in response to movement of the release wires 1024 and 1025 due to frictional forces imposed on the end loops 1081-1083 by the release wires, the point at which the distal ends of the release wires 1084 and 1085 pass from within the end loops 1081-1083 would vary depending on the amount of movement of the end loops 1081-1083.

If the end loops 1081-1083 were to be axially displaced from their normal position relative to the distal ends of the release wires prior to deployment, the timing of the release of the belts 1021-1023 could be adversely affected. Thus, the prevention of axial displacement of the belts 1021-1023 during proximal retraction of the release wires 1024 and 1025 facilitates accurate release of the belts by keeping the overlap joint of the belt looped end portions in a constant axial position during such retraction.

In addition, it may be desirable to keep belts 1021-1023 positioned at or near the general center of a given constrained self-expanding members 1031-1033 so that the self-expanding member 1031-1033 is substantially uniformly and evenly constrained over its axial length. If belts 1021-1023 constrain the self-expanding members 1031-1033 at a non-centered axial position on the member, an end of the member opposite that of the non-centered position may be less constrained and may interfere with axial movement of the outer tubular member 1053 (and consequently deployment of the endovascular graft 1011).

Figure 16:
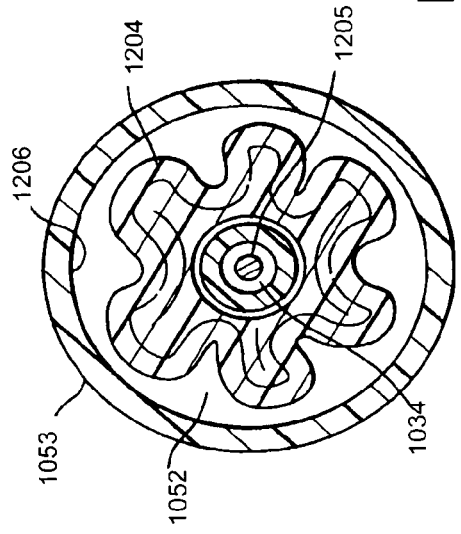
FIG. 16 is a transverse cross sectional view of the delivery system of FIG. 14 taken along lines 16-16 of FIG. 14.

Tubular body member 1205 of the endovascular graft 1011 is disposed between and secured to the second distal self-expanding member 1033 and the proximal self-expanding member 1031. The tubular body member comprised of flexible material 1204, is shown constrained in an idealized view in FIGS. 14, 16 and 19, for clarity. In practice, tubular body member 1205 while constrained is tightly compressed with minimal air space between layers of flexible material 1204 so as to form a tightly packed configuration as shown in FIG. 16. Tubular body member 1205 is optionally radially constrained by an inside surface 1206 of the inner lumen 1052 of outer tubular member 1053.

An inner tubular member 1207 is slidably disposed within the inner lumen 1052 of outer tubular member 1053. Release wires 1024 and 1025, guidewire tube 1017 and an inflation tube 1211 are disposed within an inner lumen 1212 of the inner tubular member 1207. Inner lumen 1212 is optionally sealed with a sealing compound, depicted in FIGS. 14, 15 and 19 by reference numeral 1213 at distal end 1214. The sealing compound 1213 prevents leakage of fluids such as blood, etc., from a proximal end 1215, shown in FIG. 21, of the inner tubular member 1207. Sealing compound 1213 fills the space within the inner lumen 1212 of the inner tubular member 1207 between an outer surface 1216 of the guidewire tube 1017, the outer surface 1217 of the inflation tube 1211 and outer surfaces 1221 and 1222 of a tubular guide 1223 for the first release wire 1024 and a tubular guide 1224 for the second release wire 1025. The sealing compound 1213 can be any suitable material, including epoxies, silicone sealer, ultraviolet cured polymers, or the like.

In FIG. 15, the tubular guides 1223 and 1224 for the first release wire 1024 and the second release wire 1025 allow axial movement of the release wires with respect to the sealing compound 1213 and inner tubular member 1207. The inside diameter of the inner lumens of the tubular guides 1223 and 1224 are sized to fit closely with an outer diameter or transverse dimension of the release wires 1024 and 1025. Alternatively, tubular guides 1223 and 1224 may be replaced by a single tubular guide that houses one or more release wires, such as wires 1024 and 1025.

Turning to FIG. 21, the inner tubular member 1207 terminates proximally with the proximal adapter 1042 having a plurality of side arms 1225, 1226 and 1227 and a proximal exit port 1231 for the inner lumen 1034 of the guidewire tube 1017. First release wire side arm 1225 branches from a proximal adapter body portion 1233 and has an inner lumen 1234 and proximal end 1086 of the first release wire 1024. A proximal extremity 1236 of the first release wire 1024 is anchored to the first release wire proximal handle 1093 which is threaded onto the proximal end 1238 of the first release wire side arm 1225. The proximal extremity 1236 of first release wire 1024 is configured as an expanded bushing or other abutment that captures the handle 1093 and translates proximal axial movement of the handle 1093 to the first release wire 1024 but allows relative rotational movement between the handle 1093 and the proximal end 1086 of the first release wire 1024.

A similar configuration exists for the proximal end 1087 of the second release wire 1025. There, a second release wire side arm 1226 branches from the proximal adapter body portion 1233 and has an inner lumen 1244 that houses the proximal end 1087 of the second release wire 1025 which is free to slide in an axial orientation within the lumen 1244. A proximal extremity 1246 of the second release wire 1025 is configured as an expanded bushing or other abutment that captures the second release wire handle and translates axial proximal movement of the second release wire handle 1094 to the second release wire 1025, but allows relative rotational movement between the proximal end 1087 of the second release wire 1025 and the second release wire handle 1094.

The first release wire handle 1093 and second release wire handle 1094 may optionally be color coded by making each, or at least two, release wire handles a color that is distinctly different from the other. For example, the first release wire handle 1093 could be made green in color with the second release wire handle 1094 being red in color. This configuration allows the operator to quickly distinguish between the two release wire handles and facilitates deployment of the belts in the desired order.

In another embodiment, instead of color coding of the release wire handles 1093 and 1094, the spatial location of the handles can be configured to convey the proper order of deployment of the release wires to the operator of the delivery system. For example, if three release wire handles are required for a particular embodiment, the corresponding three side arms can be positioned along one side of the proximal adapter. In this configuration, the release wire handle that needs to be deployed first can extend from the distal-most side arm. The release wire handle that needs to be deployed second can extend from the middle side arm. The release wire handle that is to be deployed last can extend from the proximal-most side arm. For such a configuration, the operator is merely instructed to start deployment of the release wires at the distal-most release wire handle and work backward in a proximal direction to each adjacent release wire handle until all are deployed. Of course, an opposite or any other suitable configuration could be adopted. The configuration should adopt some type of spatially linear deployment order, either from distal to proximal or proximal to distal, in order to make reliable deployment of the release wires in the proper order easy to understand and repeat for the operator of the delivery system. Other types of release order indicators such as those discussed above could also be used, such as numbering each release wire handle or side arm with a number that indicates the order in which that handle is to be deployed.

The proximal end 1036 of the guidewire tube 1017 terminates and is secured to an inner lumen 1251 of the proximal end 1259 of the proximal adapter 1042. Inner lumen 1251 typically has a longitudinal axis 1253 that is aligned with a longitudinal axis 1254 of the proximal section 1013 elongate shaft 1012 so as to allow a guidewire to exit the proximal end 1015 of the elongate shaft 1012 without undergoing bending which could create frictional resistance to axial movement of the guidewire. A proximal port 1255 of the proximal adapter 1042 may be directly fitted with a hemostasis valve, or it may be fitted with a Luer lock fitting which can accept a hemostasis valve or the like (not shown).

The proximal adapter 1042 may be secured to the proximal end 1215 of the inner tubular member 1207 by adhesive bonding or other suitable method. A strain relief member 1256 is secured to the distal end 1257 of the proximal adapter 1042 and the inner tubular member 1207 to prevent kinking or distortion of the inner tubular member 1207 at the joint.

As seen in FIG. 14, the proximal end 1261 of the outer tubular member 1053 is secured to a proximal fitting 1262 that slides over an outer surface 1258 of the inner tubular member 1207. A seal 1263 located in proximal fitting 1262 provides a fluid seal for the lumen 1265 formed between the outer surface 1258 of the inner tubular member 1207 and the inner surface 1206 of the inner lumen 1052 of the outer tubular member 1053. The fit between the outer surface 1258 of the inner tubular member 1207 and the inner surface 1206 of the outer tubular member 1053 is typically close, but still allows for easy relative axial movement between outer tubular member 1053 and inner tubular member 1207. A stop 1266 is disposed and secured to the outer surface 1258 of the inner tubular member 1207 distal of the proximal adapter 1042 to limit the amount of proximal axial movement of the outer tubular member 1053 relative to the inner tubular member 1207.

When the outer tubular member 1053 is positioned on the proximal shoulder 1048 of the distal nose piece 1044 prior to deployment of endovascular graft 1011, the distance between a proximal extremity 1267 of proximal fitting 1262 and a distal extremity 1268 of stop 1266 is approximately equal to or slightly greater than an axial length of the endovascular graft 1011 in a constrained state. This configuration allows the outer tubular member 1053 to be proximally retracted to fully expose the endovascular graft 1011 in a constrained state prior to deployment of the graft. This distance may be greater, but should not be less than the length of the endovascular graft 1011 in a constrained state in order to completely free the constrained graft 1011 for radial expansion and deployment.

Retraction limiters may alternatively be used to prevent excessive axial movement of the release wires 1024 and 1025 in a proximal direction during deployment. Particularly in embodiments of the invention where single release wires are used to constrain and deploy multiple belts such as with first release wire 1024, retraction limiters may be used to allow enough axial movement of the release wire 1024 to deploy a first belt 1021, but prevent deployment of a second more proximally located belt 1022. For example, as shown in FIG. 21, a retraction limiter in the form of a filament 1268 could be disposed between the proximal adapter 1042 and the handle 1093 of the first release wire 1024 such that proximal retraction of the first release wire 1024 sufficient for deployment of the first distal belt 1021 could be achieved, but not so much as to allow deployment of the second distal belt 1022. In order to deploy the second distal belt 1022, the filament 1268 would have to be severed or otherwise released. This type of configuration can allow more control over deployment of the endovascular graft 1011 and allow deployment in stages which are sequentially controlled to prevent inadvertent deployment of a portion of the graft 1011 in an undesirable location within the patient's vessels.

Figure 22:
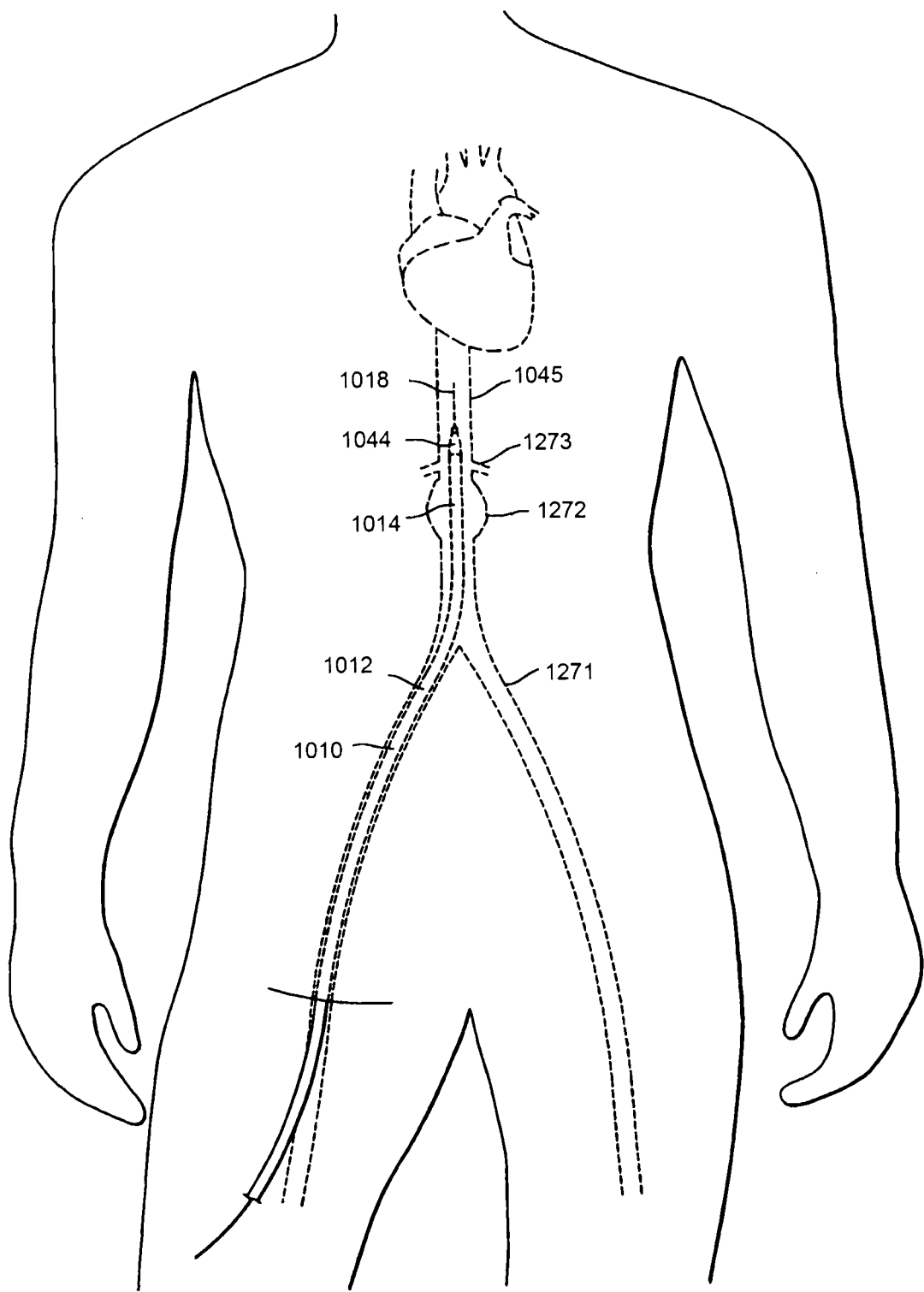
FIG. 22 is a diagrammatic view of a patient's body illustrating the patient's heart, aorta, iliac arteries, femoral arteries, and a delivery system having features of the invention disposed within the femoral artery and aorta.

In use, the delivery system 1010 is advanced into a patient's arterial system 1271 percutaneously as shown in FIG. 22 and positioned so that the endovascular graft 1011 spans an aneurysm 1272 in the patient's aorta 1045 as illustrated in FIGS. 14 and 22-25. It is generally desirable to have the tubular body portion 1205 of the graft 1011 positioned below the renal arteries 1273 in order to prevent significant occlusion of the renal arteries. The procedure typically begins with the placement of guidewire 1018 into the patient's target vessel 1045 across the target location, e.g., the aneurysm 1272. Common percutaneous techniques known in the art may be used for the initial placement of the guidewire 1018. For example, as shown in FIG. 22, percutaneous access to the aorta may be had through the femoral or iliac artery, although other access sites may be used. The delivery system 1010 may then be advanced over the guidewire 1018 to a desired position within the patient's vessel 1045. Alternatively, delivery system 1010 and guidewire 1018 could be advanced together into the patient's vasculature 1272 with the guidewire 1018 extending distally from the distal port 1038 of the guidewire tube 1017. In addition, it may be desirable in some cases to advance the delivery system 1010 to a desired location within the patient without the use of a guidewire 1018.

Figure 24:
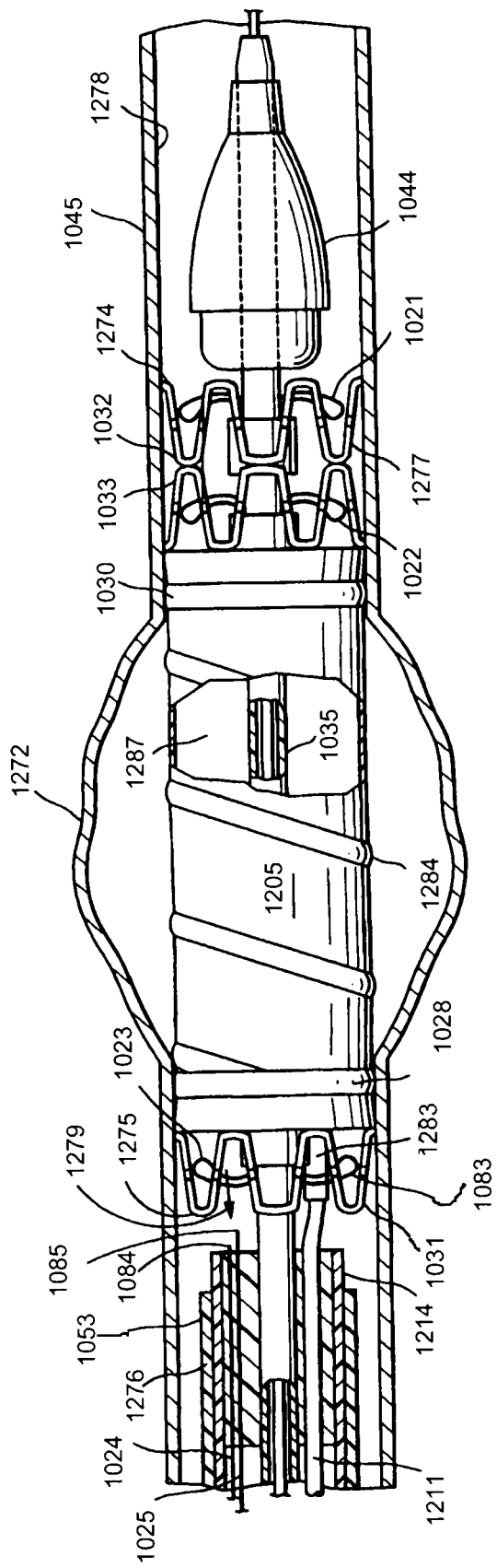
FIG. 24 is a diagrammatic view of a delivery system having features of the invention disposed within an artery of a patient with an expandable intracorporeal device being deployed within the artery.

Generally, the position of the delivery system 1010 is determined using fluoroscopic imaging or the like. As such, it may be desirable to have one or more radiopaque markers (not shown) secured to the delivery system at various locations. For example, markers may be placed longitudinally coextensive with the respective distal and proximal extremities 1274 and 1275, as shown in FIG. 24. In this way, it can be readily determined whether the graft 1011 is spanning the aneurysm 1272 of the patient's artery. Imaging markers, such as radiopaque markers, may also be secured to desirable positions on the endovascular graft 1011 itself. Other types of imaging and marking systems may be used such as computed tomography (CT), magnetic resonance imaging (MRI) and nuclear magnetic resonance (NMR) imaging systems and markers.

Once the distal section 1014 of the delivery system 1010 is properly positioned within the patient's artery 1045, the operator moves the proximal end 1261 of outer tubular member 1053 in a proximal direction relative to inner tubular member 1207. The relative axial movement is carried out by grasping the proximal end 1215 of the inner tubular member 1207 or proximal adapter 1042, and grasping the proximal end 1261 of the outer tubular member 1053, and moving the respective proximal ends towards each other. This retracts the distal section 1276 of the outer tubular member 1053 from the constrained endovascular graft 1011 and frees the graft for outward radial expansion and deployment. However, in this deployment scheme, note that the operator is free to reinsert graft 1011 back into the outer tubular member 1053 if necessary, as the release bands have not yet released the graft.

Once the distal section 1276 of the outer tubular member 1053 has been retracted, handle 1093 of the first release wire 1024 may then be unscrewed or otherwise freed from the proximal adapter 1042 and retracted in a proximal direction indicated by arrow 1279 in FIG. 23 until the distal end 1084 of the first release wire 1024 passes from within the end loops 1081 of the first distal belt 1021. When this occurs, the looped ends 1081 of the first distal belt 1021 are released and the first distal belt 1021 ceases to radially constrain the first distal self-expanding member 1032 which thereafter self-expands in a radial direction into an inner surface 1278 of the patient's aorta 1045 as shown in FIG. 23.

If the operator of the delivery system 1010 is not satisfied with the position, particularly the axial position, of the endovascular graft 1011 after deployment of the first distal self-expanding member 1032, it may then be possible to re-position the endovascular graft 1011 by manipulating the proximal end 1015 of the elongate shaft 1015. Movement of the elongate shaft 1012 can move the endovascular graft 1011, even though physical contact between the expanded member 1032 and the vessel inner surface 1278 generates some static frictional forces that resist such movement. It has been found that the endovascular graft 1011 can be safely moved within a blood vessel 1045 even in the state of partial deployment discussed above, if necessary.

Once the operator is satisfied with the position of the graft 1011, the first release wire 1024 may then be further proximally retracted so as to deploy the second distal belt 1022 in a manner similar to the deployment of the first distal belt 1021. The deployment of the second distal belt 1022 occurs when the distal end 1084 of the first release wire 1024 passes from within end loops 1082 of the second distal belt 1022 which are held in a radially constraining configuration by the first release wire 1024. Upon release of the second distal belt 1022, the second distal self-expanding member 1033 expands in a radial direction such that it may engage inner surface 1278 of the patient's aorta 1045. The amount of outward radial force exerted by the self-expanding members 1032 and 1033 on the inside surface 1278 of the patient's aorta 1045, which may vary between members 1032 and 1033, is dependent upon a number of parameters such as the thickness of the material which comprises the self-expanding members 1032 and 1033, the nominal diameter which the self-expanding members 1032 and 1033 would assume in a free unconstrained state with no inward radial force applied, material properties of the members and other factors as well.

Once the distal members 1032 and 1033 are deployed, the handle 1094 for the second release wire 1025 can be disengaged and axially retracted in a proximal direction from the proximal adapter 1042 until the distal end 1085 of the second release wire 1025 passes from within the end loops 1083 of the proximal belt 1023. Once the proximal belt 1023 is released, the proximal self-expanding member 1031 is deployed and expands in an outward radial direction, such that it may engage or be in apposition with the inner surface 1278 of the patient's aorta 1045 as shown in FIG. 24. Thereafter, the endovascular graft 1011 may be inflated with an inflation material (not shown) introduced into the proximal injection port 1282 in the proximal adapter 1042, through the inflation tube 1211, and into the inflation port 1283 of the endovascular graft 1011. Inflation material may be injected or introduced into the inflation port 1283 until the proximal and distal inflatable cuffs 1028 and 1030 and inflatable channels 1284 of the graft 1011 have been filled to a sufficient level to meet sealing and other structural requirements necessary for the tubular body to meet clinical performance criteria.

Before or during the deployment process, and preferably prior to or simultaneous with the step of inflating the endovascular graft 1011, it may be beneficial to optionally treat vessel 1045 in which the graft 1011 is deployed so to obtain a better seal between the graft 1011 and the vessel inner surface 1278, thus improving the clinical result and helping to ensure a long term cure.

One approach to this treatment is to administer a vasodilator, or spasmolytic, to the patient prior to deploying graft 1011. This has the effect of reducing the tone of the smooth muscle tissue in the patient's arteries; specifically, the smooth muscle tissue in the wall of vessel 1045 into which graft 1011 is to be deployed. Such tone reduction in turn induces the dilation of vessel 1045, reducing the patient's blood pressure. Any number of appropriate vasoactive antagonists, including the direct acting organic nitrates (e.g., nitroglycerin, isosorbide dinitrate, nitroprusside), calcium channel blocking agents (e.g., nifedipine), angiotensin-converting enzyme inhibitors (e.g., captopril), alpha-adrenergic blockers (e.g., phenoxybenzamine, phentolamine, prasozin), beta-adrenergic blockers (e.g., esmolol) and other drugs may be used as appropriate. Particularly useful are those vasodilators that can be administered intravenously and that do not have unacceptable contraindications such as aoritic aneurysm dissection, tachycardia, arrhythmia, etc.

The degree of vasodilatation and hypotensive effect will depend in part on the particular vessel in which graft 1011 is to be placed and the amount of smooth muscle cell content. Generally, the smaller the vessel, the larger percentage of smooth muscle cell present and thus the larger effect the vasodilator will have in dilating the vessel. Other factors that will effect the degree of vasodilatation is the health of the patient; in particular, the condition of the vessel 1011 into which graft 1011 is to be placed.

In practice, once the vasodilator has been administered to the patient, graft 1011 may be deployed and filled with inflation material so that graft 1011 reaches a larger diameter than would otherwise be possible if such a vasodilator was not used. This allows the inflation material to expand the diameter of graft 1011, for a given inflation pressure, beyond that which would be achievable if the vessel 1045 were in a non-dilated state (and nominal diameter). Alternatively, a larger diameter graft 1011 may be chosen for deployment. We anticipate that an increased vessel diameter of between two and twenty percent during vasodilatation may be optimal for-achieving an improved seal.

The vessel 1045 in which graft 1011 is to be placed may optionally be monitored pre- and/or post-dilation but before deployment of graft 1011 (via computed tomography, magnetic resonance, intravenous ultrasound, angiography, blood pressure, etc.) so to measure the degree of vasodilatation or simply to confirm that the vasodilator has acted on the vessel 1045 prior to deploying graft 1011.

Once the vasodilator wears off, preferably after between about five and thirty minutes from the time the drug is administered, the vessel 1045 surrounding graft 1011 returns to its normal diameter. The resultant graft-vessel configuration now contains an enhanced seal between graft 1011 and vessel inner surface 1278 and provides for reduced luminal intrusion by graft 1011, presenting an improved barrier against leakage and perigraft blood flow compared to that obtainable without the sue of vasodilators or the like.

Such vasodilating techniques may be used with all of the embodiments of the present invention, including the tubular graft 1011 as well as a bifurcated graft version of the expandable intracorporeal device of the present invention as is discussed in detail below.

Once graft 1011 is fully deployed, a restraining or retention device, such as retention wire 1285 that binds the distal end 1286 of the inflation tube 1111 to the inflation port 1283, as shown in FIGS. 25 and 26, is activated. The retention wire 1185 is activated by pulling the proximal end of the wire in a proximal direction so as to disengage the distal ends 1293 and 1294 from the holes 1295 and 1296. This eliminates the shear pin function of the distal ends 1293 and 1294 and allows the distal end 1286 of the inflation tube 1211 to be disengaged from the inflation port 1283. The release wires 1024 and 1025 may then be fully retracted from the elongate shaft 1012 in a proximal direction and the delivery system 1010 retracted in a proximal direction from the deployed endovascular graft 1011. The unconstrained distal belts 1021-1023 slip through the openings in the expanded members 1031, 1032 and 1033 as the delivery system 1010 is retracted and are withdrawn through the inner passageway 1287 of the deployed graft 1011. The distal nosepiece 1044 is also withdrawn through the inner passageway 1287 of the deployed graft 1011 as the delivery system 1010 is withdrawn as shown in FIGS. 23-25.

FIG. 26 illustrates the junction between the distal end 1286 of inflation tube 1211 and inflation port 1283. Typically, retention wire 1285 extends from the inflation port 1283 proximally to the proximal end 1015 of delivery system 1010. In this way, an operator can disengage the distal end 1286 of the inflation tube 1211 from the inflation port 1283 by pulling on the proximal end 1283 of retention wire 1285 from a proximal end 1015 of delivery system 1010. The retention wire 1285 can be a small diameter wire made from a material such as a polymer, stainless steel, nickel titanium, or other alloy or metal; in a particular embodiment of the invention, retention wire 1285 may be a spring formed of a variety of suitable spring materials. Alternatively retention wire 1285 may have a braided or stranded configuration.

FIG. 26 shows a single retention filament or wire 1285 disposed within the lumen 1291 of the inflation tube 1211. The distal end 1292 of retention wire 1285 may have one or more loops 1293 and 1294, respectively, disposed within one or more side holes disposed in the inflation port 1283 of the distal end 1286 of the inflation tube 1211. A number of side hole configurations may be utilized. The embodiment of FIG. 26 has two sets of opposed side hole locations 1295 and 1296. The distal loops 1293 and 1294 of the retention wire 1285 act to interlock the side holes 1295 and 1296 by creating a removable shear pin element which prevents relative axial movement between the distal end 1286 of the inflation tube 1211 and the inflation port 1283. Alternate embodiments may include multiple retention filaments or wires disposed within the lumen 1291 of the inflation tube 1211. An external sleeve (not shown) may be added over this assembly to further secure the interface and prevent leakage of inflation material through side holes 1295 and 1296. This sleeve is attached to inflation tube 1211 and is received with it.

Figure 27:
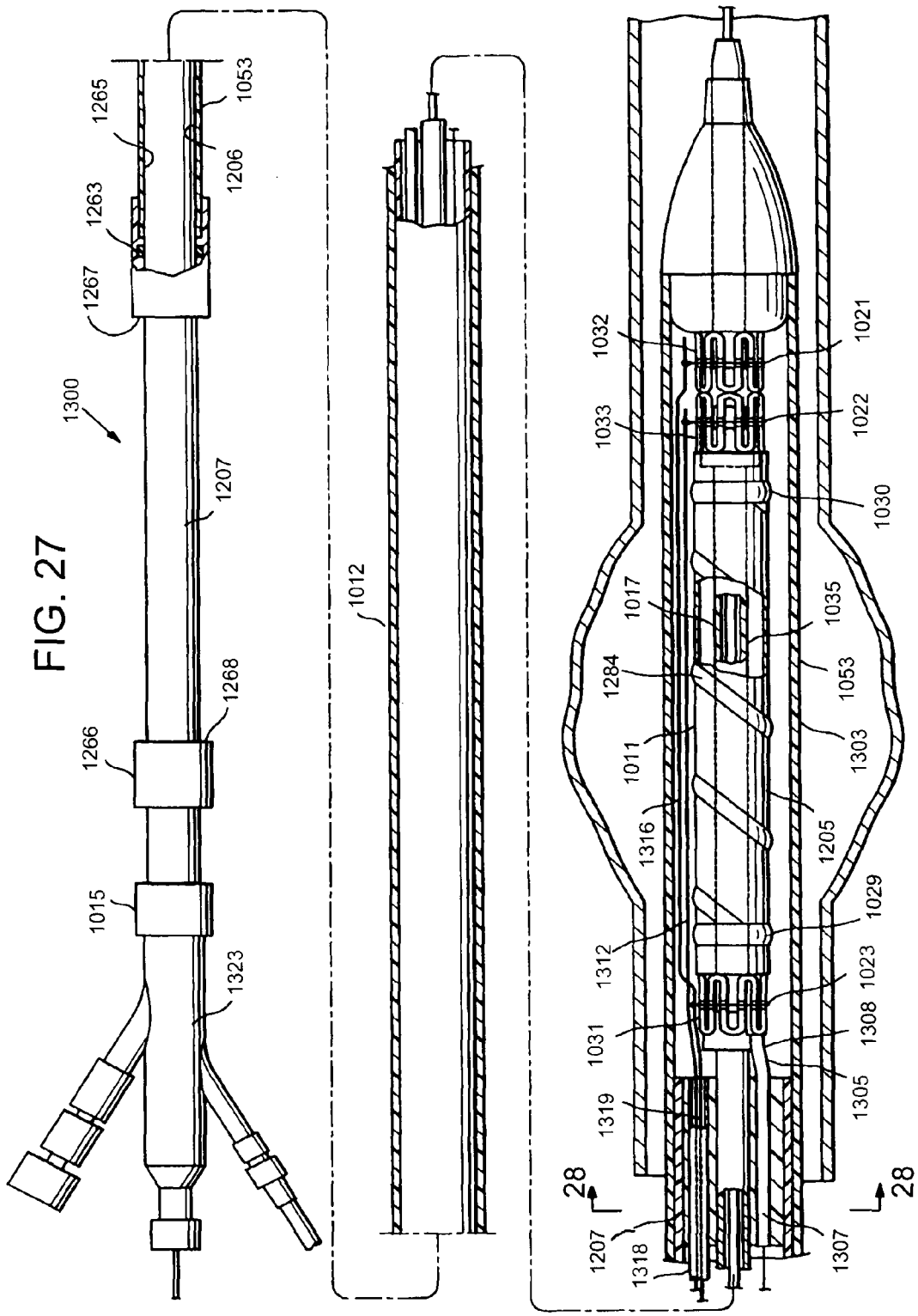
FIG. 27 is an elevational view in partial longitudinal section illustrating an embodiment of a delivery system for an expandable intracorporeal device having features of the invention.
Figure 28:
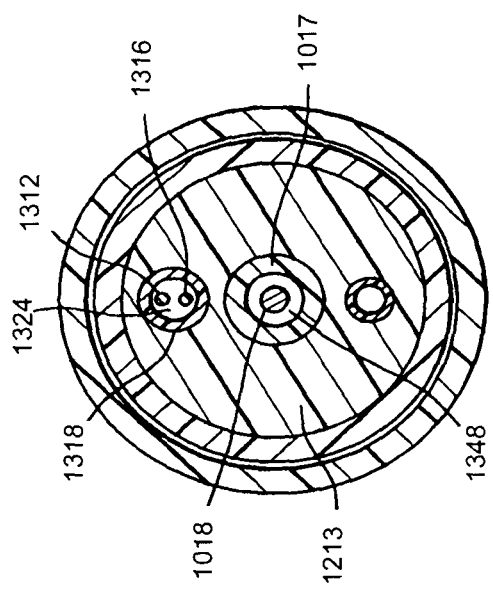
FIG. 28 is a transverse cross sectional view of the delivery system of FIG. 27 taken along lines 28-28 in FIG. 27.
Figure 29:
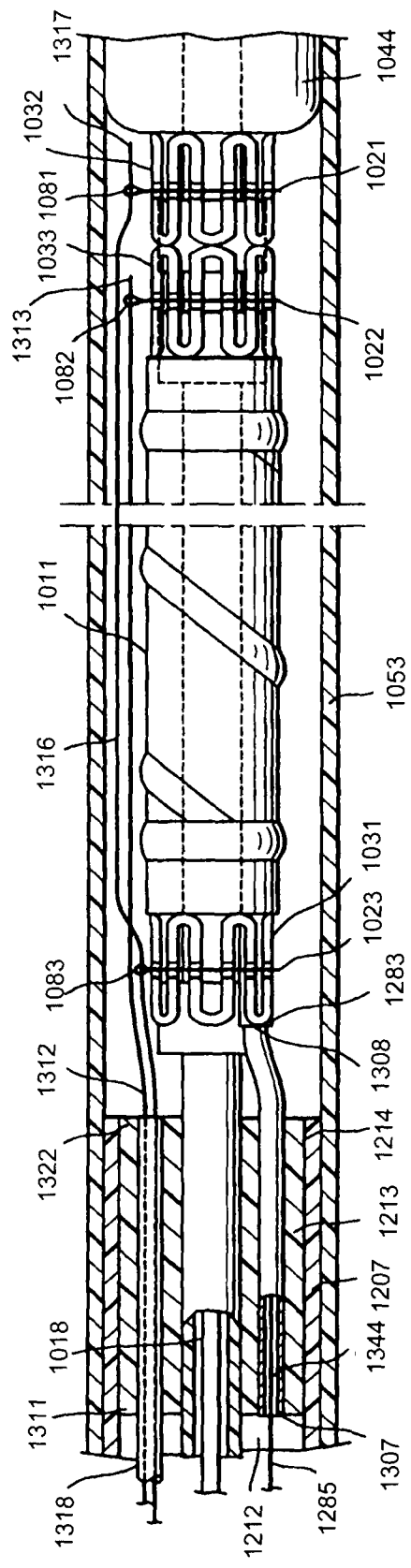
FIG. 29 is an enlarged elevational view in partial section of the delivery system shown in FIG. 27.

FIGS. 27-30 illustrate an alternative embodiment of the delivery system shown in FIG. 14. In FIGS. 27-30, like elements with respect to the embodiment of FIG. 14 will be shown with like reference numerals where appropriate. The delivery system 1300 has an outer tubular member 1053 and inner tubular member 1207 at a distal section 1303 of the delivery system 1300. An endovascular graft 1011 is disposed within the outer tubular member in the distal section 1303. An inflation tube 1305, similar to that of the embodiment shown in FIG. 14 is coupled to an inflation port 1283 of the endovascular graft 1011. However, the inflation tube 1305, having a proximal end 1307 and a distal end 1308, does not extend the majority of the length of the delivery system 1300. Instead, the proximal end 1307 of the inflation tube 1305 terminates at a proximal end 1311 of the potted section 1213 as shown in FIGS. 27-29.

Figure 30:
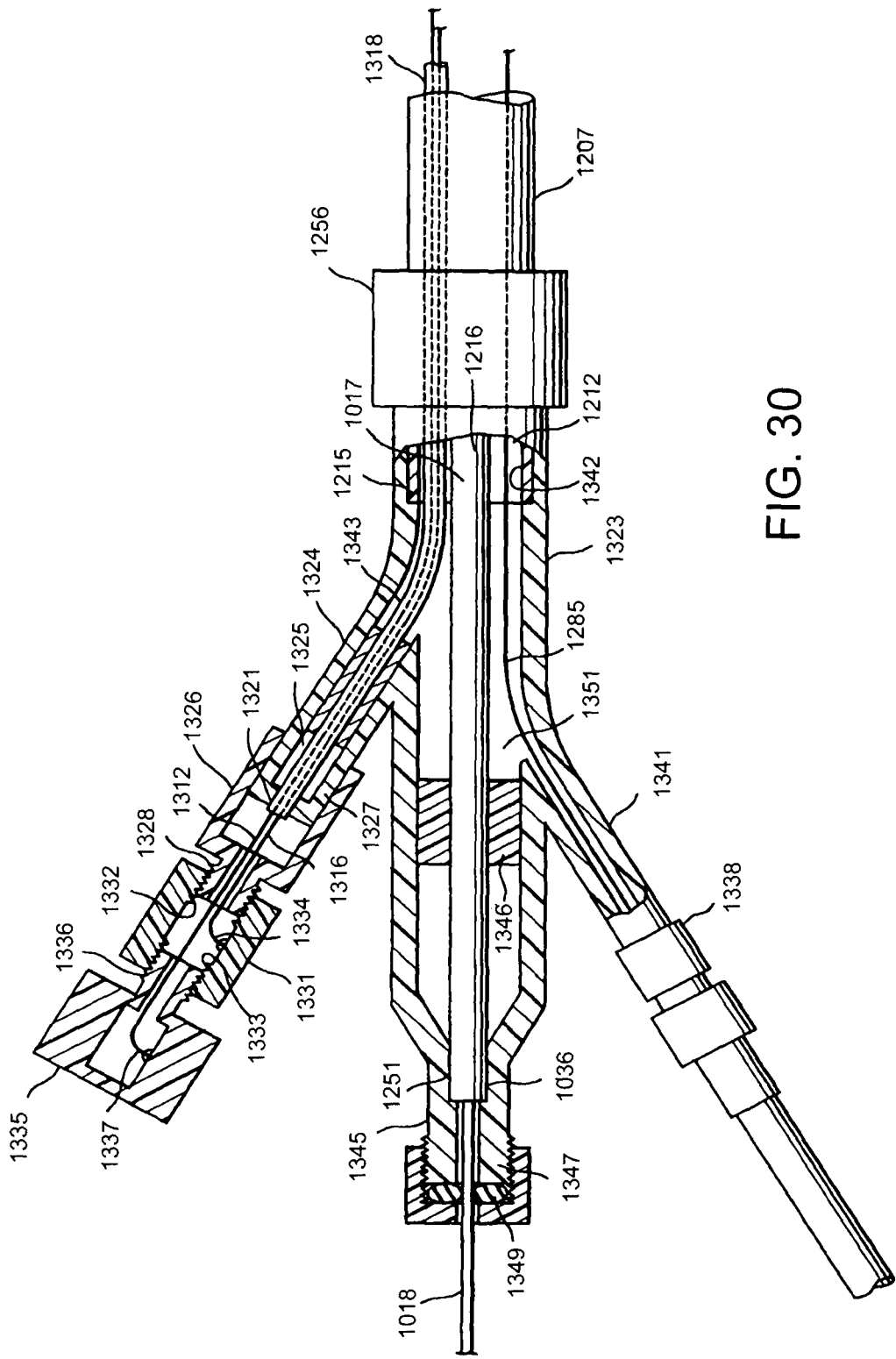
FIG. 30 is an elevational view in partial section of the proximal adapter of the delivery system shown in FIG. 27.

Referring to FIGS. 27 and 29, first release wire 1312 having distal end 1313 engages end loops 1082 of second distal belt 1022. The second distal belt 1022 is disposed about and constrains the second distal self-expanding member 1033. A second release wire 1316 having a distal end 1317 engages the end loops 1081 of the first distal belt 1021 and the end loops 1083 of the proximal belt 1023. The first distal belt 1021 is disposed about and constrains the first distal self-expanding member 1032. The proximal belt 1023 is disposed about and constrains the proximal self-expanding member 1031. A release wire tube 1318, having a proximal end 1321, as shown in FIG. 30, and a distal end 1322, shown in FIG. 29, extends from the potted section 1213 of the distal section 1303 of the delivery system 1300 to the proximal adapter 1323 shown in FIG. 30. The release wire tube 1318 has a lumen 1324, as shown in FIG. 28, that contains the first release wire 1312 and the second release wire 1316.

The proximal adapter 1323 has a first side arm 1324 with an inner lumen 1325 that secures the proximal end 1321 of the release wire tube 1318. A threaded end cap 1326 is secured to a proximal end 1327 of the first side arm 1324 and has a threaded portion 1328. A second release wire handle 1331, having a distal threaded portion 1332 and a proximal threaded portion 1333, is threaded onto the threaded end cap 1326. A proximal end 1334 of the second release wire 1316 is secured to the second release wire handle 1331. A first release wire handle 1335 has a threaded portion 1336 which is releasably threaded onto the proximal threaded portion 1333 of the second release wire handle 1331. A proximal end 1337 of the first release wire 1312 is secured to the first release wire handle 1335.

Once the outer tubular member 1053 has been proximally retracted, belts 1021-1023 can be released. This configuration allows the operator of the delivery system 1300 to first disengage and proximally retract the first release wire handle 1335 so as to first release the second distal self-expanding member 1033 without releasing or otherwise disturbing the constrained state of the first distal self-expanding member 1032 or the proximal self-expanding member 1031. Once the second distal self-expanding member 1033 has been deployed or released, the endovascular graft 1011 may be axially moved or repositioned to allow the operator to adjust the position of the graft 1011 for final deployment.

This is advantageous, particularly in the treatment of abdominal aortic aneurysms, because it allows the physician to accurately place graft 1011 into position. In many cases, it is desirable for the physician to place the graft 1011 such that the distal end of the tubular body portion 1205 of the graft is just below the renal arteries 1273, shown in FIG. 22, to prevent occlusion of the renal arteries by the tubular body portion 1205. If a self-expanding member, such as self-expanding member 1032 is radiopaque and the delivery procedure is performed using fluoroscopic imaging, adjustment of the position of the graft after release of self-expanding member is readily achievable. Because self-expanding member 1032 is immediately adjacent the distal end of the tubular body portion 1205 of the graft 1011, the ability to visualize and reposition the self-expanding member 1032 is particularly useful in order to position the distal end of the tubular body portion 1205 just below the renal arteries without occluding the renal arteries, if such positioning is indicated for the patient being treated.

Thereafter, the second release wire handle 1331 may be unscrewed or otherwise released from the end cap 1326 and proximally retracted so as to first release the first distal belt end loops 1081 and then the proximal belt end loops 1083. Of course, the position of the graft 1011 may still be adjustable even with both distal self-expanding members 1032 and 1033 deployed, depending on the particular configuration of the graft 1011 and the self-expanding members 1032 and 1033. The release of the belts 1021, 1022 and 1023 is the same or similar to that of the belts of the embodiment of FIG. 14 and occurs when the distal end of the release wires 1313 and 1317 which lock the end loops 1081-1083 together is proximally retracted past the end loops 1081-1083 of the belts 1021-1023 which are constrained.

Once the self-expanding members 1031-1033 of the endovascular graft 1011 have been deployed or released, and the graft 1011 is in a desired location, the graft 1011 can then be inflated by injection of an inflation material (not shown) into the injection port 1338 on a second side arm 1341 of the proximal adapter 1323. The inflation material is introduced or injected directly into an inner lumen 1212 of the inner tubular member 1207, as shown in FIG. 30, and travels distally between an inside surface 1342 of the inner tubular member 1207, outside surface 1343 of the release wire tube 1318 and outside surface 1216 of the guidewire tube 1017. This allows the inflation material, which can be highly viscous, to flow through the cross sectional area between the inside surface 1342 of the inner tubular member 1207 and the outside surfaces 1216 and 1343 of the release wire tube 1318 and guidewire tube 1017. This cross sectional area is large relative to the cross sectional area of the inner lumen of the inflation tube 1211 of the embodiment of FIG. 14. This results in more rapid flow of inflation material to the inflatable cuffs 1028 and 1030 and channels 1284 of the endovascular graft 1011 and decreases inflation time.

Once the inflation material, which is travelling distally in the delivery system 1300 during inflation, reaches the potted portion 1213 of the distal section 1303 of the delivery system, it then enters and flows through a lumen 1344, as shown in FIG. 29, at the proximal end 1307 of the inflation tube 1305 and into the inflation port 1283 of the graft 1011. Upon inflation of the graft 1011 with an inflation material, a release device, such as retention wire 1285 can be retracted or otherwise activated so as to de-couple the inflation tube 1305 from the inflation port 1283 of the endovascular graft 1011.

A proximal end 1036 of the guidewire tube 1017 is secured within a central arm 1345 of the proximal adapter 1323 which has a potted section 1346. A seal 1349 is disposed on a proximal end 1347 of the central arm 1345 for sealing around the guidewire 1018 and preventing a backflow of blood around the guidewire. A hemostasis adapter (not shown) can be coupled to the proximal end 1347 of the central arm 1345 in order to introduce fluids through the guidewire tube lumen 1348, as shown in FIG. 28, around an outside surface of the guidewire 1018. The potted section 1346 of the central arm 1345 prevents any injected fluids from passing into the inflation material lumen 1351 within the proximal adapter 1323 or the inner tubular member 1207.

FIG. 31 illustrates an alternative embodiment to the proximal adapters 1042 and 1323 used in the embodiments of the invention of FIG. 14 and FIG. 27. In this embodiment, the proximal adapter 1360 has a first release wire handle 1361 and a second release wire handle 1362 which are in a nested configuration. The proximal end 1334 of the second release wire 1316 is secured to the second release wire handle 1362. The proximal end 1337 of the first release wire 1312 is secured to the first release wire handle 1361. This configuration prevents the operator from inadvertently deploying or activating the second release wire 1316 prior to deployment or activation of the first release wire 1312 which could result in an undesirable endovascular graft deployment sequence.

In use, the operator first unscrews or otherwise detaches a threaded portion 1363 of the first release wire handle 1361 from an outer threaded portion 1364 of a first side arm end cap 1365 of a first side arm 1366. The first release wire handle 1361 is then proximally retracted which releases the end loops 1082 of the second distal belt 1022 as discussed above with regard to the embodiment of the invention shown in FIG. 27.

Once the first release wire handle 1361 is removed from the first side arm end cap 1365, the second release wire handle 1362 is exposed and accessible to the operator of the delivery system. A threaded portion 1367 of the second release wire handle 1362 can then be unscrewed or otherwise detached from an inner threaded portion 1368 of the first side arm end cap 1365. The second release wire handle 1362 can then be retracted proximally so as to sequentially deploy the first distal belt 1021 and self-expanding member 1032 and proximal belt 1023 and proximal self-expanding member 1031, respectively. The other functions and features of the proximal adapter 1360 can be the same or similar to those of the proximal adapters 1042 and 1323 shown in FIG. 14 and FIG. 30 and discussed above.

Optionally, this embodiment may comprise reverse or oppositely threaded portions, 1363 and 1367 respectively, of the first and second release wire handles 1361 and 1362. Thus, for instance, a counter-clockwise motion may be required to unthread threaded portion 1363 of the first release wire handle 1361 from the outer threaded portion 1364, while a clockwise motion is in contrast required to unthread threaded portion 1367 of the second release wire handle 1367 from the inner threaded portion 1368. This feature serves as a check on the overzealous operator who might otherwise prematurely unscrew or detach the threaded portion 1367 of the second release wire handle 1362 by unscrewing in the same direction as required to release the threaded portion 1363 of the first release wire handle 1361.

In another aspect of the invention, a delivery system 1400 for delivery and deployment of a bifurcated intracorporeal device, specifically, an embodiment of the invention directed to delivery and deployment of a bifurcated endovascular graft or stent is contemplated. As with all the delivery systems disclosed herein, the delivery system 1400 for a bifurcated device is configured for delivery and deployment a wide variety of intracorporeal devices. Although the focus of the specific embodiments are directed to systems for delivery of endovascular grafts or stent grafts, embodiments of the delivery systems disclosed herein can are also suitable for delivery of intravascular filters, stents, including coronary stents, other types of shunts for intracorporeal channels, aneurysm or vessel occluding devices and the like.

The structure, materials and dimensions of the delivery system 1400 for bifurcated devices can be the same or similar to the structure, materials and dimensions of the delivery systems discussed above. In addition, the structure, materials and dimensions of bifurcated grafts contemplated herein can have structure, materials and dimensions similar to those of grafts having a primarily tubular shape discussed above.

FIGS. 32-35 illustrate an embodiment of an expandable intracorporeal device in the form of a bifurcated stent-graft 1401. This embodiment includes a main body portion 1402 at a distal end 1403 of the graft 1401 that has a generally tubular cross-sectional profile when the graft takes on an expanded or deployed configuration. An ipsilateral leg 1404 and contralateral leg 1405 (short leg), both having a substantially tubular configuration when expanded or deployed, branch from the main body portion 1402 at bifurcation 1406 and extend in a proximal direction from the bifurcation 1406. The ipsilateral leg 1404 terminates proximally with a proximal self-expanding member 1407 and the contralateral leg 1405 terminates proximally with a proximal self-expanding member 1408.

The main body portion 1402 of the graft may have a transverse dimension when in an expanded or deployed state ranging from about 10 mm to about 40 mm, specifically from about 15 mm to about 30 mm. The legs 1404 and 1405 of the graft 1401 may have a transverse dimension when in an expanded or deployed state ranging from about 5 mm to about 16 mm, specifically from about 8 mm to about 27 mm. The main body portion 1402 of the graft 1401 may have a length ranging from about 2 cm to about 12 cm, specifically from about 4 cm to about 8 cm.

A second distal self-expanding member 1411 is disposed at a distal end 1412 of the main body portion 1402 of the graft 1401 as with the graft embodiments previously discussed. Also, as with other endovascular graft embodiments discussed herein, the graft 1401 may have inflatable channels and inflatable cuffs that serve, among other functions, to provide support for the graft 1401 and the inflatable channels and cuffs can have configurations which are the same or similar to those inflatable channels and cuffs of other graft embodiments discussed herein, as well as other configurations. A distal inflatable cuff 1413 is disposed at the distal end 1412 of the main body portion 1402. Proximal inflatable cuffs 1414 and 1415 are disposed on a proximal end 1416 of the ipsilateral leg 1404 and a proximal end 1417 of the contralateral leg 1405 respectively. Inflatable channels 1418 are fluid tight conduits which connect the inflatable cuffs 1413, 1414 and 1415. The inflatable channels 1418 and inflatable cuffs 1413 and 1414 are inflatable through an inflation port 1421 that may be disposed at or near the proximal end 1416 of the ipsilateral leg 1404. The inflation port 1421 may also be disposed at or near the proximal end 1417 of the contralateral leg 1405, or it may be disposed on other portions of the device as necessary. Generally, the structure and the materials used in the graft 1401 (both the graft portion and the self-expanding members) can be similar to the structure and materials of the other graft embodiments discussed above. In one particular embodiment, the main body portion and legs of the graft are made of expanded polytetrafluoroethylene (ePTFE) and the self-expanding members are made of nickel titanium, stainless steel or the like.

A first distal self-expanding member 1422 is secured to the second distal self-expanding member 1411 as shown in FIG. 32. This configuration is similar to that of endovascular graft 1011 illustrated in FIGS. 14-19B, 23-25 and 27-29 above. Graft 1011 has first and second distal self-expanding members 1032 and 1033 which may be deployed in any desired sequence. In a particular embodiment having first and second distal self-expanding members, it may be desirable to first deploy the second distal self-expanding member 1033 prior to deploying the first distal self-expanding member 1032. As discussed above, deploying the second distal self-expanding member 1033 first may allow the operator to accurately adjust the axial position of the graft in the body lumen or vessel to within one to several millimeters before deploying the first distal self-expanding member 1032. Using this technique, deployment of the second distal self-expanding member 1033 alone provides sufficient resistance to axial displacement of the graft 1011 for the graft position to be maintained in normal blood flow, but still allows deliberate axial displacement by the operator to achieve a desired axial position. This may be particularly important if tissue-penetrating members are included on the distal-most or first distal self-expanding member 1032. If such tissue penetrating members are used on the first distal self-expanding member 1032, axial movement may be difficult or even impossible once this member 1032 is deployed without risking damage to the body lumen or vessel. As such, accurate axial placement of the graft 1011 prior to deployment of the first distal self-expanding member 1032 can be critical.

In addition, although not shown in the figures, this graft embodiment 1401 may include two or more proximal self-expanding members disposed on one or both of the ipsilateral leg 1404 and/or contralateral leg 1405. These self-expanding members may have a configuration similar to that of the first and second distal self-expanding members 1411 and 1422

Figure 36:
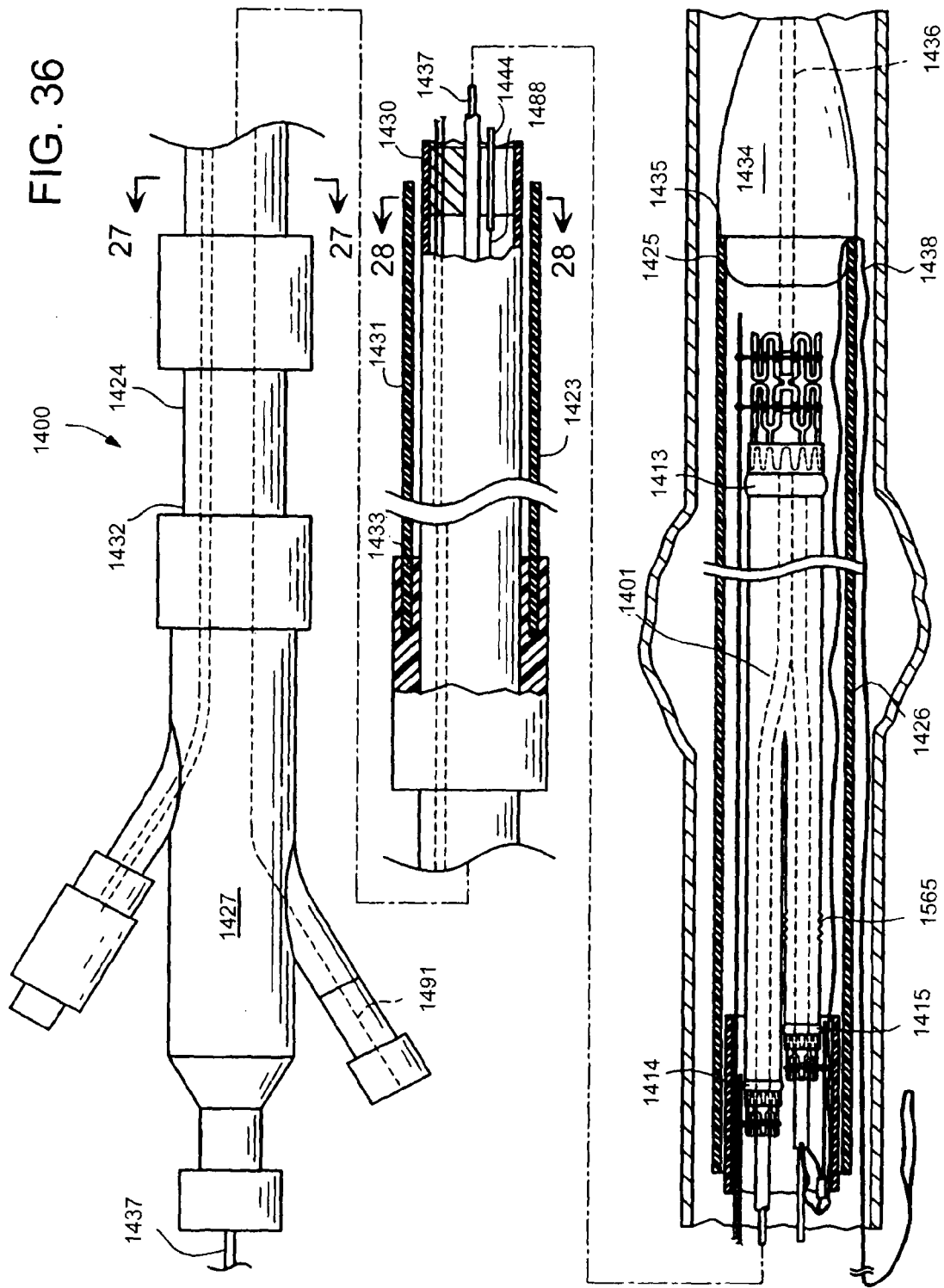
FIG. 36 is an elevational view in partial section of an embodiment of a delivery system having features of the invention.

FIGS. 36-45 illustrate an embodiment of a delivery system 1400 having features of the invention. FIG. 36 shows delivery system 1400 in partial section having an elongate shaft 1423 with a proximal end 1424, a distal end 1425 and a distal section 1426. A proximal adapter 1427 is disposed at the proximal end 1424 of the elongate shaft 1423 and houses the controls that enable the operator to manipulate elements at the distal section 1426 of delivery system 1400 to release and deploy the graft 1401, including inflating the graft channels 1418 and cuffs 1413, 1414 and 1415. The elongate shaft 1423 has an inner tubular member 1430 and an outer tubular member 1431 disposed about the inner tubular member 1430. The outer tubular member 1431 is generally configured to slide in an axial direction over the inner tubular member 1430. A proximal end 1432 of the inner tubular member 1430 is secured to or disposed on the proximal adapter 1427. The inner and outer tubular members 1430 and 1431 may be made of polymeric materials, e.g., polyimides, polyester elastomers (Hytrel®), or polyether block amides (Pebax®), and other thermoplastics and polymers. The outside diameter of the outer tubular member 1431 may range from about 0.1 inch to about 0.4 inch; specifically from about 0.15 inch to about 0.20 inch. The wall thickness of the outer tubular member 1431 may range from about 0.002 inch to about 0.015 inch, specifically from about 0.004 inch to about 0.008 inch. The proximal adapter 1427 is generally fabricated from a polymeric material such as polyethylene, acetal resins (Delrin®), etc., but can also be made from any other suitable material.

Bifurcated stent graft 1401 is shown in FIGS. 36-41 disposed within the distal section 1426 of the elongate shaft 1423 in a constrained configuration. The outer tubular member 1431 is disposed about the graft 1401 in the constrained state but can be retracted proximally so as to expose the constrained graft 1401 by proximally retracting a proximal end 1433 of the outer tubular member 1431. As illustrated more fully in FIG. 50, a distal nosepiece 1434 may be disposed on a distal end 1435 of the outer tubular member 1431 and forms a smooth tapered transition from a guidewire tube 1436 to the outer tubular member 1431. This transition helps to facilitate the tracking of the outer tubular member 1431 over a guidewire 1437. In order to form this smooth transition, the nosepiece 1434 may have a length to major diameter ratio ranging from about 3:1 to about 10:1 (the "major diameter" being defined as the largest diameter of the nosepiece). The outer tubular member 1431 is not typically permanently secured to the nosepiece 1434 and may be retractable from the nosepiece 1434 during the deployment sequence. A secondary release cable 1438 extends from an opening in the distal section of the elongate shaft.

Figure 37:
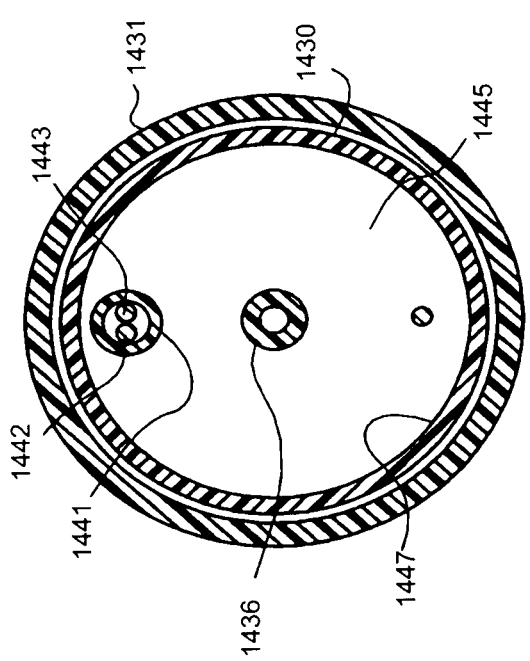
FIG. 37 is a transverse cross sectional view of the delivery system of FIG. 36 taken along lines 37-37 of FIG. 36.

FIG. 37 shows the inner tubular member 1430 disposed within the outer tubular member 1431 and the guidewire tube 1436 disposed within the inner tubular member 1430. The guidewire tube 1436 may be made from polymeric materials such as polyimide, polyethylene, polyetheretherketones (PEEK™), or other suitable polymers, and may have an outside diameter ranging from about 0.02 inch to about 0.08 inch, specifically about 0.035 inch to about 0.055 inch. The guidewire tube 1436 wall thickness may range from about 0.002 inch to about 0.025 inch, specifically from about 0.004 inch to about 0.010 inch.

A release member tube in the form of a release wire tube 1441 is disposed about a distal primary release member in the form of a distal primary release wire 1442. The release wire tube 1441 is also disposed about a proximal primary release member in the form of a proximal primary release wire 1443. Both the release member tube 1441 and an inflation tube 1444 are disposed within an inner lumen 1445 of the inner tubular member 1430. The outside diameter of the release wire tube 1441 may range from about 0.01 inch to about 0.05 inch, specifically about 0.015 inch to about 0.025 inch. The wall thickness of the release wire tube 1441 may range from about 0.001 inch to about 0.006 inch, specifically from about 0.002 inch to about 0.004 inch.

The outside diameter of the inflation tube 1444 may range from about 0.02 inch to about 0.10 inch; specifically from about 0.04 inch to about 0.08 inch. The inflation tube 1444 wall thickness may range from about 0.002 inch to about 0.025 inch; specifically from about 0.003 inch to about 0.010 inch.

Figure 38:
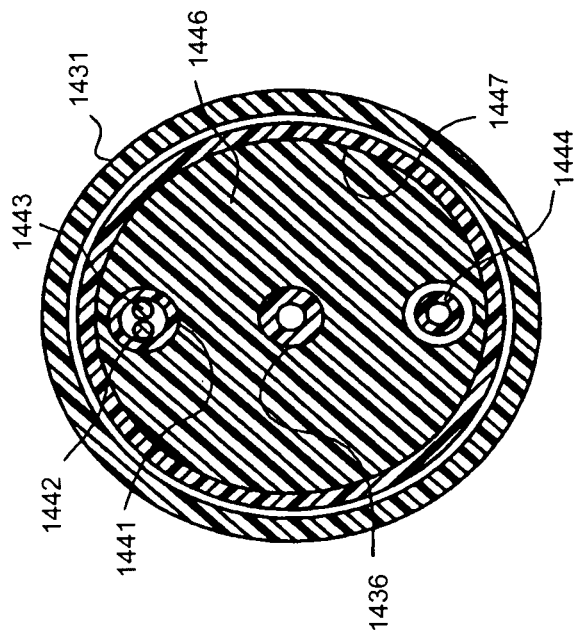
FIG. 38 is a transverse cross sectional view of the delivery system of FIG. 36 taken along lines 38-38 of FIG. 36.

In FIG. 38, a potted portion 1446 is disposed between an inner surface 1447 of a distal end 1448 of the inner tubular member 1430, the release wire tube 1441, the guidewire tube 1436 and the inflation tube 1444. The potted portion 1446 seals the inner lumen 1445 of the inner tubular member 1430 from bodily fluids that are exposed to the constrained graft 1401 and potted portion 1446 once the outer tubular member 1431 is proximally retracted. The potted portion 1446 may be made from adhesives, thermoforming plastics, epoxy, metals, or any other suitable potting material. Alternatively, a molded or machined plug may be bonded or affixed to the distal end of the inner tubular member, with lumens to accommodate the passage of tubes 1441, 1436 and 1444.

Figure 39:
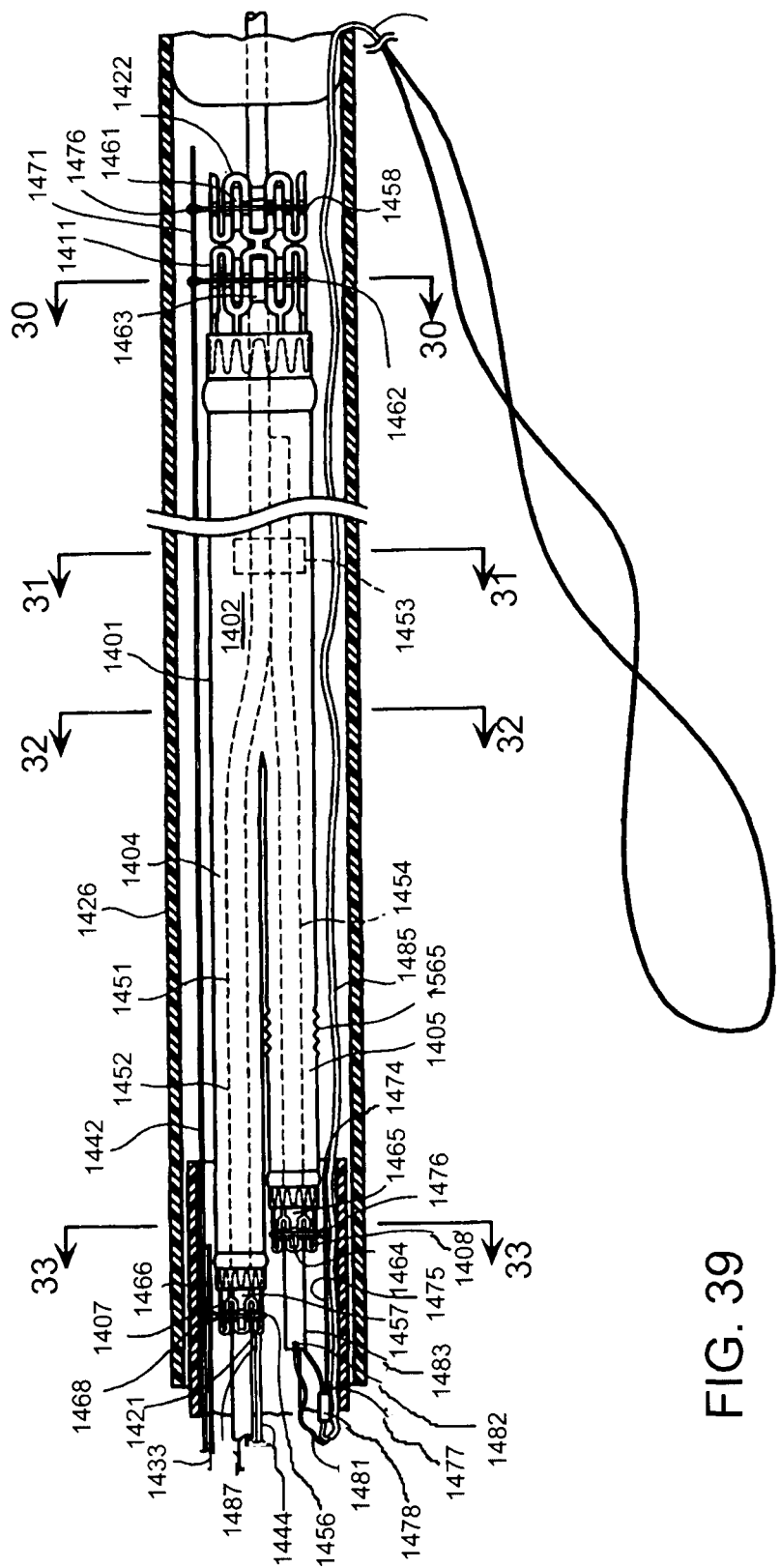
FIG. 39 is an elevational view in partial section showing an enlarged view of a distal portion of the delivery system of FIG. 36.

A more detailed view of the distal section 1426 of the elongate shaft 1423 is shown in partial section in FIGS. 39-43. A distal section 1451 of the guidewire tube 1436 serves as a primary belt support member 1452 and is disposed within the main body portion 1402 and ipsilateral leg 1404 of the graft 1401. Alternatively, the primary belt support member 1452 may be disposed adjacent the graft main body portion 1402 and ipsilateral leg 1404. A secondary belt support member housing 1453 is secured to the primary belt support member 1452. An additional length of guidewire tube or other elongate member serving as a secondary belt support member 1454 is slidably disposed within an appropriately configured lumen 1455 of the housing 1453. The secondary belt support member 1454 is shown in FIG. 39 disposed within the graft main body portion 1402 and contralateral leg 1405; however, the secondary belt support member 1454 may also be disposed adjacent the contralateral leg 1405, regardless of whether the primary belt support member 1452 is disposed adjacent or within the main body portion 1402 and ipsilateral leg 1404.

The secondary belt support member housing lumen 1455 and secondary support member 1454 cross sections may be keyed, singly or in combination, to allow relative sliding motion without relative rotation motion and therefore limit any twisting of the secondary support member 1454 and the contralateral leg 1405. The secondary belt support member 1454 may be made from alloys such as nickel titanium, stainless steel, or polymeric materials such as polyimide and can have an outside transverse dimension ranging from about 0.01 inch to about 0.06 inch.

A proximal primary belt 1456 is shown in FIG. 39 disposed about and radially constraining the proximal self-expanding member 1407 of the ipsilateral leg 1404. This proximal self-expanding member 1407 in turn is disposed about a bushing 1457 that is shown as cylindrical in form, but which may have other configurations as well. The bushing 1457 is secured to the primary belt support member 1452 adjacent the proximal self-expanding member 1407 of the ipsilateral leg 1404.

A first distal primary belt 1458 is disposed about and radially constraining the first distal self-expanding member 1422, which itself is disposed about a cylindrical bushing 1461. A second distal primary belt 1462 is disposed about and radially constraining the second distal self-expanding member 1411 and the second distal self-expanding member 1411 is disposed about a cylindrical bushing 1463.

A secondary belt 1464 is shown disposed about and radially constraining the proximal self-expanding member 1408 of the contralateral leg 1405. This proximal self-expanding member 1408 is disposed about a bushing 1465 which is cylindrical in shape.

As with the other embodiments of the present invention, the belts 1456, 1458, 1462 and 1464 are typically made from nickel titanium, an alloy that is capable of exhibiting a unique combination of high strain without elastic deformation, high strength and biocompatability. However, any other suitable materials may be used including other metallic alloys such as stainless steel, high strength fibers such as carbon, Kevlar®, polytetrafluoroethylene (PTFE), polyimide, or the like. The outer transverse dimension or diameter of the belts 1456, 1458, 1462 and 1464 can be from about 0.002 inch to about 0.012 inch; specifically about 0.004 inch to about 0.007 inch.

A distal portion 1466 of the proximal primary release wire 1443 is disposed within end loops 1468 of the proximal primary belt 1456 so as to releasably secure the proximal self-expanding member 1407 of the ipsilateral leg 1404 in a constrained state. The proximal primary belt 1456 may be disposed about the self-expanding member 1407 in a hoop-like configuration. The proximal self-expanding member 1407 exerts outward radial pressure on the releasably secured belt 1456. The primary proximal release wire 1443 is axially moveable within the end loops 1468 of the proximal primary belt 1456 to allow for release of the belt by proximal retraction of the primary proximal release wire 1443 in the same manner as described above with respect to other embodiments of the present invention.

Likewise, a distal portion 1471 of the distal primary release wire 1442 is disposed within end loops 1472 of the second distal primary belt 1462 which radially constrains the second distal self-expanding member 1411. The second distal primary belt 1462 is formed in a hoop configuration about the second distal self-expanding member 1411 and the second distal self-expanding member 1411 exerts outward radial force on the second distal primary belt 1462. The distal primary release wire 1442 is axially moveable within the end loops 1472 of the second distal primary belt 1462 to allow for release of the radial constraint as discussed above with respect to the proximal primary release wire 1443 and as discussed above for other embodiments of the present invention. The distal portion 1471 of the distal primary release wire 1442 is also disposed within end loops 1473 of the first distal primary belt 1458 and radially constrains the first distal self-expanding member 1422 in a similar fashion.

Although the distal primary release wire 1442 and proximal primary release wire 1443 are shown as two separate components, the release wires 1442 and 1443 could be combined into a single release member, such as the branched release wire 1150 shown in FIG. 20I above. A branched release wire is capable of releasing multiple belts in a desired sequence by proper configuration of the lengths of the various branches of the wire. The relative amount of the release wire extending beyond the looped ends of the belt as indicated by reference numeral 1156 in FIG. 20I controls the timing of the release of the belts. Alternatively, a single release wire may engage both distal and proximal primary belts 1456, 1458 and 1462. As this single release wire 1150 is moved proximally, the first distal primary belt 1458 is first released, followed by the release of the second distal primary belt 1462 and then release of the proximal primary belt 1456.

A distal portion 1474 of a secondary release member in the form of a secondary release wire 1475 is disposed within end loops 1476 of a secondary belt 1464 which radially constrains the proximal self-expanding member 1408 of the contralateral leg 1405. The proximal self-expanding member 1408 of the contralateral leg 1405 exerts outward radial force on the secondary belt 1464 when the self-expanding member 1408 is in a constrained configuration. The secondary release wire 1475 is axially moveable within the end loops 1476 of the secondary belt 1464.

A proximal end 1477 of the secondary release wire 1475 is secured to an actuator hub 1478. A release strand 1481 is secured to the actuator hub 1478 and is attached to the secondary belt support member 1454, and is shown by way of example in the embodiment of FIG. 39 as being looped through a hole 1482 in the proximal end 1483 of the secondary belt support member 1454. Both portions of the release strand 1481 that are looped through the proximal end 1483 of the secondary belt support member 1454 pass into an inner lumen 1484 of a release strand tube 1485 as seen in FIG. 40. The release strand tube 1485 passes through an aperture 1486 in the distal end 1435 of the outer tubular member 1431. Release strand 1481 may comprise any filamentary thread or wire, metallic, polymeric, or otherwise, suitable for manipulation as will be herein described. It also may be braided or twisted if desired. The release strand 1481 may be made of a filamentary thread of ePTFE.

As discussed above with respect to other embodiments, the release wires 1442, 1443 and 1475 are generally made from a biocompatible high strength alloy such as stainless steel, but can also be made from any other suitable materials. Examples include other metallic alloys such as nickel titanium, non-metallic fibers such as carbon, polymeric materials, composites thereof, and the like. As discussed above, the diameter and stiffness of the release wires 1442, 1443 and 1475 can be important with respect to the diameter and stiffness of the belts 1456, 1458, 1462 and 1464.

The configuration of the end loops 1468, 1472, 1473 and 1476 of the belts 1456, 1458, 1462 and 1464 may vary to suit the particular embodiment of the delivery system 1400 and device to be delivered. For example, FIGS. 20C-20H illustrate a variety of belt and end loop configurations that may be suitable for delivery systems for bifurcated devices. Referring to FIG. 20C, belts 1112 and 1114 are shown having a twisted configuration which has a tendency to reduce snagging or entanglement of the belts 1112 and 1114 after deployment and release of the belts from a constrained configuration. In addition, FIG. 20C illustrates an angle a that belts 1112 and 1114 make with respect to line 1125. In one embodiment, belts 1112 and 1114 would be substantially parallel to each other when in an unconstrained state such that this angle is approximately ninety degrees. It may also be desirable to use belts that have end loops that have different cross sectional areas (or transverse dimensions). For example, FIG. 20E shows end loops 1081' and 1081" constrained by release wire 1024. We have found that, depending on the transverse dimension and material of loop 1081' disposed within loop 1081", elastic deformation of loop 1081' can hinder the release process when release wire 1024 is proximally retracted. Therefore, it may be desirable to make loop 1081' from a material that is substantially smaller in cross sectional area or transverse dimension that that of loop 1081". In a particular example, loop 1081' is made from nickel titanium wire having a diameter of about 0.003 to about 0.005 inch, and loop 1081" is made from the same material having a diameter ranging from about 0.005 to about 0.007 inch.

Figure 44:
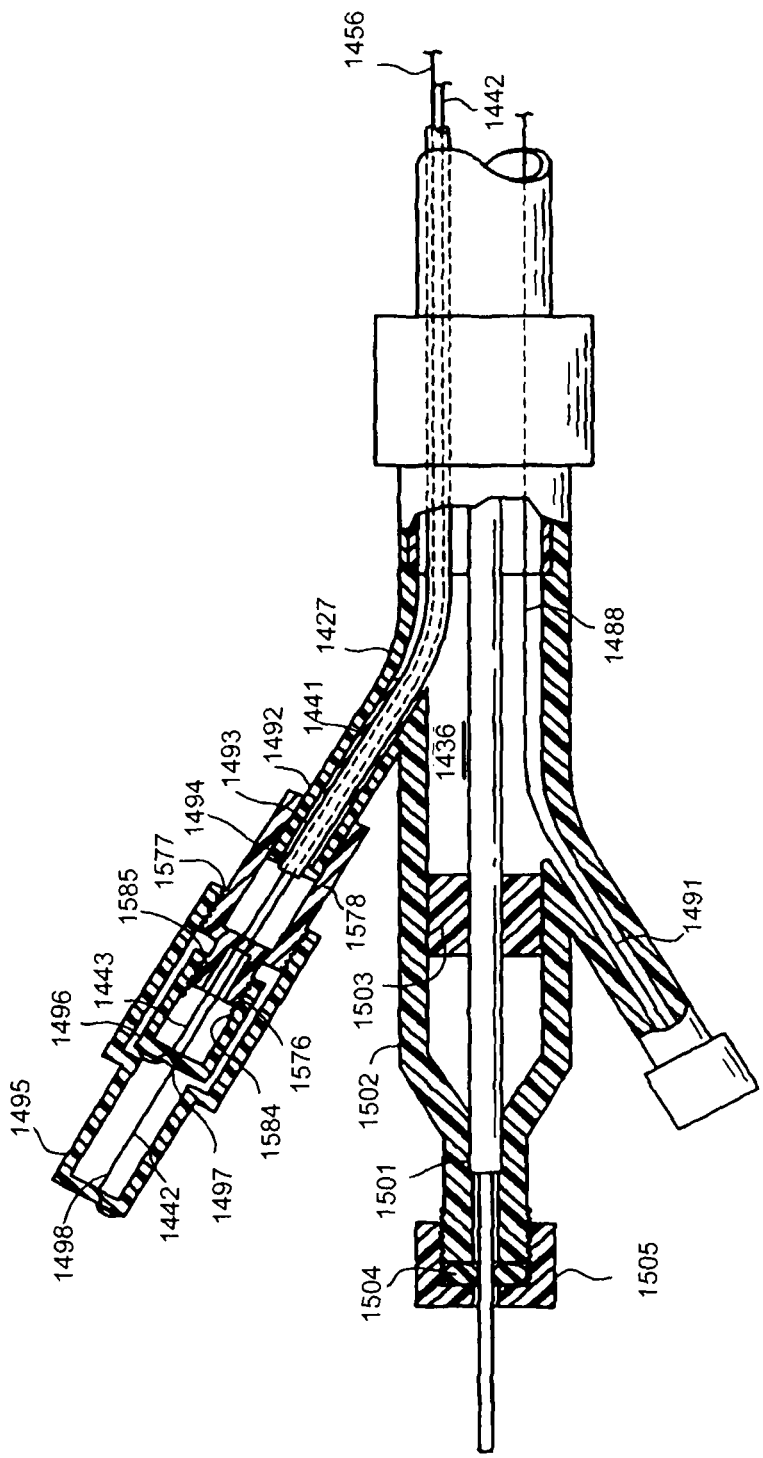
FIG. 44 is an elevational view in partial section of the proximal adapter of the delivery system of FIG. 36.

Inflation port 1421 extends proximally from the proximal end 1416 of the ipsilateral leg 1404 of the graft 1401. The inflation port 1421 is coupled to a distal end 1487 of the inflation tube 1444 by a retention mechanism, such as a retention wire 1488, the operation of which can be the same or similar to like embodiments of retention wire 1285 discussed above. Typically, the retention wire 1488 extends from the inflation port 1421 proximally to the proximal adapter 1427 of delivery system 1400. The distal end 1487 of the inflation tube 1444 can be disengaged from the inflation port 1421 by pulling on a proximal end 1491 of retention wire 1488, as shown in FIG. 44. The retention wire 1488 may be a small diameter wire made from a material such as a polymer, stainless steel, nickel titanium, other alloy or metal, or composite; in a particular embodiment of the invention, retention wire 1488 may be a spring formed of a variety of suitable spring materials. Alternatively, the retention wire 1488 may have a braided or stranded configuration.

FIG. 44 illustrates proximal adapter 1427 which is suitable for use with embodiments of the present invention. The proximal adapter 1427 houses the proximal termination of the primary release wires 1442 and 1443, guidewire tube 1444, retention wire 1488 and release wire tube 1441. The proximal adapter 1427 has a first side arm 1492 with an inner lumen 1493 that secures the proximal end 1494 of the release wire tube 1441. The proximal adapter 1427 has a distal primary release wire handle 1495 and a proximal primary release wire handle 1496 that are disposed in a nested configuration on the first side arm 1492. A proximal end 1497 of the proximal primary release wire 1443 is secured to the proximal primary release-wire handle 1496. A proximal end 1498 of the distal primary release wire 1442 is secured to the distal primary release wire handle 1495. This configuration prevents the operator from inadvertently deploying or activating the proximal primary release wire 1443 prior to deployment or activation of the distal primary release wire 1442 which could result in an undesirable graft 1401 deployment sequence.

A proximal end 1501 of the guidewire tube 1436 is secured within a central arm 1502 of the proximal adapter 1427 that has a potted section 1503. A seal 1504 may be disposed on a proximal end 1505 of the central arm 1502 for sealing around the guidewire lumen and preventing a backflow of fluid. The potted section 1503 of the central arm 1502 prevents any injected fluids from passing into the inflation material lumen 1506 within the proximal adapter 1427 or the inner tubular member 1430. The other functions and features of the proximal adapter 1427 may be the same or similar to those of the proximal adapters 1042 and 1323 shown in FIG. 14 and FIG. 30 and discussed above.

Figure 45:
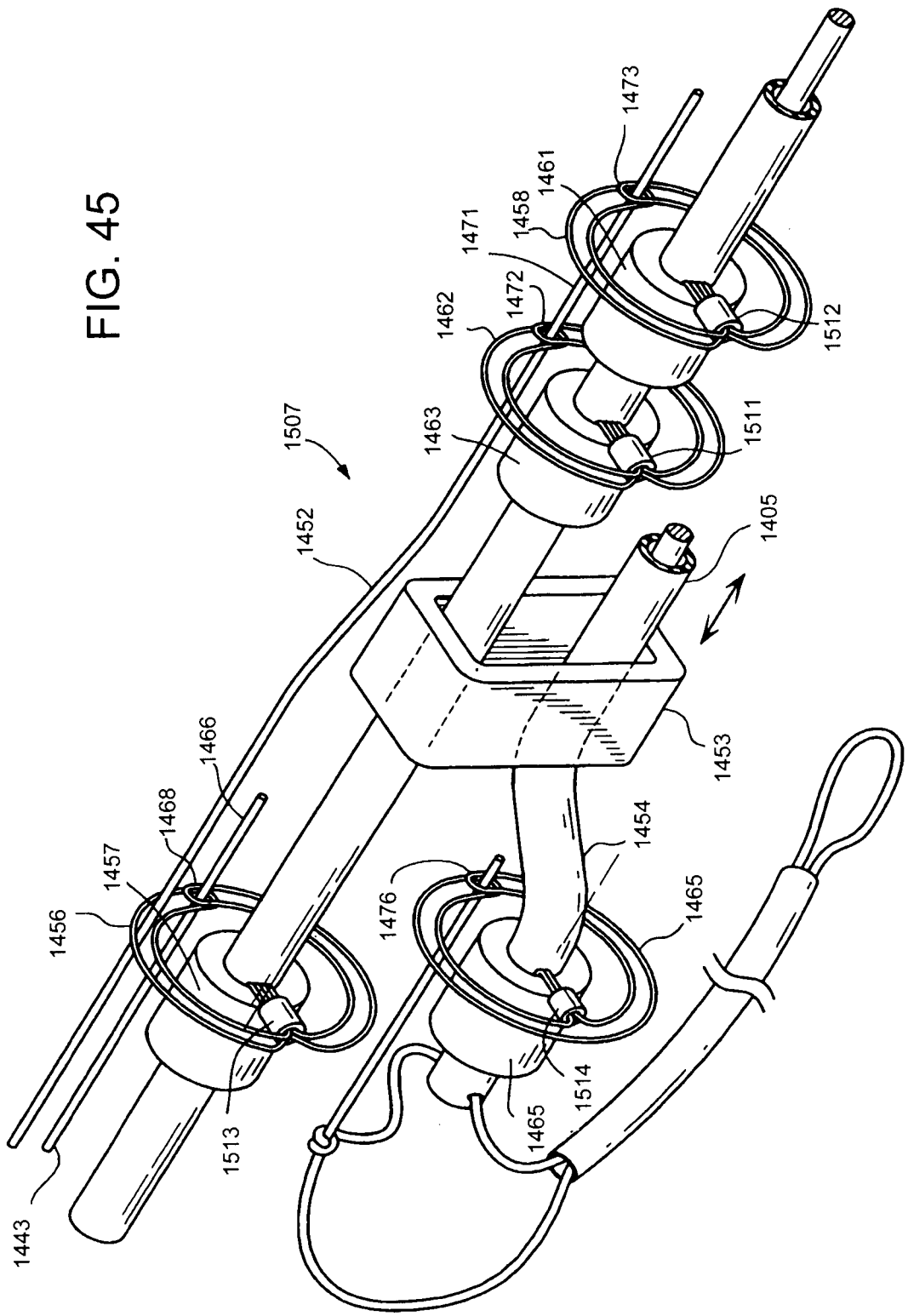
FIG. 45 is a perspective view of the belt support member assembly at a distal portion of the delivery system of FIG. 36.

FIG. 45 illustrates a belt support member assembly 1507 of the delivery system 1400. The distal end 1508 of the secondary belt support member 1454 is slidingly disposed within the secondary belt support member housing 1453 which is secured to the primary belt support member 1452. The second distal primary belt 1462 is secured to the primary belt support member 1452 (which in this embodiment is the guidewire tube 1436) and extends radially therefrom through an optional second distal primary standoff tube 1511. Similar optional first distal primary standoff tube 1512, proximal primary standoff tube 1513 and optional secondary standoff tube 1514 are disposed on the first distal primary belt 1458, proximal primary belt 1456 and secondary belt 1464, respectively.

In general, the various features and components (including, e.g., details of various embodiments of the release wires, the self-expanding members, belts, inflation port and tube, guidewire tube, standoff tubes, proximal adapter and its associated components, the materials and dimensions for each of the various components, etc.) as discussed herein with respect to those embodiments of FIGS. 14-31 may be used in the bifurcated embodiments of the present invention as discussed herein and as illustrated in FIGS. 32-45.

Figure 46:
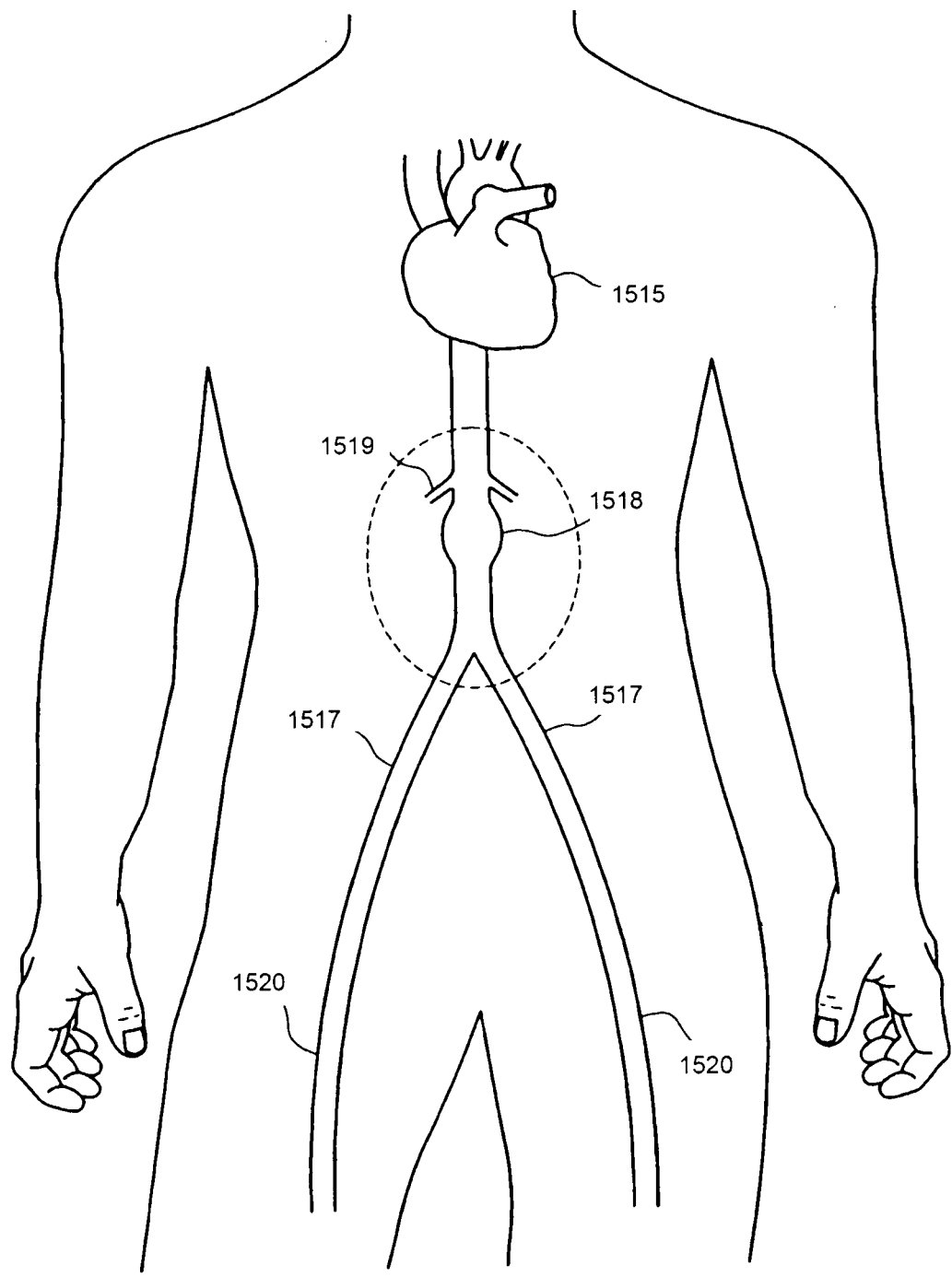
FIG. 46 illustrates a portion of the internal vasculature of a patient, including the aorta, iliac and femoral arteries branching therefrom.

In use, the delivery system 1400 for delivery of a bifurcated intracorporeal device, specifically, a bifurcated graft 1401, can be operated in a similar fashion to the delivery systems discussed above. FIG. 46 illustrates generally the anatomy of a patient's heart 1515, aorta 1516 and iliac arteries 1517. The aorta extends from the heart 1515 and descends into the abdomen of the patient's body. An aneurysm 1518 is disposed in the aorta 1516 just below the renal arteries 1519. The aorta 1516 branches into the right and left iliac arteries 1517 below the aneurysm, which then become the femoral arteries 1520.

Figure 47:
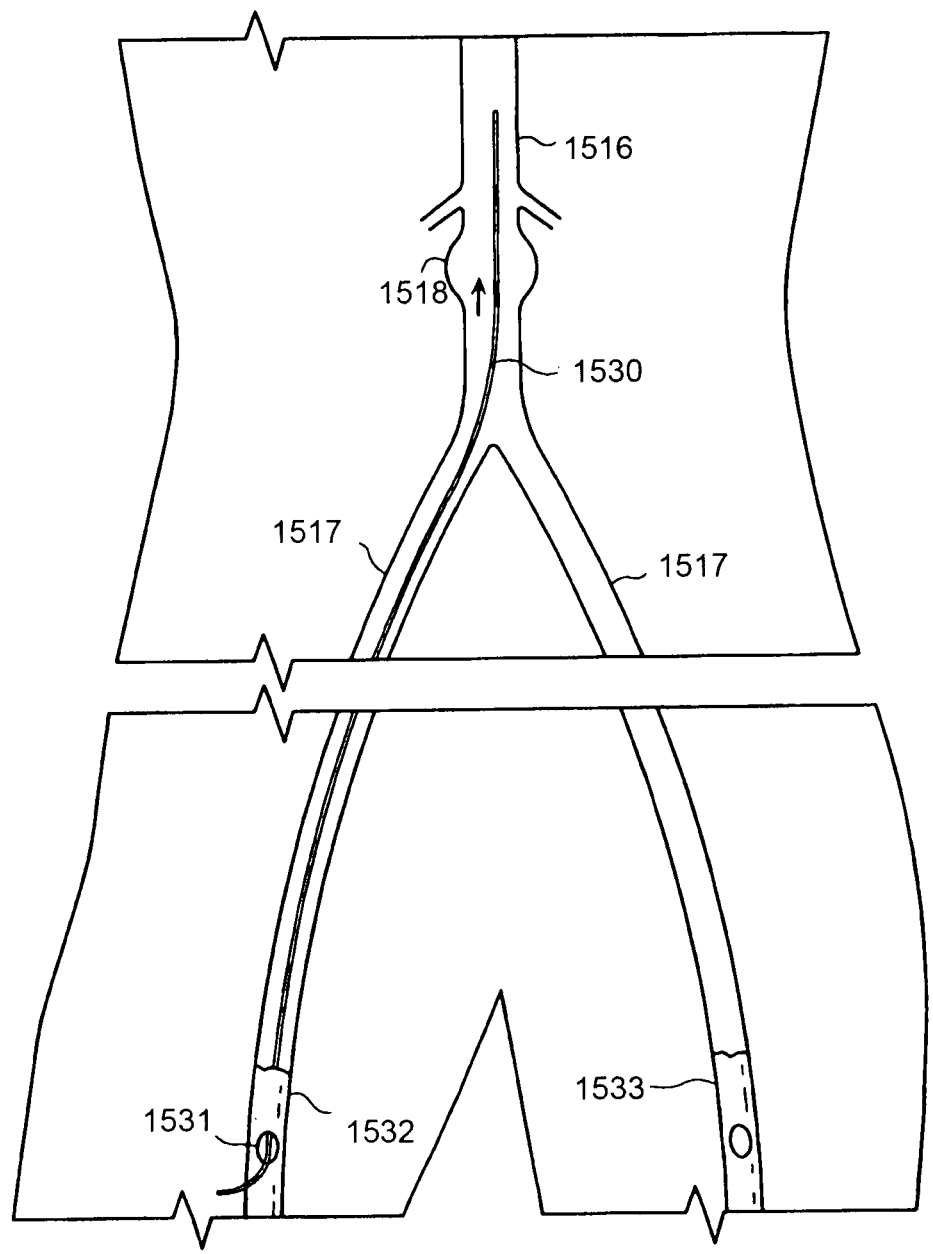
FIG. 47 is a magnified view of the abdominal aorta area of the patient shown in FIG. 46 and shows a guidewire positioned in the aorta from the right iliac artery.

One delivery procedure of the present invention begins with delivery of a first guidewire 1530 into an access hole 1531 in a femoral artery, the right femoral artery 1532 for the procedure depicted in FIG. 47, and advanced distally through the iliac artery 1517 and into the patient's aorta 1516. Access into the femoral artery 1532 is generally accomplished with a standard sheath and trocar kit, although sheathless access may also be employed. It should be noted that although the procedure described herein and illustrated in FIGS. 47-65 is initiated in the right femoral artery 1532, the same procedure could be carried out beginning in the left femoral artery 1532 with the orientation reversed. A vasodilator may optionally be administered to the patient at this point as previously discussed. If desired, a vasodilator may also be administered later in the procedure, but preferably prior to or simultaneous with the step of introducing inflation material into the graft 1401.

Figure 48:
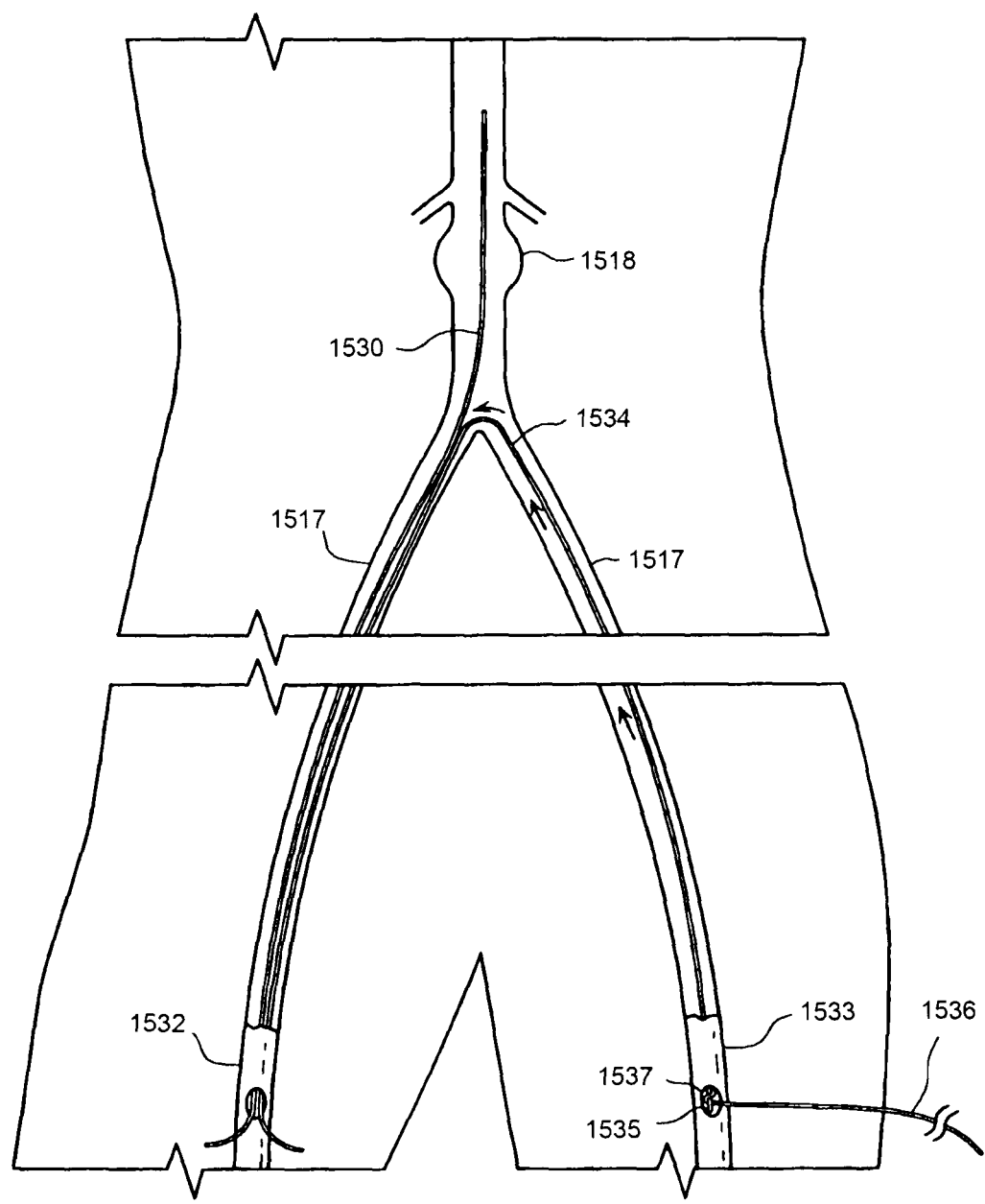
FIGS. 48-50 illustrate the magnified view of the abdominal aorta of the patient shown in FIG. 46 and depict a deployment sequence of the bifurcated endovascular stent graft of FIG. 32 with the delivery system of FIG. 36.

With the first guidewire 1530 positioned across the aneurysm 1518, a second guidewire 1534 is then introduced into the ipsilateral or right femoral artery 1532 and guided into the iliacs 1517 and then back down into the contralateral or left femoral artery 1533 as shown in FIG. 48. A distal end 1535 of the second guidewire 1534 may then be captured with a snare 1536 or similar device inserted through an access hole 1537 in the left femoral artery 1533. The distal end 1535 of the second guidewire 1534 may then be pulled out of the left femoral artery 1533 through the same left femoral artery access hole 1537, providing a continuous length of wire passing through each iliac artery 1517 via the left and right femoral artery access holes 1531 and 1537 as shown in FIG. 48.

Figure 49:
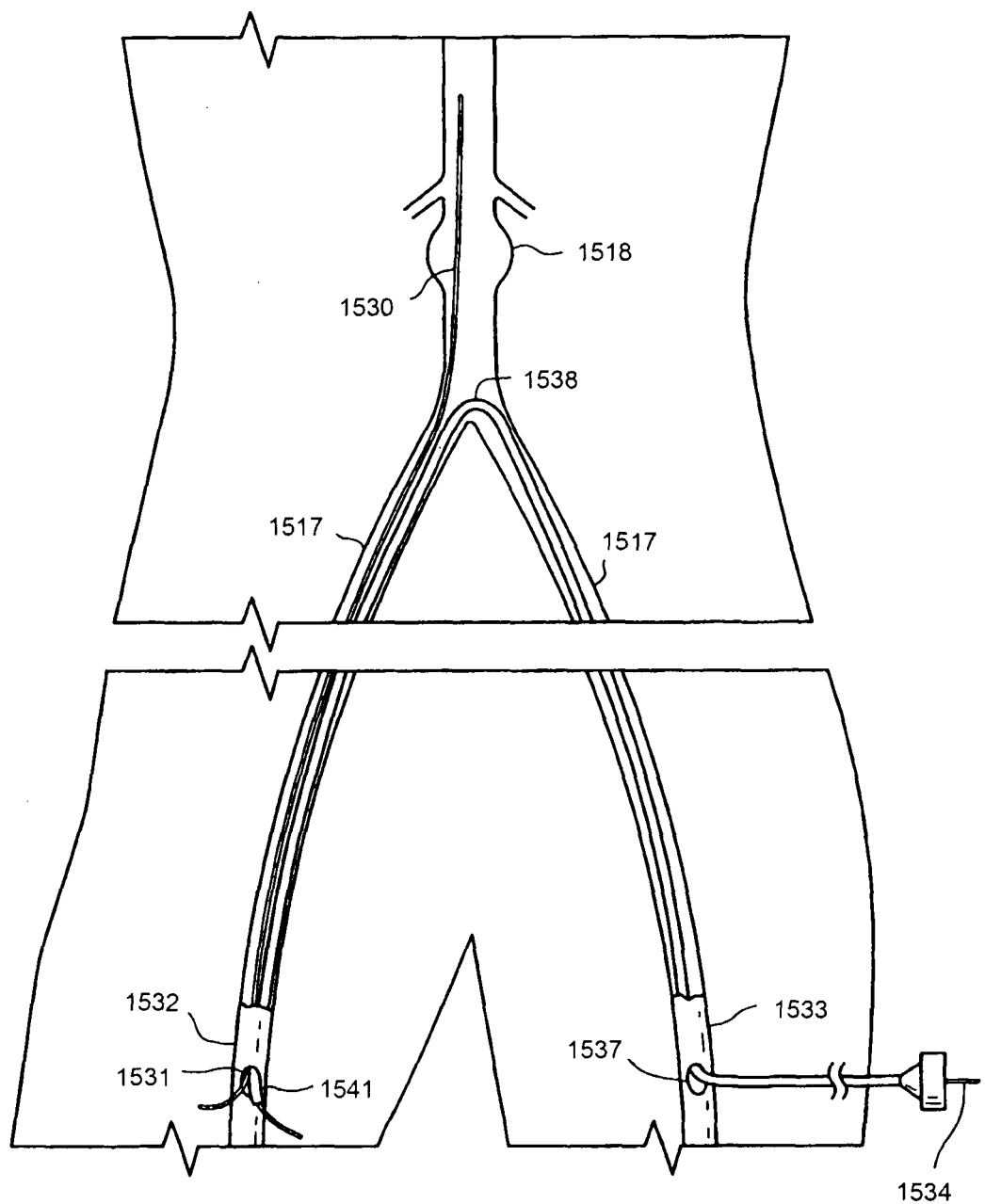
Figure 50:
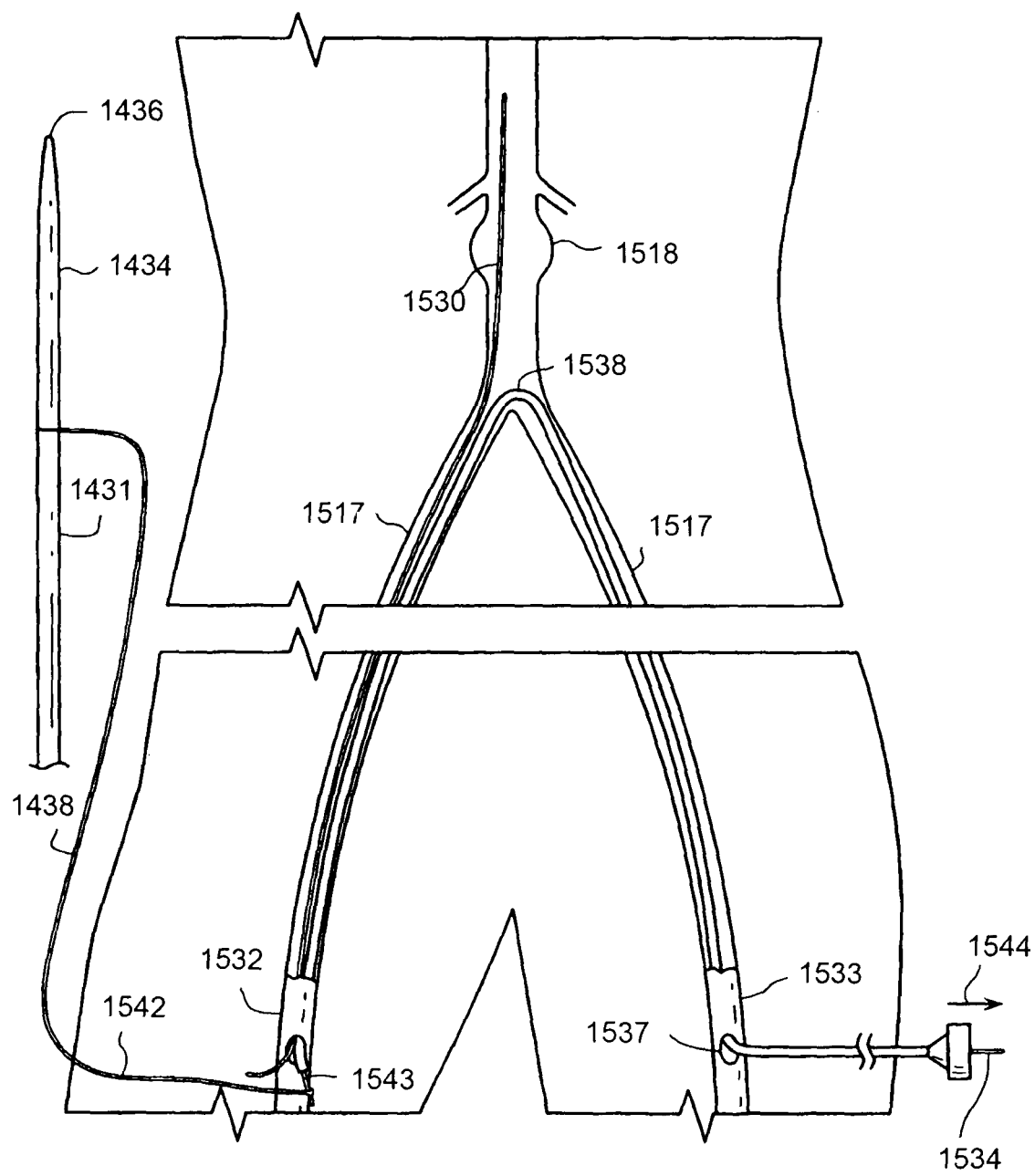

Once the second guidewire 1534 exits the access hole 1537 in the left femoral artery 1533, a tubular catheter 1538 may be advanced over the second guidewire 1534 through the left femoral artery access hole 1537 so as to extend out of the body from the access hole 1531 in the right femoral artery 1532 as shown in FIG. 49. This provides a continuous conduit between the right and left iliac arteries 1517. With a distal end 1541 of the tubular catheter 1538 extending from the access hole 1531 in the right femoral artery 1532, a distal end 1542 of the secondary release cable 1438 may then be affixed to a proximal end 1543 of the second guidewire 1534 as shown in FIG. 50. For purposes of simplicity, the secondary release cable 1438 is shown in, e.g., FIGS. 50-53 in schematic form as a single strand. However, it is understood that the term "secondary release cable" encompasses a single or multiple-component feature of the present invention that may be used to assist in the deployment of the graft. For instance, in the embodiment depicted herein, the secondary release cable 1438 represents the combination of the release strand 1481 and release strand tube 1441 discussed above in conjunction with, e.g., FIG. 39. Other variations of this combination are within the scope of the present invention.

Figure 51:
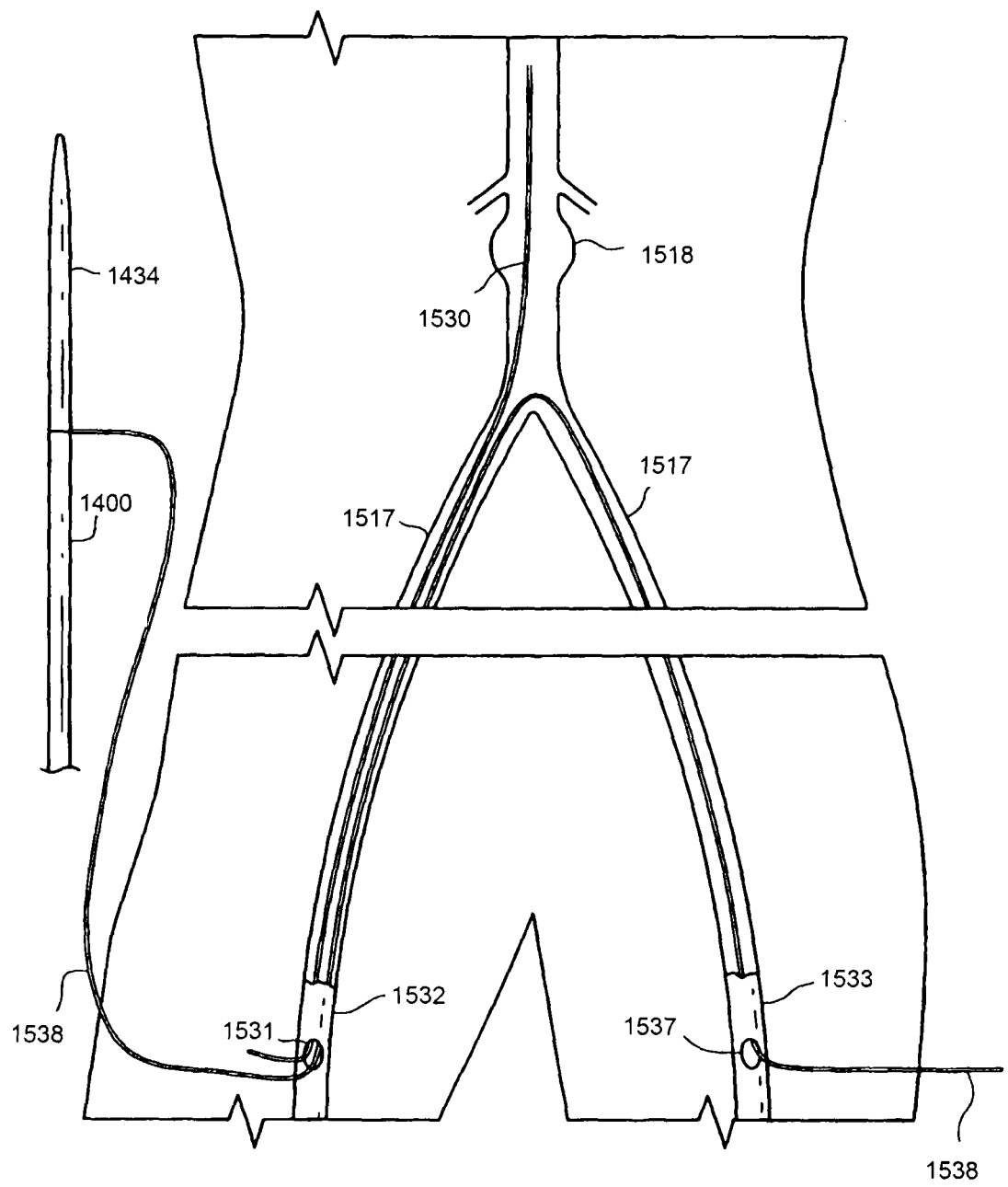
FIGS. 51-65 continue to illustrate a deployment sequence of the bifurcated endovascular stent graft of FIG. 32.

The second guidewire 1534 is then pulled out of the tubular catheter 1538 from the left femoral artery access hole 1537, in the direction indicated by the arrow 1544 in FIG. 50, so that the secondary release cable 1438 then extends through the tubular catheter 1538 from the right iliac artery to the left iliac artery. The tubular catheter 1538 may then be withdrawn, leaving the secondary release cable 1438 extending through the left and right iliac arteries 1517 from the access hole 1531 in the right femoral artery 1532 to the access hole 1537 in the left femoral artery 1533 as shown in FIG. 51. The first guidewire 1530 remains in position across the aneurysm 1518.

Figure 52:
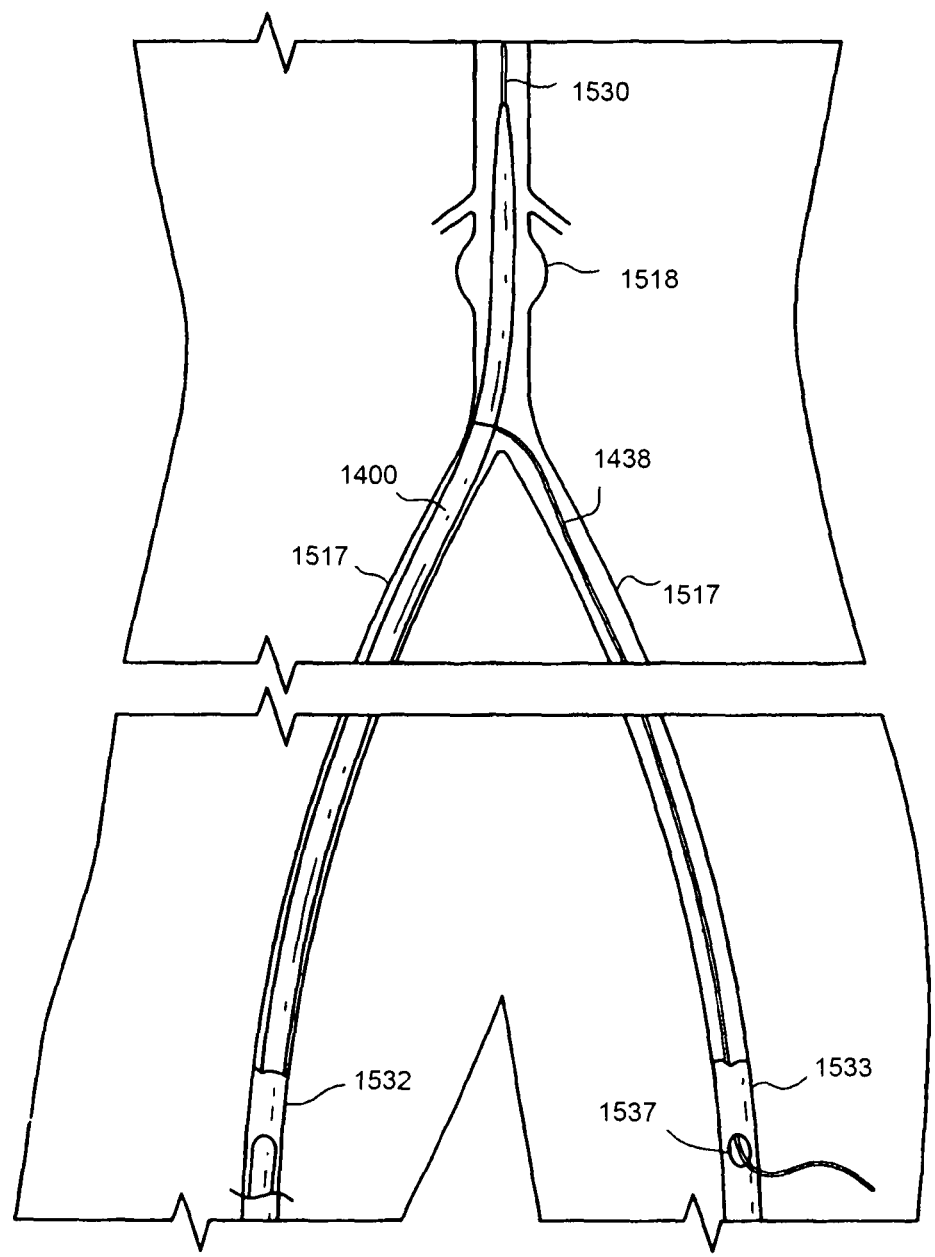

The delivery system 1400 is then advanced into the patient's right femoral artery 1532 through the access hole 1531 over the first guidewire 1530 as shown in FIG. 52. It may be desirable to apply tension to the secondary release cable 1438 as the delivery system 1400 is advanced to the vicinity of the aneurysm 1518 so as to remove slack in the cable 1438 and prevent tangling of the cable 1438 or the like. Tension on the secondary release cable 1438 may also help to prevent twisting of the delivery system 1400 during insertion.

Figure 50A:
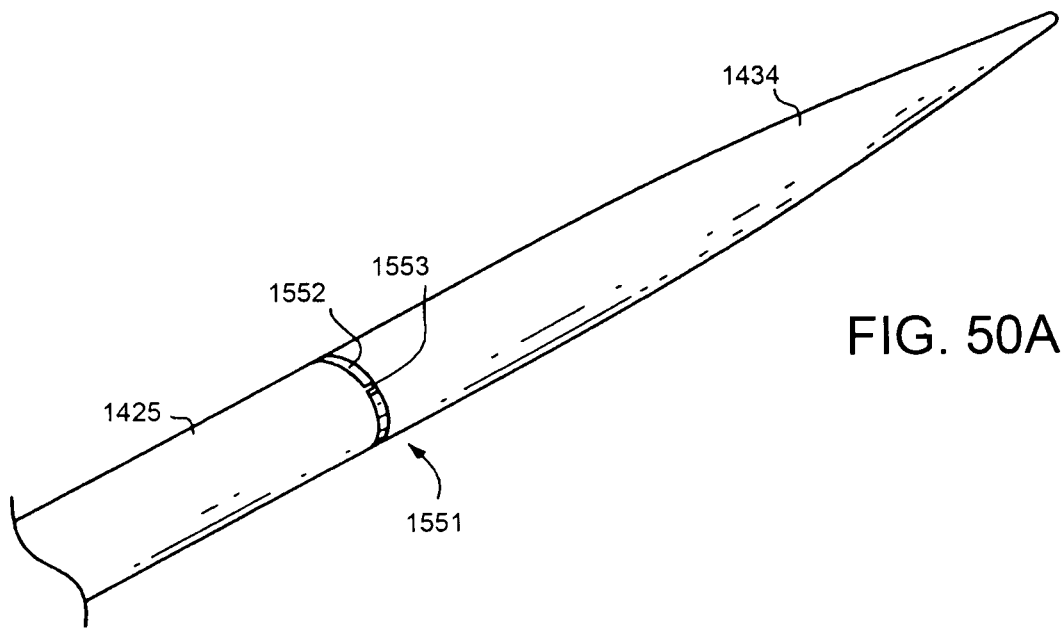
FIG. 50A is a perspective view of a marker disposed on the delivery system distal section in the vicinity of the nosepiece.
Figure 50B:
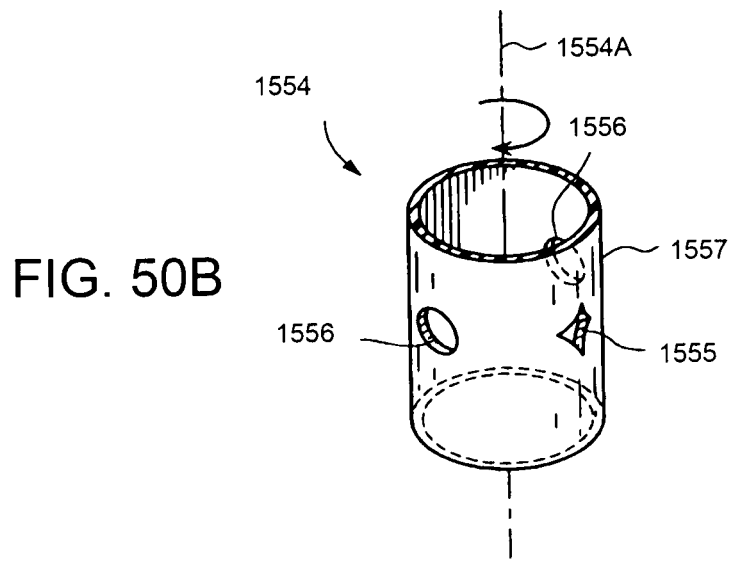
FIG. 50B is a perspective view of an alternative embodiment of a marker for use in the delivery system of the present invention.

FIGS. 50A-B show an optional marker band that may disposed adjacent nosepiece 1434 or generally in the vicinity of the distal end of the delivery system 1425. Such a marker band 1551 may also be integral with the delivery system 1400; for example, it may be incorporated as part of the distal nosepiece 1434. A useful marker 1551 can be one that does not add to the profile of the delivery system 1400 as shown in FIG. 50A (i.e., one that does not give the delivery system 1400 a higher diameter). The embodiments of FIGS. 50A-B are useful in the present embodiment, although they may be used in the embodiments discussed above. Such a marker may be used to aid the operator in introducing the delivery system 1400 without twisting.

For example, the marker embodiment 1551 of FIG. 50A comprises a marker body 1552 in the form of a simple discontinuous ring made of an appropriate radiopaque material (e.g., platinum, gold, etc.) visible under fluoroscopy, etc. The cross section of the ring may be asymmetric so that under fluoroscopy the cross section may be seen in the vicinity of the discontinuity 1553. The operator will be able to tell if the delivery system 1400 is twisted by how the ring 1552 is presented under fluoroscopy. Alternatively, ring 1552 may be continuous but have a notch or similar cutout to serve the same purpose.

The embodiment 1554 of FIG. 50B is an example of such a marker. Here, both a notch 1555 and two circular holes 1556 have been cut out of the marker body 1557 for easier determination of its orientation when disposed on the notch or other part of the delivery system 1400. For instance, in an orientation where the two circular holes 1556 are aligned with respect to the fluoroscope field of view, the user will see a single circular hole to the left of a triangular or vee-shape cutout 1555 on the side of the marker 1554. As the angular orientation of the device 1400 (and thus the marker 1554) about the longitudinal axis changes, the appearance of the two circular holes 1556 and side notch 1555 will change. If the device is twisted clockwise ninety degrees from this orientation along its central longitudinal axis 1554A, for instance, the circles 1556 will largely disappear from view and the side notch 1555 will generally appear in the front of the field of view as a symmetric diamond. Comparing these views will allow the user to know that the entire delivery system 1400 has twisted about ninety degrees. Keeping the same orientation, then, will be made easier with such a marker 1554.

For each of the embodiments of FIGS. 50A-B, variations in the shape, number, orientation, pattern and location of the notch 1553 and 1555, holes 1556 or other discontinuity, as well as various marker body dimensions cross sectional shape, etc., may be realized, as long as the marker 1551 and 1554 is configured so that the angular orientation of the delivery system 1400 may readily be determined by the user under fluoroscopy or similar imaging technique.

Figure 53:
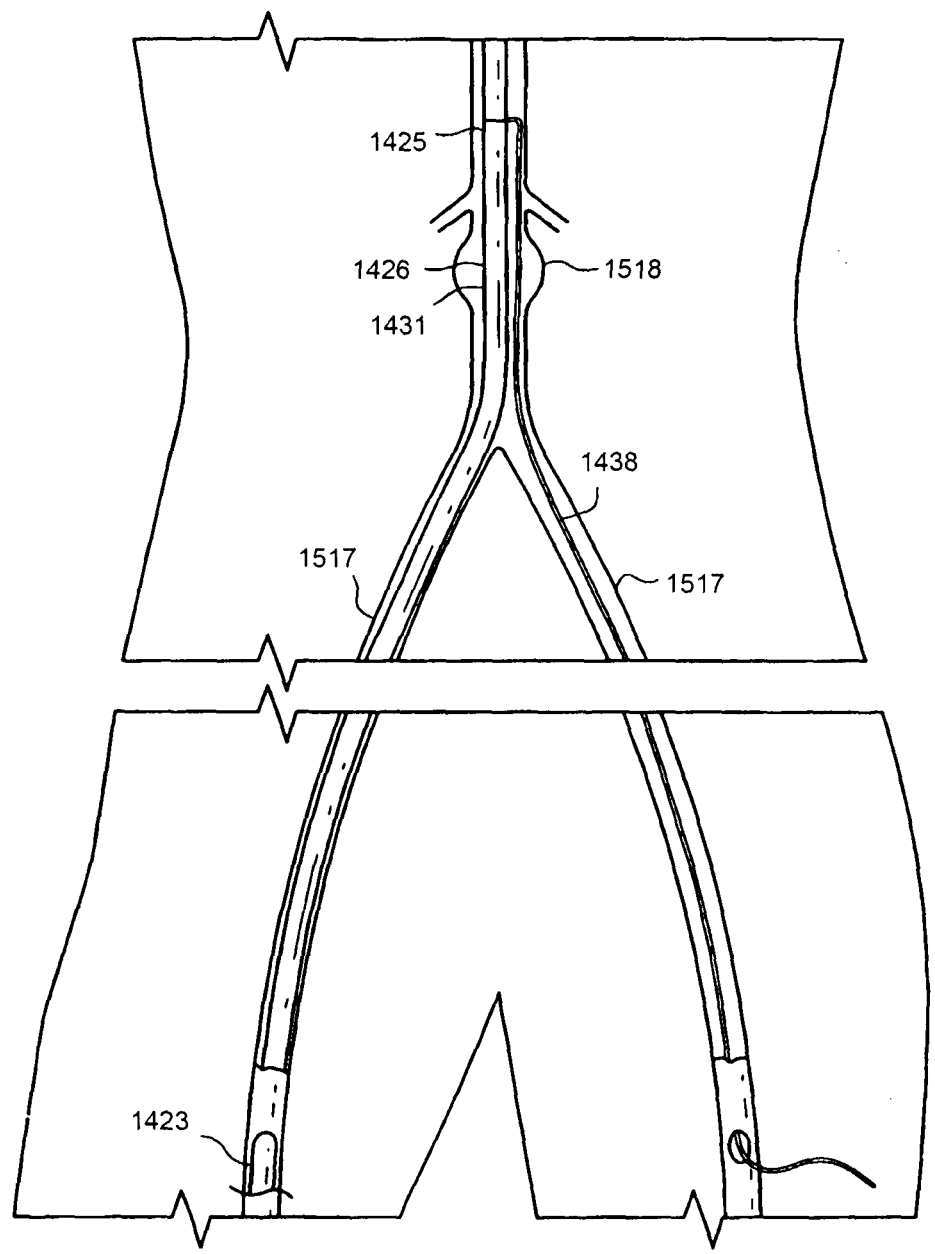
Figure 57:
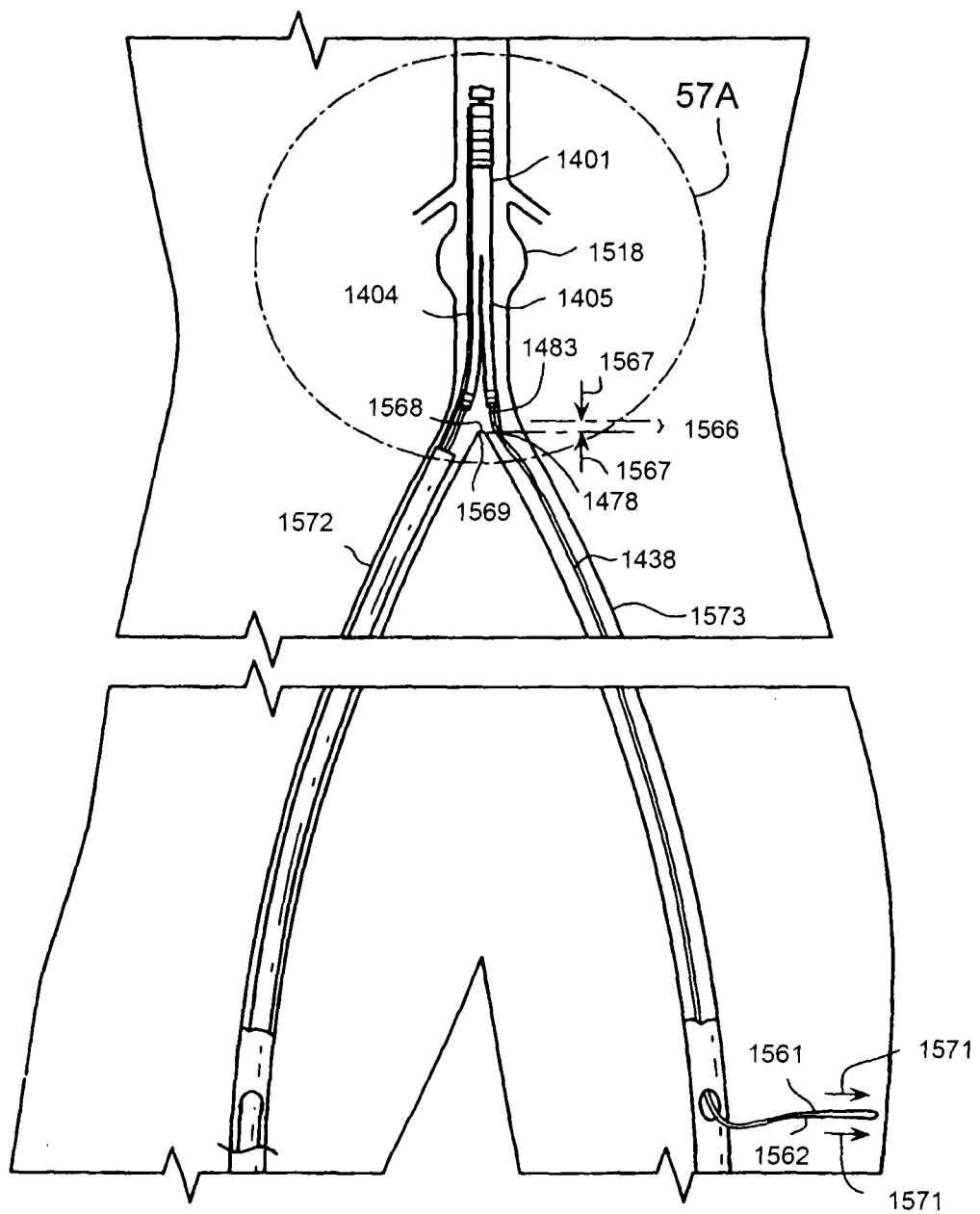
Figure 57A:
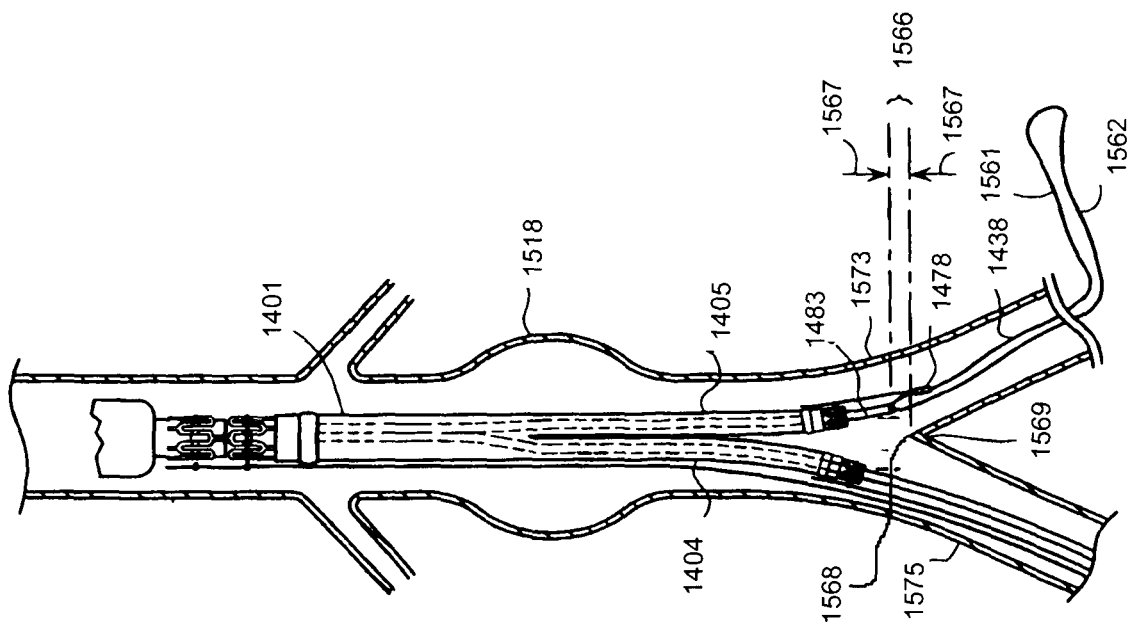

The delivery system 1400 is positioned in a location suitable for initiating the deployment process, such as one in which the distal end 1425 of the delivery system 1400 is disposed beyond, or distal to the position in which the graft 1401 will be placed, as shown in FIG. 53. This position allows the proximal end 1483 of the secondary belt support member 1454 to be laterally displaced without mechanical interference from the patient's vasculature. Such clearance for lateral displacement is shown in FIG. 57.

Once the distal section 1426 of the elongate shaft 1423 and the endovascular graft 1401 are positioned, the deployment process is initiated. First, the outer tubular member 1431 is proximally retracted by pulling on the proximal end 1433 of the outer tubular member 1431 relative to the inner tubular member 1430. The inner tubular member 1430 should be maintained in a stable axial position, as the position of the inner tubular member 1430 determines the position of the constrained bifurcated graft 1401 prior to deployment. Upon retraction of the outer tubular member 1431, the constrained bifurcated graft 1401 is exposed and additional slack is created in the secondary release cable 1438 as shown in more detail in FIG. 54.

Alternatively, a variety of different components may be substituted for the outer tubular member 1431 in some of the embodiments of the invention. For instance, a shroud, corset, mummy-wrap, or other cover may be released or actuated to expose the constrained graft 1401 after the delivering system 1400 is introduced into the vasculature.

Figure 41B:
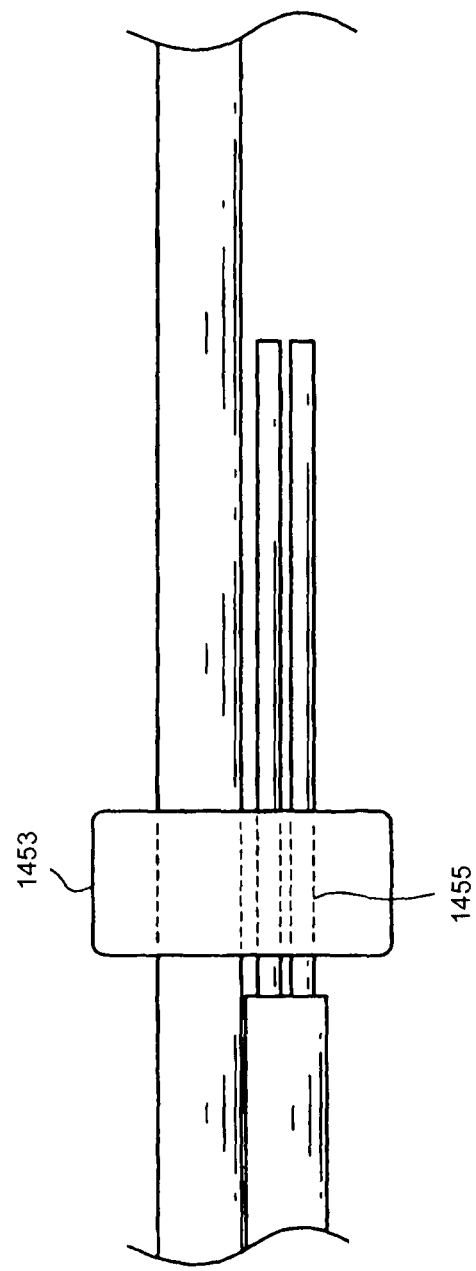
FIG. 41B is an elevational view of the alternative embodiment of the secondary belt support member of FIG. 41A.
Figure 54:
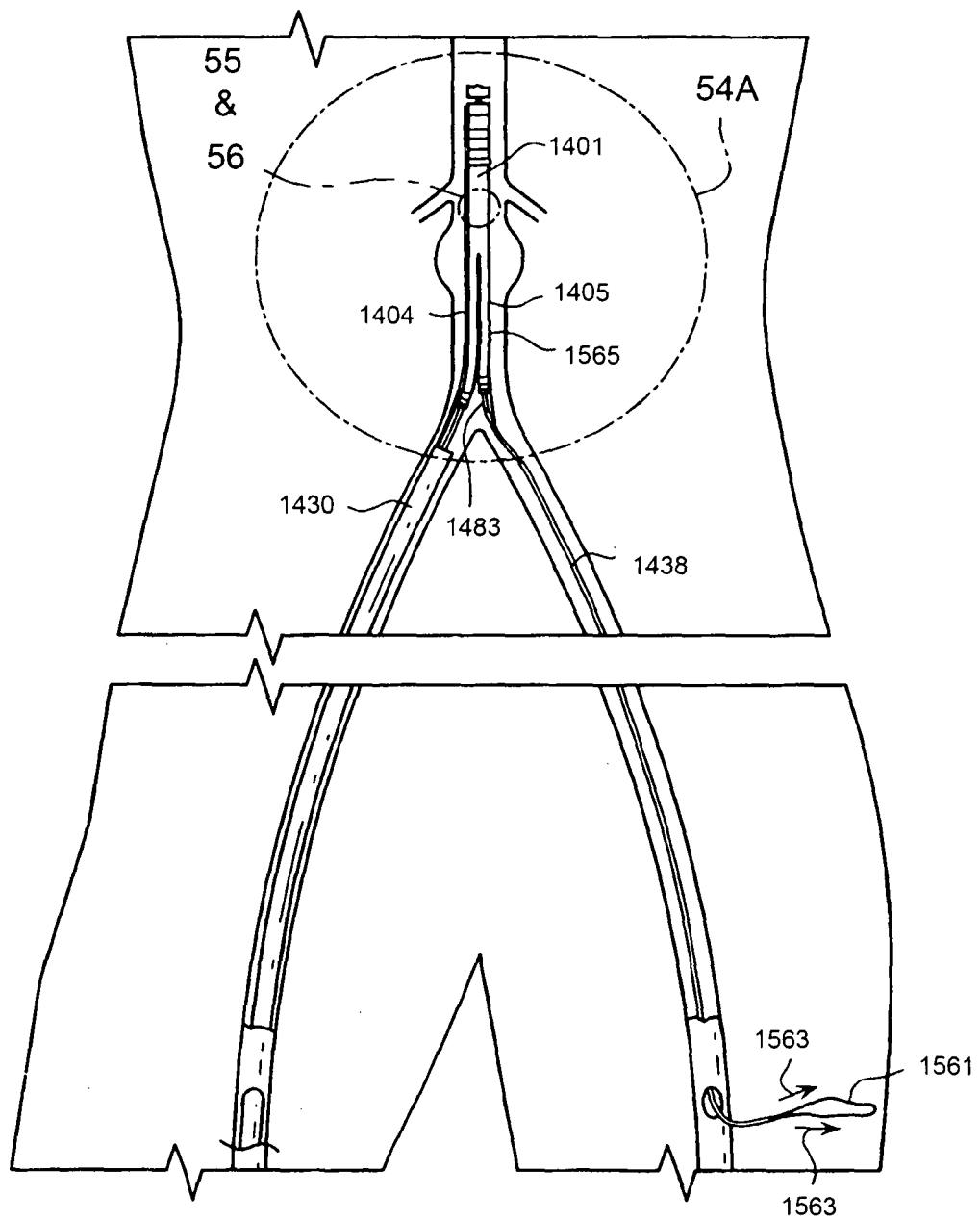
Figure 55:
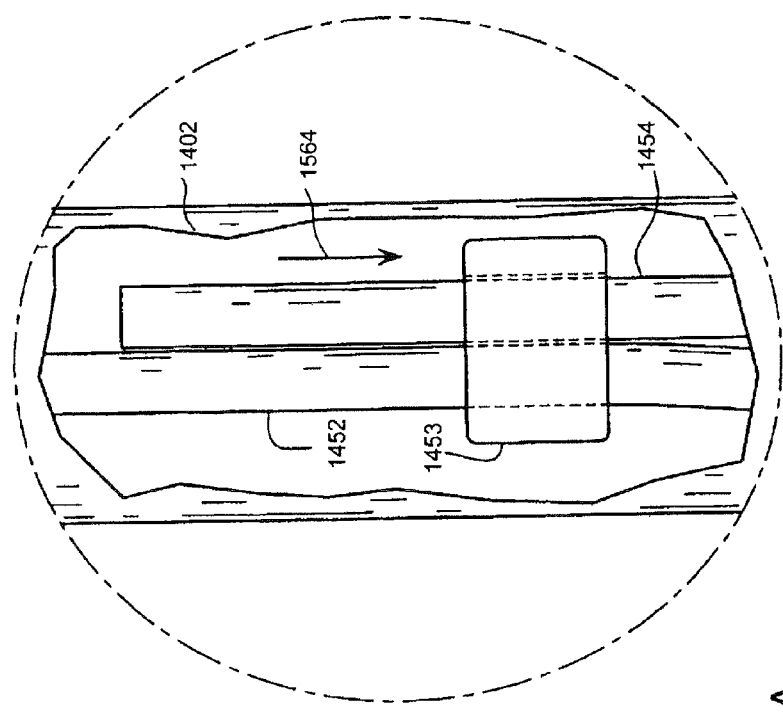
Figure 54A:
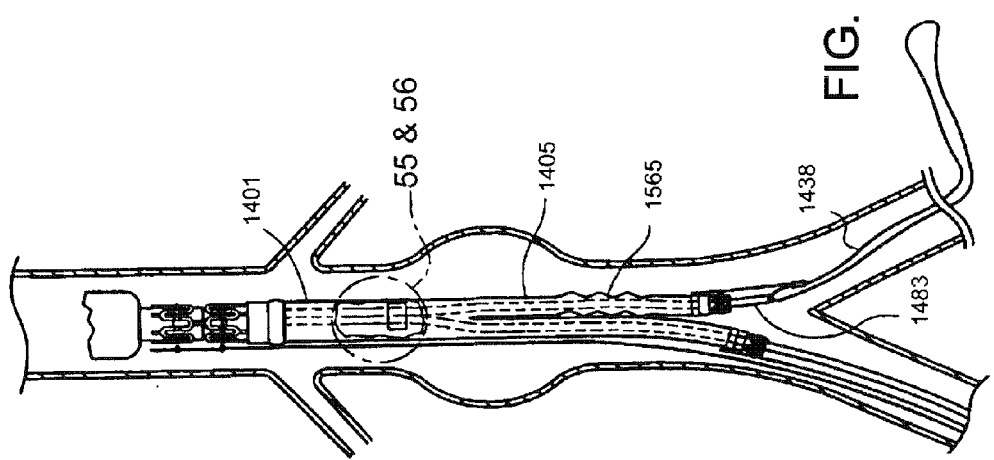
Figure 56:
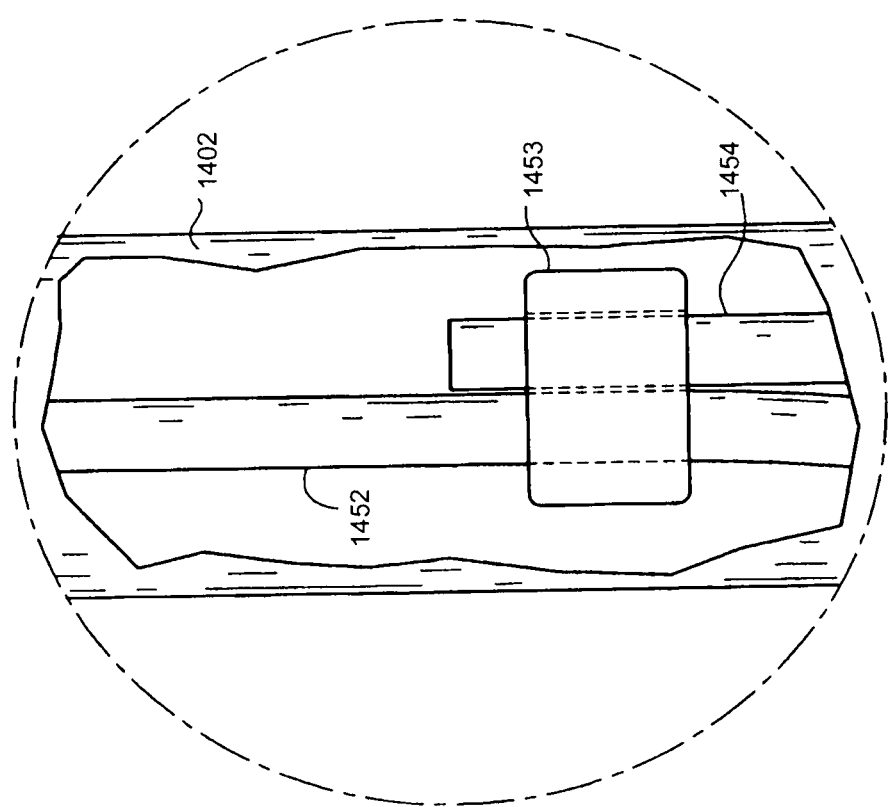

The slack in the secondary release cable 1438 is taken up by applying tension to both lengths 1561 and 1562 of the release strand 1481 as shown by the arrows 1563 in FIG. 54. As tension continues to be applied to both lengths 1561 and 1562 of the release strand 1481, the secondary belt support member 1454 begins to slide within the secondary belt support member housing 1453 in a proximal direction as shown by the arrow 1564 in FIG. 55. The secondary belt support member 1454 continues to slide proximally until all the slack is removed from an axially compressed or folded portion 1565 of the contralateral leg 1405 of the graft 1401 shown in FIG. 54 and the primary and secondary belt support members 1452 and 1454 are oriented relative to the secondary belt support member housing 1453 as generally shown in FIG. 56. Rotational movement of the secondary belt support member 1454 relative to the secondary belt support member housing 1453 is prevented by the non-circular or asymmetric cross section of the member 1454 as shown in FIGS. 41-28B. This prevents the contralateral leg 1405 from twisting or becoming entangled with other components of the graft 1401 or delivery system 1400 during deployment.

Axial compression of all or a portion of the contralateral leg 1405 while the graft 1401 is in a constrained state within the delivery system 1400 prior to deployment allows the axial position of the two proximal self-expanding members 1407 and 1408 to be axially offset from each other. Alternatively, graft legs 1404 and 1405, having different lengths may be used to prevent overlap of the self-expanding members 1407 and 1408 within the delivery system 1400. The cross sectional profile or area of the overlap self-expanding members 1407 and 1408 is generally greater than that of the adjacent polymer material portion of the legs 1404 and 1405 of the graft 1401, so eliminating the overlap can be desirable. The self-expanding members 1407 and 1408 are typically made of a metal or metallic alloy and maintain a cylindrical configuration, even when in a constrained state. The polymer material of the legs 1404 and 1405 or main body portion 1402 of the graft 1401, by contrast, is relatively soft and malleable and can conform to the shape of whatever lumen in which it may be constrained. Placing both proximal self-expanding members 1407 and 1408 adjacent each other in a compressed state at a single axial position within the delivery system 1400 would require a configuration in which two objects having an approximately circular cross section are being placed within another circular lumen. Such a configuration generates a significant amount of wasted or unused cross sectional area within that axial position of the delivery system 1400 and would likely result in less flexibility and greater cross section than a delivery system 1400 in which the proximal self-expanding members 1407 and 1408 are axially offset.

A gap 1566 indicated by the arrows 1567 in FIG. 57 allows the proximal end 1483 of the secondary belt support member 1454 and secondary release wire actuator hub 1478 to move in a lateral direction without mechanical interference from the carina 1568 of the iliac artery bifurcation 1569. Gap 1566 may vary depending on the patient's particular anatomy and the specific circumstances of the procedure.

The lateral movement of the contralateral leg 1405 and secondary belt support member 1454 is accomplished by application of tension on both lengths 1561 and 1562 of the release strand 1481 as shown by the arrows 1571 in FIG. 57. This movement away from the primary belt support member 1452 allows the secondary belt support member 1454 to transition from alignment with the right iliac artery 1572 to alignment with the left iliac artery 1573 as shown in FIG. 57.

Figure 58:
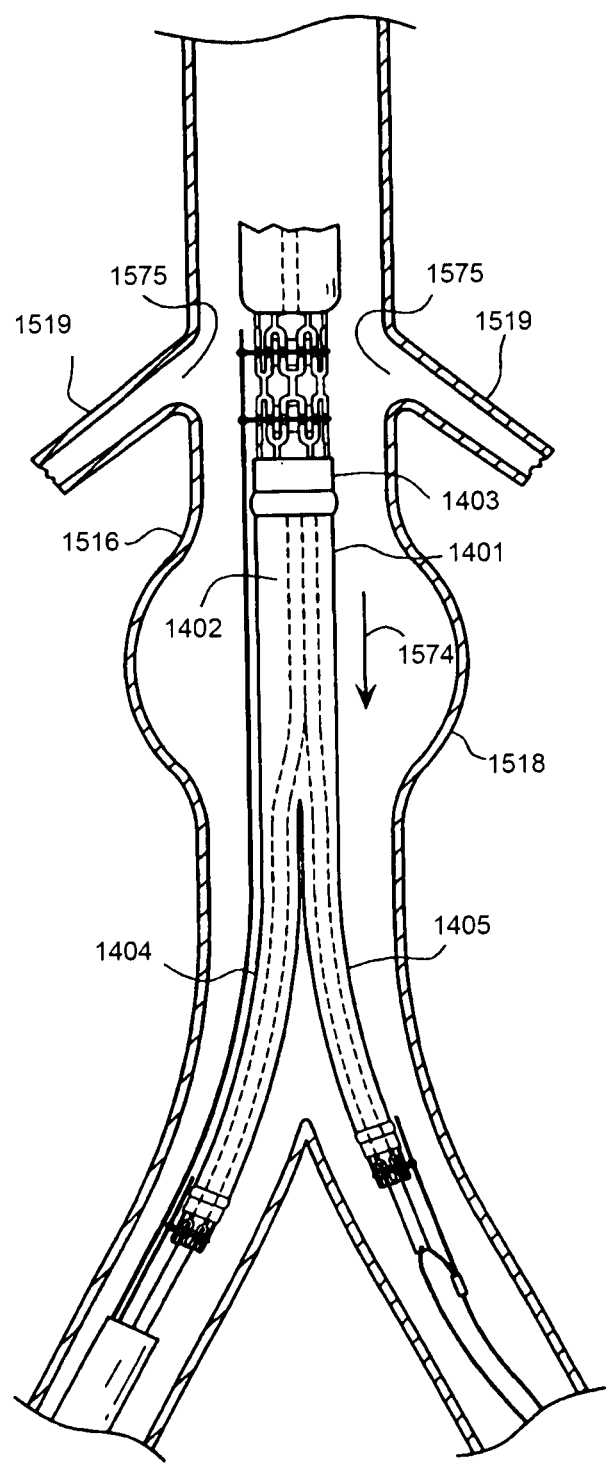

Once the ipsilateral leg 1404 of the graft 1401 and contralateral leg 1405 of the graft 1401 are aligned with the right and left iliac arteries 1572 and 1573, respectively, the delivery system 1400 may then be retracted proximally, as shown by the arrow 1574 in FIG. 58, so as to reposition the distal section 1426 of the elongate shaft 1423 and the bifurcated graft 1401 into the desired position for deployment as shown in FIG. 58.

As discussed above with respect to placement of a tubular graft 1011 embodiment of the present invention, when deploying the graft 1401 in the abdominal aorta 1516 it is generally desirable to ensure that the distal end 1403 of the graft main body portion 1402 is installed proximal to, or below, the renal arteries 1519 in order to prevent their significant occlusion.

However, the distal self-expanding members 1411 and 1422 of the graft 1401 may, depending upon the anatomy of the patient and the location of the aneurysm 1518, partially or completely span the ostia 1575 of one or both renal arteries 1519. It can be desirable, however, to ensure that ostia 1575 of the renal arteries 1519 are not blocked by the distal end 1403 of the graft main body portion 1402. As discussed previously, a variety of imaging markers 1551 and 1554 may be used on either or both the delivery system 1400 and the graft 1401 itself to help guide the operator during the graft positioning process.

After proper positioning, the first and second distal self-expanding members 1411 and 1422 may then be deployed. The operator first unscrews or otherwise detaches a threaded portion 1576 of the distal primary release wire handle 1495 from an outer threaded portion 1577 of a first side arm end cap 1578 shown in FIG. 44. Next, the distal primary release wire handle 1495 is proximally retracted, which in turn retracts the distal primary release wire 1442 in a proximal direction, as shown by the arrow 1581 in FIG. 59. As the distal end 1582 of the distal primary release wire 1442 passes through the end loops 1472 and 1473 of the first distal primary belt 1458 and second distal primary belt 1462, the end loops 1472 and 1473 are released, freeing the first distal self-expanding member 1422 and second distal self-expanding member 1411 to self-expand in an outward radial direction so to contact an inner surface 1583 of the patient's aorta 1516. The first and second distal primary belts 1458 and 1462 remain secured to the primary belt support member 1452 and will eventually be retracted from the patient with the delivery system 1400 after deployment is complete.

Figure 59:
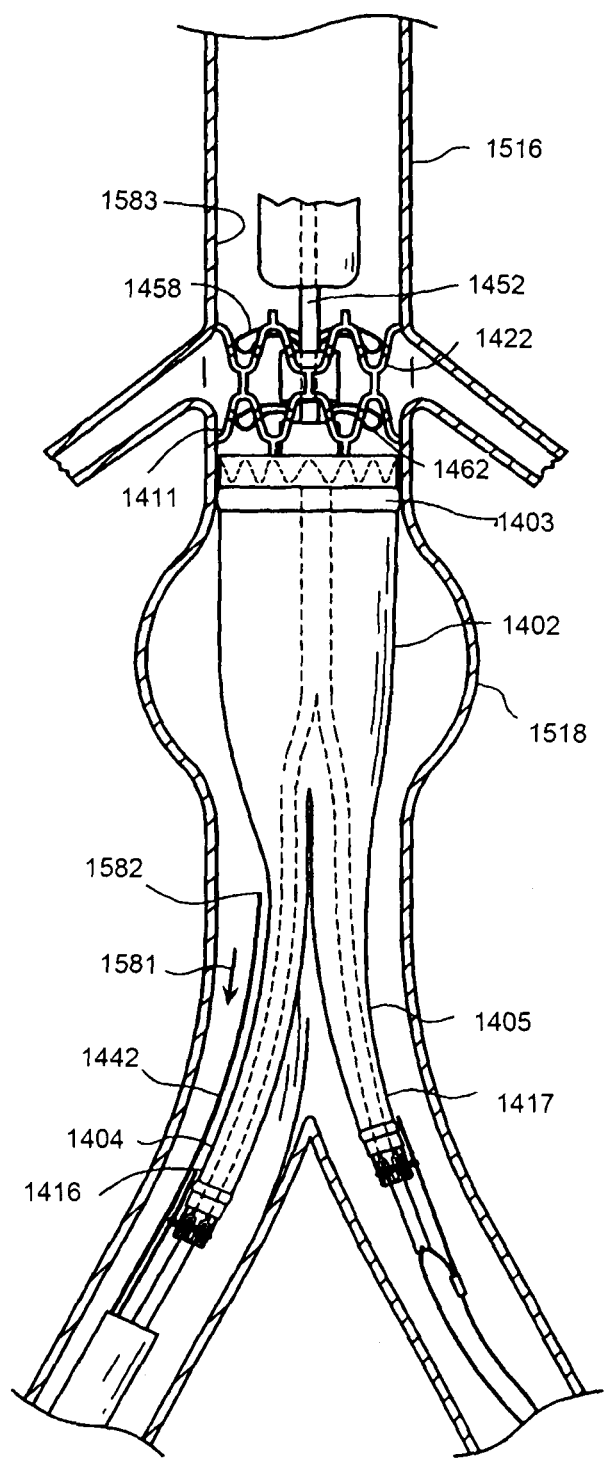

As the first and second distal self-expanding members 1411 and 1422 expand and contact the aorta 1516, a distal end 1403 of the graft main body portion 1402 opens with the self-expanding members 1411 and 1422 and promotes opening of the graft polymer material portion from the flow of blood into the distal end 1403 of the graft main body portion 1402 with a "windsock" effect. As a result, once the first and second distal self-expanding members 1411 and 1422 are expanded to contact the aorta inner surface 1583, the graft main body portion 1402 and legs 1404 and 1405 balloon out or expand while the proximal ends 1416 and 1417 of the legs 1404 and 1405 of the graft 1401 remain constricted due to the constrained configuration of the proximal self-expanding members 1407 and 1408 of the ipsilateral and contralateral legs 1404 and 1405, as shown in FIG. 59. At this point, there typically will be partial or restricted blood flow through and around the graft 1401.

Figure 60:
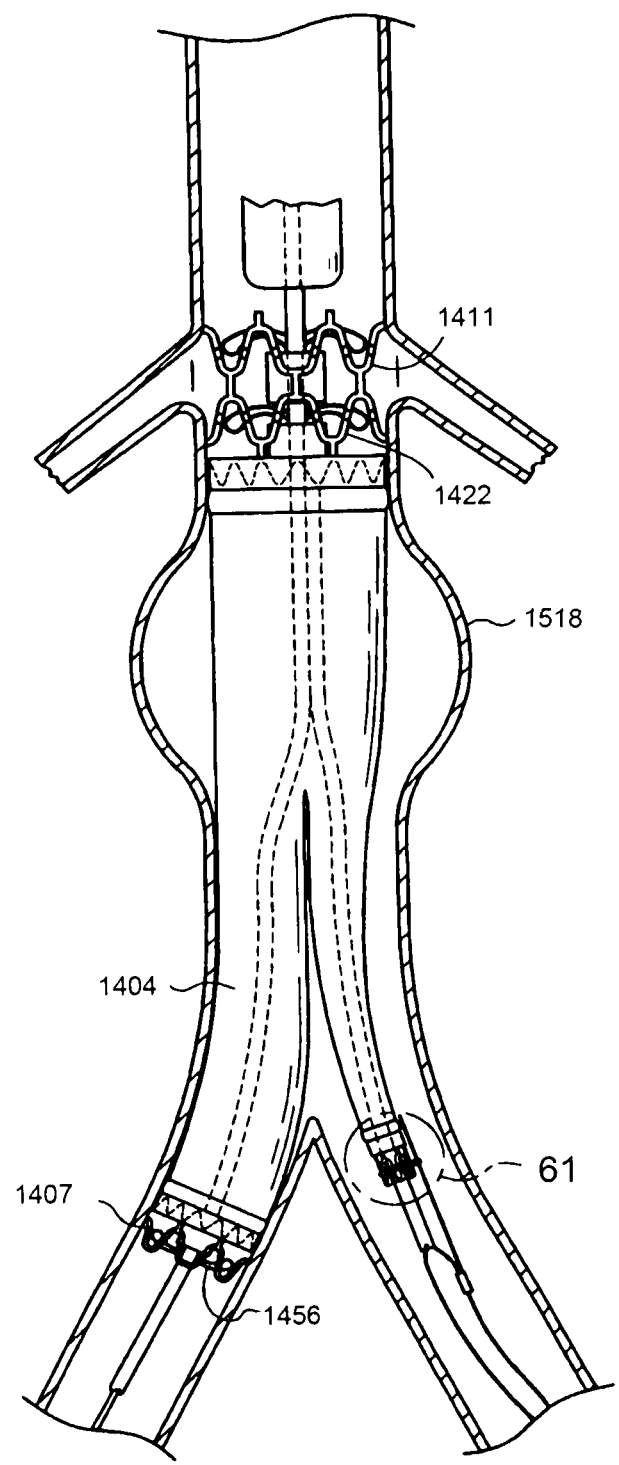

Next, the proximal self-expanding member 1407 of the ipsilateral leg 1404 is deployed. Deployment of the first and second distal self-expanding member 1411 and 1422 has exposed the proximal primary release wire handle 1496, making it accessible to the operator. A threaded portion 1584 of the proximal primary release wire handle 1496 is unscrewed or otherwise detached from an inner threaded portion 1585 of the first side arm end cap 1578. The proximal primary release wire handle 1496 may then be retracted proximally so as to deploy the proximal primary belt 1456 and proximal self-expanding member 1407 of the ipsilateral leg 1404 as shown in FIG. 60.

Figure 61:
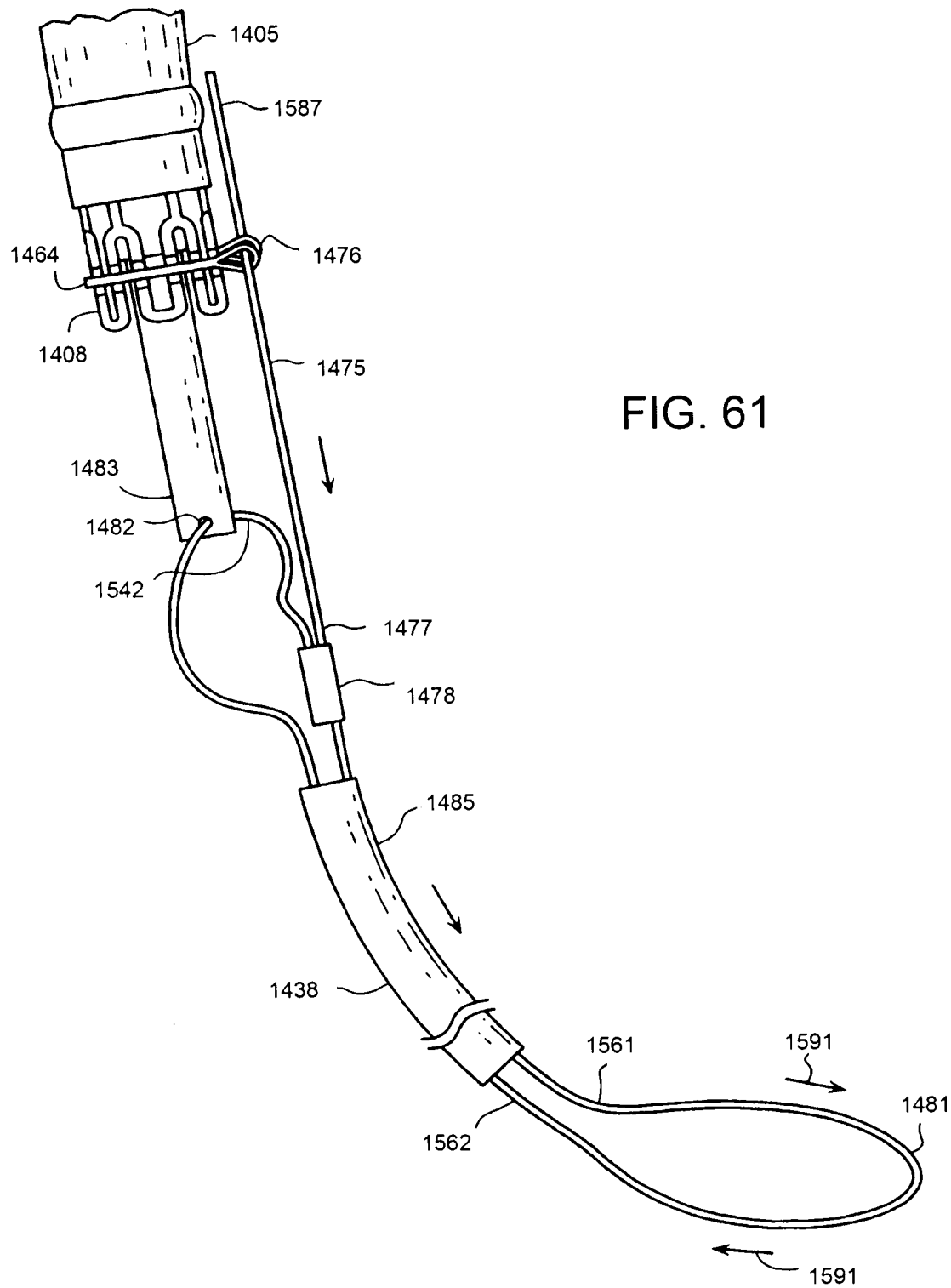

FIG. 61 depicts an enlarged view of the proximal end 1483 of the secondary belt support member 1454. The proximal self-expanding member 1408 of the contralateral leg 1405 is secured to the proximal end 1417 of the contralateral leg 1405. The proximal self-expanding member 1408 is constrained in a radial direction by the secondary belt 1464, which has end loops 1476 releasably constrained by the distal end 1587 of the secondary release wire 1475. The proximal end 1477 of the secondary release wire 1475 terminates with and is secured to the actuator hub 1478. The release strand is secured to the actuator hub 1478 and loops through an aperture or hole 1482 in the proximal end 1483 of the secondary belt support member 1454. As discussed above, a portion of the release strand 1481 is disposed within the release strand tube 1485 to form the secondary release cable 1438.

When both a first length 1561 and second length 1562 of the release strand 1481 are pulled together in a proximal direction from a proximal end 1588 of the secondary release cable 1438, the entire pulling force is exerted on the proximal end 1483 of the secondary belt support member 1454 because the looped distal end 1542 of the release strand 1481 pulls on the proximal end 1483 of the secondary belt support member 1454 without displacing the actuator hub 1478.

Figure 62:
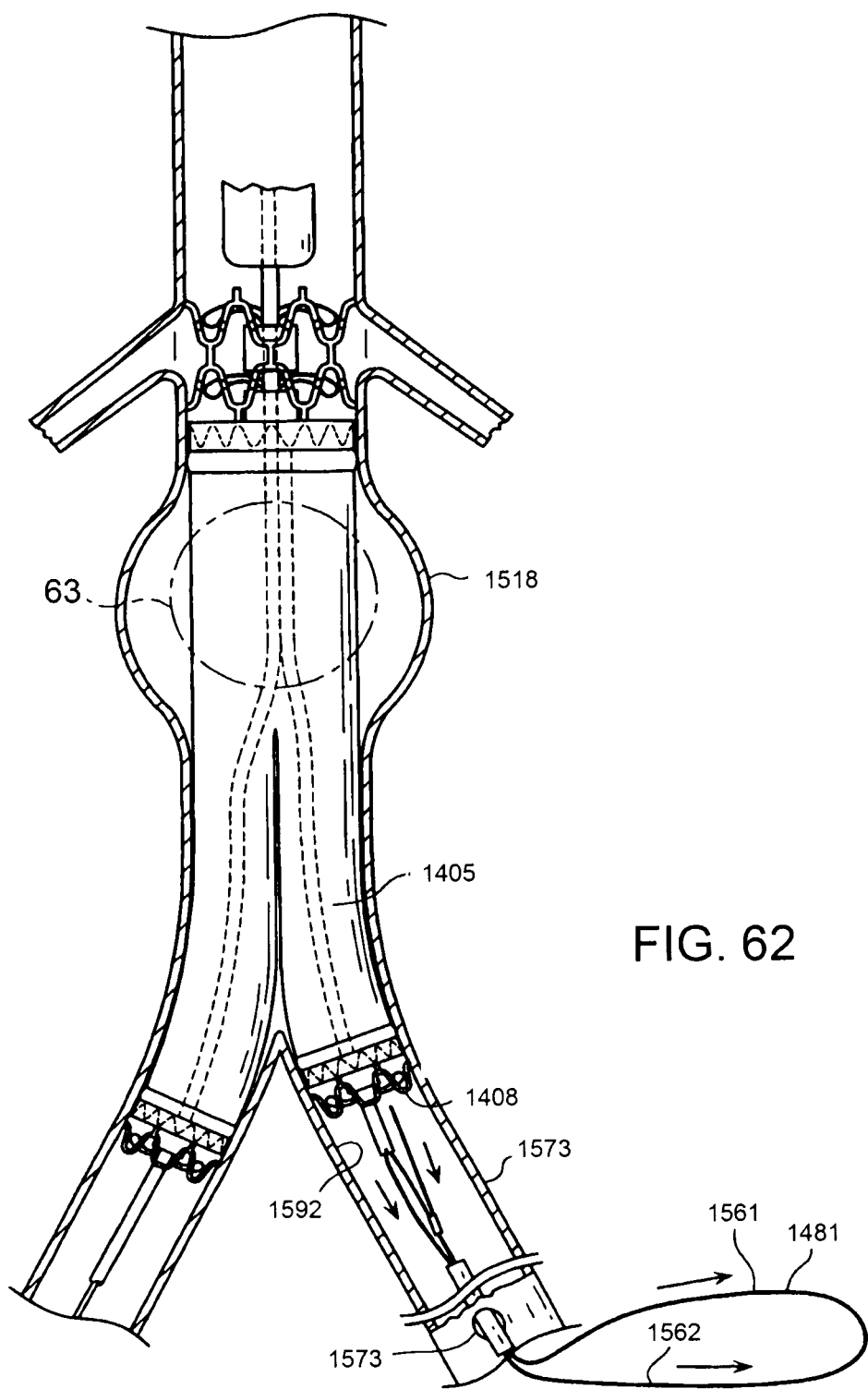
Figure 63:
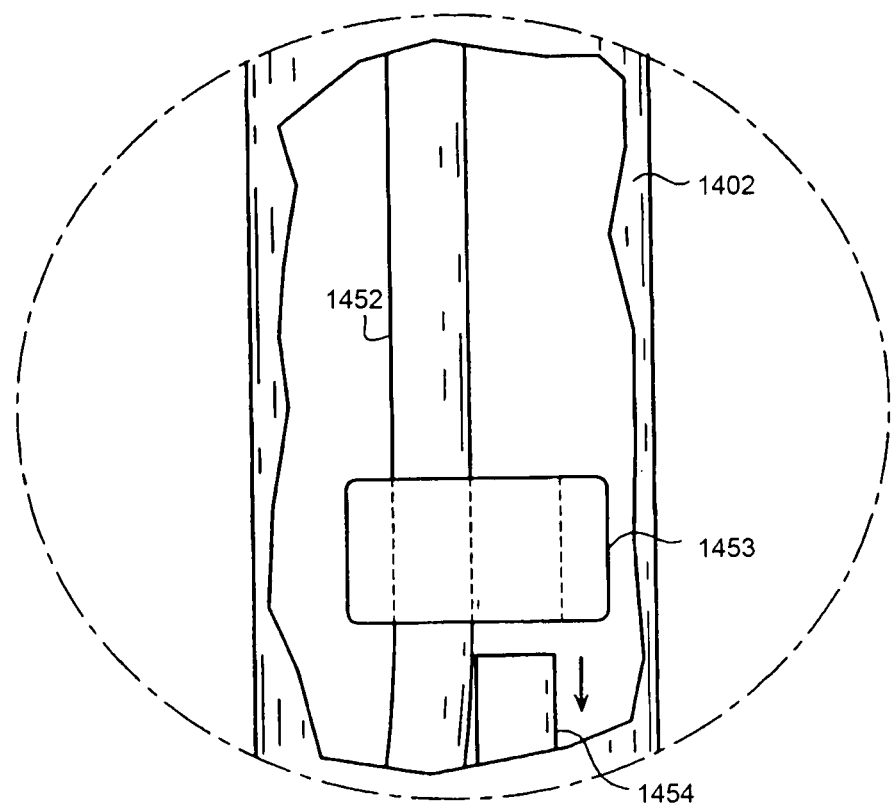

When deployment of the proximal self-expanding member 1408 of the contralateral leg 1405 is desired, the operator applies tension in a proximal direction only to the first length 1561 of the release strand 1481, which extends proximally from the actuator hub 1478. The direction of such tension is indicated in FIG. 61 by the arrows 1591. Upon the application of this proximal tension, the actuator hub 1478 is moved proximally, as is the secondary release wire 1475 which is secured to the actuator hub 1478. The proximal self-expanding member 1408 of the contralateral leg 1405 deploys when the distal end 1587 of the secondary release wire 1475 passes through the end loops 1468 of the secondary belt 1464 so as to release the radial constraint on the proximal self-expanding member 1408 imposed by the secondary belt 1464. Upon release of the radial constraint, the proximal selfexpanding member 1408 expands so as to contact an inside surface 1592 of the left iliac artery 1573 as shown in FIG. 62. Once the proximal self-expanding member 1408 of the contralateral leg 1405 is expanded, the operator may then apply tension to both lengths 1561 and 1562 of the release strand 1481 to withdraw the secondary belt support member 1454 from the housing 1453 (as shown in FIG. 63) and remove it from the patient's vasculature through the left femoral artery access hole 1537.

Figure 64:
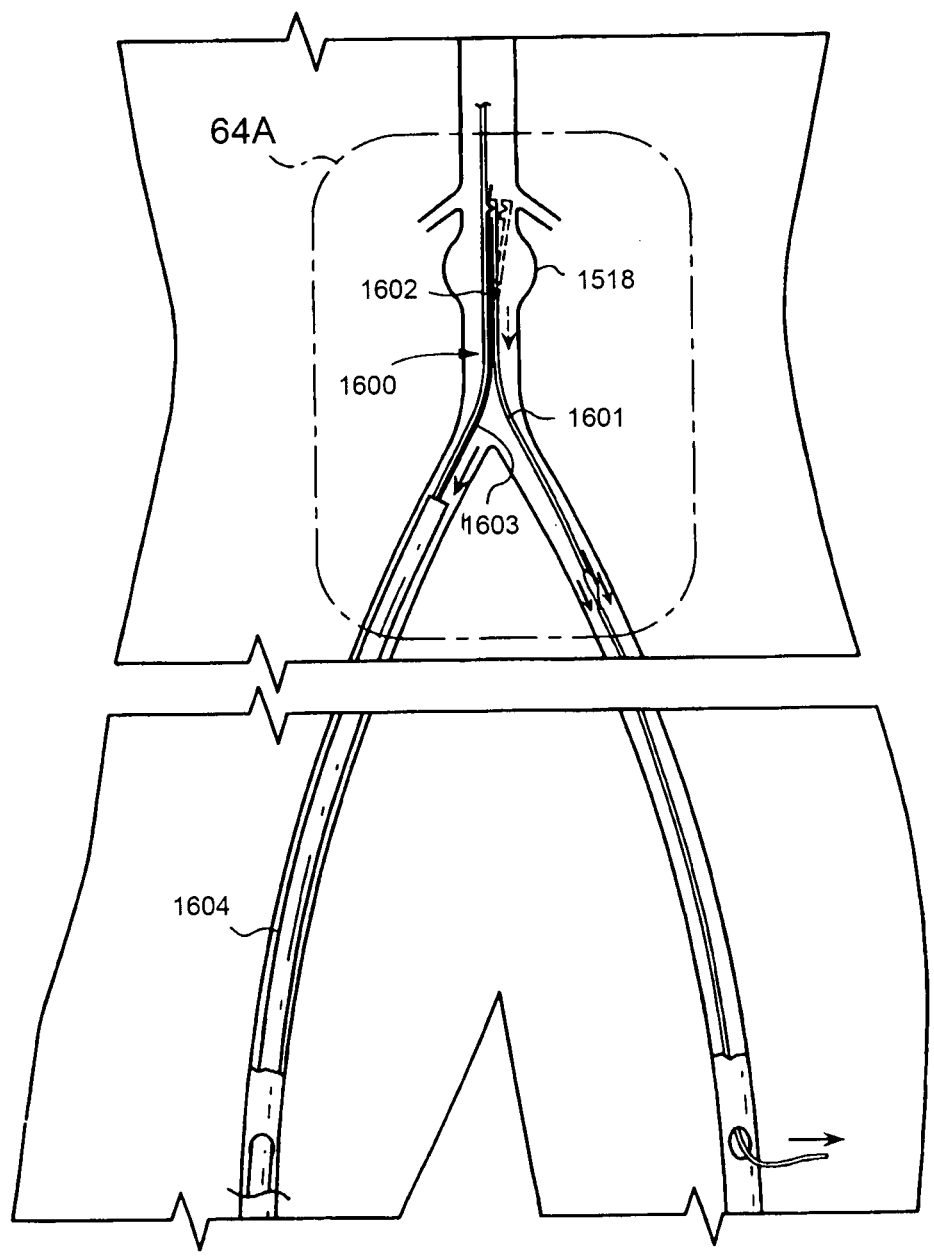
Figure 64A:
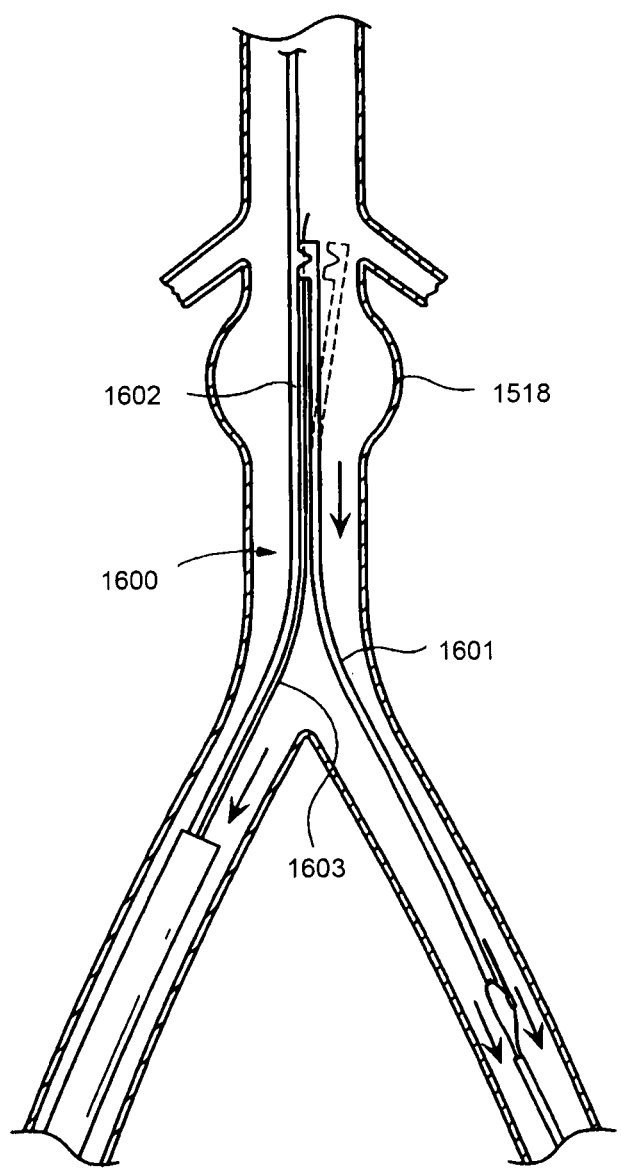

FIG. 64 depicts an alternative embodiment of a belt support member assembly 1600 in which the secondary belt support member 1601 is detached from the primary belt support member 1602 by withdrawal of a latch wire 1603. Generally, all other features of the delivery system 1604 of the embodiment of FIG. 64 can be the same as the delivery systems discussed above. It should be noted, however, that the embodiment shown in FIG. 64 does not allow the secondary belt support member 1601 to slide in an axial direction relative to the primary belt support member 1602. As such, it may be desirable to use this embodiment to deliver and deploy a graft having legs that are not substantially equal in length. Otherwise, if proximal self-expanding members are to be axially offset, the secondary belt support member 1601 would have to be detached from the primary belt support member 1602 prior to deploying and releasing the secondary belt (not shown).

Figure 65:
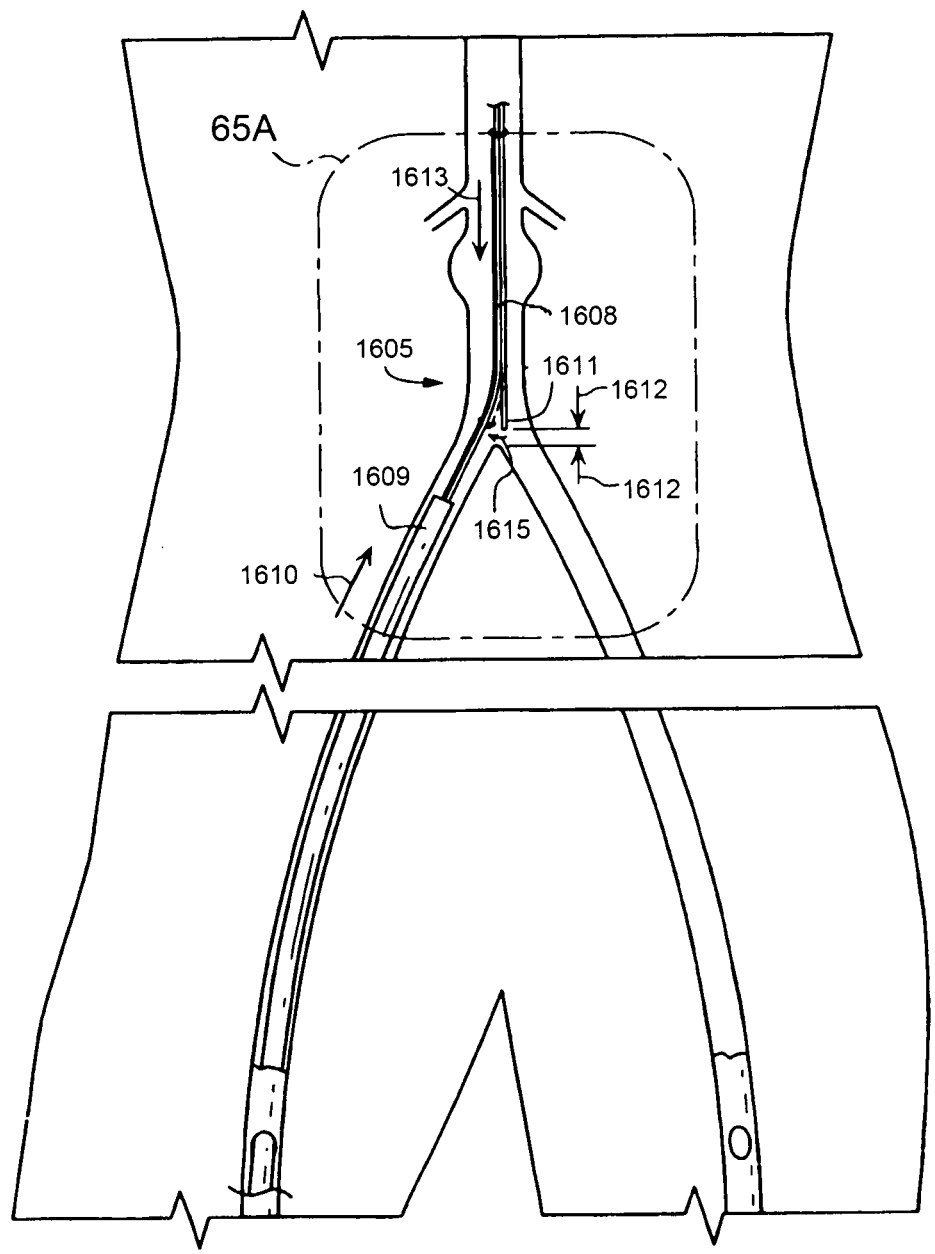
Figure 65A:
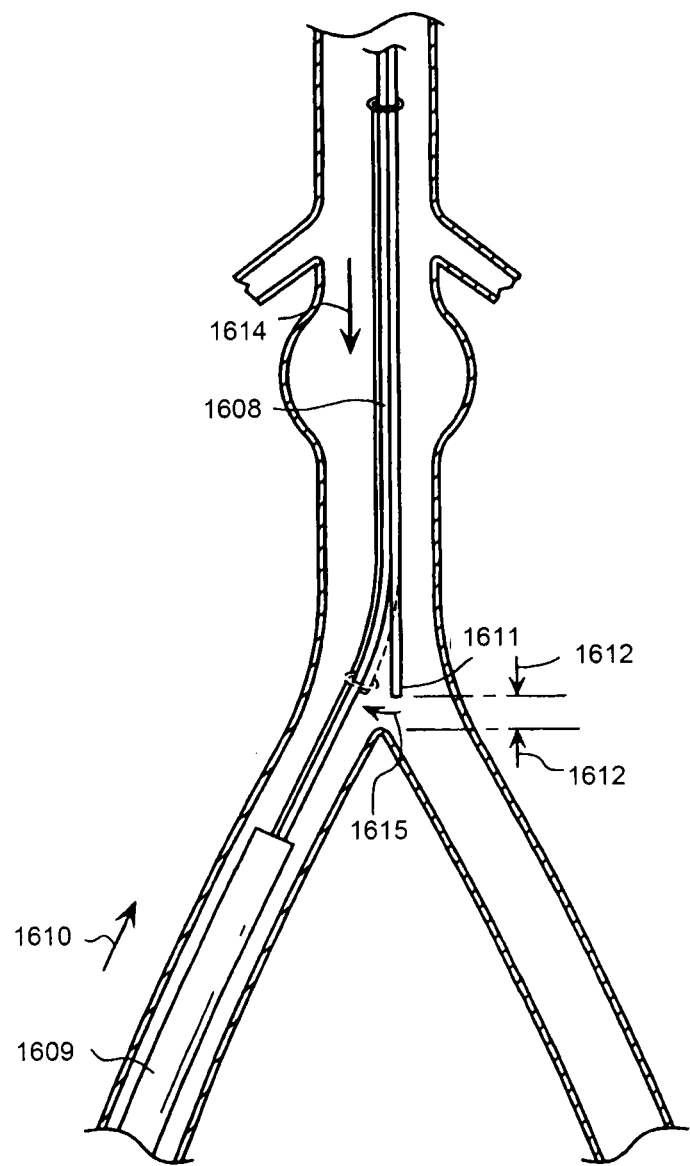

FIG. 65 shows an alternative belt support member assembly 1606 wherein the secondary belt support member 1607 is laterally displaced and locked into a position parallel with the primary belt support member 1608 prior to removal of the delivery system 1609 from the patient's vasculature.

All other features of the delivery system 1609 of the embodiment of FIG. 65 can be the same as the delivery systems discussed above. In use, after all self-expanding members have been deployed, the delivery system 1609 is advanced distally into the patient's vasculature, as shown by the arrow 1610 in FIG. 65, in order to achieve a gap between a proximal end 1611 of the secondary belt support member 1607 and the patient's vasculature as shown by the arrows 1612 in FIG. 65. A constraining ring 1613 is then retracted proximally, as indicated by the arrow 1614, so as to force the secondary belt support member 1607 to be laterally displaced as shown by the arrow 1615, also in FIG. 65. Once the secondary belt support member 1607 has been fully retracted in a lateral direction so as to be substantially parallel to the primary belt support member 1608, the delivery system 1609 can then be retracted from the patient's vasculature.

As previously described with respect to the tubular graft embodiment 1011, thereafter, the bifurcated graft 1401 may be inflated with an inflation material (not shown) via the inflation tube 1444 and inflation port 1421 until the inflatable channels 1418 and inflatable cuffs 1413, 1414 and 1415 have been filled to a sufficient level to meet sealing and other structural requirements necessary for the bifurcated graft main body portion 1402 and the ipsilateral and contralateral legs 1407 and 1408 to meet clinical performance criteria.

For all the embodiments described, both tubular and bifurcated, inflation is generally accomplished by inserting or injecting, via one or more device such as a syringe or other suitable mechanism, the inflation material under a pressure- or volume-control environment.

For instance, in one embodiment of a pressure-control technique, a volume of inflation material is first injected into the delivery system 1400 (which at this point may include the graft, but may also include the inflation tube 1444). The particular desired volume of inflation material will depend on several factors, including, e.g., the composition and nature of the inflation and polymer graft material, the size of the graft 1401 to be deployed, the vessel or lumen diameter into which the graft 1401 is deployed, the configuration of the graft 1401 (tubular, bifurcated, etc.), the features of the graft main body 1402 and (if present) legs 1407 and 1408, and the conditions during the procedure (such as temperature).

Thereafter, the operator may affix a pressure control device, such as an Endoflator® or the like, to the injection port 1621 of the proximal adapter 1427 of the inflation tube and apply a pressure to the delivery system 1400 and a graft 1401 for a period of time. This serves to ensure that the fill material previously introduced enters the graft 1401 and fills it to the desired pressure level.

We have found that a useful pressure-control approach involves a series of such constant pressure applications, each for a period of time. For instance, the graft 1401 may first be pressurized at a level from about 5 psi to about 12 psi or higher, preferably about 9 psi, for between about 5 seconds and 5 minutes, preferably about 3 minutes or more. Optional monitoring of the fluid and the device during the fill procedure may be used to help ensure a proper fill. Such monitoring may be accomplished under fluoroscopy or other technique, for instance, if the fill material is radiopaque.

Thereafter, the fill protocol may be completed, or the pressure may be increased to between about 10 psi and about 15 psi or higher, preferably about 12 psi, for an additional period of time ranging from between about 5 seconds and 5 minutes or more, preferably about 1 minute. If the graft 1401 so requires, the pressure may be increased one or more additional times in the same fashion to effect the proper fill. For instance, subsequent pressure may be applied between about 12 and 20 psi or more, preferably about 16 psi to 18 psi, for the time required to satisfy the operator that the graft 1401 is sufficiently filled.

The details of particular pressure-time profiles, as well as whether a single pressure-time application or a series of such applications is used to fill embodiments of the graft 1401 will depend on the factors described above with respect to the volume of fill material used; the properties and composition of the fill material tend to be of significance in optimizing the fill protocol. For example, a stepped series of pressure-time profiles as described above is useful when the fill material comprises a hardenable or curable material whose physical properties may be time-dependent and which change after being introduced into the graft 1401 and its delivery system 1400.

Alternatively, a volume-control method may be utilized to fill embodiments of the grafts 1011 and 1401, including both tubular and bifurcated. Here, a volume of fill material is again introduced into the delivery system 1400 as described above. In this method, however, the volume of fill material used is precisely enough material to fill the graft 1401, the inflation tube 1444, and any other component in the delivery system 1400 through which the fill fluid may travel on its way to the graft 1401. The operator introduces the predetermined quantity of fill material, preferably with a syringe or similar mechanism, into the inflation tube 1444 and graft 1401. A precise amount of fill material may be measured into a syringe, for example, so that when the syringe is emptied into the delivery system 1400 and graft 1401, the exact desired amount of fill material has reached the graft 1401. After a period of time (which period will depend on the factors previously discussed), the syringe or equivalent may be removed from the inflation tube 1444 or injection port 1621 of proximal adapter 1427 and the procedure completed.

A pressurized cartridge of gas or other fluid may be used in lieu of a syringe to introduce the fill material into the delivery system and graft under this volume-control regime so to provide a consistent and reliable force for moving the fill material into the graft 1401. This minimizes the chance that variations in the force and rate of fill material introduction via a syringe-based technique affect the fill protocol and possibly the clinical efficacy of the graft 1401 itself.

For each of the pressure- and volume-control configurations, an optional pressure relief system may be included so to bleed any air or other fluid existing in the delivery system 1400 prior to the introduction of the fill material (such as the inflation tube 1444 or graft 1401) so to avoid introducing such fluid into the patient. Such an optional system may, for example, comprise a pressure relief valve at the graft 1401/inflation tube 1444 interface and a pressure relief tube disposed through the delivery system 1400 (e.g., adjacent the inflation tube 1444) terminating at the proximal adapter 1427 and vented to the atmosphere.

Figure 66:
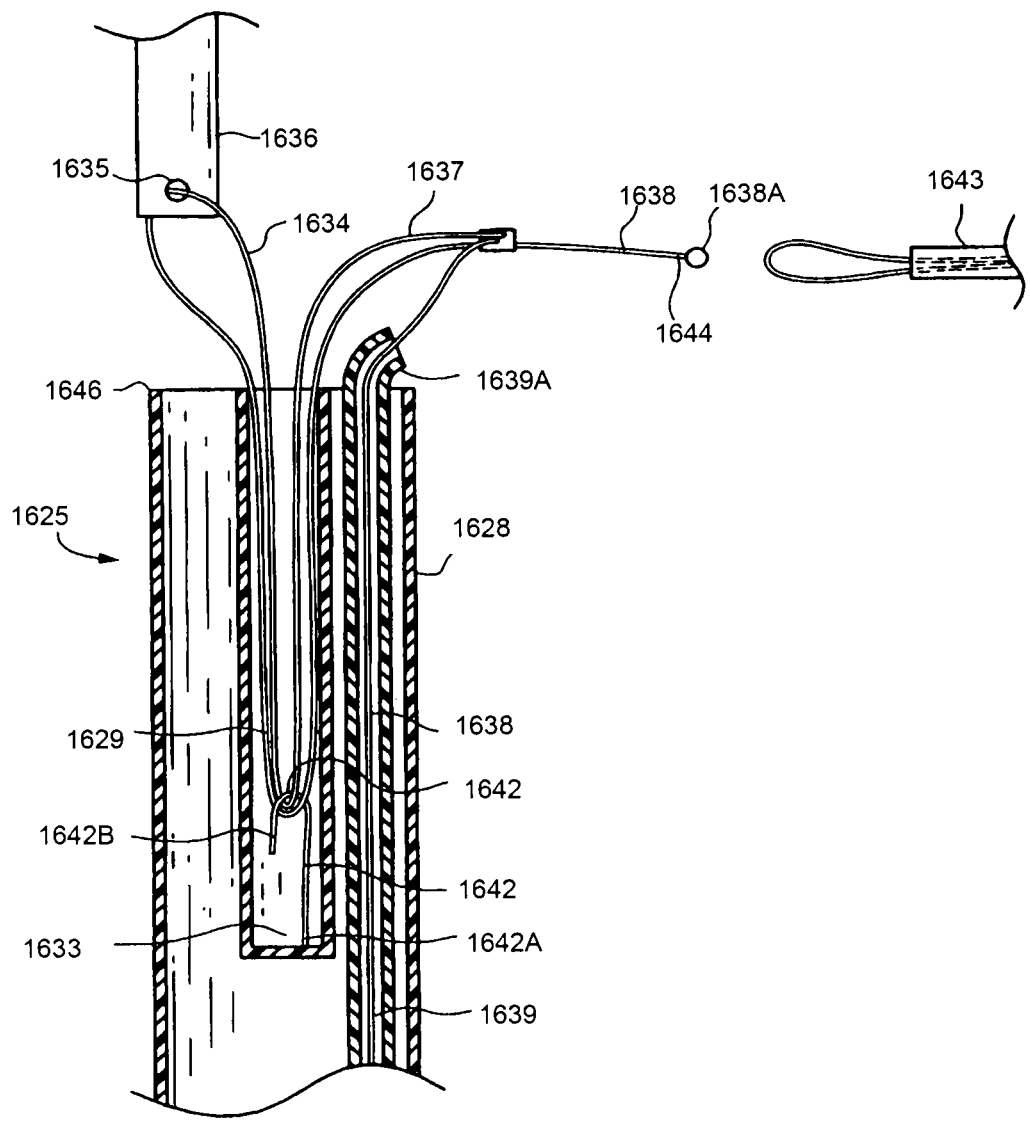

Turning now to FIG. 66, an embodiment of a bifurcated graft delivery system 1625 and method is illustrated. This embodiment is tailored to provide for a controlled withdrawal of a secondary release cable from a lumen of an inner tubular member 1628 so to help eliminate the possibility that the release cable 1626 becomes entangled or otherwise twisted during deployment.

Shown in FIG. 66 is a well 1633 is disposed in the inner tubular member 1628. Well 1633 contains a release strand 1629 that is looped at its proximal end 1634 outside the well 1633 through an aperture 1635 in the secondary belt support member 1636 and that is affixed or attached at its distal end 1637 to a second guidewire 1638. The second guidewire 1638 is shown in the embodiment of FIG. 66 as disposed in its own optional lumen 1639 within the inner tubular member 1628.

Within the well 1633, the release strand 1629 is arranged to form a "u-turn" in which it changes direction to double back on itself at juncture 1641 as shown in FIG. 66. At juncture 1641, a friction line 1642 is looped around all or a portion of the release strand 1629. This friction line 1642 is fixed to the bottom of the well 1633 on one end 1642A and is free on another end 1642B. The friction line 1642 is preferably a polymeric monofilament such as polyimide, etc., but may be metallic and may be braided as necessary to achieve the desired friction characteristic needed to interact with release strand 1629. Friction line 1642 has a length sufficient to interact with the release strand 1629 during the deployment process until the release strand 1629 has been completely removed from the well 1633 as will now be described in detail.

In use, the configuration of FIG. 66 works as follows. Once the left and right femoral access holes 1531 and 1537, discussed above, have been created, the delivery system 1625 is introduced into and through the patient's vasculature. A snare catheter 1643 is introduced into the left femoral artery access hole, such as the left femoral artery access hole 1537 discussed above. The operator then captures the tip 1644 of the second guidewire 1638 with the snare 1643. In the embodiment of FIG. 66, the second guidewire 1638 is shown as pre-attached to the release strand 1629 at the distal end 1637.

A ball capture tip 1638A or similar member may optionally be disposed on the tip 1644 of second guidewire 1638 to facilitate its capture by snare catheter 1643 and prevent possible injury to the vessel intima. In addition, tip 1638A may be made radiopaque so that it may be readily located by the operator during the procedure. When in the form of a ball, tip 1638A may have a diameter ranging from between about 0.020 inch to about 0.120 inch, specifically, between about 0.040 inch to about 0.060 inch. Although not shown in the figures, second guidewire 1638 may also have one or more additional sections branching therefrom, each having a tip or member similar to tip 1644, including tip 1638A, so to provide the operator with one or more alternative sites for capture with snare 1643 in case tip 1638A is inaccessible.

An angled extension 1639A may optionally be provided on one or both of the top of optional lumen 1639 and/or the top of well 1633. Angled extension 1639A may be made of any suitable polymeric or metallic material such as stainless steel. As seen in FIGS. 66-67, extension 1639A disposed on the top of lumen 1639 is generally biased towards the artery in which snare 1643 is disposed at an angle of between about 20 degrees and about 120 degrees, specifically, between about 40 degrees and about 95 degrees, so to guide the release strand 1629 and 1653 in the proper direction and thus facilitate ease of capture by snare 1643.

As the second guidewire 1638 is pulled out of the inner tubular member 1628 from the left femoral artery access hole 1537 in the direction shown by the arrow 1544 in FIG. 50, the release strand 1629 feeds out of the well 1633 in an orderly and linear fashion in a direction from the release strand distal end 1637 to its proximal end 1634. This is made possible by the forces created at the "u-turn" or juncture 1641 by the physical interface with the friction line 1642. The friction force (which can be tailored by the proper combination of release strand 1629 and friction line 1642 diameters and their materials and by properly dimensioning of the well 1633, for example) provides enough resistance to counter the force applied by the operator so that the "u-turn" or juncture 1641 moves in an orderly fashion in a direction from the well bottom 1633 to the distal end 1646 of the inner tubular member 1628 until it exits out of the outer tubular member 1628. At this point, any remaining friction line 1642 at the juncture 1641 is superfluous as it has served its purpose of facilitating an orderly withdrawal of the release strand 1629. The operator continues to pull on the second guidewire 1638 as previously described so that the release strand 1629 extends through the left femoral artery access port 1537. We have found the embodiment of FIG. 66 to be useful in achieving an orderly and tangle-free deployment.

Alternatively, any number of other arrangements in which the release strand 1629 may be fed out of the outer tubular member 1628 in an orderly manner is within the scope of the present invention. For instance, the well 1651 shown in FIGS. 67-69 is, for instance, an extruded polymeric part having a unique cross-sectional configuration that eliminates the need for the friction line 1642 in the embodiment shown in FIG. 66. Here, a narrowing constraint or gap 1652 runs the length of the well interior 1651, forming a physical barrier between first and second opposing portions 1654 and 1655 of the release strand 1653, shown in FIGS. 67-69. The constraint or gap 1652 is sized to allow the passage therethrough of the release strand juncture or "u-turn" 1656. As the operator pulls the release strand 1653 out of the well 1651, the constraint or gap 1652 prevents the opposing portions 1654 and 1655 of the release strand 1653 from crossing into the other side of the well 1651. Said another way, the constraint or gap 1652 keeps the juncture or "u-turn" 1656 within its vicinity to facilitate an orderly withdrawal of the release strand 1653 from the well 1651. In this embodiment, the release strand 1653 can have a diameter of between about 0.004 and 0.010 inch; specifically between about 0.006 and 0.007 inch. The gap or constraint 1652 should be between about 0.003 and about 0.009 inch; preferably between about 0.005 and about 0.006 inch.

Figure 70:
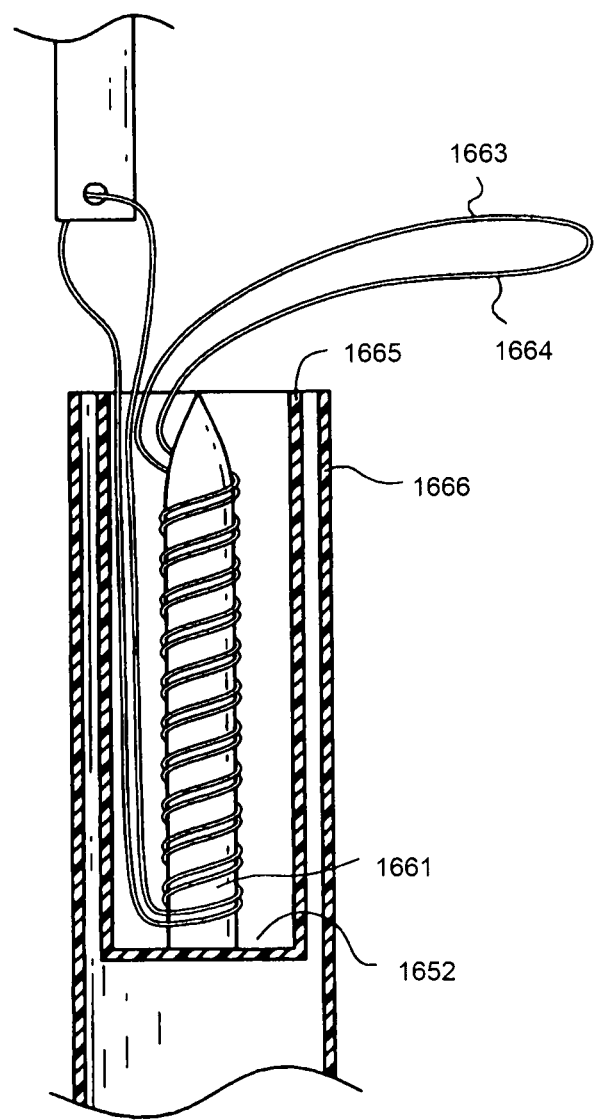

Yet another variation of this embodiment, shown in FIG. 70, includes a post 1661 disposed in a well 1652 around which the release strand 1663 is wound such that as the operator pulls the distal portion 1664 of the release strand 1663 out of the distal end 1665 of the well 1652, the release strand 1663 unwinds in an orderly fashion from the post 1661. The post 1661 may be optionally configured to spin on its longitudinal axis, similar to that of a fishing reel spinner, to facilitate the exit of the release strand 1663.

Other variations, such as a block and tackle arrangement (not shown), are envisioned in which the release strand 1663 is looped through a grommet or similar feature. The grommet provides the necessary friction to prevent the entire release strand 1663 from pulling out of the well 1652 in one mass as soon as the operator applies a force on a distal end thereof. Any arrangement in which a frictional or similar force is utilized to allow for the orderly dispensation of the release strand 1663 from the shaft or post 1661 is within the scope of the embodiment contemplated.

While particular forms of the invention have been illustrated and described, it will be apparent that various modifications can be made without departing from the spirit and scope of the invention.

What is claimed is:

1. An endovascular graft delivery system configured to deliver an endovascular graft to a target location within a patient's vasculature and deploy the endovascular graft at the target location, comprising:
    an endovascular graft comprising:
        a proximal end, a distal end, a tubular graft body section disposed between the proximal end and the distal end; and
        a first distal self-expanding member that is disposed distally of: (i) a second self-expanding member and (ii) the distal end of the graft body section;
    wherein the first distal self-expanding member comprises:
        a proximal end, a distal end, a plurality of struts and a plurality of apices at each of the proximal and distal ends;
        a barb integrally formed as a part of at least one strut without a joint and without other mechanical connection thereat and extending outwardly from a position on said at least one strut, wherein said at least one strut comprises an outer surface and an opposed inner surface, thereby defining a strut wall therein between; and
        at least one slot formed as an opening directly through only one longitudinal portion of said one of at least one of the struts from said outer surface of said at least one strut to said opposed inner surface of said at least one strut, said opening being bounded only by the one longitudinal portion of said strut wall of said at least one strut, said at least one strut containing said portion being disposed between one of said plurality of apices at said proximal end and one of said plurality of apices at said distal end, wherein at least one of the proximal and distal apices are curved apices; and
    a delivery system comprising:
        an elongate shaft having a proximal section and a distal section;
        an outer tubular member with the graft body section being disposed within the outer tubular member in a radially constrained state;
        a constraint disposed at the first distal self-expanding member; and
        a release member for releasing the constraint;
    wherein the outer tubular member is configured to be retracted proximally to expose the graft body section; and
    wherein the release member is operable to release the constraint from the first distal self-expanding member after the outer tubular member is retracted proximally to at least partially expose the graft body section.

2. The endovascular graft delivery system of claim 1, further comprising a handle for manipulation to move the release member to release the constraint disposed at the first distal self-expanding member.

3. The endovascular graft delivery system of claim 1, wherein the endovascular graft delivery system has a delivery profile from about 10 French to about 16 French.

4. The endovascular graft delivery system of claim 1, wherein the endovascular graft delivery system has a delivery profile of about 16 French.

5. The endovascular graft delivery system of claim 1, wherein the at least one slot is configured to the shape of the at least one barb.

6. The endovascular graft delivery system of claim 1, wherein the self-expanding members comprises NiTi.

7. The endovascular graft delivery system of claim 1, wherein the first distal self-expanding member is a two-stage stent having interconnected intermediate stent portions.

8. The endovascular graft delivery system of claim 1, wherein the at least one barb is oriented in a proximal direction and has an elevation angle with respect to a longitudinal axis of a strut from which the barb extends of about 10 degrees to about 45 degrees.

9. The endovascular graft delivery system of claim 1, wherein the at least one barb is proximal to an apex.

10. The endovascular graft delivery system of claim 1, wherein some of said struts and some of said apices are free of barbs.

11. The endovascular graft delivery system of claim 1, wherein some of said apices are free of barbs.

12. The endovascular graft delivery system of claim 1, wherein the elongate shaft of the delivery system further comprises a guidewire lumen.

13. The endovascular graft delivery system of claim 1, wherein the at least one barb is configured to engage tissue of the patient's vasculature to prevent migration of the endovascular graft within the patient's vasculature.

14. The endovascular graft delivery system of claim 1, wherein the endovascular graft is bifurcated such that the tubular graft body section further comprises a main body portion and a bifurcation from which extend in a proximal direction (i) an ipsilateral leg terminating proximally with a first proximal self-expanding member and (ii) a contralateral leg terminating proximally with a second proximal self-expanding member.

15. The endovascular graft delivery system of claim 1, further comprising a radiopaque marker secured thereto.

16. The endovascular graft delivery system of claim 1, further comprising a radiopaque marker secured to the endovascular graft.

17. The endovascular graft delivery system of claim 14, wherein the first and second proximal self-expanding members comprise NiTi.

18. The stent of claim 1, wherein the proximal and distal apices are curved apices.

19. The stent of claim 1, wherein the graft body section comprises polyester.

20. A method of treating a patient's vasculature by using the endovascular graft delivery system of claim 1, comprising:
providing the endovascular graft delivery system of claim 1;
delivering the endovascular graft in the radially constrained state to a target location within a patient's body passageway with the delivery system;
moving the outer tubular member proximally relative to the endovascular graft;
deploying the second distal self-expanding member of the endovascular graft, whereby the second distal self-expanding member self-expands while the first distal self-expanding member remains in at least partially the radially constrained state; and
deploying the first distal self-expanding member by releasing the constraint such that the first distal self-expanding member engages tissue of the patient's body passageway in which the endovascular graft is at least partially deployed and prevents axial migration of the endovascular graft.

21. An endovascular graft delivery system configured to deliver an endovascular graft to a target location within a patient's vasculature and deploy the endovascular graft at the target location, comprising:
an endovascular graft comprising:
a proximal end, a distal end, a tubular graft body section disposed between the proximal end and the distal end; and
a first distal self-expanding member that is disposed distally of: (i) a second self-expanding member and (ii) the distal end of the graft body section;
wherein the first distal self-expanding member comprises:
a proximal end, a distal end and a plurality of struts and joined by curved apices at the proximal and distal ends of said stent;
at least one barb on at least one strut, the barb being an extension of the strut in which no joint and no other connection to the strut exists, wherein said at least one strut comprises an outer surface and an opposed inner surface, thereby defining a strut wall therein between; and
at least one slot formed as an opening directly through only one longitudinal portion of said one of at least one of the struts from said outer surface of said at least one strut to said opposed inner surface of said at least one strut, said opening being bounded only by the one longitudinal portion of said strut wall of said at least one strut, said at least one strut containing said portion being disposed between one of said plurality of apices at said proximal end and one of said plurality of apices at said distal end, the slot being configured to the shape of the at least one barb, wherein the first distal self-expanding member is a two-stage stent having interconnected intermediate stent portions, and wherein said curved apices have an outer lateral surface with a radius of curvature; and
a delivery system comprising:
an elongate shaft having a proximal section and a distal section;
an outer tubular member with the graft body section being disposed within the outer tubular member in a radially constrained state;
a constraint disposed at the first distal self-expanding member; and
a release member for releasing the constraint;
wherein the outer tubular member is configured to be retracted proximally to expose the graft body section; and
wherein the release member is operable to release the constraint from the first distal self-expanding member after the outer tubular member is retracted proximally to at least partially expose the graft body section.

22. The endovascular graft delivery system of claim 21, further comprising a handle for manipulation to move the release member to release the constraint disposed at the first distal self-expanding member.

23. The endovascular graft delivery system of claim 21, wherein the endovascular graft is bifurcated such that the tubular graft body section further comprises a main body portion and a bifurcation from which extend in a proximal direction (i) an ipsilateral leg terminating proximally with a first proximal self-expanding member and (ii) a contralateral leg terminating proximally with a second proximal self-expanding member.

24. A method of treating a patient's vasculature by using the endovascular graft delivery system of claim 21, comprising:
providing the endovascular graft delivery system of claim 21;
delivering the endovascular graft in the radially constrained state to a target location within a patient's body passageway with the delivery system;
moving the outer tubular member proximally relative to the endovascular graft;
deploying the second distal self-expanding member of the endovascular graft, whereby the second distal self-expanding member self-expands while the first distal self-expanding member remains in at least partially the radially constrained state; and deploying the first distal self-expanding member by releasing the constraint such that the first distal self-expanding member engages tissue of the patient's body passageway in which the endovascular graft is at least partially deployed and prevents axial migration of the endovascular graft.

25. An endovascular graft delivery system configured to deliver an endovascular graft to a target location within a patient's vasculature and deploy the endovascular graft at the target location, comprising:
   an endovascular graft comprising:
      a proximal end, a distal end, a tubular graft body section disposed between the proximal end and the distal end; and
      a first distal self-expanding member that is disposed distally of: (i) a second self-expanding member and (ii) the distal end of the graft body section;
   wherein the first distal self-expanding member comprises:
      a proximal end, a distal end and a plurality of struts and apices at the proximal and distal ends of said stent;
      at least one barb on a strut, the barb and strut comprising a barb/strut interface in which there is no mechanical connection to join the barb to the strut, wherein said at least one strut comprises an outer surface and an opposed inner surface, thereby defining a strut wall therein between; and
      at least one slot formed as an opening directly through only one longitudinal portion of said one of at least one of said struts from said outer surface of said at least one strut to said opposed inner surface of said at least one strut, said opening being bounded only by the one longitudinal portion of said strut wall of said at least one strut, said at least one strut containing said portion being disposed between one of said plurality of apices at said proximal end and one of said plurality of apices at said distal end, the at least one slot being configured to the shape of the at least one barb, wherein said apices have an outer lateral surface with a radius of curvature; and
   a delivery system comprising:
      an elongate shaft having a proximal section and a distal section;
      an outer tubular member with the graft body section being disposed within the outer tubular member in a radially constrained state;
      a constraint disposed at the first distal self-expanding member; and
      a release member for releasing the constraint;
   wherein the outer tubular member is configured to be retracted proximally to expose the graft body section; and
   wherein the release member is operable to release the constraint from the first distal self-expanding member after the outer tubular member is retracted proximally to at least partially expose the graft body section.

26. The endovascular graft delivery system of claim 25, further comprising a handle for manipulation to move the release member to release the constraint disposed at the first distal self-expanding member.

27. The endovascular graft delivery system of claim 25, wherein the endovascular graft is bifurcated such that the tubular graft body section further comprises a main body portion and a bifurcation from which extend in a proximal direction (i) an ipsilateral leg terminating proximally with a first proximal self-expanding member and (ii) a contralateral leg terminating proximally with a second proximal self-expanding member.

28. A method of treating a patient's vasculature by using the endovascular graft delivery system of claim 25, comprising:
   providing the endovascular graft delivery system of claim 25;
   delivering the endovascular graft in the radially constrained state to a target location within a patient's body passageway with the delivery system;
   moving the outer tubular member proximally relative to the endovascular graft;
   deploying the second distal self-expanding member of the endovascular graft, whereby the second distal self-expanding member self-expands while the first distal self-expanding member remains in at least partially the radially constrained state; and
   deploying the first distal self-expanding member by releasing the constraint such that the first distal self-expanding member engages tissue of the patient's body passageway in which the endovascular graft is at least partially deployed and prevents axial migration of the endovascular graft.

29. An endovascular graft delivery system configured to deliver an endovascular graft to a target location within a patient's vasculature and deploy the endovascular graft at the target location, comprising:
   an endovascular graft comprising:
      a proximal end, a distal end, a tubular graft body section disposed between the proximal end and the distal end; and
      a first distal self-expanding member that is disposed distally of: (i) a second self-expanding member and (ii) the distal end of the graft body section;
   wherein the first distal self-expanding member comprises:
      a proximal end, a distal end and a plurality of struts joined by curved apices at the proximal and distal ends of said stent;
      at least one barb on at least one strut, the barb being located on the strut between two apices, the barb being an extension of the strut in which no joint and no other connection to the strut exists, wherein said at least one strut comprises an outer surface and an opposed inner surface, thereby defining a strut wall therein between; and
      at least one slot formed as an opening directly through only one longitudinal portion of said one of at least one of the struts from said outer surface of said at least one strut to said opposed inner surface of said at least one strut, said opening being bounded only by the one longitudinal portion of said strut wall of said at least one strut, said at least one strut containing said portion being disposed between one of said plurality of apices at said proximal end and one of said plurality of apices at said distal end, the slot being configured to the shape of the at least one barb, wherein the first distal self-expanding member is a two-stage stent having interconnected intermediate stent portions, and wherein said curved apices have an outer lateral surface with a radius of curvature; and
   a delivery system comprising:
      an elongate shaft having a proximal section and a distal section;
      an outer tubular member with the graft body section being disposed within the outer tubular member in a radially constrained state;

a constraint disposed at the first distal self-expanding member; and a release member for releasing the constraint;

wherein the outer tubular member is configured to be retracted proximally to expose the graft body section; and wherein the release member is operable to release the constraint from the first distal self-expanding member after the outer tubular member is retracted proximally to at least partially expose the graft body section.

30. A method of treating a patient's vasculature by using the endovascular graft delivery system of claim 29, comprising:

providing the endovascular graft delivery system of claim 29;

delivering the endovascular graft in the radially constrained state to a target location within a patient's body passageway with the delivery system;

moving the outer tubular member proximally relative to the endovascular graft;

deploying the second distal self-expanding member of the endovascular graft, whereby the second distal self-expanding member self-expands while the first distal self-expanding member remains in at least partially the radially constrained state; and deploying the first distal self-expanding member by releasing the constraint such that the first distal self-expanding member engages tissue of the patient's body passageway in which the endovascular graft is at least partially deployed and prevents axial migration of the endovascular graft.

* * * * *